(12) United States Patent
Li et al.

(10) Patent No.: US 11,465,984 B2
(45) Date of Patent: Oct. 11, 2022

(54) COMPOUND HAVING ERK KINASE INHIBITORY ACTIVITY AND USE THEREOF

(71) Applicants: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

(72) Inventors: Lei Li, Shanghai (CN); Meiyu Geng, Shanghai (CN); Ying Huang, Shanghai (CN); Jian Ding, Shanghai (CN); Qiong Zhang, Shanghai (CN); Min Huang, Shanghai (CN); Shuai Tang, Shanghai (CN); Ning Shen, Shanghai (CN); Yi Chen, Shanghai (CN)

(73) Assignees: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/652,148

(22) PCT Filed: Sep. 29, 2018

(86) PCT No.: PCT/CN2018/108762
§ 371 (c)(1),
(2) Date: Mar. 30, 2020

(87) PCT Pub. No.: WO2019/062949
PCT Pub. Date: Apr. 4, 2019

(65) Prior Publication Data
US 2020/0247781 A1 Aug. 6, 2020

(30) Foreign Application Priority Data
Sep. 30, 2017 (CN) .......................... 201710915493.5

(51) Int. Cl.
*C07D 401/14* (2006.01)
*C07D 403/14* (2006.01)
*C07D 405/14* (2006.01)

(52) U.S. Cl.
CPC ......... *C07D 401/14* (2013.01); *C07D 403/14* (2013.01); *C07D 405/14* (2013.01)

(58) Field of Classification Search
CPC ............................ C07D 401/14; C07D 403/14
See application file for complete search history.

(56) References Cited

FOREIGN PATENT DOCUMENTS

| WO | 2017114510 | * | 7/2017 |
| WO | 2017114510 A1 | * | 7/2017 |
| WO | WO 2017/114510 | | 7/2017 |
| WO | WO 2017/125530 | | 7/2017 |
| WO | WO 2017/125534 | | 7/2017 |

OTHER PUBLICATIONS

WO 2017/114510, Shanghai Institute of Materia Medica, Chinese Academy of Sciences, "Compound Having ERK Kinase Inhibitory Activity, Method for Preparation Thereof, and Use Thereof," Jul. 6, 2017, English language machine translation of abstract, Espacenet, date obtained: Jun. 30, 2020, 1 page <https://worldwide.espacenet.com/patent/search/family/059224677/publication/WO2017114510A1?q=WO%202017%2F114510>.

\* cited by examiner

*Primary Examiner* — Paul V Ward
(74) *Attorney, Agent, or Firm* — Hoxie & Associates LLC

(57) ABSTRACT

The invention relates to a compound of formula (I):

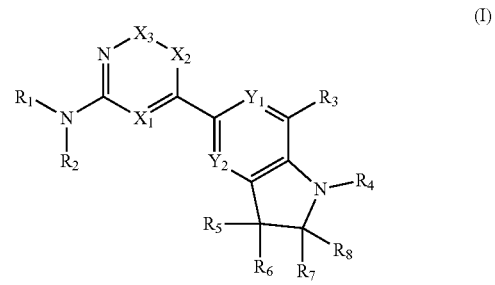

wherein variables are as defined in the specification. The compound is an inhibitor of an ERK kinase, e.g. ERK1 and/or ERK2 kinase. The invention also relates to the use of the compound and a method for preparing the compound, and a pharmaceutical composition containing the compound.

25 Claims, 1 Drawing Sheet

COMPOUND HAVING ERK KINASE INHIBITORY ACTIVITY AND USE THEREOF

CROSS REFERENCE TO RELATED APPLICATIONS

This application is a United States Application under 35 U.S.C. 371 claiming benefit of PCT Application No. PCT/CN2018/108762, filed on Sep. 29, 2018, which claims the benefit of priority from Chinese Patent Application No. 201710915493.5, filed on Sep. 30, 2017, the contents of each of which are incorporated herein by reference.

FIELD OF THE INVENTION

The invention belongs to the field of pharmaceutical chemistry. Specifically, the invention relates to novel compounds or pharmaceutically acceptable salts thereof, and a pharmaceutical composition comprising said compounds or pharmaceutically acceptable salts thereof, which are useful as modulators of the extracellular signal-regulated kinase (ERK) pathway, in particular as inhibitors of ERK kinases such as ERK1 and/or ERK2 kinase.

BACKGROUND OF THE INVENTION

The Ras-Raf-MEK-ERK pathway is a mitogen activated protein kinase (MAPK) signaling pathway and regulates multiple functions such as proliferation, differentiation, and apoptosis of cells. Mutations of this pathway are present in more than one third of all human cancers. Therefore, the nodal proteins on this pathway have become a hotspot for the development of targeting anti-cancer drugs in recent years. Specific B-Raf inhibitors vemurafenib and dabrafenib were approved by the U.S. FDA for the treatment of melanoma in 2011 and 2013, respectively. The MEK1/2 inhibitor trametinib was approved by the U.S. FDA for the treatment of melanoma in 2013. The combination of vemurafenib and the MEK inhibitor cobimetinib was approved by the U.S. FDA for the treatment of B-Raf V600E or V600K mutant melanoma in 2015. The U.S. FDA also approved the combination of dabrafenib and trametinib for the treatment of B-Raf V600E mutant non-small cell lung cancer in 2017. However, there are limitations for the inhibition of these upstream pathway nodes. Tumors can rapidly become resistant to B-Raf and MEK inhibitors, and the mechanisms of the resistance include a variety of ways such as point mutation, change of multimeric form of proteins, and change of peptide chain length of proteins. This is a great challenge for the development of next generation of drugs against Raf and MEK. Meanwhile, as a terminal key node of MAPK, the activated ERK can transmit extracellular signals to cell nucleus, promote the phosphorylation of cytoplasmic target proteins or regulate the activity of other protein kinases, thereby regulating gene expression. It is undoubtedly important in the development of anti-tumor drugs. Especially when the majority of the current MAPK upstream targeting therapies eventually show drug resistance, the ERK inhibitors will probably become a more effective therapeutic means because of being less prone to generate acquired drug resistance. Since ERK was discovered in the 1990s, there has been much extensive and intensive research on it, but to date no ERK inhibitors have been approved for marketing as pharmaceuticals. Currently the highly selective ERK inhibitor BVD-523 (Ulixertinib) in Phase 2 clinic trial is at the leading level worldwide. In early 2017, it is reported that BVD-523 at the dose of 600 mg twice a day showed acceptable safety in patients and produced a lasting efficacy in patients having melanoma with NRAS mutation and solid tumors with BRAF V600 and non-V600 mutants (including melanoma, glioblastoma multiforme, brain metastatic cancer, gallbladder adenocarcinoma, and head and neck tumor). These data further support the clinical development of ERK inhibitors.

In conclusion, the ERK inhibitors alone or in combination can be expected to have wide prospects in the anti-tumor field, and the development of a novel ERK inhibitor is urgently needed in this field. Patent application WO2017/114510A1 discloses a series of ERK inhibitors, but the inventors of the present application found that in said patent application, some compounds, especially those having the structure of

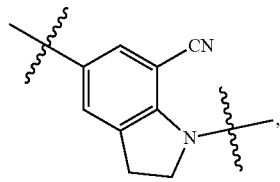 [SMILES: *c1cc(C#N)c2c(c1)CCN2*]

had a poor chemical stability, and easily generate impurities, especially under alkaline conditions, which properties of these compounds bring certain difficulties to drug development; and some compounds having the structure of

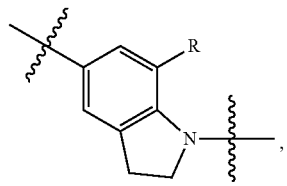

wherein R is amino, carboxyl or amido etc., although active in preliminary in vitro tests, had unsatisfactory pharmacokinetic parameters, which brings certain difficulties to drug development. In short, comprehensive evaluation (for example, in terms of chemical stability and/or pharmacokinetic properties, etc.) revealed that some compounds disclosed in the patent application WO2017/114510A1 showed difficulties in drug development. Therefore, there is a need to look for highly selective compounds with ERK kinase inhibitory activity, which are more suitable for drug development, through comprehensive evaluation.

DESCRIPTION OF THE INVENTION

Through many experimental research, the inventors finally found that the compounds having the core structure

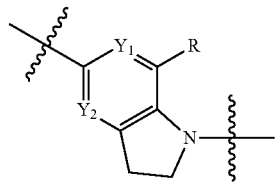

and wherein $R_3$ is halogen, unsubstituted alkyl, haloalkyl, deuterated alkyl or the like had a good chemical stability as well as better solubility and permeability, all showed ERK kinase inhibitory activity in the enzyme and cell assays, and had good pharmacokinetic parameters, so they were particularly suitable for drug development.

Embodiments

In one aspect, the invention provides novel ERK kinase inhibitors. Specifically, the invention provides the following embodiments:

Embodiment 1. A compound of formula (I), or a stereoisomer, racemate, geometric isomer, tautomer, prodrug, hydrate, solvate, or pharmaceutically acceptable salt thereof,

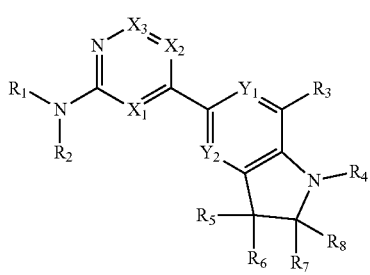

(I)

Wherein $X_1$ is selected from the group consisting of $CR_{9a}$ and N;
$X_2$ is selected from the group consisting of $CR_{9b}$ and N;
$X_3$ is selected from the group consisting of $CR_{9c}$ and N;
and at most one of $X_1$, $X_2$ and $X_3$ is N;

$Y_1$ and $Y_2$ are each independently selected from the group consisting of $CR_9'$ and N;

$R_{9a}$, $R_{9b}$ and $R_{9c}$ are each independently selected from the group consisting of H, D, halo, —OH, cyano, optionally substituted alkyl, optionally substituted alkoxy, optionally substituted alkylcarbonyl, optionally substituted alkoxycarbonyl, optionally substituted cycloalkyl, amino, optionally substituted mono- or di-(alkyl) amino and —$CONR_aR_b$;

$R_9'$ is selected from the group consisting of H, D, halo, —OH, cyano, optionally substituted alkyl, optionally substituted alkoxy, optionally substituted alkylcarbonyl, optionally substituted alkoxycarbonyl, optionally substituted cycloalkyl, amino, optionally substituted mono- or di-(alkyl) amino and $CONR_aR_b$;

$R_1$ is selected from the group consisting of H and D;

$R_2$ is selected from the group consisting of optionally substituted alkyl, optionally substituted cycloalkyl, optionally substituted heterocyclyl, optionally substituted aryl, and optionally substituted heteroaryl, or $R_2$ together with $X_1$ forms optionally substituted heterocyclyl;

$R_3$ is selected from the group consisting of halo and optionally substituted alkyl;

$R_4$ is selected from the group consisting of H, D, optionally substituted alkyl, optionally substituted alkoxy, —CO$(CR_{10}R_{11})_mR_{12}$, —SO$_2(CR_{10}R_{11})_mR_{12}$, —CONR$_{13}$$(CR_{10}R_{11})_mR_{12}$, —COO$(CR_{10}R_{11})_mR_{12}$, —$CR_{13}R_{13}'$$(CR_{10}R_{11})_mR_{12}$ and $C_{1-8}$ alkylcarbonyl-; wherein m is 0, 1, 2 or 3, and wherein $R_{10}$ and $R_{11}$ are each independently selected from the group consisting of H, D, halo, optionally substituted alkyl, and optionally substituted alkoxy; or $R_{10}$ and $R_{11}$ are joined together to form optionally substituted cycloalkyl, cycloalkenyl, aryl, heteroaryl and heterocyclyl; and $R_{12}$ is each independently selected from the group consisting of H, optionally substituted alkyl, optionally substituted cycloalkyl, optionally substituted heterocyclyl, optionally substituted aryl, and optionally substituted heteroaryl; and $R_{13}$ and $R_{13}'$ are each independently selected from the group containing of H and optionally substituted alkyl; or $R_{13}$ and $R_{13}'$ together with the adjacent carbon form optionally substituted cycloalkyl, cycloalkenyl and heterocyclyl;

$R_5$, $R_6$, $R_7$ and $R_8$ are each independently selected from the group consisting of —H, -D, halo, —OH, amino, cyano, optionally substituted alkyl, optionally substituted alkoxy, —$(CH_2)_{0-3}CONR_aR_b$, —$(CH_2)_{0-3}COOH$, optionally substituted cycloalkyl, and optionally substituted heterocyclyl; or any two of $R_5$, $R_6$, $R_7$ and $R_8$ together with the adjacent carbon form optionally substituted cycloalkyl, cycloalkenyl, aryl, heteroaryl and heterocyclyl; and $R_a$ and $R_b$ are each independently selected from the group consisting of H, D and optionally substituted alkyl;

Wherein the optional substituents are independently selected from the group consisting of deuterium (D), halo, —OH, mercapto, cyano, —$CD_3$, —$C_1$-$C_6$ alkyl, $C_2$-$C_6$ alkenyl, $C_2$-$C_6$ alkynyl, 3-8 membered cycloalkyl, aryl, 3-8 membered heterocyclyl, heteroaryl, aryl-$C_1$-$C_6$alkyl, heteroaryl-$C_1$-$C_6$haloalkyl-, $C_1$-$C_6$haloalkyl-, —$OC_1$-$C_6$alkyl, —$OC_2$-$C_6$alkenyl, —$OC_1$-$C_6$alkylphenyl, —$C_1$-$C_6$ alkyl-OH, —$C_1$-$C_6$alkyl-SH, —$C_1$-$C_6$alkyl-O—$C_1$-$C_6$alkyl, —$OC_1$-$C_6$haloalkyl, —$NH_2$, —$C_1$-$C_6$alkyl-$NH_2$, —$N(C_1$-$C_6$alkyl)$_2$, —$NH(C_1$-$C_6$alkyl), —$N(C_1$-$C_6$alkyl)($C_1$-$C_6$alkylphenyl), —$NH(C_1$-$C_6$alkylphenyl), nitro, —$C(O)$—OH, —$C(O)OC_1$-$C_6$alkyl, —CONRiRii (wherein Ri and Rii are each independently selected from the group consisting of H, D and $C_{1-6}$alkyl), —$NHC(O)(C_1$-$C_6$alkyl), —NHC(O) (phenyl), —$N(C_1$-$C_6$alkyl)$C(O)(C_1$-$C_6$alkyl), —$N(C_1$-$C_6$alkyl)$C(O)$ (phenyl), —$C(O)C_1$-$C_6$alkyl, —$C(O)$-5-7 membered heteroaryl), —$C(O)C_1$-$C_6$alkylphenyl, —$C(O)$$C_1$-$C_6$haloalkyl, —$OC(O)C_1$-$C_6$alkyl, —$S(O)_2$-$C_1$-$C_6$alkyl, —$S(O)$—$C_1$-$C_6$alkyl, —$S(O)_2$-phenyl, —$S(O)_2$-$C_1$-$C_6$haloalkyl, —$S(O)_2NH_2$, —$S(O)_2NH(C_1$-$C_6$alkyl), —$S(O)_2NH$(phenyl), —$NHS(O)_2(C_1$-$C_6$alkyl), —$NHS(O)_2$(phenyl), and —$NHS(O)_2(C_1$-$C_6$haloalkyl), wherein each of said alkyl, cycloalkyl, phenyl, aryl, heterocyclyl and heteroaryl is optionally further substituted with one or more substituents selected from the group consisting of halo, —OH, —$NH_2$, cycloalkyl, 3-8 membered heterocyclyl, $C_1$-$C_4$alkyl, $C_1$-$C_4$haloalkyl-, —$OC_1$-$C_4$alkyl, —$C_1$-$C_4$alkyl-OH, —$C_1$-$C_4$alkyl-O—$C_1$-$C_4$alkyl, —$OC_1$-$C_4$haloalkyl, cyano, nitro, —$C(O)$—OH, —$C(O)OC_1$-$C_6$alkyl, —$CON(C_1$-$C_6$alkyl)$_2$, —$CONH(C_1$-$C_6$alkyl), —$CONH_2$, —$NHC(O)(C_1$-$C_6$alkyl), —$NH(C_1$-$C_6$alkyl)$C(O)(C_1$-$C_6$alkyl), —$SO_2(C_1$-$C_6$alkyl), —$SO_2$(phenyl), —$SO_2(C_1$-$C_6$haloalkyl), —$SO_2NH_2$, —$SO_2NH(C_1$-$C_6$alkyl), —$SO_2NH$(phenyl), —$NHSO_2(C_1$-$C_6$alkyl), —$NHSO_2$(phenyl) and —$NHSO_2(C_1$-$C_6$haloalkyl), provided that the compound is not 2-(2-chloropyridin-3-yl)-1-(7-fluoro-2-(hydroxymethyl)-5-(2-(isopropylamino)pyrimidin-4-yl)indolin-1-yl)ethan-1-one.

Embodiment 2. The compound according to Embodiment 1, or a stereoisomer, racemate, geometric isomer, tautomer, prodrug, hydrate, solvate, or pharmaceutically acceptable salt thereof, characterized in that:

$X_1$ is selected from the group consisting of $CR_{9a}$ and N;
$X_2$ is selected from the group consisting of $CR_{9b}$ and N;
$X_3$ is selected from the group consisting of $CR_{9c}$ and N;
and at most one of $X_1$, $X_2$ and $X_3$ is N;

$Y_1$ and $Y_2$ are each independently selected from the group consisting of $CR_9'$ and N;

$R_{9a}$, $R_{9b}$ and $R_{9c}$ are each independently selected from the group consisting of H, D, halo, —OH, cyano, optionally substituted $C_{1-3}$alkyl, optionally substituted $C_{1-3}$alkoxyl, optionally substituted $C_{1-3}$alkylcarbonyl, optionally substituted $C_{1-3}$alkoxylcarbonyl, optionally substituted $C_{3-8}$cycloalkyl, amino, optionally substituted mono- or di-($C_{1-3}$alkyl)amino, and —$CONR_aR_b$;

$R_9'$ is selected from the group consisting of H, D, halo, —OH, cyano, optionally substituted $C_{1-3}$alkyl, optionally substituted $C_1$-3alkoxyl, optionally substituted $C_{1-3}$alkylcarbonyl, optionally substituted $C_{1-3}$alkoxylcarbonyl, optionally substituted $C_{3-8}$cycloalkyl, amino, optionally substituted mono- or di-($C_{1-3}$alkyl)amino, and $CONR_aR_b$;

$R_1$ is selected from the group consisting of H and D;

$R_2$ is selected from the group consisting of optionally substituted $C_{1-8}$alkyl, optionally substituted $C_{3-8}$cycloalkyl, optionally substituted 3-8 membered heterocyclyl, optionally substituted 6-12 membered aryl, and optionally substituted 5-12 membered heteroaryl such as 5-7 membered heteroaryl, or $R_2$ together with $X_1$ forms optionally substituted 3-8 membered heterocyclyl;

$R_3$ is selected from the group consisting of halo and $C_{1-8}$alkyl optionally substituted with one or more substituents independently selected from the group consisting of D and halo;

$R_4$ is selected from the group consisting of H, D, optionally substituted $C_{1-8}$alkyl, optionally substituted $C_{1-8}$alkoxyl, —$CO(CR_{10}R_{11})_mR_{12}$, —$SO_2(CR_{10}R_{11})_mR_{12}$, —$CONR_{13}(CR_{10}R_{11})_mR_{12}$, —$COO(CR_{10}R_{11})_mR_{12}$, —$CR_{13}R_{13}'(CR_{10}R_{11})_mR_{12}$ and $C_{1-8}$alkylcarbonyl-; wherein m is 0, 1, 2 or 3, and wherein $R_{10}$ and $R_{11}$ are each independently selected from the group consisting of H, D, halo, optionally substituted $C_{1-8}$alkyl, and optionally substituted $C_{1-8}$alkoxyl, or $R_{10}$ and $R_{11}$ are joined together to form optionally substituted cycloalkyl, cycloalkenyl, aryl, heteroaryl and heterocyclyl; and $R_{12}$ are each independently selected from the group consisting of H, optionally substituted $C_{1-3}$alkyl, optionally substituted $C_{3-8}$cycloalkyl, optionally substituted 3-8 membered heterocyclyl, optionally substituted 6-12 membered aryl, and optionally substituted 5-12 membered heteroaryl such as 5-7 membered heteroaryl; and $R_{13}$ and $R_{13}'$ are each independently selected from the group consisting of H and optionally substituted $C_{1-3}$alkyl; or $R_{13}$ and $R_{13}'$ together with the adjacent carbon form optionally substituted $C_{3-8}$cycloalkyl, $C_{4-8}$cycloalkenyl and $C_{5-8}$heterocyclyl;

$R_5$, $R_6$, $R_7$ and $R_8$ are each independently selected from the group consisting of —H, -D, halo, —OH, amino, cyano, optionally substituted $C_{1-3}$alkyl, optionally substituted $C_{1-3}$alkoxyl, —$(CH_2)_{0-3}CONR_aR_b$, —$(CH_2)_{0-3}COOH$, optionally substituted $C_{3-8}$cycloalkyl, and optionally substituted 3-8 membered heterocyclyl; or any two of $R_5$, $R_6$, $R_7$ and $R_8$ together with the adjacent carbon form optionally substituted cycloalkyl, cycloalkenyl, aryl, heteroaryl and heterocyclyl; and $R_a$ and $R_b$ are each independently selected from the group consisting of H, D and optionally substituted $C_{1-3}$alkyl.

Embodiment 3. The compound according to any one of Embodiments 1 to 2, or a stereoisomer, racemate, geometric isomer, tautomer, prodrug, hydrate, solvate, or pharmaceutically acceptable salt thereof, characterized in that: the compound is represented by formula Ia, Ib, Ic or Id:

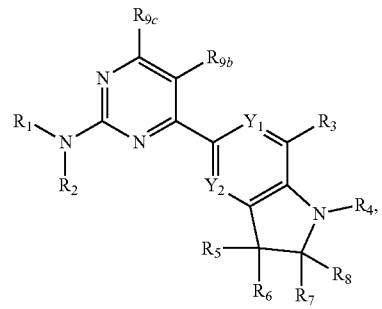

Ia

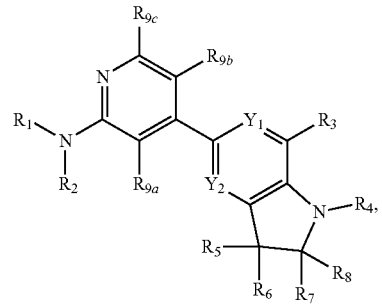

Ib

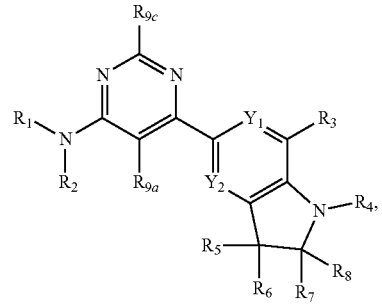

Ic

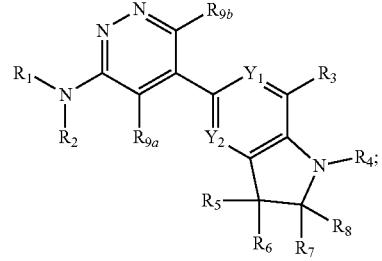

Id $R_{9a}$, $R_{9b}$ and $R_{9c}$ are each independently selected from the group consisting of H, D, $C_{1-3}$alkyl, $C_{1-3}$haloalkyl, $C_{1-3}$alkoxyl, —OH, cyano, halo, amino, mono- or di-($C_{1-3}$alkyl)amino, $C_{1-3}$alkylcarbonyl, $C_{1-3}$alkoxylcarbonyl and $C_{3-8}$cycloalkyl; preferably, $R_{9a}$, $R_{9b}$ and $R_{9c}$ are each independently selected from the group consisting of H, D and $C_{1-3}$alkyl; more preferably, $R_{9a}$, $R_{9b}$ and $R_{9c}$ are each independently selected from the group consisting of H and D; and Other variables are as defined in Embodiment 1 or 2.

Embodiment 4. The compound according to any one of Embodiments 1 to 3, or a stereoisomer, racemate, geometric isomer, tautomer, prodrug, hydrate, solvate, or pharmaceutically acceptable salt thereof, characterized in that:

$Y_1$ is $CR_9'$, $Y_2$ is $CR_9'$, and wherein $R_9'$ is selected from the group consisting of H, D, halo and $C_{1-3}$alkyl; more preferably, $Y_1$ is $CR_9'$, $Y_2$ is $CR_9'$, and wherein $R_9'$ is H, D, F or methyl;

or $Y_1$ is $CR_9'$, $Y_2$ is N, and wherein $R_9'$ is selected from the group consisting of H, D, halo and $C_{1-3}$alkyl; more preferably, $Y_1$ is $CR_9'$, $Y_2$ is N, and wherein $R_9'$ is H, D, F or methyl;

or $Y_1$ is N, $Y_2$ is $CR_9'$, and wherein $R_9'$ is selected from the group consisting of H, D, halo and $C_{1-3}$alkyl; more preferably, $Y_1$ is N, $Y_2$ is $CR_9'$, and wherein $R_9'$ is H, D, F or methyl;

or $Y_1$ is N, and $Y_2$ is N.

Embodiment 5. The compound according to Embodiment 1, or a stereoisomer, racemate, geometric isomer, tautomer, prodrug, hydrate, solvate, or pharmaceutically acceptable salt thereof, characterized in that: the compound is represented by formula Ie:

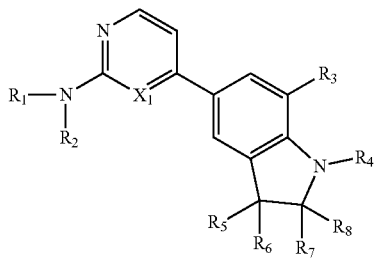

Ie

Wherein the variables are as defined in claim 1.

Embodiment 6. The compound according to any one of Embodiments 1, 2 and 5, or a stereoisomer, racemate, geometric isomer, tautomer, prodrug, hydrate, solvate, or pharmaceutically acceptable salt thereof, characterized in that: $X_1$ is selected from the group consisting of $CR_{9a}$ and N, wherein $R_{9a}$ is selected from the group consisting of H, D, halo, —OH, cyano, $C_{1-3}$alkyl, $C_{1-3}$haloalkyl, $C_{1-3}$alkoxyl, $C_{1-3}$alkylcarbonyl, $C_{1-3}$alkoxylcarbonyl, $C_{3-8}$cycloalkyl, amino, and mono- or di-($C_{1-3}$alkyl)amino; preferably, $X_1$ is selected from the group consisting of $CR_{9a}$ and N, wherein $R_{9a}$ is selected from the group consisting of H, D and $C_{1-3}$alkyl; more preferably, $X_1$ is selected from the group consisting of CH, CD and N.

Embodiment 7. The compound according to any one of Embodiments 1 and 5, or a stereoisomer, racemate, geometric isomer, tautomer, prodrug, hydrate, solvate, or pharmaceutically acceptable salt thereof, characterized in that:

$R_2$ is selected from the group consisting of optionally substituted $C_{1-6}$alkyl, optionally substituted $C_{3-8}$cycloalkyl, optionally substituted 3-8 membered heterocyclyl, and optionally substituted 5-12 membered heteroaryl such as 5-7 membered heteroaryl, wherein the optional substituent is one or more substitutents independently selected from the group consisting of D, halo, hydroxyl, —$CD_3$, $C_{1-6}$alkyl and hydroxyl$C_{1-6}$alkyl, preferably is one or more substitutents independently selected from the group consisting of D, halo, hydroxyl, —CD3, —$CH_3$ and —$CH_2OH$;

or $R_2$ is selected from the group consisting of $C_{1-6}$alkyl optionally substituted with one or more hydroxyl, $C_{3-8}$cycloalkyl optionally substituted with one or more hydroxyl, 3-8 membered heterocyclyl, and 5-12 membered heteroaryl such as 5-7 membered heteroaryl optionally substituted with one or more substituents selected from —$CD_3$, $C_{1-6}$alkyl and hydroxyl$C_{1-6}$alkyl;

or $R_2$ is selected from the group consisting of $C_{1-4}$alkyl,

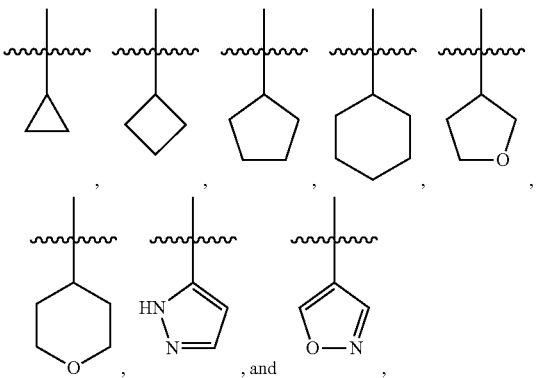

which are optionally substituted with one or more substituents independently selected from the group consisting of D, halo, hydroxyl, $C_{1-4}$alkyl, —$CD_3$ and hydroxyl$C_{1-4}$alkyl, preferably with one or more substituents independently selected from the group consisting of D, halo, hydroxyl, —$CH_3$, —$CD_3$ and —$CH_2OH$;

or $R_2$ is selected from the group consisting of isopropyl,

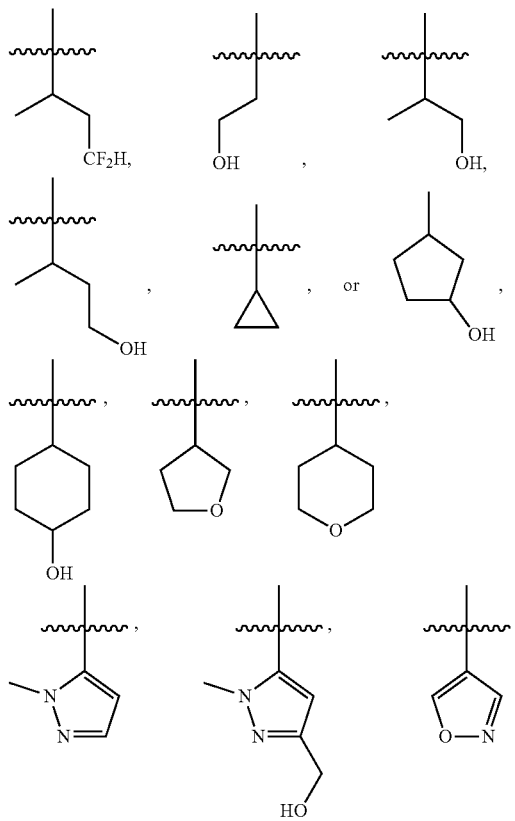

-continued

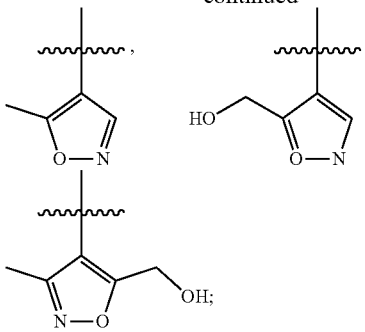

or
$R_2$ is selected from the group consisting of

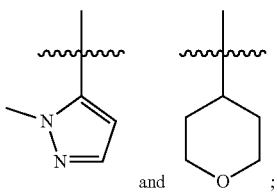

or
$R_2$ is selected from the group consisting of

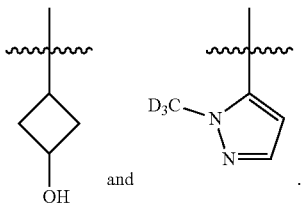 [SMILES: *C1CC(O)C1 ; *c1ccnn1C([2H])([2H])[2H]]

Embodiment 8. The compound according to any one of Embodiments 1 to 7, or a stereoisomer, racemate, geometric isomer, tautomer, prodrug, hydrate, solvate, or pharmaceutically acceptable salt thereof, characterized in that: $R_3$ is selected from the group consisting of halo and $C_{1-6}$alkyl optionally substituted with one or more substituents independently selected from the group consisting of D and halo; or $R_3$ is selected from the group consisting of halo and $C_{1-3}$alkyl optionally substituted with one or more substituents independently selected from the group consisting of D and halo; or $R_3$ is selected from the group consisting of halo and $C_{1-6}$alkyl; or $R_3$ is selected from the group consisting of fluoro, chloro, bromo, iodo, —$CH_3$, —$CH_2CH_3$, —$CH(CH_3)_2$, —$CH_2CH_2CH_3$, —$CF_3$, —$CHF_2$, $CF_3CH_2$—, and $CD_3$-; or $R_3$ is selected from the group consisting of fluoro, chloro, and —$CH_3$; or $R_3$ is fluoro.

Embodiment 9. The compound according to any one of Embodiments 1 to 8, or a stereoisomer, racemate, geometric isomer, tautomer, prodrug, hydrate, solvate, or pharmaceutically acceptable salt thereof, characterized in that:

$R_4$ is selected from the group consisting of —CO($CR_{10}R_{11})_mR_{12}$ and —$CR_{13}R_{13}'(CR_{10}R_{11})_mR_{12}$; wherein m is 0, 1, 2 or 3, and wherein $R_{10}$ and $R_{11}$ are each independently selected from the group consisting of H, D and $C_{1-4}$alkyl optionally substituted with hydroxyl;

$R_{12}$ is each independently selected from the group consisting of optionally substituted 6-12 membered aryl, and optionally substituted 5-12 membered heteroaryl such as 5-7 membered heteroaryl;

$R_{13}$ and $R_{13}'$ are each independently selected from the group consisting of H, $C_{1-3}$alkyl and $C_{1-3}$haloalkyl.

Embodiment 10. The compound according to Embodiment 9, or a stereoisomer, racemate, geometric isomer, tautomer, prodrug, hydrate, solvate, or pharmaceutically acceptable salt thereof, characterized in that: $R_{12}$ is each independently selected from the group consisting of optionally substituted 6-12 membered aryl, and optionally substituted 5-12 membered heteroaryl such as 5-7 membered heteroaryl, wherein the optional substituent is one or more substituents independently selected from the group consisting of D, halo, $C_{1-4}$alkyl, cyano, and $C_{3-8}$heterocyclyl-$(CH_2)_{0-4}$— (for example, morpholinyl such as morpholino, piperazinyl, tetrahydropyranyl such as tetrahydropyran-4-yl, morpholinylmethyl such as morpholinomethyl, or piperazinylmethyl);

or $R_{12}$ is selected from the group consisting of optionally substituted phenyl and optionally substituted pyridinyl such as pyridin-3-yl, wherein the optional substituent is one or more substitutents independently selected from the group consisting of D, halo, $C_{1-4}$alkyl (for example, methyl or ethyl), cyano, and $C_{3-8}$heterocyclyl-$(CH_2)_{0-4}$— (for example, morpholinyl such as morpholino, piperazinyl, tetrahydropyranyl such as tetrahydropyran-4-yl, morpholinylmethyl such as morpholinomethyl, or piperazinylmethyl);

or $R_{12}$ is selected from the group consisting of

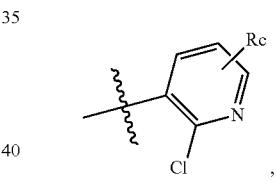

wherein Rc is selected from the group consisting of halo such as fluoro or chloro, $C_{1-4}$alkyl such as methyl,

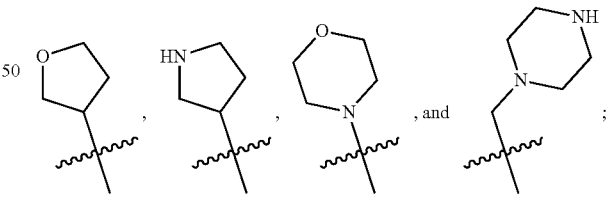

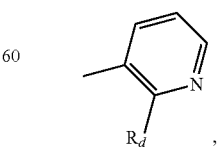

wherein $R_d$ is selected from the group consisting of H, $C_{1-4}$alkyl such as methyl or ethyl, and

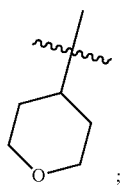

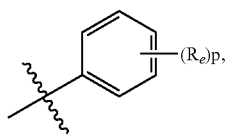

wherein $R_e$ is selected from the group consisting of halo such as fluoro and chloro, and p is 1 or 2; and

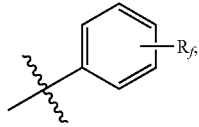

wherein $R_f$ is selected from the group consisting of

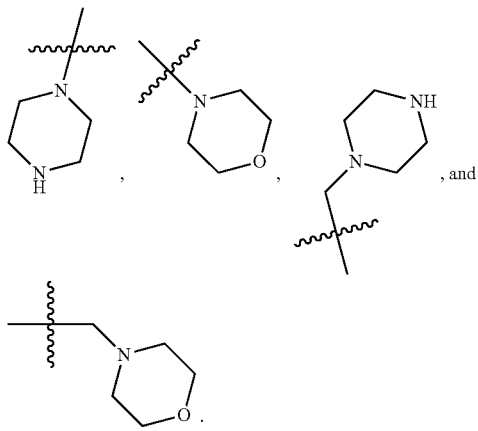

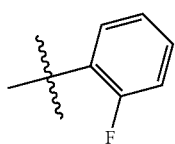 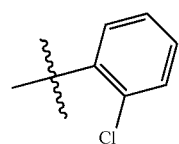

Embodiment 11. The compound according to any one of Embodiments 1 to 8, or a stereoisomer, racemate, geometric isomer, tautomer, prodrug, hydrate, solvate, or pharmaceutically acceptable salt thereof, characterized in that: $R_4$ is selected from the group consisting of —CO(CR$_{10}$R$_{11}$)$_m$R$_{12}$, wherein m is 0, 1, 2 or 3, and wherein $R_{10}$ and $R_{11}$ are each independently selected from the group consisting of H; and $R_{12}$ is selected from the group consisting of

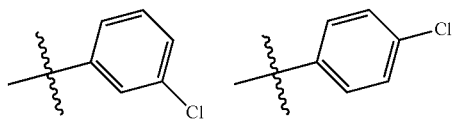

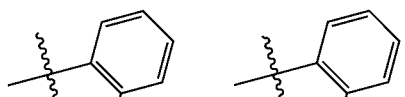

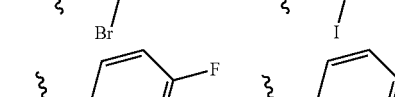

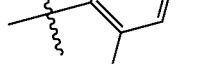

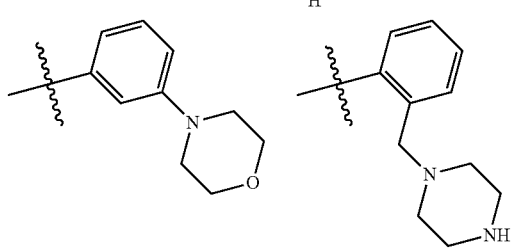

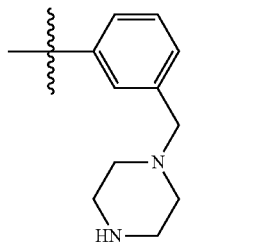

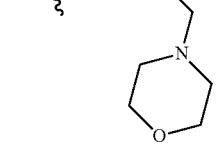

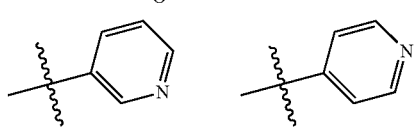

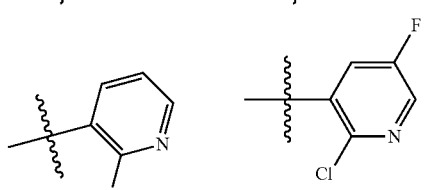

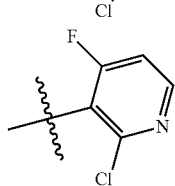

-continued

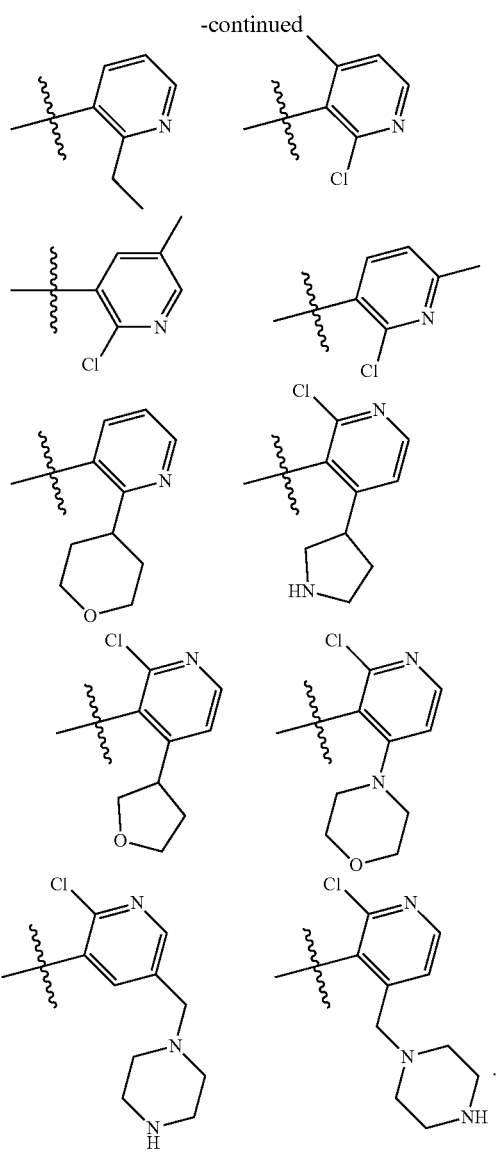

Embodiment 12. The compound according to any one of Embodiments 1 to 8, or a stereoisomer, racemate, geometric isomer, tautomer, prodrug, hydrate, solvate, or pharmaceutically acceptable salt thereof, characterized in that: $R_4$ is selected from the group consisting of —CO(CR$_{10}$R$_{11}$)$_m$R$_{12}$, wherein m is 0, 1, 2 or 3, and wherein $R_{10}$ and $R_{11}$ are each independently selected from the group consisting of H; $R_{12}$ is selected from the group consisting of 2-cyanophenyl, 5-chloro-2-fluorophenyl, 2-chloro-3-fluorophenyl, 2-chloro-4-fluorophenyl, 2-chloro-5-fluorophenyl, 2,5-difluorophenyl, 3-chloropyridin-2-yl, 6-chloropyridin-2-yl, 3-chloropyridin-4-yl, or 4-chloropyridin-3-yl.

Embodiment 13. The compound according to any one of Embodiments 1 to 12, or a stereoisomer, racemate, geometric isomer, tautomer, prodrug, hydrate, solvate, or pharmaceutically acceptable salt thereof, characterized in that:

$R_5$, $R_6$, $R_7$ and $R_8$ are each independently selected from the group consisting of —H, -D, halo, —OH, amino, cyano, optionally substituted $C_{1-6}$alkyl, optionally substituted $C_{1-6}$alkoxyl, —(CH$_2$)$_{0-3}$ CONR$_a$R$_b$, —(CH$_2$)$_{0-3}$COOH, optionally substituted $C_{3-8}$cycloalkyl, and optionally substituted 3-8 membered heterocyclyl, wherein the optional substituent is one or more substitutents independently selected from the group consisting of D, —OH, —OC$_1$-C$_6$alkyl and NH$_2$, and wherein R$_a$ and R$_b$ are each independently selected from the group consisting of H, D and C$_{1-3}$alkyl;

or $R_5$, $R_6$, $R_7$ and $R_8$ are each independently selected from the group consisting of H and C$_{1-6}$alkyl optionally substituted with hydroxyl or —OC$_1$-C$_6$alkyl;

or $R_5$ and $R_6$ are each independently selected from the group consisting of H and C$_{1-6}$alkyl; and $R_7$ and $R_8$ are each independently selected from the group consisting of H and C$_{1-6}$alkyl optionally substituted with hydroxyl or —OC$_1$-C$_6$alkyl;

or $R_5$, $R_6$, $R_7$ and $R_8$ are each independently selected from the group consisting of —H, —CH$_3$ and —CH$_2$OH;

or $R_5$, $R_6$ and $R_7$ are H, and $R_8$ is H, —CH$_3$ or —CH$_2$OH.

Embodiment 14. A compound selected from the group consisting of Examples P1-P20, P23-P25, P28-51, P53-P64:

P1

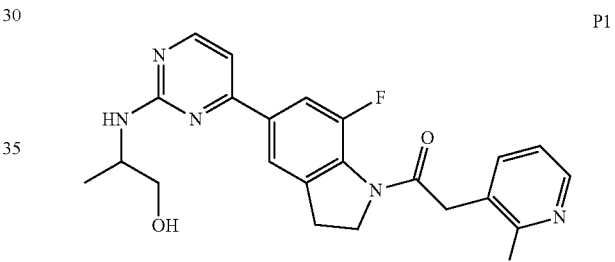

P2

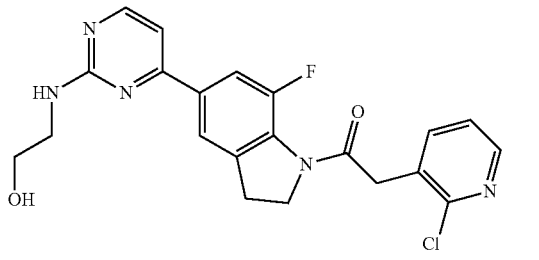

P3

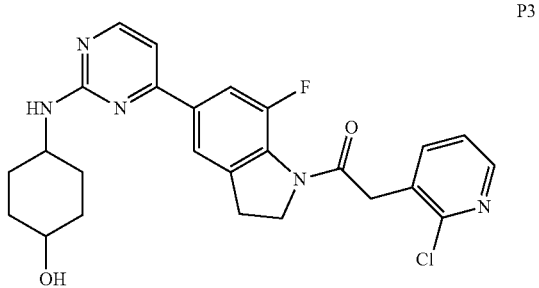

-continued
P4
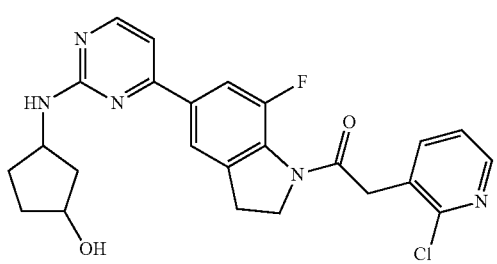
P5
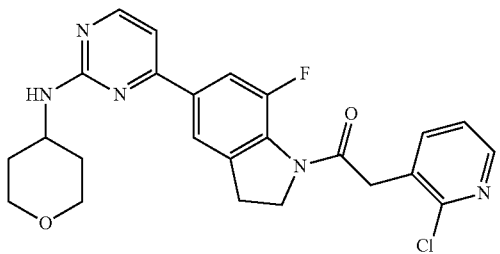
P6
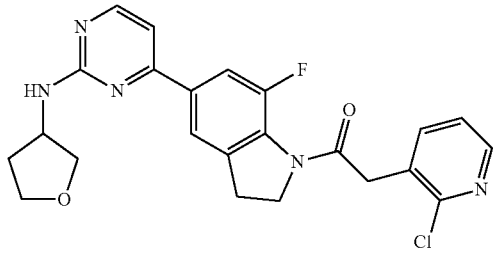
P7
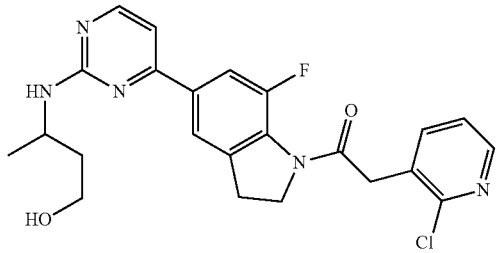
P8
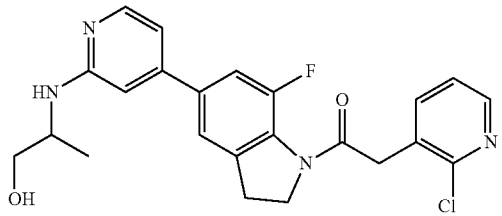
-continued
P9
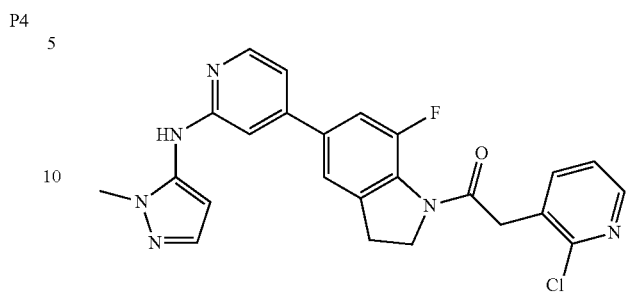
P10
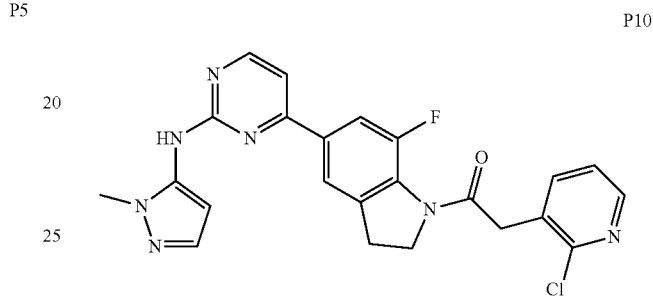
P11
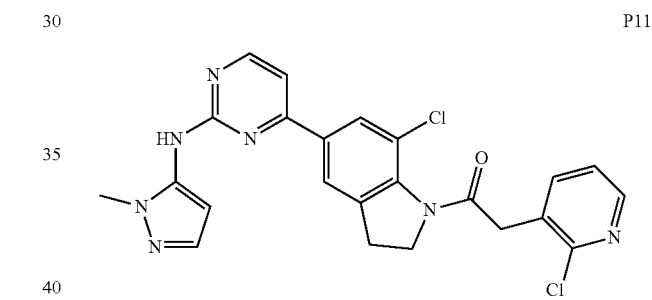
P12
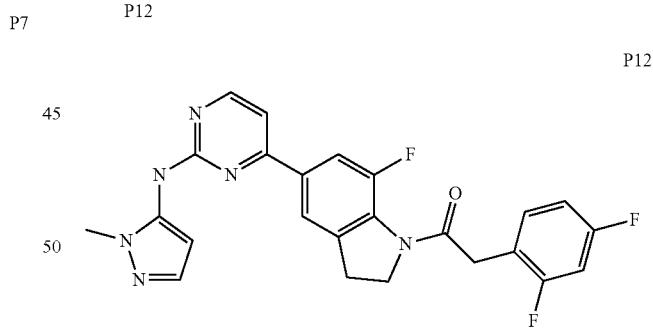
P13
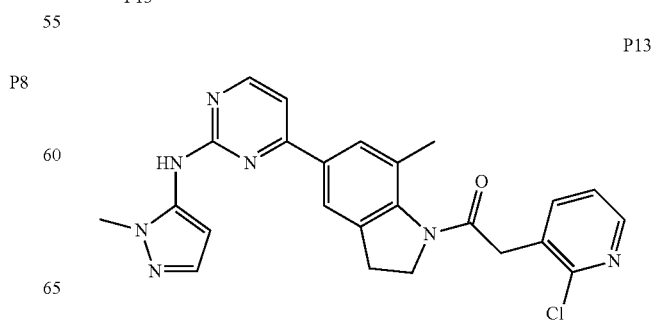

-continued
P14
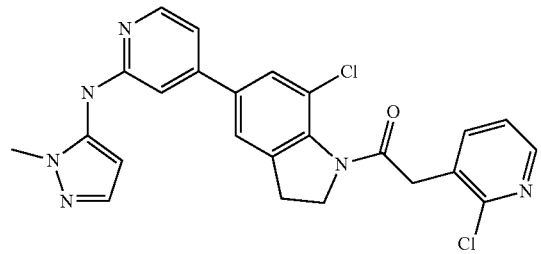
P15
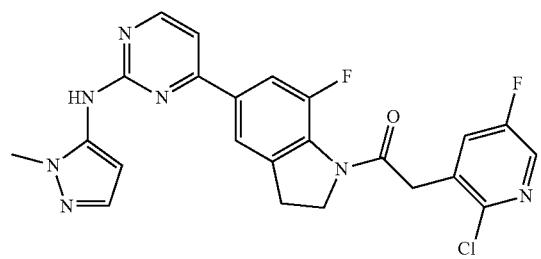
P16
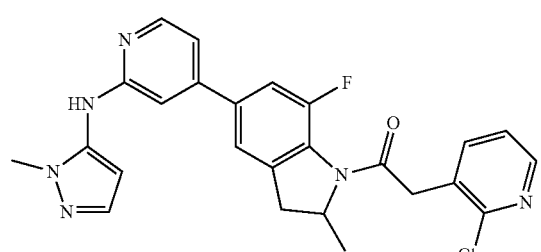
P17
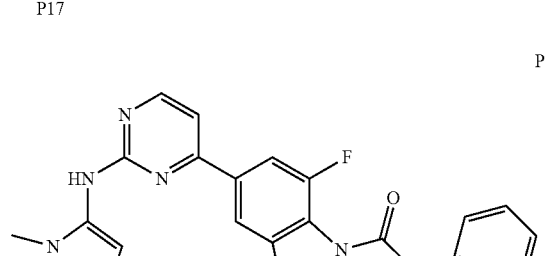
P18
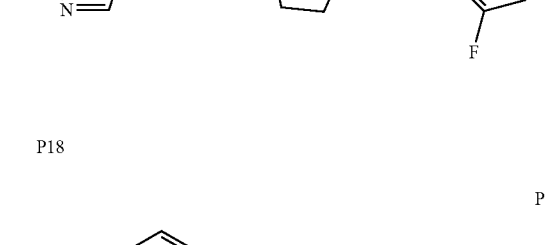
-continued
P19
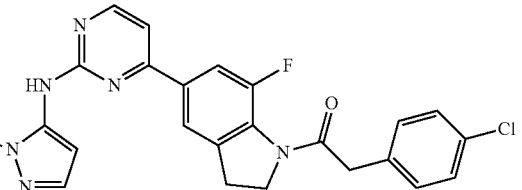
P20
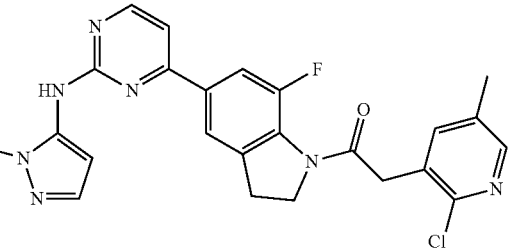
P23
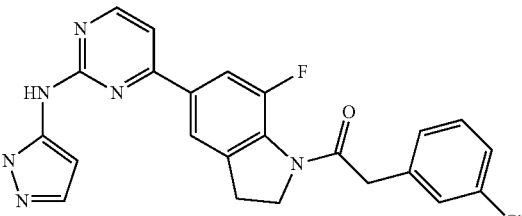
P24
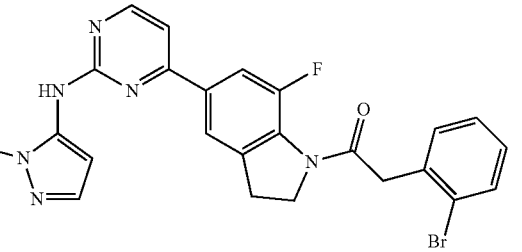
P25
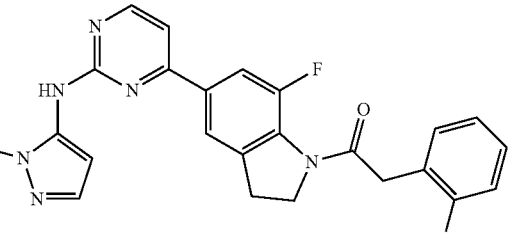
P28
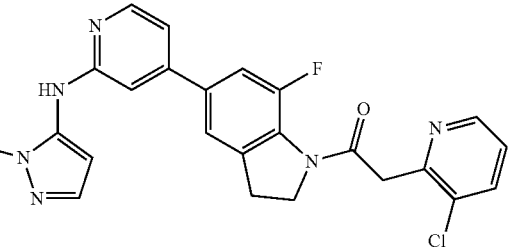

P29
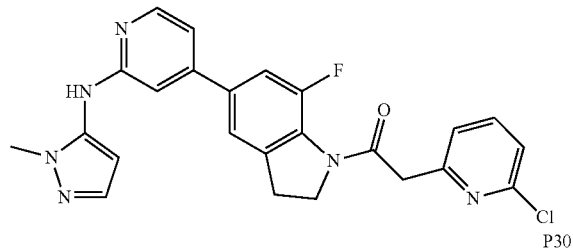
P30
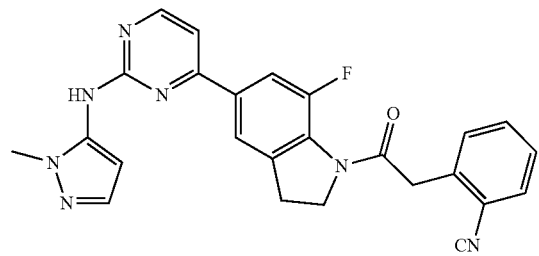
P31
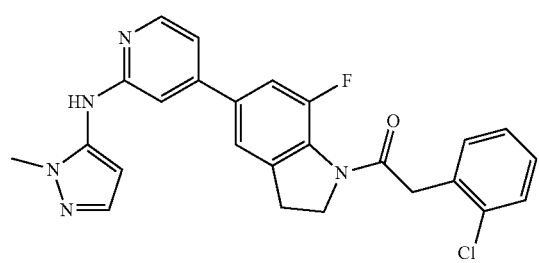
P32
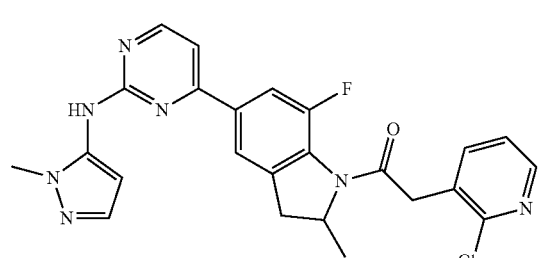
P33
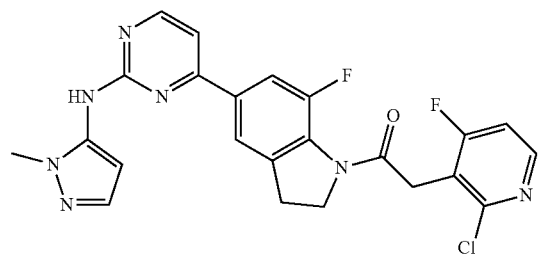
P34
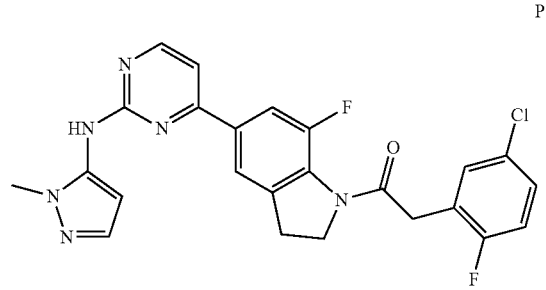
P35
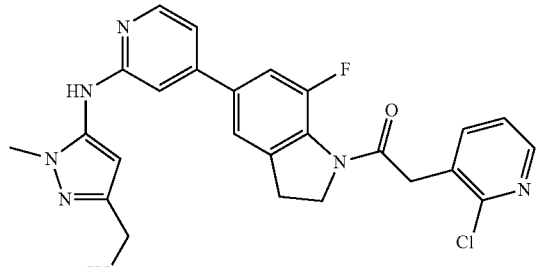
P36
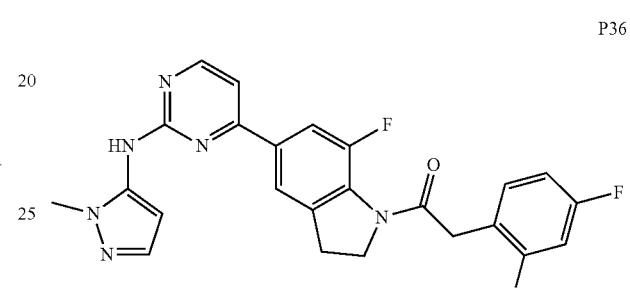
P37
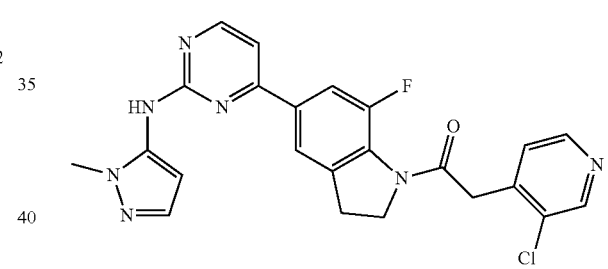
P38
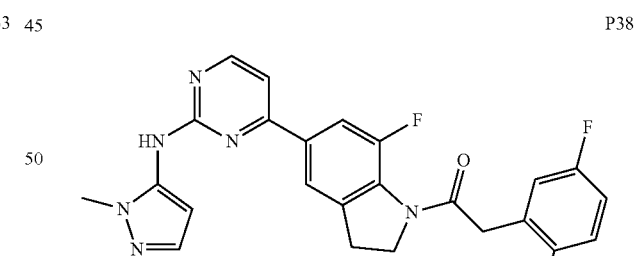
P39
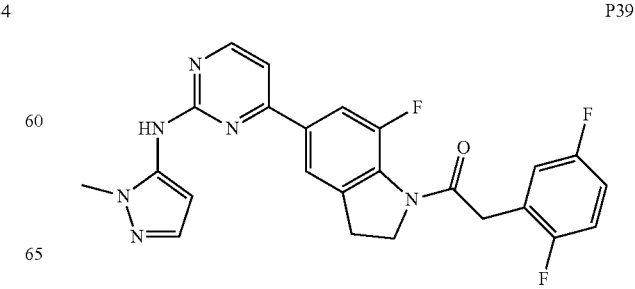

P40 and P41
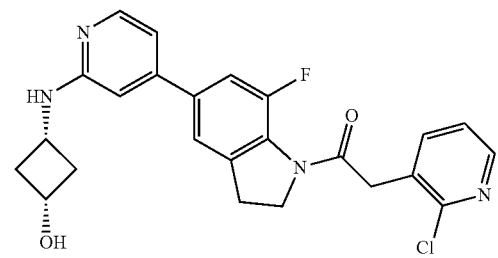
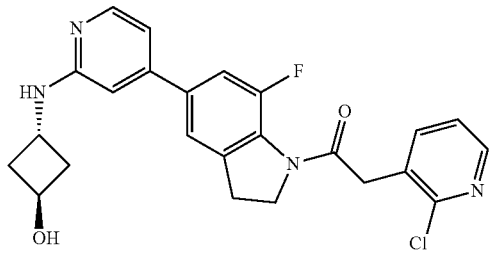
P42 and P43
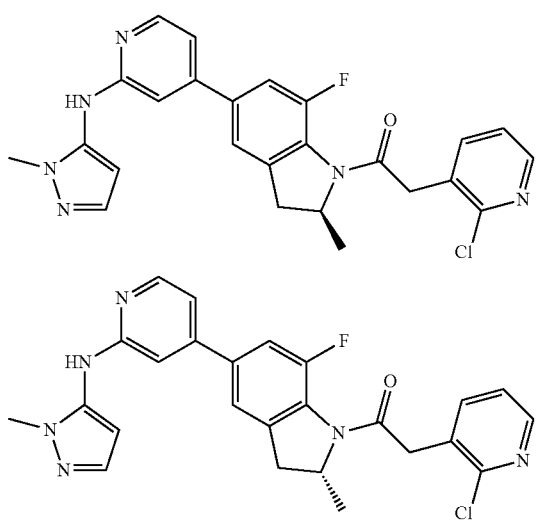
P44
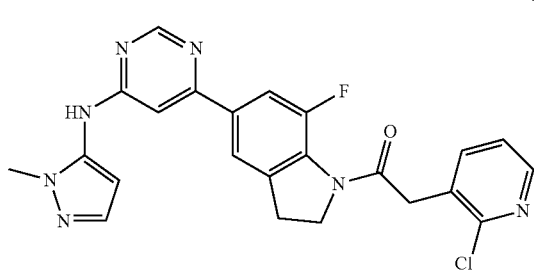
P45
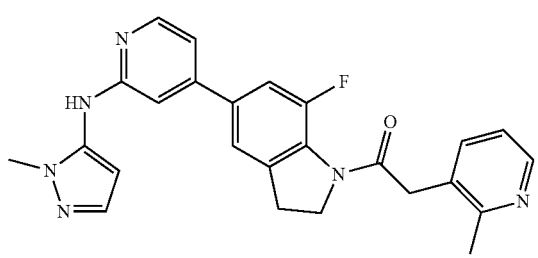
P46
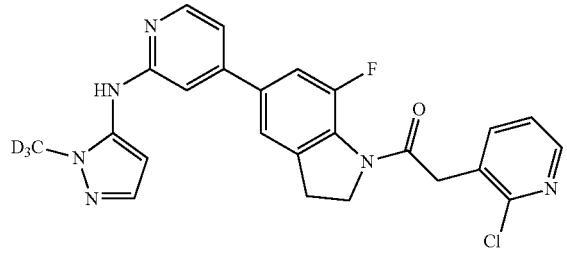
P47
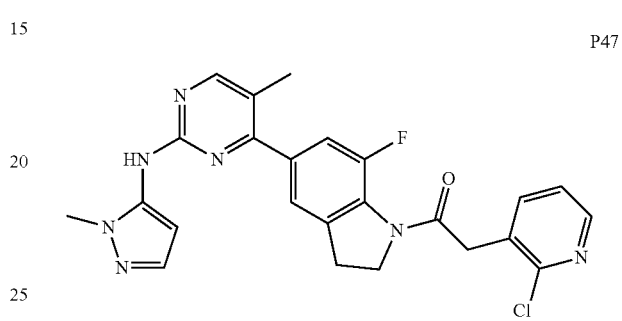
P48
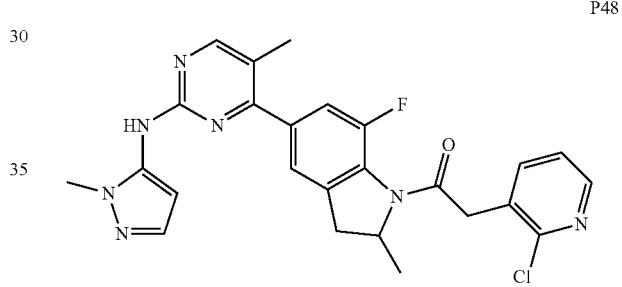
P49
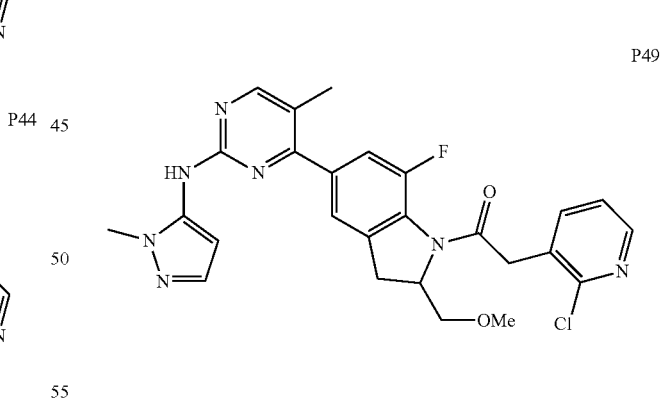
P50
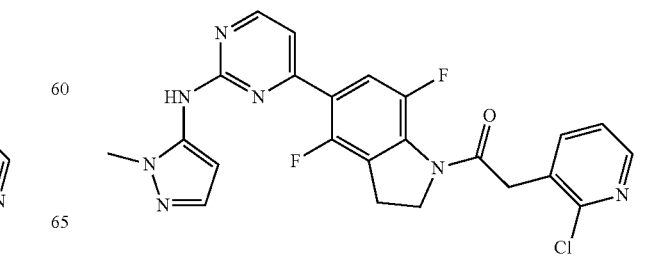

-continued
P51
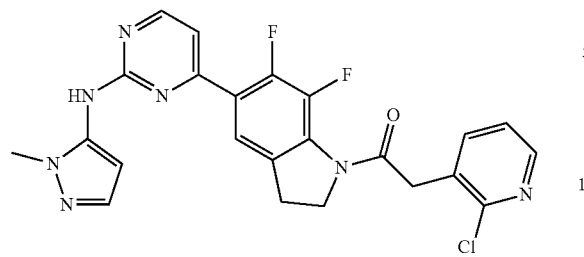
P53
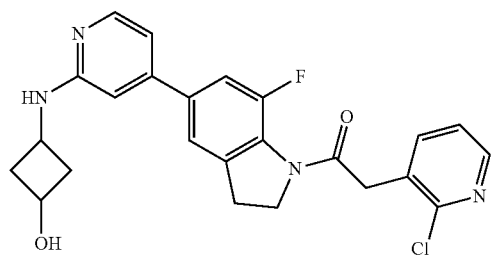
(racemate)
P54
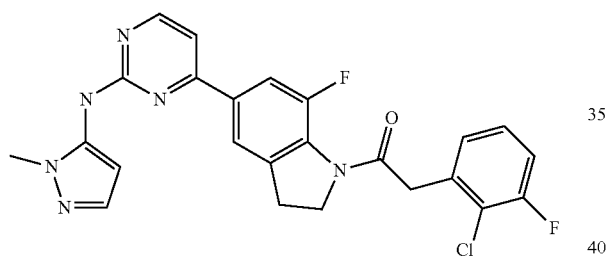
P55
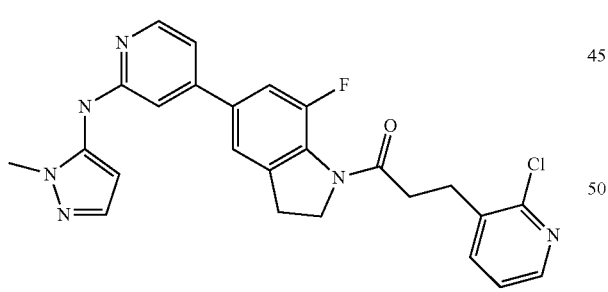
P56
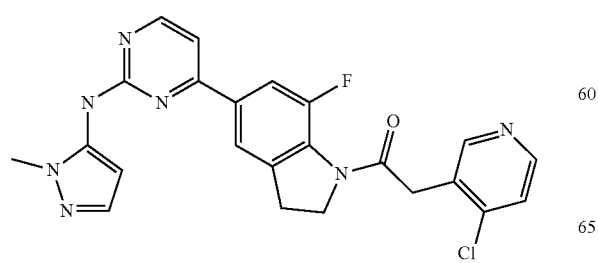
-continued
P57
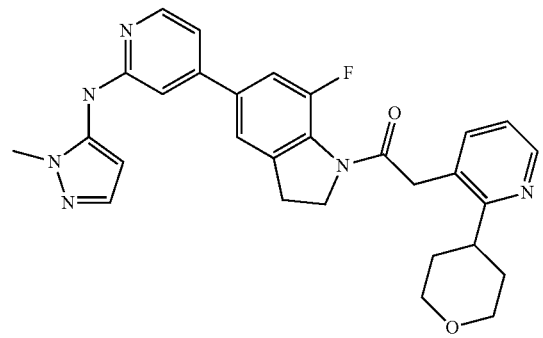
P58
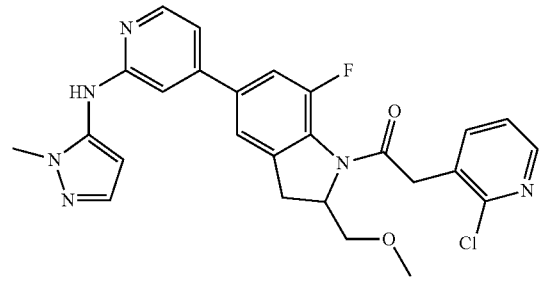
P59
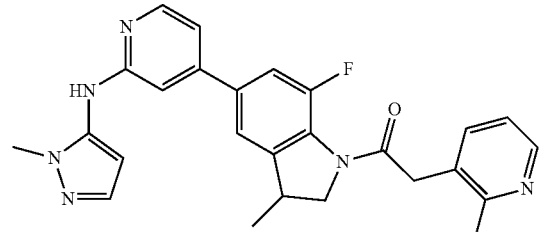
P60
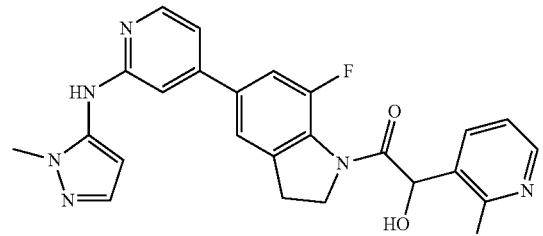
P61
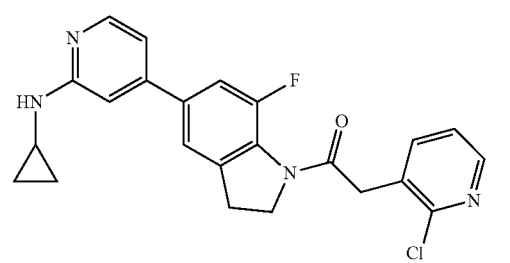

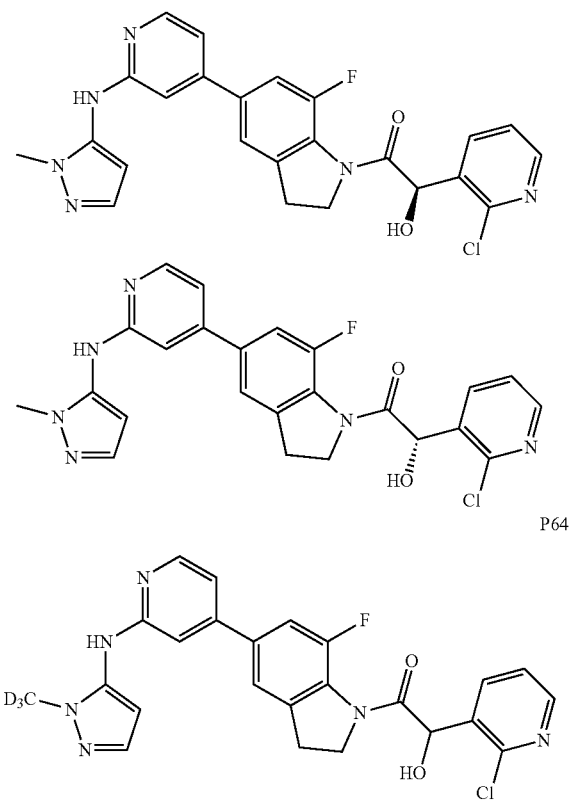

or a pharmaceutically acceptable salt thereof.

In another aspect, the invention provides a pharmaceutical composition comprising the novel compounds above, uses of the novel compounds above, and methods for treatment using the novel compounds above:

Embodiment 15. The compound according to any one of Embodiments 1 to 14, or a pharmaceutically acceptable salt thereof, for use as a medicament.

Embodiment 16. A pharmaceutical composition, comprising the compound according to any one of Embodiments 1 to 14, or a pharmaceutically acceptable salt thereof, and optionally a pharmaceutically acceptable carrier.

Embodiment 17. Use of the compound according to any one of Embodiments 1 to 14, or a pharmaceutically acceptable salt thereof, in the manufacture of a medicament for prevention and/or treatment of a disease related to an ERK kinase, or use of the compound according to any one of Embodiments 1 to 14, or a pharmaceutically acceptable salt thereof, for use as a product as an ERK kinase inhibitor.

Embodiment 18. A non-therapeutic method of inhibiting an ERK kinase activity, comprising contacting an effective amount of the compound according to any one of claims 1 to 14, or a pharmaceutically acceptable salt thereof, with an ERK kinase, thereby inhibiting the ERK kinase.

In another aspect, the invention provides intermediates (for example, intermediates 1-82, particularly intermediate 25, disclosed herein) and methods (for example, the methods shown in FIGS. 1-4, particularly the method shown in FIG. 3) for preparing the novel compounds above:

Embodiment 19. The compound t-butyl (4-(7-fluoroindolin-5-yl)pyridin-2-yl)(1-methyl-1H-pyrazol-5-yl)carbamate represented by the formula:

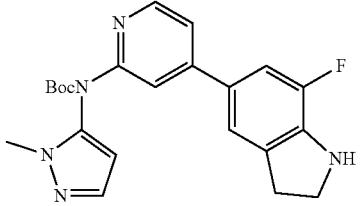 [SMILES: Cn1nccc1N(C(=O)OC(C)(C)C)c1cc(-c2cc(F)c3c(c2)CCN3)ccn1]

or a stereoisomer, racemate, geometric isomer, tautomer, hydrate, solvate, or pharmaceutically acceptable salt thereof.

Embodiment 20. A method for preparing the compound of formula (I) according to Embodiment 1, or a stereoisomer, racemate, geometric isomer, tautomer, prodrug, hydrate, solvate or pharmaceutically acceptable salt thereof, said compound of formula (I) is the compound of formula C3:

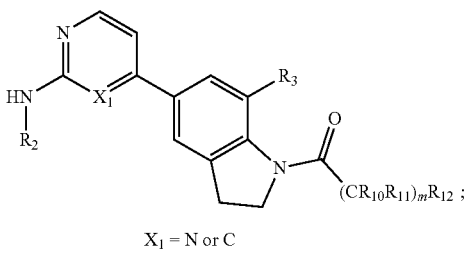

wherein $X_1$, $R_2$, $R_3$, $R_{10}$, $R_{11}$, $R_{12}$ and m are as defined in Embodiment 1, comprising the steps of:

(a) subjecting the compound of formula C1

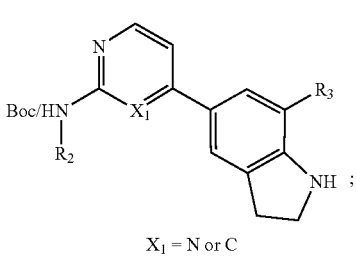

and the compound

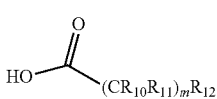

to amide coupling reaction, to give the compound of formula C2,

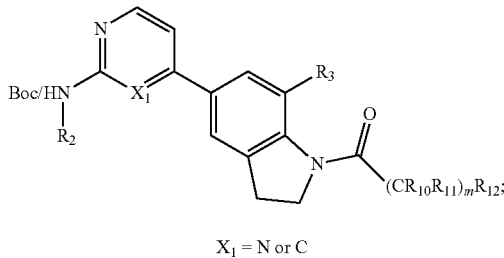

C2

$X_1$ = N or C and
(b) when the compound of formula C2 is Boc-protected, deprotecting it, to give the compound of formula C3,

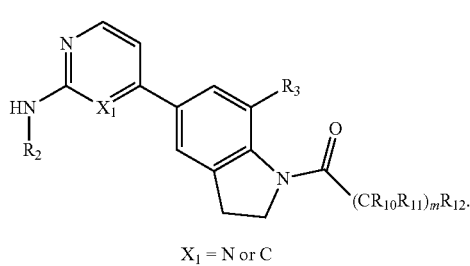

C3

$X_1$ = N or C

Embodiment 21. The method according to Embodiment 20, wherein the amide coupling reaction is carried out in the presence of a condensing agent and a base in an inert solvent.

Embodiment 22. The method according to Embodiment 20, wherein the deprotection is carried out in the presence of an acid in an inert solvent.

Embodiment 23. The method according to Embodiment 21 or 22, wherein the inert solvent is selected from the group consisting of ethyl acetate, tetrahydrofuran, methyltetrahydrofuran, acetonitrile, dimethyl sulfoxide, N,N-dimethylformamide, dichloromethane, 1,2-dichloroethane, N-methyl-2-pyrolidone, or a combination thereof.

Embodiment 24. The method according to Embodiment 21, wherein the condensing agent is one or more selected from the group consisting of 1-hydroxylbenzotriazole (HOBT), 1-hydroxyl-7-azobenzotriazole (HOAT), benzotriazol-1-yl-oxytripyrrolidino-phosphonium hexafluorophosphate (PyBOP), benzotriazol-1-yloxytris(dimethylamino) phosphonium hexafluorophosphate (BOP), 1,1-carbonyldiimidazole (CDI), 1-propylphosphonic anhydride ($T_3P$), 1-ethyl-3-(3-dimethylaminopropyl)carbodiimide hydrochloride (EDC.HCl), N,N-dicyclohexylcarbodiimide (DCC), acetic anhydride, acetyl chloride, oxalyl chloride, O-(7-azabenzotriazol-1-yl)-N,N,N',N'-tetramethyluronium hexafluorophosphate (HATU), and O-(benzotriazol-1-yl)-N,N,N',N'-tetramethyluronium hexafluorophosphate (HBTU).

Embodiment 25. The method according to Embodiment 21, wherein the base is one or more selected from the group consisting of triethylamine, DIPEA, pyridine, 2,4-dimethylpyridine, NaOH, KOH, LiOH, $Na_2CO_3$, $K_2CO_3$, $NaHCO_3$, $Cs_2CO_3$, $Na_3PO_4$, or $K_3PO_4$.

Embodiment 26. The method according to Embodiment 20, wherein the amide coupling reaction is carried out at a temperature from room temperature to reflux for 0.5-24 h.

Embodiment 27. The method according to Embodiment 22, wherein the acid is one or more selected from the group consisting of hydrochloric acid, sulfuric acid, trifluoroacetic acid, acetic acid, formic acid, and phosphoric acid.

Embodiment 28. The method according to Embodiment 20, wherein the deprotection is carried out at a temperature from −10° C. to 80° C. for 0.5-24 h.

Definitions

The following terms and symbols used in the present application have the meanings as described below, unless otherwise specified in the context.

A dash ("-") that is not between two letters or symbols indicates a point of attachment of a substituent. For example, —O($C_{1-3}$alkyl) refers to $C_{1-3}$alkyl which is attached to the rest of the molecule through an oxygen atom. However, when the attachment point of a substituent is apparent to those skilled in the art, for example, for a halogen substituent, the dash "-" may be omitted.

When a group carries a wavy line "〜", the wavy line indicates the point of attachment of the group to the rest of the molecule.

As used herein, the term "alkyl" refers to a straight or branched chain saturated monovalent hydrocarbon radical having from 1 to 8 carbon atoms, such as from 1 to 6 carbon atoms, such as from 1 to 4 carbon atoms, such as 1, 2 or 3 carbon atoms. For example, "$C_{1-8}$ alkyl" refers to alkyl having from 1 to 8 carbon atoms. Similarly, "$C_{1-4}$ alkyl" refers to alkyl having from 1 to 4 carbon atoms, and "$C_{1-3}$ alkyl" refers to alkyl having from 1 to 3 carbon atoms. Examples of alkyl include, but are not limited to, methyl ("Me"), ethyl ("Et"), n-propyl ("n-Pr"), isoproyl ("i-Pr"), n-butyl ("n-Bu"), isobutyl ("i-Bu"), sec-butyl ("s-Bu"), t-butyl ("t-Bu"), etc. Whether the term "alkyl" is used alone or as part of another group such as haloalkyl, alkoxyl, etc., this definition applies.

As used herein, the term "alkenyl" refers to a straight or branched chain monovalent hydrocarbon radical having from 2 to 8 carbon atoms, such as 2 to 6 carbon atoms, for example 2, 3 or 4 carbon atoms, and containing one or more, for example 1, 2 or 3, carbon-carbon double bonds (C═C). For example, "$C_{2-6}$ alkenyl" denotes alkenyl having from 2 to 6 carbon atoms and containing 1 or 2, preferably 1, carbon-carbon double bonds. Similarly, "$C_{2-3}$ alkenyl" denotes alkenyl having from 2 to 3 carbon atoms and containing 1 carbon-carbon double bond. Examples of alkenyl include, but are not limited to, ethenyl, 2-propenyl, and 2-butenyl.

As used herein, the term "alkynyl" refers to a straight or branched chain monovalent hydrocarbon radical having from 2 to 8 carbon atoms, such as from 2 to 6 carbon atoms, such as from 2 to 4 carbon atoms, and containing one or more, for example 1, 2 or 3, carbon-carbon triple bonds (C≡C). For example, "$C_{2-6}$ alkynyl" refers to alkynyl having from 2 to 6 carbon atoms and containing 1 or 2, preferably 1, carbon-carbon triple bonds. Similarly, "$C_{2-3}$ alkynyl" refers to alkynyl having from 2 to 3 carbon atoms and containing 1 carbon-carbon triple bond. Examples of alkynyl include, but are not limited to, ethynyl, 2-propynyl and 2-butynyl.

As used herein, the term "alkoxyl" refers to the group —O-alkyl, wherein alkyl is as defined above. For example, "$C_{1-8}$alkoxyl" refers to —O—$C_{1-8}$alkyl, i.e., alkoxyl having from 1 to 8 carbon atoms. Similarly, "$C_{1-3}$alkoxyl" refers to —O—$C_{1-3}$alkyl, i.e., alkoxyl having from 1 to 3 carbon atoms. Examples of alkoxyl include, but are not limited to, methoxy, ethoxy, n-propoxy, isopropoxy, n-butoxy, isobutoxy, t-butoxy, pentoxy and hexoxy etc. Whether the term "alkoxyl" is used alone or as part of another group, this definition applies.

As used herein, the term "halo" or "halogen" refers to fluoro (F), chloro (Cl), bromo (Br) and iodo (I), preferably fluoro and chloro, most preferably fluoro.

As used herein, the term "haloalkyl" refers to alkyl as defined herein wherein one or more hydrogen atoms, for example 1, 2, 3, 4 or 5 hydrogen atoms, are replaced by halogen, and when more than one hydrogen atom is replaced by a halogen atom, said halogen atoms may be the same or different from one another. Examples of haloalkyl include, but are not limited to, —$CF_3$, —$CHF_2$ and —$CH_2CF_3$ etc.

As used herein, the term "hydroxyl" refers to the group —OH.

As used herein, the term "mercapto" refers to the group —SH.

As used herein, the term "cyano" refers to the group —CN.

As used herein, the term "carboxyl" refers to the group —C(O)—OH, and may also be represented by —COOH.

As used herein, the term "carbonyl" refers to the group —C(O)—, and may also be represented by —CO—.

As used herein, the term "hydrogen" refers to the group —H.

As used herein, the symbol "D" refers to deuterium.

As used herein, the term "amino" refers to the group —$NH_2$.

As used herein, the term "alkylamino" or "mono-alkylamino" refers to the group alkyl-NH—, wherein alkyl is as defined herein.

As used herein, the term "di-alkylamino" refers to the group (alkyl)$_2$-N—, wherein alkyl is as defined herein.

As used herein, the term "alkylcarbonyl" refers to alkyl attached to another group through carbonyl, i.e., alkyl-C(O)—, wherein alkyl is as defined herein.

As used herein, the term "alkoxylcarbonyl" refers to alkoxyl attached to another group through carbonyl, i.e., alkoxyl-C(O)—, wherein alkoxyl is as defined herein.

As used herein, the term "oxo" refers to the group =O.

As used herein, the term "nitro" refers to the group —$NO_2$.

As used herein, the term "cycloalkyl" refers to a saturated, monovalent monocyclic or bicyclic hydrocarbon radical having from 3 to 12 ring carbon atoms, such as from 3 to 8 ring carbon atoms, such as from 3 to 6 ring carbon atoms. For example, "$C_{3-8}$cycloalkyl" refers to cycloalkyl having from 3 to 8 ring carbon atoms. Similarly, "$C_{3-6}$cycloalkyl" refers to cycloalkyl having from 3 to 6 ring carbon atoms. Examples of cycloalkyl include, but are not limited to, cyclopropyl, cyclobutyl, cyclopentyl, cyclohexyl, cycloheptyl and cyclooctyl.

As used herein, the term "cycloalkenyl" refers to cycloalkyl as defined herein containing one or more double bonds, such as 1, 2, 3 or 4 double bonds, the ring of which is non-aromatic. For example, "$C_{3-8}$cycloalkenyl" refers to cycloalkenyl having from 3 to 8 ring carbon atoms. Similarly, "$C_{3-6}$cycloalkenyl" refers to cycloalkenyl having from 3 to 6 ring carbon atoms. Examples of cycloalkenyl include, but not limited to cyclopropenyl, cyclobutenyl, cyclopentenyl, cyclohexenyl, cycloheptenyl and cyclooctenyl.

As used herein, the term "heterocyclyl" or "heterocyclic" or "heterocycle" refers to monocyclic, bicyclic or tricyclic, saturated and partially unsaturated non-aromatic rings having from 3 to 20 ring atoms, such as from 3 to 12 ring atoms, such as from 3 to 8 ring atoms, such as from 3 to 6 ring atoms, which contain at least one carbon atom in addition to from 1 to 4, such as from 1 to 3, such as 1 or 2, such as 1, heteroatoms selected from the group consisting of O, S and N. In one example, said "heterocyclyl" or "heterocyclic" or "heterocycle" is monocyclic and has from 3 to 8 ring atoms, such as 3, 4, 5 or 6 ring atoms, which contain at least one carbon atom in addition to from 1 to 4, such as from 1 to 3, such as 1 or 2, such as 1, heteroatoms selected from the group consisting of O, S and N. In one example, said "heterocyclyl" or "heterocyclic" or "heterocycle" contains 0, 1, 2 or 3 double bonds. Any nitrogen or sulfur heteroatom may be optionally oxidized (e.g., NO, SO, $SO_2$), and any nitrogen heteroatom may be optionally quaternized (e.g., $[NR_4]^+Cl^-$, $[NR_4]^+OH^-$). Heterocyclyl having from 3 to 8 ring atoms is also referred to simply as 3-8 membered heterocyclyl, and heterocyclyl having other numbers of carbon atoms can be similarly abbreviated. Examples of heterocyclyl include, but are not limited to, oxiranyl, aziridinyl, thiiranyl, azetidinyl, oxetanyl, thietanyl, 1,2-dithietanyl, 1,3-dithietanyl, pyrrolidinyl (pyrrolidin-1-yl, pyrrolidin-2-yl, pyrrolidin-3-yl), dihydro-1H-pyrrolyl, dihydrofuranyl, tetrahydrofuranyl (e.g., tetrahydrofuran-2-yl, tetrahydrofuran-3-yl, tetrahydrofuran-4-yl), dihydrothienyl, tetrahydrothienyl, imidazolidinyl, piperidinyl, piperazinyl (e.g., piperazin-1-yl, piperazin-2-yl, piperazin-3-yl, piperazin-4-yl), isoquinolinyl, tetrahydroisoquinolinyl, morpholinyl (e.g., morpholino (i.e., morpholin-1-yl), morpholin-2-yl, morpholin-3-yl), thiomorpholinyl, 1,1-dioxo-thiomorpholinyl, dihydropyranyl, tetrahydropyranyl (e.g., tetrahydropyran-2-yl, tetrahydropyran-3-yl, tetrahydropyran-4-yl), hexahydrothiopyranyl, hexahydropyrimidyl, oxazitanyl, thiazinanyl, thioxanthyl, homopiperazinyl, homopiperidinyl, azepanyl, oxepanyl, thiepanyl, azepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidonyl, oxazolidinonyl, imidazolidinonyl, 4,5,6,7-tetrahydro[2H]indazolyl, tetrahydrobenzimidazolyl, 4,5,6,7-tetrahydrobenzo[d]imidazolyl, 1,6-dihydroimidazo[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatrazinyl, dithiadiazinyl, imidazolinyl, dihydropyrimidyl, tetrahydropyrimidinyl, 1-pyrrolinyl, 2-pyrrolinyl, 3-pyrrolinyl, indolinyl, thiopyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinyl, imidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptanyl, azaspiro[3.5]nonanyl, azaspiro[2.5]octanyl, azaspiro[4.5]decanyl, 1-azaspiro[4.5] decan-2-onyl, azaspiro[5.5]undecanyl, tetrahydroindolyl, octahydroindolyl, tetrahydroisoindolyl, tetrahydroindazolyl, 1,1-dioxohexahydrothiopyranyl. Examples of 5 membered heterocylyl containing sulfur or oxygen atom and from 1 to 3 nitrogen atoms are: thiazolyl, including thiazol-2-yl and thiazol-2-yl N-oxide; thiadiazolyl, including 1,3,4-thiadiazol-5-yl and 1,2,4-thiadiazol-5-yl; oxazolyl, such as oxazol-2-yl; and oxadiazolyl, such as 1,3,4-oxadiazol-5-yl and 1,2,4-oxadiazol-5-yl. Examples of 5-membered heterocyclyl containing from 2 to 4 nitrogen atoms include: imidazolyl, such as imidazol-2-yl; triazolyl, such as 1,3,4-triazol-5-yl; 1,2,3-triazol-5-yl, 1,2,4-triazol-5-yl; and tetrazolyl, such as 1H-tetrazol-5-yl. Examples of benzo-fused 5-membered heterocyclyl are: benzoxazol-2-yl, benzothiazol-2-yl and benzimidazol-2-yl. Exemplary 6-membered heterocyclyl containing from 1 to 3 nitrogen atoms and optionally sulfur or oxygen atoms are: pyridinyl, such as pyridin-2-yl, pyridin-3-yl and pyridin-4-yl; pyrimidinyl, such as pyrimidin-2-yl and pyrimidin-4-yl; triazinyl, such as 1,3,4-triazin-2-yl and 1,3,5-triazin-4-yl; pyridazinyl, especially pyridazin-3-yl; and pyrazinyl. Further examples of heterocycyl are pyridine N-oxide and pyridazine N-oxide as well as pyridinyl, pyrimidin-2-yl, pyrimidin-4-yl, pyridazinyl and 1,3,4-triazin-2-yl.

As used herein, the term "hydroxylalkyl" refers to alkyl substituted with hydroxyl, i.e., -alkyl-OH, wherein alkyl is as defined herein. Examples of said group include, but not limited to hydroxylmethyl, hydroxylethyl (such as 2-hydroxylethyl, 1-hydroxylethyl), hydroxylpropyl (such as 1-hydroxylprop-2-yl, 1-hydroxylprop-3-yl, 1-hydroxylprop-1-yl etc.), hydroxylbutyl (such as 4-hydroxylbut-2-yl etc.).

As used herein, the term "aryl" refers to a carbocyclic hydrocarbon radical consisting of one ring or fused rings, wherein at least one ring is aromatic, and having from 6 to 14 ring carbon atoms, such as from 6 to 12 ring carbon atoms, such as from 6 to 10 ring carbon atoms. Example of aryl include, but not limited to phenyl, naphthyl, 1,2,3,4-tetrahydronaphthyl, indenyl, preferably phenyl and naphthyl.

As used herein, the term "heteroaryl" refers to:

A monocyclic aromatic hydrocarbon radical having 5, 6 or 7 ring atoms, such as having 6 ring atoms, and containing one or more, such as 1, 2 or 3, such as 1 or 2, ring heteroatoms independently selected from the group consisting of N, O and S (e.g. N) in the ring, with the remaining ring atoms being carbon atoms; and A bicyclic aromatic hydrocarbon radical having from 8 to 12 ring atoms, such as having 9 or 10 ring atoms, and containing one or more, such as 1, 2, 3 or 4, such as 1 or 2, ring heteroatoms independently from the group connecting of N, O and S (e.g. N) in the rings, with the remaining ring atoms being carbon atoms, wherein at least one of the rings is aromatic.

When the total number of S and O atoms in the heteroaryl group exceeds 1, those heteroatoms are not adjacent to one another.

The heteroaryl group also includes those wherein the N heteroatom occurs as N-oxide, such as pyrimidinyl N-oxides.

In some embodiments, the heteroaryl above in which the heteroatom(s) in the ring(s) is N atom(s) is defined herein as "nitrogen-containing heteroaryl". The nitrogen-containing heteroaryl also includes those wherein the N heteroatom occurs as N-oxide, such as pyridyl N-oxides. For example, the nitrogen-containing heteroaryl is a monocyclic heteroaryl having 5 ring atoms and containing 1 or 2 N heteroatoms in the ring, with the remaining ring atoms being carbon atoms; and as another example, the nitrogen-containing heteroaryl is a monocyclic heteroaryl having 6 ring atoms, and containing 1, 2 or 3 heteroatoms in the ring, with the remaining ring atoms being carbon atoms.

Examples of heteroaryl include, but are not limited to, pyridyl (such as pyridin-2-yl, pyridin-3-yl, pyridin-4-yl, pyridin-5-yl, pyridin-6-yl), pyridyl N-oxide; pyrazinyl; pyrimidinyl; pyrazolyl (such as pyrazol-5-yl, pyrazol-1-yl, pyrazol-2-yl, pyrazol-3-yl, pyrazol-4-yl); imidazolyl; oxazolyl; isoxazolyl; thiazolyl; isothiazolyl; thiadiazolyl; tetrazolyl; triazolyl; thienyl; furyl; pyranyl; pyrrolyl; pyridazinyl; benzo[d]thiazolyl; bezodioxolyl, such as benzo[d][1,3]dioxolyl; benzoxazolyl, such as benzo[d]oxazolyl; imidazopyridyl, such as imidazo[1,2-a]pyridyl; triazolopyridyl, such as [1,2,4]triazolo[4,3-a]pyridyl and [1,2,4]triazolo[1,5-a]pyridyl; indazolyl, 2H-indazolyl; pyrrolopyrimidinyl, such as pyrrolo[3,4-d]pyrimidinyl, 7H-pyrrolo[2,3-d]pyrimidinyl; pyrazolopyrimidinyl, such as pyrazolo[1,5-a]pyrimidinyl; tetrazolopyridyl, such as tetrazolo[1,5-a]pyridyl; benzothienyl; benzofuryl; benzoimidazolinyl; indolyl; indolinyl; purinyl, such as 9H-purinyl and 7H-purinyl; quinolinyl; isoquinolinyl; 1,2,3,4-tetrahydroquinolinyl; and 5,6,7,8-tetrahydroisoquinolinyl.

Examples of the nitrogen-containing heteroaryl include, but are not limited to, pyrrolyl; pyrazolyl; imidazolyl; pyridyl; pyrazinyl; pyrimidinyl, pyrimidinyl N-oxide; pyridazinyl; pyrrolopyrimidinyl, such as pyrrolo[3,4-d]pyrimidinyl, 7H-pyrrolo[2,3-d]pyrimidinyl; purinyl, such as 9H-purinyl and 7H-purinyl; quinolinyl; indolyl; and indazolyl.

As used herein, "aryl" or "aromatic" follows Hückel's rule wherein the number of i-electrons equals 4n+2 where n is zero or any positive integer up to 6.

As used herein, the term "optional" or "optionally" means that the subsequently described substitution pattern, event, or circumstance may or may not occur, and that the description includes instances where the substitution pattern occurs and instances where it does not. For example, "optionally substituted alkyl" encompasses both "unsubstituted alkyl" and "substituted alkyl" as defined herein. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

As used herein, the term "substituted" or "substituted with" means that one or more hydrogen atoms on the designated atom or group are replaced with one or more substituents selected from the indicated group of substituents, provided that the designated atom's normal valence is not exceeded. When a substituent is oxo (i.e., =O), then two hydrogens on a single atom are replaced by the oxo. Combinations of substituents and/or variables are permissible only if such combinations result in a chemically correct and stable compound. A chemically correct and stable compound means a compound that is sufficiently robust to survive isolation from a reaction mixture for the identification of the chemical structure of the compound, and subsequently to be prepared into a formulation having at least one practical utility. For example, under the circumstances that the substituents are not specifically indicated, the term "substituted" or "substituted with . . . " as used herein means that one or more hydrogen atoms on a given atom or group are independently replaced by one or more, for example 1, 2, 3 or 4 substituents independently selected from the group consisting of deuterium (D), halo, —OH, mercapto, cyano, —CD$_3$, —C$_1$-C$_6$alkyl (preferably —C$_{1-3}$alkyl), C$_2$-C$_6$ alkenyl, C$_2$-C$_6$ alkynyl, cycloalkyl (preferably 3-8 membered cycloalkyl), aryl, heterocyclyl (preferably 3-8 membered heterocyclyl), heteroaryl, aryl-C$_1$-C$_6$alkyl-, heteroaryl-C$_1$-C$_6$alkyl-, C$_1$-C$_6$haloalkyl-, —OC$_1$-C$_6$alkyl (preferably —OC$_1$-C$_3$ alkyl), —OC$_2$-C$_6$alkenyl, —OC$_1$-C$_6$alkylphenyl, —C$_1$-C$_6$alkyl-OH (preferably —C$_1$-C$_4$alkyl-OH), —C$_1$-C$_6$alkyl-SH, —C$_1$-C$_6$alkyl-O—C$_1$-C$_6$alkyl, —OC$_1$-C$_6$haloalkyl, —NH$_2$, —C$_1$-C$_6$alkyl-NH$_2$ (preferably —C$_1$-C$_3$ alkyl-NH$_2$), —N(C$_1$-C$_6$alkyl)$_2$ (preferably —N(C$_1$-C$_3$ alkyl)$_2$), —NH(C$_1$-C$_6$alkyl) (preferably —NH(C$_1$-C$_3$alkyl)), —N(C$_1$-C$_6$alkyl)(C$_1$-C$_6$alkylphenyl), —NH(C$_1$-C$_6$alkylphenyl), nitro, —C(O)—OH, —C(O) OC$_1$-C$_6$alkyl (preferably —C(O)OC$_1$-C$_3$alkyl), —CONRiRii (wherein Ri and Rii are selected from the group consisting of H, D and $C_{1-6}$alkyl, preferably $C_{1-3}$ alkyl), —NHC(O)($C_1$-$C_6$alkyl), —NHC(O)(phenyl), —N($C_1$-$C_6$alkyl)C(O)($C_1$-$C_6$alkyl), —N($C_1$-$C_6$alkyl)C(O)(phenyl), —C(O)$C_1$-$C_6$alkyl, —C(O) heteroaryl (preferably —C(O)-5-7 membered heteroaryl), —C(O)$C_1$-$C_6$alkylphenyl, —C(O)$C_1$-$C_6$haloalkyl, —OC(O)$C_1$-$C_6$alkyl (preferably —OC(O)$C_1$-$C_3$alkyl), —S(O)$_2$-$C_1$-$C_6$alkyl, —S(O)—$C_1$-$C_6$alkyl, —S(O)$_2$-phenyl, —S(O)$_2$-$C_1$-$C_6$haloalkyl, —S(O)$_2$NH$_2$, —S(O)$_2$NH($C_1$-$C_6$alkyl), —S(O)$_2$NH(phenyl), —NHS(O)$_2$($C_1$-$C_6$alkyl), —NHS(O)$_2$(phenyl), and —NHS(O)$_2$($C_1$-$C_6$haloalkyl), wherein said alkyl, cycloalkyl, phenyl, aryl, heterocyclyl and heteroaryl are each optionally further substituted with one or more substituents selected from the group consisting of halo, —OH, —NH$_2$, cycloalkyl, 3-8 membered heterocyclyl, $C_1$-$C_4$alkyl, $C_1$-$C_4$haloalkyl-, —O$C_1$-$C_4$alkyl, —$C_1$-$C_4$alkyl-OH, —$C_1$-$C_4$alkyl-O—$C_1$-$C_4$alkyl, —O$C_1$-$C_4$haloalkyl, cyano, nitro, —C(O)—OH, —C(O)O$C_1$-$C_6$alkyl, —CON($C_1$-$C_6$alkyl)$_2$, —CONH($C_1$-$C_6$alkyl), —CONH$_2$, —NHC(O)($C_1$-$C_6$alkyl), —NH($C_1$-$C_6$alkyl)C(O)($C_1$-$C_6$alkyl), —SO$_2$($C_1$-$C_6$alkyl), —SO$_2$(phenyl), —SO$_2$($C_1$-$C_6$haloalkyl), —SO$_2$NH$_2$, —SO$_2$NH($C_1$-$C_6$alkyl), —SO$_2$NH(phenyl), —NHSO$_2$($C_1$-$C_6$alkyl), —NHSO$_2$(phenyl), and —NHSO$_2$($C_1$-$C_6$haloalkyl). When an atom or group is substituted with more than one substitutents, the substituents may be same or different.

As used herein, the term "pharmaceutically acceptable" means non-toxic, biologically tolerable and suitable for administration to a subject.

As used herein, the term "pharmaceutically acceptable salt" refers to a base or acid addition salt of the compound of formula (I) that is non-toxic, biologically tolerable and suitable for administration to a subject. The "Pharmaceutically acceptable salt" includes, but are not limited to, acid addition salts formed by the compound of formula (I) with an inorganic acid, such as hydrochloride, hydrobromide, carbonate, bicarbonate, phosphate, sulfate, sulfite, nitrate, and the like, as well as with an organic acid, such as formate, acetate, malate, maleate, fumarate, tartrate, succinate, citrate, lactate, methanesulfonate, p-toluenesulfonate, 2-hydroxyethanesulfonate, benzoate, salicylate, stearate, and salts with alkane-dicarboxylic acid of formlua HOOC—(CH$_2$)$_n$—COOH (wherein n is 0-4), etc. Also, "pharmaceutically acceptable salt" includes base addition salts formed by the compound of formula (I) carrying an acidic moiety with a pharmaceutically acceptable cations such as sodium, potassium, calcium, aluminum, lithium and ammonium.

In addition, if a compound described herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. Those skilled in the art will be able to determine, without undue experimentation, a variety of synthetic methods, which are used to prepare non-toxic pharmaceutically acceptable acid addition salts.

The compounds of the invention may exist in the form of solvates. The term "solvates" means solvent addition forms that contain either stoichiometric or non-stoichiometric amounts of solvent. If the solvent is water, the solvate formed is a hydrate, and when the solvent is alcohol, the solvate formed is an alcoholate. Hydrates are formed by the combination of one or more molecules of water with one molecule of the substance in which the water retains its molecular state as $H_2O$. Such combination may form one or more kinds of hydrates, for example, hemihydrates, monohydrate, and dihydrate.

As used herein, the term "prodrug" refers to an active or inactive compound that will be chemically modified to form the compounds of the invention by physiological effects in vivo, such as hydrolysis, metabolism, and the like, upon administration to a subject. The suitability and techniques involved in preparing and using a prodrug are well known to those skilled in the art. Exemplary prodrugs are, for example, esters of free carboxylic acids, S-acyl derivatives of thiols and O-acyl derivatives of alcohols or phenols. Suitable prodrugs are generally pharmaceutically acceptable ester derivatives which are convertible under physiological conditions by solvolysis to the parent carboxylic acid, for example, lower alkyl esters, cycloalkyl esters, lower alkenyl esters, benzyl esters, mono- or di-substituted lower alkyl esters, such as ω-(amino, mono- or di-lower alkyl amino, carboxyl, lower alkoxylcarbonyl)-lower alkyl esters, α-(lower alkanoyloxy, lower alkoxylcarbonyl or di-lower alkylaminocarbonyl)-lower alkyl esters, for example, pivaloyloxymethyl ester and the like, which are conventional in the art.

It will be appreciated by those skilled in the art that some of the compounds of formula (I) may contain one or more chiral centers and therefore exist in two or more stereoisomeric forms. Thus, the compounds of the invention may exist as individual stereoisomers (for example, enantiomers, diastereomers) and mixtures thereof in any proportion, such as racemate, and, where appropriate, as tautomers and geometric isomers.

As used herein, the term "stereoisomer" refers to compounds that have the same chemical constitution but are different in the spatial arrangement of the atoms or groups. Stereoisomers include enantiomers, diastereomers, conformers, and the like.

As used herein, the term "enantiomer" refers to two stereoisomers of a compound that are nonsuperimposable mirror images of each other.

As used herein, the term "diastereomer" refers to stereoisomers which have two or more chiral centers and whose molecules are not mirror images of one another. Diastereomers have different physical properties, e.g. melting points, boiling points, spectral properties, or biological activities. Mixtures of diastereomers may be separated under high resolution analytical procedures such as electrophoresis and chromatography such as HPLC.

Stereochemical definitions and conventions used herein follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and/or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid (such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as obtain either or both substantially free of the other, i.e., in a form having an optical purity of, for example, at least 91%, 92%, 93%, 94%, 95%, 96%, 97%, 98%, 99% or 99.5% by weight of the desired stereoisomer. Alternatively the racemates can be covalently linked to a chiral compound (auxiliary) to produce diastereomers which can be separated by chromatography or by fractional crystallization after which time the chiral auxiliary is chemically removed to afford the pure enantiomers, as is known to those skilled in the art.

As used herein, the term "conformer" refers to an isomer formed due to the different spatial position of an atom or group around a single bond in a covalent compound molecule, such as the half-chair conformer and evelope conformer of cyclopentane.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "geometric isomer" is an isomer caused by the inability of a double bond or a single bond of ring carbon atoms to rotate freely, and is also known as cis- and trans-isomers. The cis-isomer occurs when substituents are located on the same side of a plane, and the trans-isomer occurs when substituents are located on the opposite side of a plane.

As used herein, the terms "treating", "treat," or "treatment" of a disease refer to administering one or more pharmaceutical substances, especially a compound of formula (I) and/or a pharmaceutically acceptable salt thereof described herein to a subject that has the disease, or has a symptom of the disease, with the purpose to heal, alleviate, relieve, alter, remedy, ameliorate, improve, or affect the disease or the symptoms of the disease. In some embodiments, the disease is cancer.

As used herein, the terms "preventing", "prevent" or "prevention" of a disease refer to administering one or more pharmaceutical substances, especially a compound of formula (I) and/or a pharmaceutically acceptable salt thereof described herein to a subject that has a predisposition toward the disease, with the purpose to prevent the development of the disease in the subject. In some embodiments, the disease is a disease associated with an ERK kinase such as ERK1 and/or ERK2 kinase. In further embodiments, the disease is a disease associated with high expression or high activity of an ERK kinase such as ERK1 and/or ERK2 kinase. In further embodiments, the disease is cancer or tumor.

As used herein, the terms "cancer", "carcinoma" and "tumor" refer to a physiological condition typically characterized by disregulated cell proliferation in mammals Examples of the cancer include blastoma, glioma, sarcoma, seminoma, glioblastoma, melanoma, leukemia, and myeloid or lymphoid malignancies. More specific examples of the cancer include squamous cell cancer (e.g., epithelial squamous cell cancer) and lung cancer, including small-cell lung cancer, non-small cell lung cancer (NSCLC), lung adenocarcinoma, and lung squamous cell cancer. Additional cancers include skin cancer, keratoacanthoma, follicular carcinoma, hairy cell leukemia, buccal cavity, pharynx cancer, lip cancer, tongue cancer, mouth cancer, salivary gland cancer, esophageal cancer, laryngeal cancer, hepatocellular cancer, gastric cancer, gastrointestinal cancer, small intestine cancer, large intestine cancer, pancreatic cancer, cervical cancer, ovarian cancer, liver cancer, bladder cancer, hepatoma, breast cancer, colon cancer, rectal cancer, colorectal cancer, genitourinary system cancer, biliary tract cancer, gallbladder adenocarcinoma, thyroid cancer, papillary cancer, endometrial cancer, uterine cancer, salivary gland cancer, kidney cancer, prostate cancer, testicular cancer, vulval cancer, peritoneal cancer, anal cancer, penile cancer, bone cancer, multiple myeloma, B cell lymphoma, central nervous system cancer, brain cancer, head and neck cancer, Hodgkin's lymphoma. Examples also include myeloproliferative disorders such as polycythemia vera, essential thrombocythemia, myelofibrosis such as primary myelofibrosis, acute myeloid leukemia, and chronic myeloid leukemia (CML).

The terms "treating", "contacting" and "reacting" in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

As used herein, the term "effective amount" refers to an amount sufficient to generally bring about a beneficial effect in a subject. The effective amount of the compounds of the invention may be ascertained by conventional methods (such as modeling, dose escalation studies or clinical trials), and by taking into consideration conventional influencing factors (such as the mode of administration, the pharmacokinetics of the compound, the severity and course of the disease, the subject's medical history, the subject's health status and response to drugs).

The term "inhibition", "inhibitory" or "inhibiting" indicates a decrease in the baseline activity of a biological activity or process. The term "inhibition of ERK activity" or "inhibiting ERK activity" refers to a decrease in the activity of ERK as a direct or indirect response to the presence of the compound of formula (I) and/or the pharmaceutically acceptable salt thereof described herein, relative to the activity of ERK in the absence of the compound of formula (I) and/or the pharmaceutically acceptable salt thereof. The decrease in activity may be due to the direct interaction of the compound of formula (I) and/or the pharmaceutically acceptable salt thereof described herein with ERK, or due to the interaction of the compound of formula (I) and/or the pharmaceutically acceptable salt thereof described herein, with one or more other factors that in turn affect the ERK activity.

As used herein, the term "subject" refers to mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human In general, the term "about" is used herein to modify a numerical value above and below the stated value by a variance of 20%.

Technical and scientific terms used herein and not specifically defined have the meaning commonly understood by those skilled in the art to which the invention pertains.

General Synthesis Methods

The compounds of formula (I) in accordance with the invention, or a stereoisomer, racemate, geometric isomer, tautomer, prodrug, hydrate, solvate or pharmaceutically acceptable salt thereof, may be prepared by a variety of methods, including those indicated below, those exemplified in the Examples, or methods analogous thereto. Suitable general synthetic schemes are depicted below. Suitable reaction conditions for each reaction step are known to those skilled in the art. Starting materials for the preparation are commercially available or may be prepared using methods indicated below or analogous thereto, or well known to those skilled in the art. Variables in general formulae have the same meaning as above unless otherwise indicated.

The general synthesis methods for preparation of the compounds of the invention are shown in FIGS. 1 to 4.

FIG. 1 shows general synthetic scheme A for the synthesis of the compounds of the invention.

FIG. 2 shows general synthetic scheme B for the synthesis of the compounds of the invention.

FIG. 3 shows general synthetic scheme C for the synthesis of the compounds of the invention.

FIG. 4 shows general synthetic scheme D for the synthesis of the compounds of the invention.

In these schemes, it is well understood that protecting groups for sensitive or reactive groups (e.g., amino, hydroxyl and carboxyl) are used, when necessary, according to common principles or chemistry to prevent undesired chemical reactions. The protecting groups are treated according to standard methods of organic synthesis (T. W. Greenee and P. G. M. Wuts, "Protective Groups in Organic Synthesis", 5th Edition, Wiley, New York 2014). These groups are removed at a convenient stage of synthesis of a compound using methods well known to those skilled in the art. The selection of the process, the reaction conditions and the performance sequence should be in accordance with the preparation of the compounds of formula (I).

Examples of amino-protecting groups include carbamates, amides, alkyl and aryl groups, imines, as well as many N-heteroatom derivatives which can be removed to regenerate the desired amine group. Specific amino protecting groups are Pmb (p-methoxybenzyl), Boc (t-butyloxycarbonyl), Fmoc (9-fluorenylmethyloxycarbonyl) and Cbz (carbobenzyloxy). Further examples of these groups are found in T. W. Greene and P. G. M. Wuts, "Protective Groups in Organic Synthesis", $3n^d$ Edition, John Wiley & Sons, Inc., 1999.

Examples of hydroxyl-protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $3^{nd}$ Edition, John Wiley & Sons, Inc., 1999.

Examples of carboxy protecting groups include, ester groups and heterocyclyl groups. Ester derivatives of the carboxylic acid group may be employed to block or protect the carboxylic acid group while reactions are carried out on other functional groups of the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl; alkyl or substituted alkyl esters such as methyl, ethyl, t-butylallyl or t-amyl, triphenylmethyl (trityl), 4-methoxytrityl, 4,4'-dimethoxytrityl, 4,4',4"-trimethoxytrityl, 2-phenylprop-2-yl; thioesters such as t-butyl thioester; silyl esters such as trimethylsilyl esters, t-butyldimethylsilyl esters (TBSO), and the like. Further examples of these groups are found in T. W. Greene and P. G. M. Wuts, "Protective Groups in Organic Synthesis", $5^{th}$ Edition, Wiley, New York, 2014.

Those skilled in the art will recognize whether a stereocentre is present in the compounds of formula (I). Accordingly, when a compound is desired as a single enantiomer or diastereomer, it can be obtained either by stereospecific synthesis or by resolution of the final product or any appropriate intermediate. The resolution of the final product, intermediates or starting materials may be carried out using any appropriate method known in the art. See, for example, E. L. Eliel, S. H. Wilen and L. N. Mander, "Stereochemistry of Organic Compounds" (Wiley-Interscience, 1994).

In the methods of FIG. 3 and Embodiment 20, the preparation of Compound C2 is achieved by amide coupling reaction of Compound C1 with the carboxylic acid

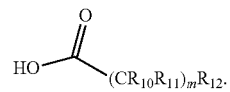

Preferably, the amide coupling reaction is carried out in an inert solvent. More preferably, the amide coupling reaction is carried out in the presence of a condensing agent and a base in an inert solvent.

The inert solvent is preferably selected from the group consisting of ethyl acetate, tetrahydrofuran, methyltetrahydrofuran, acetonitrile, dimethyl sulfoxide, N,N-dimethylformamide, dichloromethane, 1,2-dichloroethane, N-methyl-2-pyrolidone, or a combination thereof.

The condensing agent is preferably one or more selected from the group consisting of 1-hydroxylbenzotriazole (HOBT), 1-hydroxyl-7-azobenzotriazole (HOAT), benzotriazol-1-yl-oxytripyrrolidino-phosphonium hexafluorophosphate (PyBOP), benzotriazol-1-yloxytris(dimethylamino) phosphonium hexafluorophosphate (BOP), 1,1-carbonyldiimidazole (CDI), 1-propylphosphonic anhydride (T3P), 1-ethyl-3-(3-dimethylaminopropyl)carbodiimide hydrochloride (EDC.HCl), N,N-dicyclohexylcarbodiimide (DCC), acetic anhydride, acetyl chloride, oxalyl chloride, O-(7-azabenzotriazol-1-yl)-N,N,N',N'-tetramethyluronium hexafluorophosphate (HATU), and O-(benzotriazol-1-yl)-N,N,N',N'-tetramethyluronium hexafluorophosphate (HBTU), and is more preferably $T_3P$.

The base is preferably one or more selected from the group consisting of triethylamine, DIPEA, pyridine, 2,4-dimethylpyridine, NaOH, KOH, LiOH, $Na_2CO_3$, $K_2CO_3$, $NaHCO_3$, $Cs_2CO_3$, $Na_3PO_4$ or $K_3PO_4$; and is more preferably DIPEA.

Preferably, the amide coupling reaction is carried out at a temperature from room temperature to reflux.

Preferably, the amide coupling reaction is carried out for 0.5-24 h.

In the methods of FIG. 3 and Embodiment 20, when Compound C2 is Boc-protected, Compound C2 may be subjected to deprotection to give Compound C3.

Preferably, the deprotection is carried out in an inert solvent. The inert solvent is preferably selected from the group consisting of ethyl acetate, tetrahydrofuran, methyltetrahydrofuran, acetonitrile, dimethyl sulfoxide, N,N-dimethylformamide, dichloromethane, 1,2-dichloroethane, N-methyl-2-pyrolidone, or a combination thereof.

Preferably, the deprotection is carried out in the presence of an acid. The acid is preferably one or more selected from the group consisting of hydrochloric acid, sulfuric acid, trifluoroacetic acid, acetic acid, formic acid, and phosphoric acid.

Preferably, the deprotection is carried out at a temperature from −10° C. to 80° C.

Preferably, the deprotection is carried out for 0.5-24 h.

Utility and Administration

The compounds of the invention are useful for the treatment of a disease associated with an ERK kinase such as ERK1 and/or ERK2 kinase, for example a disease associated with high expression or high activity of an ERK kinase such as ERK1 and/or ERK2 kinase, such as tumor and cancer. More specifically, the tumor and cancer are selected from the group consisting of, for example, blastoma, glioma, sarcoma, seminoma, glioblastoma, melanoma, leukemia, and myeloid or lymphoid malignancies. More specific examples of the cancer include squamous cell cancer (e.g., epithelial squamous cell cancer) and lung cancer, including small-cell lung cancer, non-small cell lung cancer (NSCLC), lung adenocarcinoma, and lung squamous cell cancer. Additional cancers include skin cancer, keratoacanthoma, follicular carcinoma, hairy cell leukemia, buccal cavity, pharynx cancer, lip cancer, tongue cancer, mouth cancer, salivary gland cancer, esophageal cancer, laryngeal cancer, hepatocellular cancer, gastric cancer, gastrointestinal cancer, small intestine cancer, large intestine cancer, pancreatic cancer, cervical cancer, ovarian cancer, liver cancer, bladder cancer, hepatoma, breast cancer, colon cancer, rectal cancer, colorectal cancer, genitourinary system cancer, biliary tract cancer, gallbladder adenocarcinoma, thyroid cancer, papillary cancer, endometrial cancer, uterine cancer, salivary gland cancer, kidney cancer, prostate cancer, testicular cancer, vulval cancer, peritoneal cancer, anal cancer, penile cancer, bone cancer, multiple myeloma, B cell lymphoma, central nervous system cancer, brain cancer, head and neck cancer, Hodgkin's lymphoma. Examples also include myeloproliferative disorders such as polycythemia vera, essential thrombocythemia, myelofibrosis such as primary myelofibrosis, acute myeloid leukemia, and chronic myeloid leukemia (CML).

The compounds of the invention may be administered to a subject as a pharmaceutical composition, which may optionally comprise one or more pharmaceutically acceptable excipients.

The compounds of the invention can be administered by various known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration, different pharmaceutical formulations are required and some of those may require that protective coatings are applied to the drug formulation to prevent degradation of a compound of the invention in, for example, the digestive tract.

The compounds of the invention may be formulated as a syrup, an infusion or injection solution, a spray, a tablet, a capsule, a lozenge, a liposome, a suppository, and the like.

Particular preferred pharmaceutical forms for the administration of the compounds of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol such as glycerol, propylene glycol, polyethylene glycol, suitable mixtures thereof, surfactants or vegetable oils. The compounds of the invention can also be formulated into liposomes, in particular for parenteral administration. Liposomes provide the advantage of increased half life in the circulation, if compared to the free drug, and a prolonged more even release of the enclosed drug.

Sterilization of infusion or injection solutions can be accomplished by any techniques recognized in the art, including but not limited to addition of preservatives such as anti-bacterial or anti-fungal agents, e.g. parabens, chlorobutanol, phenol, sorbic acid or thimerosal. Further, isotonic agents, such as sugars or salts, in particular sodium chloride, may be incorporated in infusion or injection solutions.

Production of sterile injectable solutions containing one or more of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole.

Excipients which can be used with the various pharmaceutical forms of the compounds of the invention can be selected from the following non-limiting list:

a) binders such as lactose, mannitol, crystalline sorbitol, dibasic phosphates, sugars, microcrystalllne cellulose, carboxymethyl cellulose, hydroxyethyl cellulose, polyvinyl pyrrolidone and the like;

b) lubricants such as magnesium stearate, talc, calcium stearate, zinc stearate, stearic acid, hydrogenated vegetable oil, leucine, glycerides and sodium stearyl fumarates, c) disintegrants such as starches, croscarmellose, sodium methyl cellulose, agar, bentonite, alginic acid, carboxymethyl cellulose, polyvinyl pyrrolidone and the like.

In one embodiment, the formulation is for oral administration and the formulation comprises one or more or all of the following ingredients: pregelatinized starch, talc, povidone K30, croscarmellose sodium, sodium stearyl fumarate, gelatin, titanium dioxide, sorbitol, monosodium citrate, xanthan gum, titanium dioxide, flavouring agent, sodium benzoate and saccharin sodium.

In one embodiment, the compounds of the invention are administered intranasally, it may be administered in the form of a dry powder inhaler or an aerosol spray from a pressurized container, pump, spray or nebulizer with the use of a suitable propellant, e.g., dichforodifluoromethane, trichlorofluoromethane, dichlorotetrafluoroethane, a hydrofluoro-alkane such as 1,1,1,2-tetrafluoroethane (HFA 134 A™) or 1,1,1,2,3,3,3-heptafluoropropane (HFA 227EA™), carbon dioxide, or another suitable gas. The pressurized container, pump, spray or nebulizer may contain a solution or suspension of the compounds of the invention, e.g., using a mixture of ethanol and the propellant as the solvent, which may additionally contain a lubricant, e.g., sorbitan trioleate.

The typical dosage of the compounds of the invention will be in the range of 0.001-1000 mg/kg body weight/day. The daily dosage may be administered in a single dose or in multiple divided doses. The appropriate dosage is determined by the attending physician, as appropriate, depending on the type and severity of the disease being treated, the health status and past medical history of the individual, the co-drug, the specific compound to be administered, and the route of administration. If desired, the dosage of the compounds of the invention may go beyond said dosage range.

It is understood that within the scope of the invention, a technical feature defined in the individual technical solutions above can be combined with a technical feature specifically described below (e.g., in the Examples) to form a new or preferred technical solution. Such technical solutions are not reiterated one by one herein due to the length of the application.

The formula shall be relied on when there is discrepancy between the chemical name of any compound of the invention and its formula, unless the formula is obviously wrong.

As will be clearly understood by those skilled in the art, not all hydrogen atoms are explicitly depicted in the structural formulae of some compounds of the invention for the sake of simplicity. When a carbon atom or a nitrogen atom in a compound has a vacant valence, it means that hydrogen not explicitly depicted is present there. For example, the compound of Example P12 is represented by the formula

P12

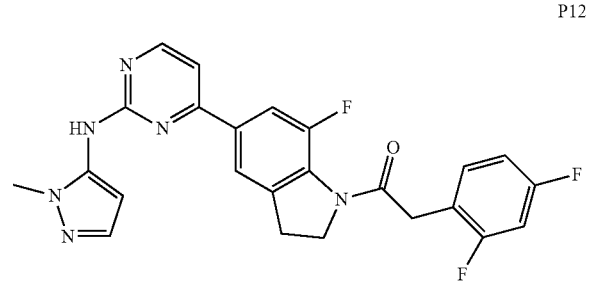 [SMILES: Cn1nccc1Nc1nccc(-c2cc(F)c3c(c2)CCN3C(=O)Cc2ccc(F)cc2F)n1]

below, wherein one hydrogen atom is omitted on the nitrogen atom between the pyrimidine ring and the pyrazole ring. Those skilled in the art can understand that said formula represents the same compound as the formula

P12

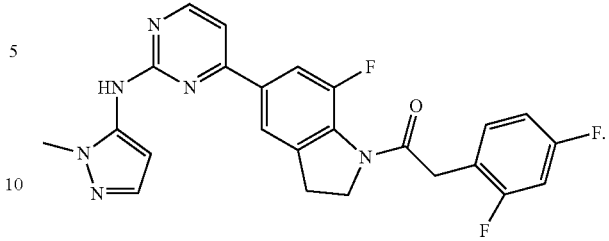

EXAMPLES

Figure 1:
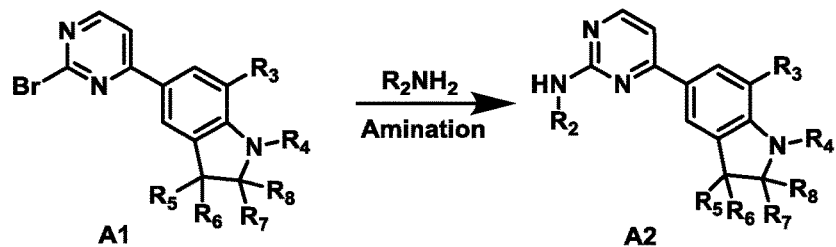
FIG. 1 shows the general synthetic scheme A for the synthesis of the compounds of the invention, wherein individual variables are as defined herein.

The following examples are merely provided for illustration of the invention and should not be construed to limit the scope of the invention.

The experimental procedures in the following examples, in which the specific conditions are not indicated, can be carried out under the conventional conditions for such reactions or under the conditions recommended by the manufacturers. Unless otherwise specified, percentages and parts are indicated by weight.

The materials and reagents used in the following examples are commercially available, unless otherwise specified.

In the following examples, $^1$H-NMR spectra were recorded using Bluker AVHD 400 MHz or Bluker AVHD 500 MHz nuclear magnetic resonance spectrometer, $^{13}$C-NMR spectra were recorded using Bluker AVHD 500 MHz or Bluker AVHD 600 MHz nuclear magnetic resonance spectrometer, with chemical shift shown in δ (ppm); Mass spectra were recorded using Waters UPLC H-Class+QDa (ESI) and Agilent 1260-6120 (ESI) mass spectrometer; and reverse phase preparative HPLC separation was carried out using Waters UV guided fully automatic purification system (Xbridge Prep C185 μm OBD column).

The abbreviations used in the examples have the following meanings:
iPrOH isopropanol
EtOH ethanol
DCM dichloromethane
TFA or CF$_3$COOH trifluoroacetic acid
MeOH methanol
NaOH sodium hydroxide
HCl hydrogen chloride or hydrochloric acid
TEA triethylamine
Raney Ni Raney nickel
dioxane dioxacyclohexane
NaH sodium hydride H₂O water
Pd/C palladium/charcoal
H₂ hydrogen gas
N₂ nitrogen gas
HATU O-(7-azabenzotriazol-1-yl)-N,N,N',N'-tetramethyl-uronium hexafluorophosphate
DMF N,N-dimethylformamide
THF tetrahydrofuran
Boc₂O di-t-butyl dicarbonate
Boc t-butoxycarbonyl
NBS N-bromosuccinimide
NCS N-chlorosuccimimide
NIS N-iodosuccimimide
MeCN or CH₃CN acetonitrile
DIPEA or DIEA N,N-diisopropylethylamine
NaBH₄ sodium borohydride
AcOH acetic acid
Ac₂O acetic anhydride
AcCl acetyl chloride
NaBH₃CN or NaBH₃(CN) sodium cyanoborohydride
K₂CO₃ potassium carbonate
Cs₂CO₃ cesium carbonate
NaHCO₃ sodium bicarbonate
nBuLi n-butyllithium
LiAlH₄ lithium aluminum hydride
Pd(dppf)Cl₂ or PdCl₂(dppf) 1,1'-bis(diphenylphospho)ferrocenelpalladium (II) dichloride
PdCl₂(PPh₃)₂ bis(triphenylphosphine)palladium(II) dichloride
KOAc potassium acetate
Fumaronitrile fumaronitrile
P(nBu)₃ tri-n-butylphosphine
LDA lithium diisopropylamide
LiOH lithium hydroxide
MeI iodomethane
EtI iodoethane
(CH₂O)ₙ paraform
HCO₂H or FA formic acid
CH₃COCl acetyl chloride
HPLC high performance liquid chromatography
CH₃COOK or AcOK potassium acetate
t-BuONa sodium t-butoxide
DMSO dimethyl sulfoxide
h hour(s)
min minute(s)
DMAP 4-dimethylamiopryidine
r.t.或 RT room temperature
T₃P 1-propylphosphonic anhydride
DMEA N,N-dimethylethanolamine
POCl₃ phosphorus oxychloride
° C. degrees centigrade
EA ethyl acetate
Bu₄NBr₃ tetra-n-butylammonium tribromide
CuI cuprous iodide
Mg magnesium
Py pyridine
TLC thin-layer chromatography
LCMS liquid chromatography-mass spectrometry
TBS t-butyldimethylsilane
TBSCl t-butyldimethylsilyl chloride
BPin₂ bis(pinacolato)diboron
PE petroleum ether
MW microwave
DEA diethylamine
HEP n-heptane
IPA isopropanol
HEX n-hexane

SYNTHESIS OF INTERMEDIATES

Intermediate 4: Synthesis of 7-fluoro-5-(4,4,5,5-tetramethyl-1,3,2-dioxaborolan-2-yl)indoline (4)

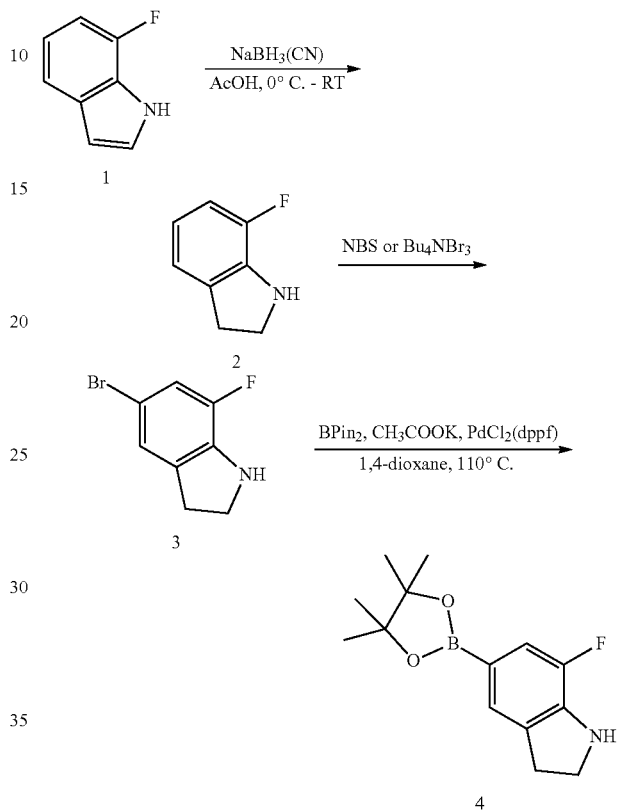

Step 1. Synthesis of 7-fluoroindoline (2)

Into a dry 50 mL round bottom flask, Compound 1 (5000 mg, 37 mmol) and AcOH (30 mL) were added at room temperature, and NaBH₃CN (5813 mg, 92.49 mmol) was added in portions at 0° C. The mixture was stirred at room temperature for 3 h. After the reaction was completed as detected by TLC plate, the reaction was concentrated under reduced pressure, added with 100 mL water, and adjusted to pH=9 with 2 mol/L aqueous sodium hydroxide solution at 0° C. The mixture was stirred for 1 hour, then warmed to 25° C., and stirred for 1 hour. The mixture was extracted with ethyl acetate, dried, and filtered. The filtrate was evaporated to dryness. The resulting residule was purified by silica gel column chromatography with eluent system (ethyl acetate/ petroleum ether=1/50 to 1/10) to give Intermediate 2 7-fluoroindoline (4.0 g, off white solid). Yield: 78.4%. LCMS: m/z 138.1 (M+H).

Step 2. Synthesis of 5-bromo-7-fluoroindoline (3)

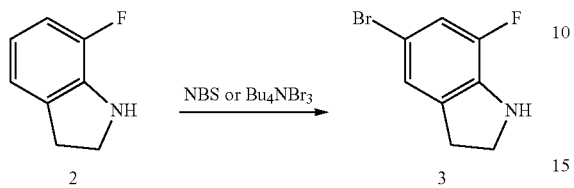

Method I:

NBS (5.2 g, 29.19 mmol) was slowly added into the solution of Intermediate 2 (4.0 g, 29.19 mmol) in acetonitrile (100 mL) in a dry 50 mL round bottom flask at 0° C. The mixture was then warmed to room temperature, and stirred for 2 h. After the reaction was completed, the reaction was concentrated under reduced pressure, added with 100 mL water, and extracted with ethyl acetate (150 mL×3). The combined organic phase washed with saturated aqueous sodium bicarbonate solution and saturated brine (100 mL×1), dried over anhydrous sodium sulfate, and filtered. The filtrate was concentrated under reduced pressure. The resulting residue was purified by silica gel column chromatography with eluent system (ethyl acetate:petroleum ether=1:8) to give Intermediate 3 (5.0 g, light purple solid). Yield: 80.6%. LCMS: m/z 215.9 (M+H).

Method II:

Into a 100 mL flask in ice-water bath, Compound 2 (9.8 g, 0.072 mol) and dichromethane (100 mL) were added, and tetra-n-butylammonium tribromide (34.5 g, 0.072 mol) was added in portions. The mixture was naturally warmed to room temperature, and stirred at room temperature for 4 h. After the reaction was completed, the reaction was concentrated under reduced pressure, slowly added with saturated aqueous sodium bicarbonate solution to adjust the pH to 6-7, and was extracted with ethyl acetate (50 mL×4). The combined organic phase was concentrated under reduced pressure. The resulting residue was purified by silica gel column chromatography with eluent system (ethyl acetate:petroleum ether=1:15) to give 5-bromo-7-fluoroindoline 3 (9.5 g, off-white solid). LCMS: m/z 215.9 (M+H).

Step 3. Synthesis of 7-fluoro-5-(4,4,5,5-tetramethyl-1,3,2-dioxaborolan-2-yl)-indoline (4)

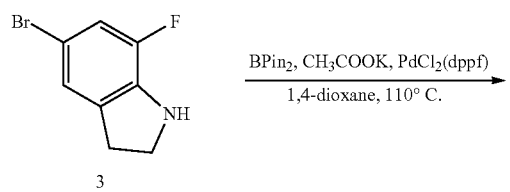

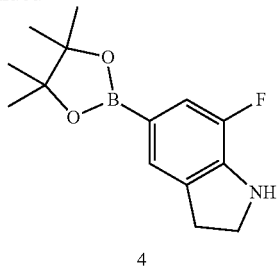

Into a dry 50 mL single-necked flask, Intermediate 3 (600 mg, 2.777 mmol), bis(pinacolato)diboron (1410 mg, 5.554 mmol), Pd(dppf)Cl$_2$ (243 mg, 0.333 mmol), potassium acetate (545 mg, 5.554 mmol) and 1,4-dioxane (4 mL) were added at room temperature. The mixture was purged with nitrogen gas three times, and heated to 110° C. with stirring under nitrogen gas for 3 h. After the reaction was completed as detected by LCMS, the reaction was filtered. The filtrate was concentrated under reduced pressure. The resulting residue was purified by silica gel column chromatography with eluent system (EA/PE=2%-10%) to give Intermediate 4, 7-fluoro-5-(4,4,5,5-tetramethyl-[1,3,2]dioxaborolan-2-yl)-2,3-dihydro-1H-indole (600 mg, yellow solid). Yield: 82.1%. Purity: about 90%. LCMS: m/z 264.1 (M+H).

Intermediate 7: Synthesis of 4-bromo-N-(1-methyl-1H-pyrazol-5-yl)pyridin-2-amine (7)

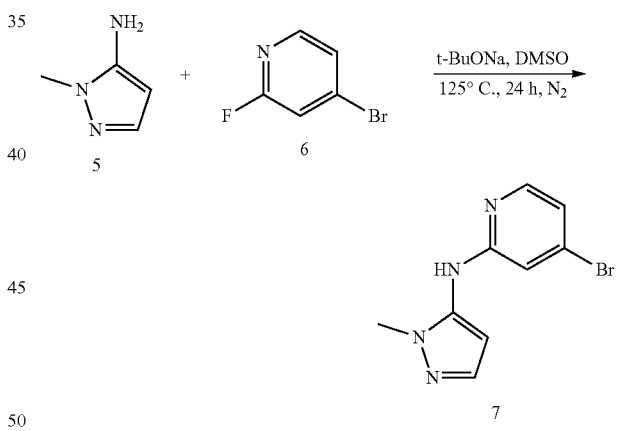

Into a dry 250 mL round bottom flask, Compound 6 (4.2 g, 23.86 mmol), Compound 5 (2.8 g, 28.83 mmol), sodium t-butoxide (4.6 g, 47.8 mmol) and DMSO (60 mL) were added at room temperature. The mixture was purged with nitrogen gas three times, and stirred under reflux at 125° C. for 24 h. After the reaction was completed as detected by LC/MS, the reaction was extracted with EA (50 mL×3), washed with saturated saline (30 mL), and then was dried and filtered. The filtrate was concentrated under reduced pressure. The resulting residue was purified by silica gel column chromatography with eluent system (PE:EA=3:7) to give Intermediate 7 (2.1 g, light yellow solid). Yield: 40%. LCMS: m/z 253.0/255.0 (M+H).

Intermediate 8: Synthesis of T-butyl (4-bromopyridin-2-yl)(1-methyl-1H-pyrazol-5-yl) carbamate (8)

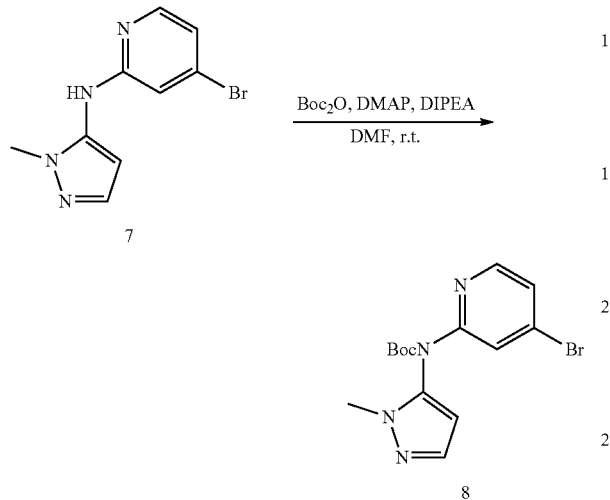

Into a dry 100 mL round bottom flask, Intermediate 7 (500 mg, 1.976 mmol), DMAP (67 mg, 0.593 mmol), DIPEA (766 mg, 5.928 mmol) and DMF (5 mL) were added at room temperature. After dissolution with stirring at room temperature, Boc₂O (1299 mg, 5.928 mmol) was slowly added, and reacted at room temperature for 3 h. After the reaction was completed, the reaction was extracted with EA. The combined organic phase washed with saturated brine, dried over anhydrous sodium sulfate, and filtered. The filtrate was concentrated under reduced pressure. The resulting residue was purified by silica gel column chromatography with eluent system (ethyl acetate/petroleum ether=15/85 to 70/30) to give Intermediate 8 (626 mg, light yellow solid). Yield: 88%. LCMS: m/z 352.9 (M+H).

Intermediate 13: Synthesis of 1-(5-(2-bromopyrimidin-4-yl)-7-fluoroindolin-1-yl)-2-(2-chloropyridin-3-yl)ethan-1-one (13)

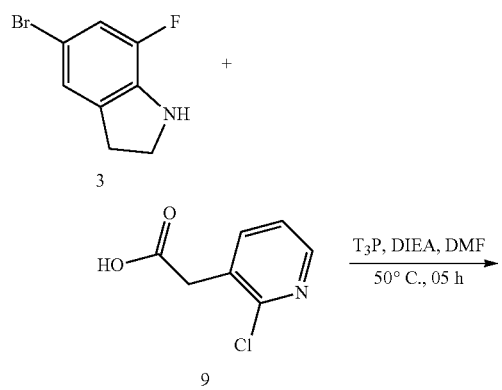

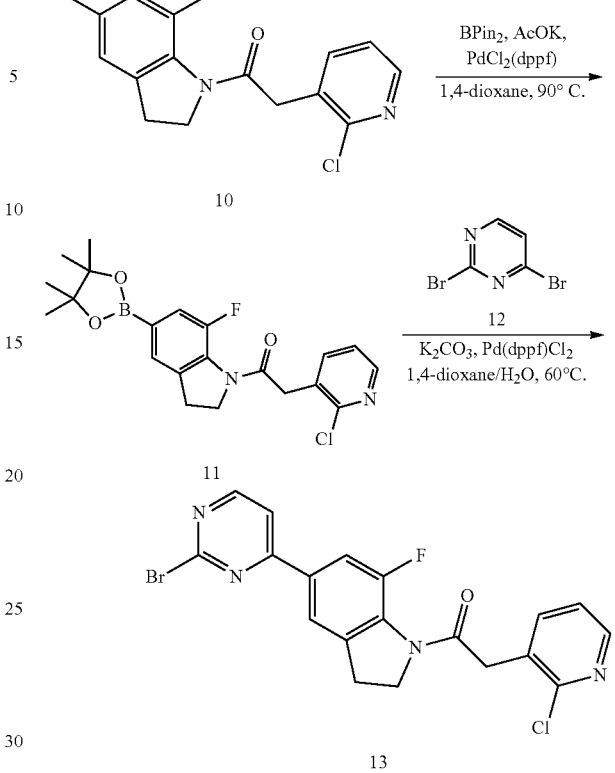

Step 1. Synthesis of 1-(5-bromo-7-fluoroindolin-1-yl)-2-(2-chloropyridin-3-yl)ethan-1-one (10)

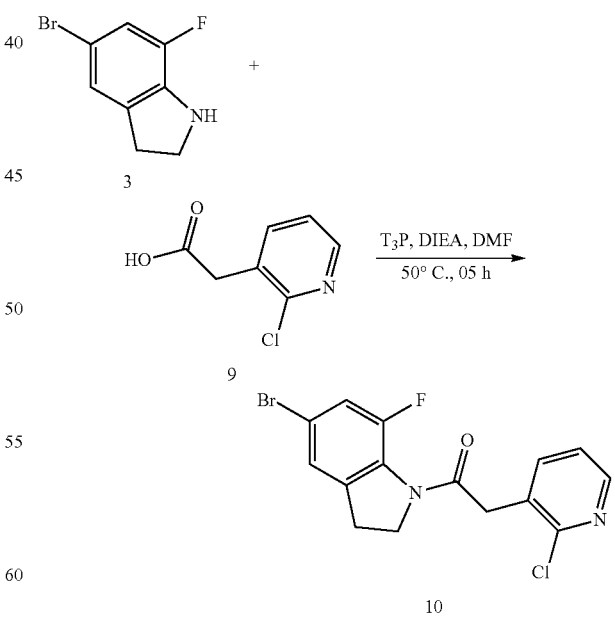

Into a dry 250 mL round bottom flask, N,N-dimethylformamide (10 mL), Intermediate 3 (1.7 g, 0.0079 mol), Compound 9 (1.23 g, 0.007 mol) and N,N-diisopropylethylamine (3.69 g, 0.028 mol) at room temperature. The mixture was purged with nitrogen gas three times, and was gradually warmed to 50° C. 1-Propylphosphonic anhydride (56 mL, 50% solution in ethyl acetate) was added and reacted for 0.5 h. After the reaction was completed as detected by TLC, the reaction was concentrated under reduced pressure. The resulting residue was poured into ice-water to precipitate. The solid was filtered to give Intermediate 10 (2.7 g, pale yellow solid). Yield: 93%. LCMS: m/z 368.8/370.8 (M+H).

Step 2. Synthesis of 2-(2-chloropyridin-3-yl)-1-(7-fluoro-5-(4,4,5,5-tetramethyl-1,3,2-dioxaborolan-2-yl)indolin-1-yl)ethan-1-one (11)

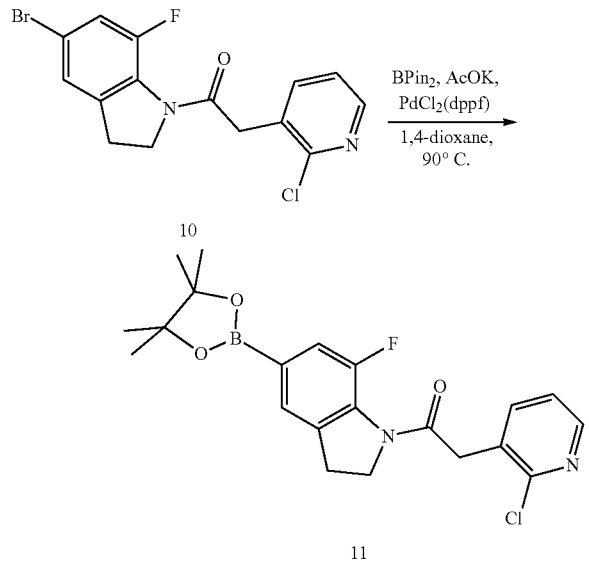

Into a dry 100 mL round bottom flask, Intermediate 10 (2 g, 0.0054 mol), bis(pinacolato)diboron (2.0 g, 0.0079 mol), potassium acetate (1.59 g, 0.016 mol) and 1,4-dioxane (36 mL) were added. The mixture was purged with nitrogen gas once, and was added with Pd(dppf)Cl₂ (442 mg, 0.0005 mol). The reaction was purged with nitrogen gas three times, heated to 90° C., and stirred for 4 h. After the reaction was completed as detected by LCMS, the reaction was concentrated under reduced pressure. The resulting residue was purified by silica gel column chromatography with eluent system (ethyl acetate:petroleum ether=1:3) to give Intermediate 11 (1.5 g, pale yellow solid). Yield: 68%. LCMS: m/z 417.1 (M+H).

Step 3. Synthesis of 1-(5-(2-bromopyrimidin-4-yl)-7-fluoroindolin-1-yl)-2-(2-chloropyridin-3-yl)ethan-1-one (13)

Into a dry 100 mL round bottom flask, Intermediate 11 (200 mg, 0.48 mmol), 2,4-dibromopyrimidine (126 mg, 0.53 mmol), potassium carbonate (200 mg, 1.44 mmol), (1,1-bis(diphenylphosphino)ferrocene)palladium (II) dichloride (70 mg, 0.096 mmol) and the mixed solvent of 1,4-dioxane and water (4:1, 10.0 mL) were added at room temperature. The reaction was purged with nitrogen gas three times, warmed to 60° C., and stirred for 2 h. After the reaction was completed, the reaction was concentrated under reduced pressure, added with 100 mL water, and extracted with ethyl acetate (150 mL×3). The combined organic phases was dried over anhydrous sodium sulfate, and filtered. The filtrate was concentrated under reduced pressure. The resulting residue was purified by silica gel column chromatography with eluent system (ethyl acetate:petroleum ether=1:1) to give the product 13 (140 mg, light yellow solid). Yield: 65.0%. LCMS: m/z 446.8 (M+H).

Intermediate 17: Synthesis of 4-chloro-N-(1-methyl-1H-pyrazol-5-yl)pyrimidin-2-amine (17)

Step 1. Synthesis of 2-(1-methyl-1H-pyrazol-5-yl)amino-pyrimidin-4(3H)-one (16)

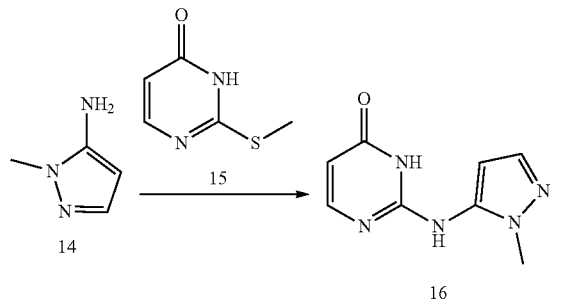

Into a dry 50 mL round bottom flask, Compound 14 (7.8 g, 80 mmol), Compound 15 (5.72 g, 40 mmol) and trimethylacetic acid (28.6 g) were added. The mixture was slowly heated to 150° C. with stirring, and reacted for 40 h. After the reaction was completed as detected by LCMS, the reaction was reduced to room temperature, and added with 30 mL dichloromethane and 5 mL methanol to fully dissolve the reaction mixture, followed by the addition of silica gel. The purification by silica gel column chromatography with eluent system (dichloromethane:methanol=3:2) gave Intermediate 16 (5 g, yellow solid). Yield: 65.8%. LCMS: m/z 191.9 (M+H).

Step 2. Synthesis of 4-chloro-N-(1-methyl-1H-pyrazol-5-yl)pyrimidin-2-amine (17)

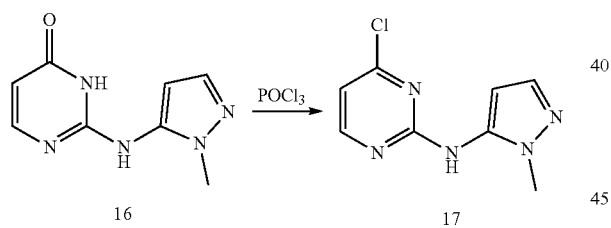

Into a dry 250 mL round bottom flask, Intermediate 16 (5 g, 26.1 mmol), phosphorus oxychloride (10 mL, 109.2 mmol) and acetonitrile (100.0 mL) were added at room temperature. The reaction was warmed to 100° C., and stirred for 2 h. After the reaction was completed, the reaction was concentrated under reduced pressure, quenched by addition of 100 mL water, and extracted with ethyl acetate (60 mL×3). The combined organic phase washed with saturated brine (40 mL×2), dried over anhydrous sodium sulfate, and filtered. The filtrate was concentrated under reduced pressure. The resulting residue was purified by silica gel column chromatography with eluent system (ethyl acetate:petroleum ether=3:2) to give Intermediate 17 (2.9 g, pale yellow solid). Yield: 53.7%. LCMS: m/z 209.9 (M+H).

$^1$H-NMR (CDCl3, 400 MHz): 8.27 (d, J=5.2 Hz, 1H), 7.53 (br, 1H), 7.48 (d, J=5.2 Hz, 1H), 6.80 (d, J=5.6 Hz, 1H), 6.28 (d, J=5.6 Hz, 1H), 3.77 (s, 3H).

Intermediate 23: Synthesis of 1-(7-chloro-5-(4,4,5,5-tetramethyl-1,3,2-dioxaborolan-2-yl)indolin-1-yl)-2-(2-chloropyridin-3-yl)ethan-1-one (23)

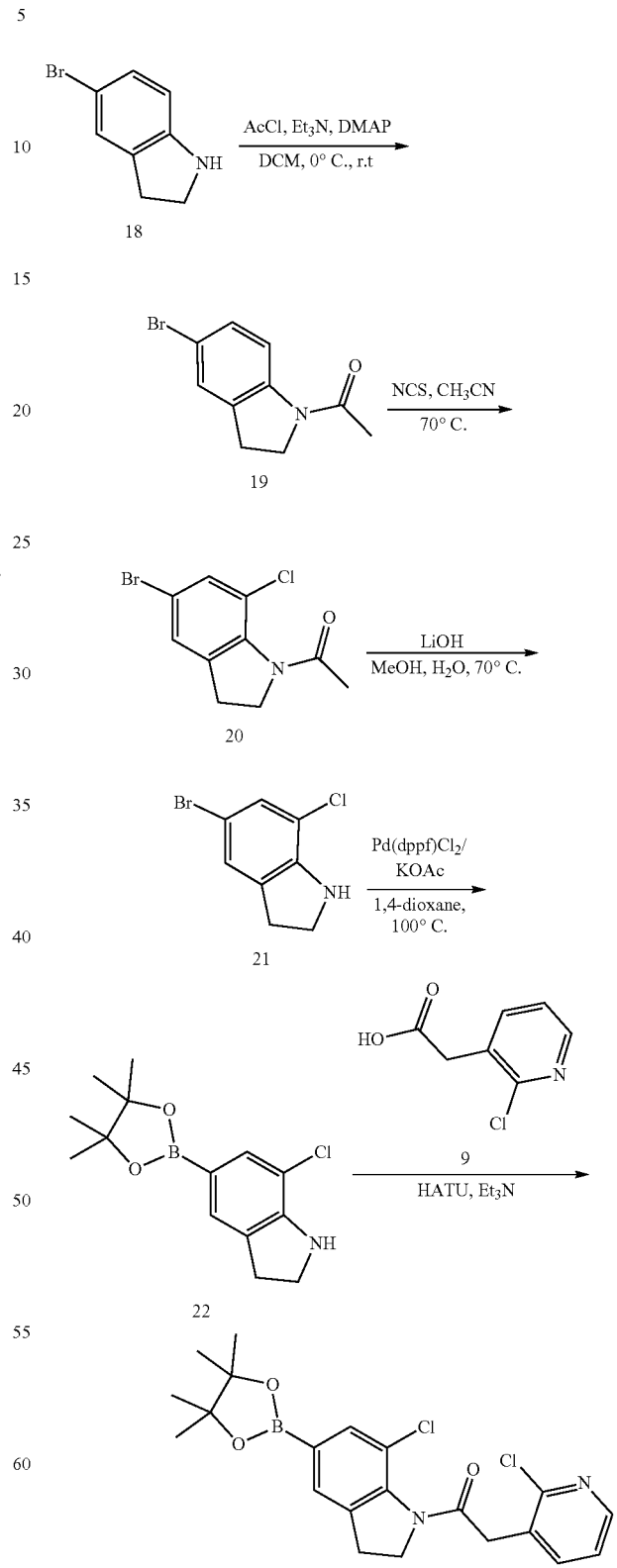

Step 1. Synthesis of 1-(5-bromo-indolin-1-yl)ethan-1-one (19)

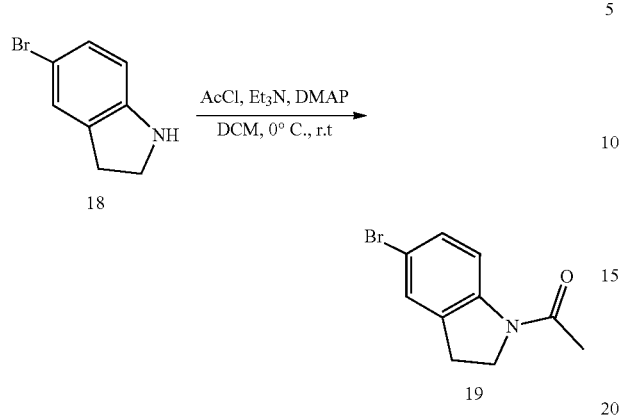

Into a dry 50 mL round bottom flask, Compound 18 (1500 mg, 7.57 mmol), DCM (20 mL), Et₃N (1915 mg, 18.93 mmol) and DMAP (30 mg) were added at room temperature, and acetyl chloride (1188 mg, 15.14 mmol) was added in portions at 0° C. After the addition, the reaction was stirred at room temperature for 3 h, and was poured into water at 0° C. and stirred for 1 h. The reaction was extracted with DCM, dried and filtered. The filtrate was evaporated to dryness to give Intermediate 19 (1.75 g, yellow solid). Yield: 96.3%. LCMS: m/z 240.0/242.0 (M+H).

Step 2. 1-(5-bromo-7-chloro-indolin-1-yl)ethan-1-one (20)

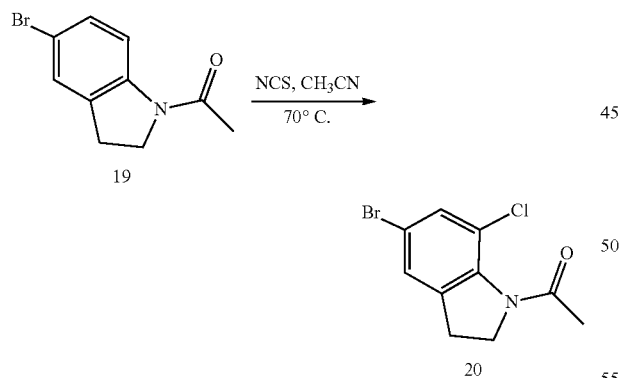

Into a dry 50 mL round bottom flask, Intermediate 19 (1600 mg, 14.58 mmol), acetonitrile (30 mL) and NCS (979 mg, 7.33 mmol) were added at room temperature. After the addition, the reaction was then stirred at 70° C. for 18 h, poured into water (20 mL), extracted with EA, dried, and filtered. The filtrate was evaporated to dryness. The resulting residue was purified by silica gel column chromatography with eluent system (ethyl acetate/petroleum ether=1/50 to 1/10) to give Intermediate 20 (1.2 g, yellow liquid). Yield: 65.6%. LCMS: m/z 274.0/276.0 (M+H).

Step 3. Synthesis of 5-bromo-7-chloro-indoline (21)

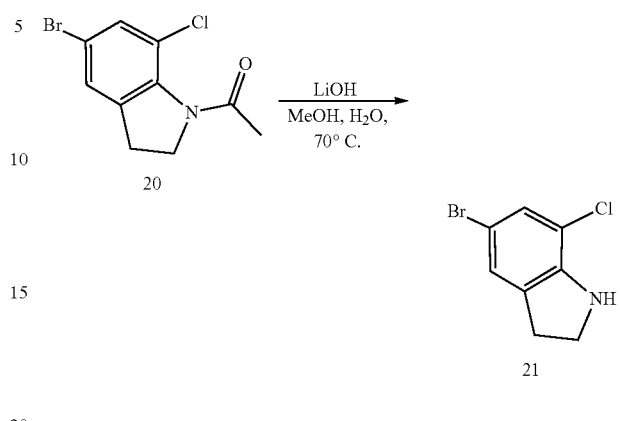

Into a dry 50 mL single-necked flask, Intermediate 20 (1200 mg, 4.37 mmol), lithium hydroxide monohydrate (550 mg, 13.11 mmol), as well as methanol (15 mL) and water (8 mL) were added at room temperature. The mixture was heated to 70° C. with stirring and reacted for 18 h. After the reaction was completed as detected by LCMS, the reaction was extracted with EA, washed, dried, and filtered. The filtrate was concentrated under reduced pressure. The resulting residue was purified by silica gel column chromatography with eluent system (EA/PE=2%-10%) to give Intermediate 21 (700 mg, yellow solid). Yield: 68.9%. Purity: about 80%. LCMS: m/z 232.0 (M+H).

Step 4. Synthesis of 7-chloro-5-(4,4,5,5-tetramethyl-1,3,2-dioxaborolan-2-yl)-indoline (22)

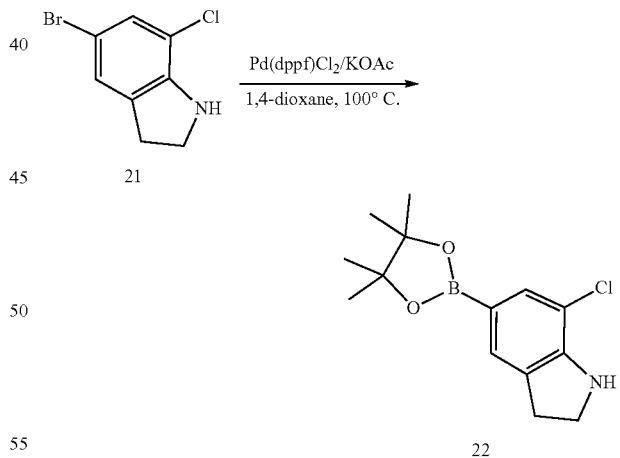

Into a dry 50 mL single-necked flask, Intermediate 21 (600 mg, 2.581 mmol), bis(pinacolato)diboron (852 mg, 3.354 mmol), Pd(dppf)Cl₂ (188 mg, 0.2581 mmol), potassium acetate (329 mg, 3.354 mmol) and 1,4-dioxane (5 mL) were added at room temperature. The mixture was purged with nitrogen gas three times, heated to 100° C. with stirring, and reacted for 3 h. After the reaction was completed as detected by LCMS, the reaction was filtered. The filtrate was concentrated under reduced pressure. The resulting residue was purified by silica gel column chromatography with eluent system (EA/PE=2%-10%) to give Intermediate 22 (480 mg, yellow solid). Yield: 66.67%. Purity: about 80%. LCMS: m/z 280.1 (M+H).

Step 5. Synthesis of Intermediate 1-(7-chloro-5-(4,4,5,5-tetramethyl-1,3,2-dioxaborolan-2-yl)indolin-1-yl)-2-(2-chloropyridin-3-yl)ethan-1-one (23)

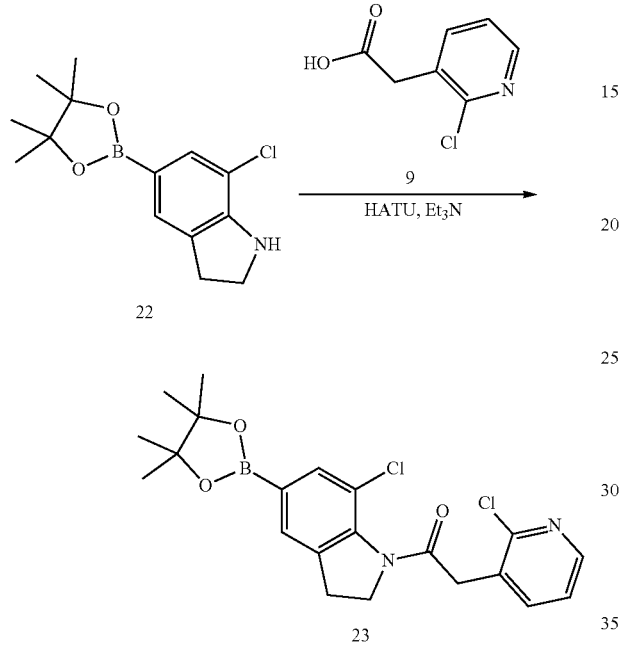

Into a dry 25 mL single-necked flask, Intermediate 22 (440 mg, 1.574 mmol), Compound 9 (540 mg, 3.147 mmol), Et₃N (318 mg, 3.147 mmol), HATU (1193 mg, 3.147 mmol) and THF (8 mL) were added at room temperature, and stirred under nigrogen gas at 32° C. for 18 h. After the reaction was completed as detected by LCMS, the reaction was extracted with EA, washed with water, dried, and evaporated to dryness. The crude producrt was purified by silica gel column chromatography with eluent system (EA/PE 10-40%) to give Intermediate 23 (290 mg, yellow solid). Yield: 42.58%. LCMS: m/z 434.1 (M+H).

Intermediate 31: Synthesis of 2-(2-chloropyridin-3-yl)-1-(7-methyl-5-(4,4,5,5-tetramethyl-1,3,2-dioxaborolan-2-yl)indolin-1-yl)ethan-1-one (31)

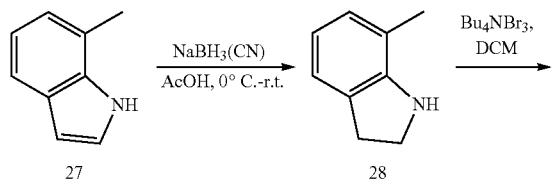

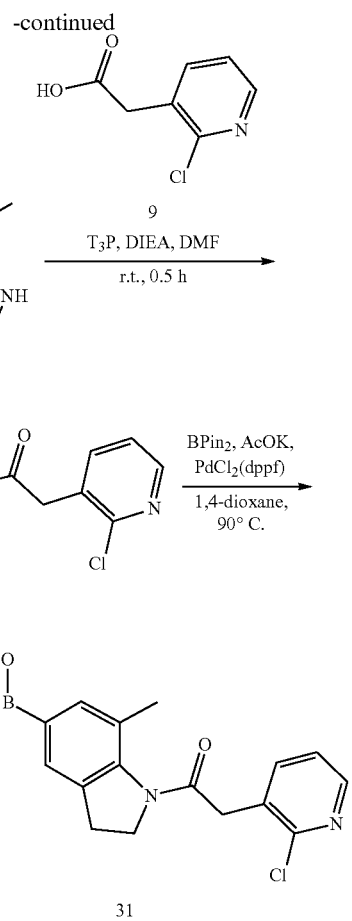

Step 1. Synthesis of 7-methylindoline (28)

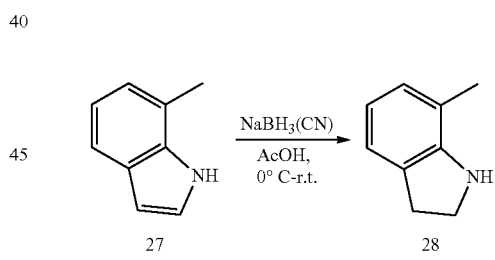

Into a dry 250 mL round bottom flask, Compound 27 7-methyl-1H-indole (2.0 g, 15.27 mmol), sodium cyanoborohydride (2.9 g, 45.81 mmol) and glacial acetic acid (40 mL) were added at 0° C. The reaction was warmed to room temperature, and stirred for 3 h. After the reaction was completed as detected by TLC plate, the reaction was concentrated under reduced pressure, added with 100 mL water, adjusted with 2 mol/L aqueous sodium hydroxide solution to pH 9, was extracted with ethyl acetate (100 mL×3). The combined organic phase washed with saturated brine (100 mL), dried over anhydrous sodium sulfate, and filtered. The filtrate was concentrated under reduced pressure. The resulting residue was purified with flash column chromatography with eluent system (ethyl acetate:petroleum ether=1:5) to give Intermediate 28 7-methylindoline (1.5 g, off white solid). Yield: 75.3%. LCMS: m/z 134.1 (M+H).

Step 2. Synthesis of 5-bromo-7-methylindoline (29)

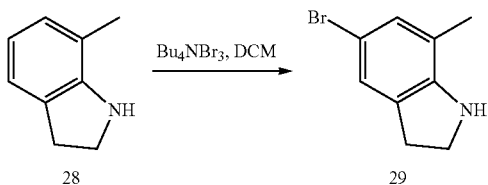

Into a dry 100 mL round bottom flask, Intermediate 28 7-methylindoline (120 mg, 0.902 mmol), tetra-n-butylammonium tribromide (464 mg, 0.902 mmol) and dichloromethane (10.0 mL) were added at room temperature. The reaction was stirred for 30 min. After the reaction was completed as detected by LCMS, the reaction was concentrated under reduced pressure, added with 100 mL water, and extracted with ethyl acetate (150 mL×3). The combined organic phase washed with saturated brine (100 mL), dried over anhydrous sodium sulfate, and filtered. The filtrate was concentrated under reduced pressure. The resulting residue was purified by silica gel column chromatography with eluent system (ethyl acetate:petroleum ether=1:5) to give Intermediate 29 5-bromo-7-methylindoline (200 mg, light purple solid). Yield: 80.6%. LCMS: m/z 211.9 (M+H).

Step 3. Synthesis of 1-(5-bromo-7-methylindolin-1-yl)-2-(2-chloropyridin-3-yl)ethan-1-one (30)

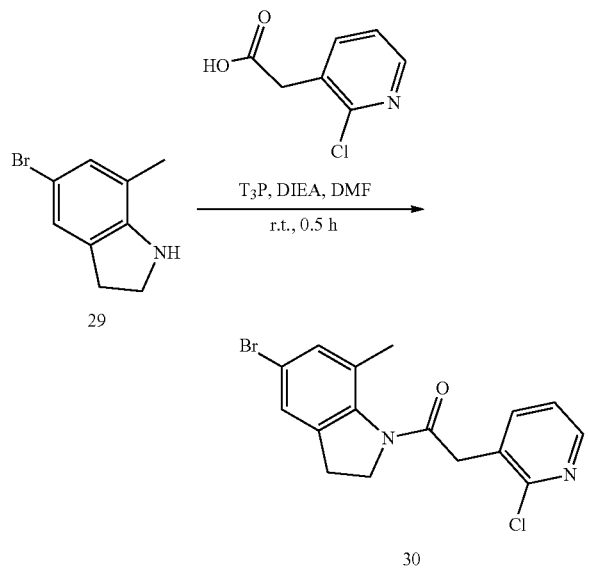

Into a dry 100 mL round bottom flask, Intermediate 29 (80 mg, 0.38 mmol), Compound 9 2-(2-chloropyridin-3-yl)acetic acid (67 mg, 0.38 mmol), N,N-diisopropylethylamine (0.25 mL, 1.52 mmol), T₃P (1.208 g, 50% (wt %) solution in ethyl acetate (1.9 mmol)) and N,N-dimethylformamide (5.0 mL) were added. The reaction was stirred at room temperature for 30 min. After the reaction was completed, the reaction was added with 100 mL water, and extracted with ethyl acetate (150 mL×3). The combined organic phase washed with saturated brine (100 mL×6), dried over anhydrous sodium sulfate, and filtered. The filtrate was concentrated under reduced pressure. The resulting residue was purified by silica gel column chromatography with eluent system (ethyl acetate:petroleum ether=1:5) to give Intermediate 30 1-(5-bromo-7-methylindolin-1-yl)-2-(2-chloropyridin-3-yl)ethan-1-one (50 mg, off white solid). Yield: 36.3%. LCMS: m/z 364.8 (M+H).

Step 4. Synthesis of 2-(2-chloropyridin-3-yl)-1-(7-methyl-5-(4,4,5,5-tetramethyl-1,3,2-dioxaborolan-2-yl)indolin-1-yl)ethan-1-one (31)

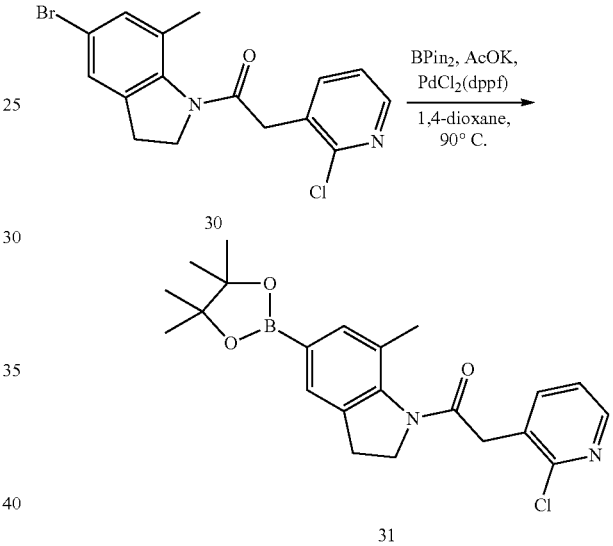

Into a dry 100 mL round bottom flask, Intermediate 30 1-(5-bromo-7-methylindolin-1-yl)-2-(2-chloropyridin-3-yl)ethan-1-one (400 mg, 1.09 mmol), bis(pinacolato)diboron (1.38 g, 5.43 mmol), potassium acetate (233 mg, 3.27 mmol), (1,1-bis(diphenylphosphino)ferrocene)palladium (II) dichloride (70 mg, 0.11 mmol) and 1,4-dioxane (20.0 mL) were added at room temperature, purged with nitrogen gas five times, warmed to 90° C., and stirred overnight. After the reaction was completed as detected by LCMS, the reaction was concentrated under reduced pressure, added with 100 mL water, and extracted with ethyl acetate (150 mL×3). The combined organic phase was dried over anhydrous sodium sulfate, and filtered. The filtrate was concentrated under reduced pressure. The resulting residue was purified by silica gel column chromatography with eluent system (ethyl acetate:petroleum ether=1:10) to give Intermediate 31 2-(2-chloropyridin-3-yl)-1-(7-methyl-5-(4,4,5,5-tetramethyl-1,3,2-dioxaborolan-2-yl)indolin-1-yl)ethan-1-one (200 mg, white solid). Yield: 44.0%. LCMS: m/z 413.0 (M+H).

Intermediate 53: Synthesis of 2-(2-chloropyridin-3-yl)-1-(7-fluoro-2-methyl-5-(4,4,5,5-tetramethyl-1,3,2-dioxaborolan-2-yl)indolin-1-yl)ethan-1-one

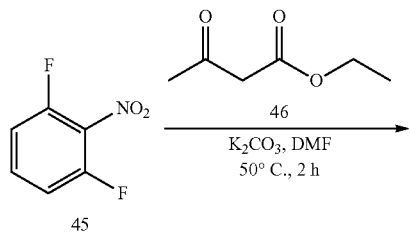

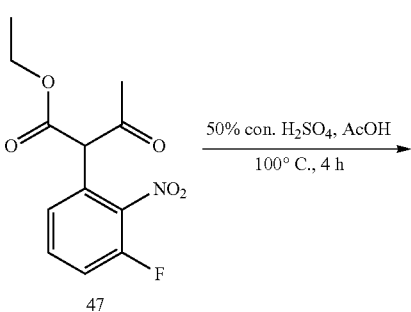

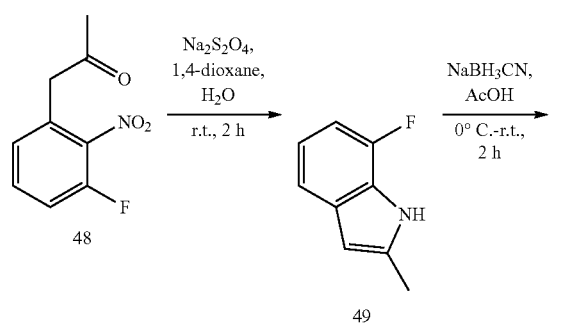

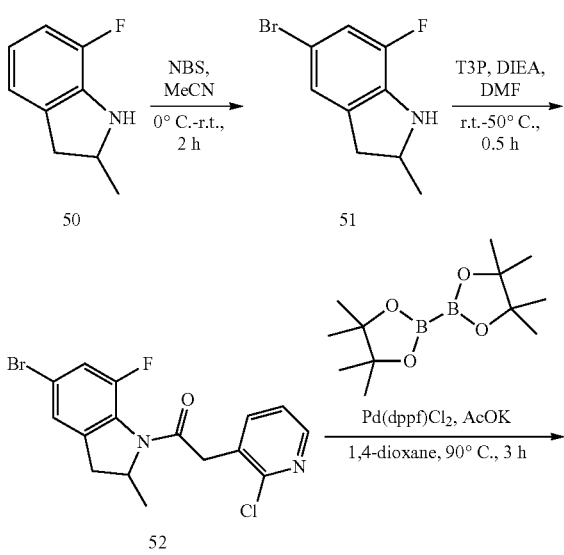

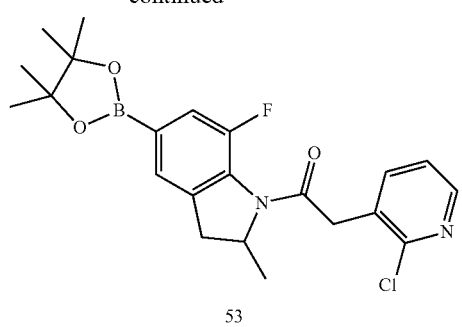

Step 1. Synthesis of ethyl 2-(3-fluoro-2-nitrophenyl)-3-oxobutyrate (47)

Into a dry 100 mL round bottom flask, ethyl acetoacetate (46)(6.1 g, 0.047 mol), potassium carbonate (8.7 g, 0.063 mol), 1,3-difluoro-2-nitrobenzene (5 g, 0.031 mol), N,N-dimethylformamide (20 mL) were sequentially added at room temperature, warmed to 50° C., and stirred for 2 h. After the reaction was completed as monitored by TLC, the reaction was diluted by addition of water (100 mL), and extracted with ethyl acetate (80 mL×3). The combined organic phase washed with saturated brine (300 mL×3), dried over anhydrous sodium sulfate, and filtered. The filtrate was concentrated under reduced pressure. The resulting residue was purified by silica gel column chromatography (ethyl acetate:petroleum ether=1:100) to give ethyl 2-(3-fluoro-2-nitrophenyl)-3-oxobutyrate 47 (2.8 g, pale yellow oil). Yield: 33%. $^1$H NMR (CDCl$_3$, 300 MHz): 13.07 (s, 1H), 7.58-7.40 (m, 1H), 7.30-7.19 (m, 1H), 7.16-7.01 (m, 1H), 4.31-4.00 (m, 2H), 1.87 (s, 3H), 1.18 (t, J=7.2 Hz, 3H).

Step 2. Synthesis of 1-(3-fluoro-2-nitrophenyl)propan-2-one (48)

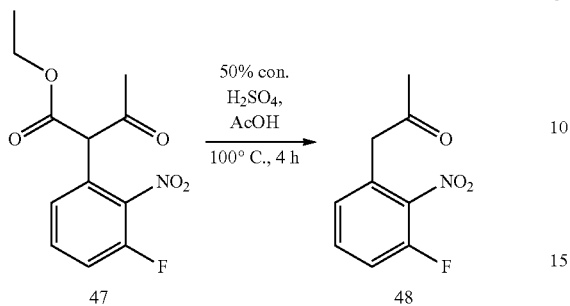

Into a dry 100 mL round bottom flask, ethyl 2-(3-fluoro-2-nitrophenyl)-3-oxobutyrate (2.8 g, 0.01 mol), acetic acid (20 mL), 50% sulfuric acid (20 mL) were added at room temperature, warmed to 100° C., and stirred for 4 h. After the reaction was completed as monitored by TLC, the reaction was diluted by addition of water (100 mL), and extracted with ethyl acetate (80 mL×3). The combined organic phase washed with saturated aqueous sodium bicarbonate solution (200 mL×2), dried over anhydrous sodium sulfate, and filtered. The filtrate was concentrated under reduced pressure. Purification by silica gel column chromatography (ethyl acetate:petroleum ether=1:5) to give 1-(3-fluoro-2-nitrophenyl)propan-2-one 48 (1.86 g, pale yellow oil). Yield: 91%. $^1$H NMR (DMSO-$d_6$, 300 MHz): 7.73-7.63 (m, 1H), 7.57-7.48 (m, 1H), 7.31 (d, J=7.5 Hz, 1H), 4.13 (s, 3H), 2.51 (s, 2H).

Step 3. Synthesis of 7-fluoro-2-methyl-1H-indole (49)

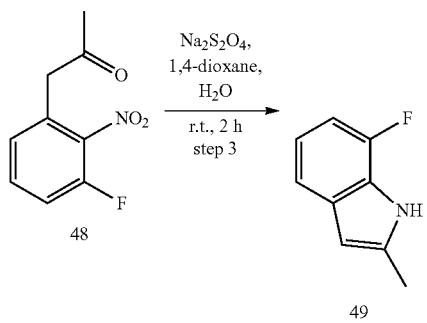

Into a dry 100 mL round bottom flask, distilled water (32 mL) and sodium hydrosulfite (13.2 g, 0.076 mol) were sequentially added, and then the solution of 1-(3-fluoro-2-nitrophenyl)propan-2-one (1.5 g, 0.0076 mmol) in 1,4-dioxane (3.4 mL) was added dropwise. The reaction was stirred at room temperature for 2 h. After the reaction was completed as monitored by TLC, the reaction was diluted by addition of water (80 mL), and extracted with ethyl acetate (60 mL×3). The combined organic phase was dried over anhydrous sodium sulfate, and filtered. The filtrate was concentrated under reduced pressure. Purification by silica gel column chromatography (pure petroleum ether) gave 7-fluoro-2-methyl-1H-indole 49 (250 mg, white solid). Yield: 22%. $^1$H NMR (DMSO-$d_6$, 300 MHz): 11.34 (s, 1H), 7.21 (d, J=6.9 Hz, 1H), 6.93-6.72 (m, 2H), 6.19 (s, 1H), 2.39 (s, 3H).

Step 4. Synthesis of 7-fluoro-2-methylindoline (50)

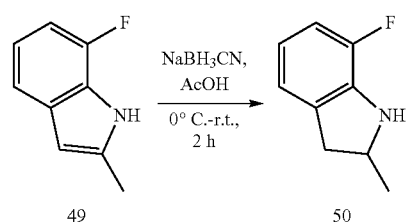

Into a dry 100 mL round bottom flask in ice bath, 7-fluoro-2-methyl-1H-indole 49 (1.8 g, 12.08 mmol), acetic acid (20 mL), sodium cyanoborohydride (2.28 g, 36.19 mmol) were sequentially added. The reaction was warmed to room temperature, and stirred for 2 h. After the reaction was completed as monitored by TLC, the reaction was concentrated under reduced pressure. Ethyl acetate (100 mL) was added to the residue to dissolve it. The solution washed with saturated aqueous sodium bicarbonate solution (80 mL×3), dried over anhydrous sodium sulfate, and filtered. The filtrate was concentrated under reduced pressure. The resulting residue was purified by silica gel column chromatography (ethyl acetate:petroleum ether=1:70) to give 7-fluoro-2-methylindoline 50 (1.4 g, colorless oil). Yield: 77%. LCMS: m/z 152.1 (M+H).

Step 5. Synthesis of 5-bromo-7-fluoro-2-methylindoline (51)

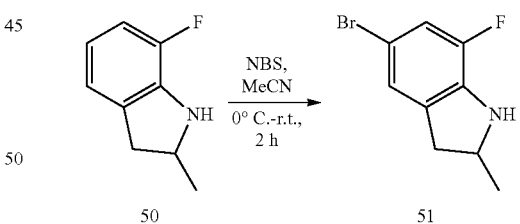

Into a dry 100 mL round bottom flask in ice bath, 7-fluoro-2-methylindoline 50 (1.4 g, 9.27 mmol), acetonitrile (20 mL), N-bromosuccinimide (1.65 g, 9.27 mmol) were sequentially added. The reaction was gradually warmed to room temperature, and stirred for 2 h. After the reaction was completed as monitored by TLC, the reaction was concentrated under reduced pressure. The resulting residue was purified by column chromatography (ethyl acetate:petroleum ether=1:70) to give the product 5-bromo-7-fluoro-2-methylindoline 51 (1.5 g, pale yellow oil). Yield: 71%. LCMS: m/z 229.9/231.9 (M+H).

Step 6. Synthesis of 1-(5-bromo-7-fluoro-2-methylindolin-1-yl)-2-(2-chloropyridin-3-yl)ethan-1-one (52)

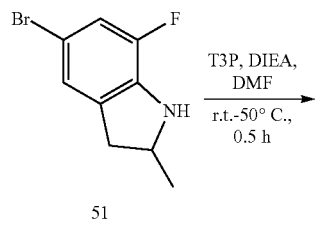

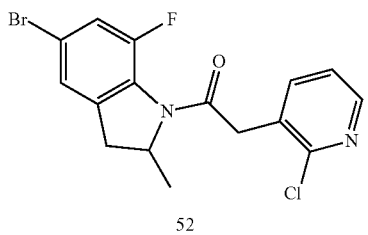

Into a dry 100 mL round bottom flask, 5-bromo-7-fluoro-2-methylindoline 7 (1.0 g, 4.35 mmol), 2-(2-chloropyridin-3-yl)acetic acid (748 mg, 4.35 mmol), N,N-dimethylformamide (10 mL), N,N-diisopropylethylamine (2.24 g, 17.36 mmol) were sequentially added at room temperature, purged with nitrogen gas three times, warmed to 50° C., added with 1-propylphosphonic anhydride (26 mL, 50% solution in ethyl acetate), and stirred for 0.5 h. After the reaction was completed as monitored by TLC, the reaction was concentrated under reduced pressure. The residue was poured into ice-water. The solid precipitated and was filtered. The filter cake was dried to give 1-(5-bromo-7-fluoro-2-methylindolin-1-yl)-2-(2-chloropyridin-3-yl)ethan-1-one 52 (1.5 g, pale brown solid). Yield: 90%. LCMS: m/z 382.8/384.8(M+H).

Step 7. Synthesis of 2-(2-chloropyridin-3-yl)-1-(7-fluoro-2-methyl-5-(4,4,5,5-tetramethyl-1,3,2-dioxaborolan-2-yl)indolin-1-yl)ethan-1-one (53)

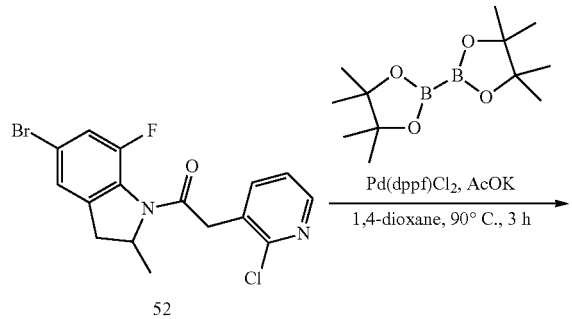

Into a dry 100 mL round bottom flask, 1-(5-bromo-7-fluoro-2-methylindolin-1-yl)-2-(2-chloropyridin-3-yl)ethan-1-one (52) (500 mg, 1.3 mmol), bis(pinacolato)diboron (496 mg, 1.95 mmol), potassium acetate (383 mg, 3.9 mmol) and 1,4-dioxane (20 mL) were sequentially added at room temperature, purged with nitrogen gas once, added with [1,1'-bis(diphenylphosphino)ferrocene]palladium (II) dichloride dichloromethane complex (10.6 mg, 0.013 mol), purged with nitrogen gas three times, heated to 90° C., and stirred for 3 h. After the reaction was completed as monitored by LCMS, the reaction was concentrated under reduced pressure. The resulting residue was purified by column chromatography (ethyl acetate:petroleum ether=1:3) to give 2-(2-chloropyridin-3-yl)-1-(7-fluoro-2-methyl-5-(4,4,5,5-tetramethyl-1,3,2-dioxaborolan-2-yl)indolin-1-yl)ethan-1-one 53 (450 mg, colorless oil). Yield: 80%. LCMS: m/z 430.9 (M+H).

Intermediate 70: Synthesis of 2-(2-chloropyridin-3-yl)-1-(4,7-difluoro-5-(4,4,5,5-tetramethyl-1,3,2-dioxaborolan-2-yl)indolin-1-yl)ethan-1-one (70)

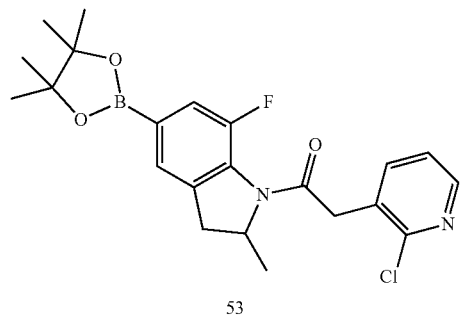

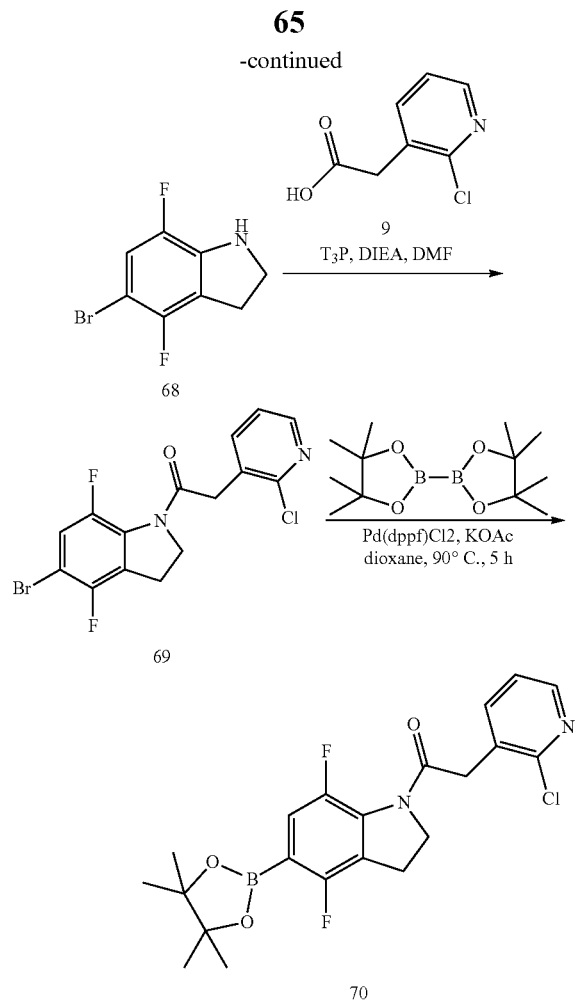

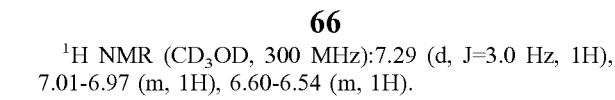

$^1$H NMR (CD$_3$OD, 300 MHz):7.29 (d, J=3.0 Hz, 1H), 7.01-6.97 (m, 1H), 6.60-6.54 (m, 1H).

Step 2. Synthesis of 5-bromo-4,7-difluoro-indoline (68)

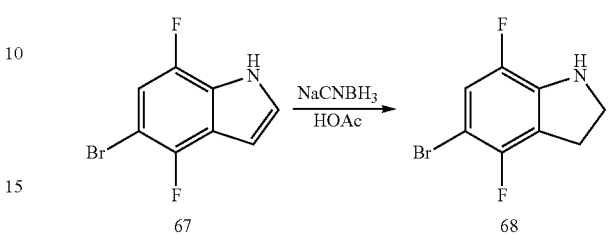

Into a 50 mL round bottom flask in ice-water bath, Compound 67 (1.45 g, 6.28 mmol) and glacial acetic acid (20 mL) were sequentially added, and sodium cyanoborohydride (0.87 g, 12.6 mol) was added in portions over about 30 min. The reaction was stirred at room temperature for 16 h. After the reaction was completed, the reaction was cooled in ice-water bath, was slowly added with saturated aqueous sodium bicarbonate solution to adjust the pH to 6-7, and was extracted with ethyl acetate (10 mL×3). The combined organic phase was dried over anhydrous sodium sulfate, and filtered. The filtrate was concentrated. The resulting residue was purified by silica gel column chromatography with eluent system (ethyl acetate:petroleum ether=1:6) to give 5-bromo-4,7-difluoro-indoline 68 (0.43 g, light yellow oil). Yield: 30.0%. LCMS: m/z 234.0/236.0 (M+H).

Step 3. Synthesis of 1-(5-bromo-4,7-difluoro-indolin-1-yl)-2-(2-chloropyridin-3-yl)ethan-1-one (69)

Step 1. Synthesis of 5-bromo-4,7-difluoro-1H-indole (67)

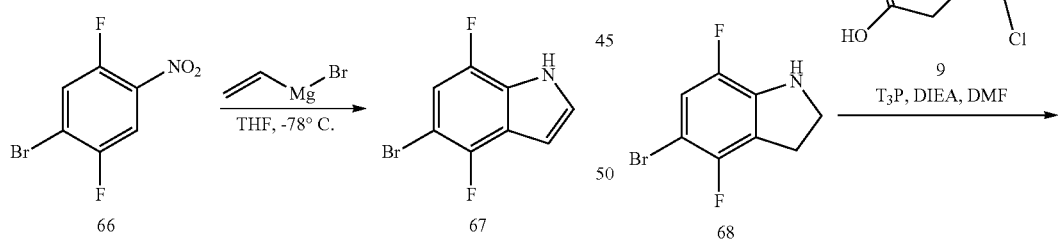

Vinylmagnesium bromide (45.6 mL, 45.6 mmol) was added into tetrahydrofuran (50 mL). The mixture was cooled to −78° C. under nitrogen gas, and was dropwise added with Compound 66 (3.9 g, 15.2 mmol, dissolved in 50 mL tetrahydrofuran). After completion of the addition, the reaction was stirred for 2 h. After the reaction was completed, the reaction was slowly added with saturated aqueous ammonium chloride solution (20 mL), and was extracted with ethyl acetate (20 mL×3). The combined organic phase was concentrated under reduced pressure. The resulting residue was purified by silica gel column chromatography with eluent system (ethyl acetate:petroleum ether=1:8) to give 5-bromo-4,7-difluoro-1H-indole 67 (1.47 g, light yellow oil). Yield: 38.7%.

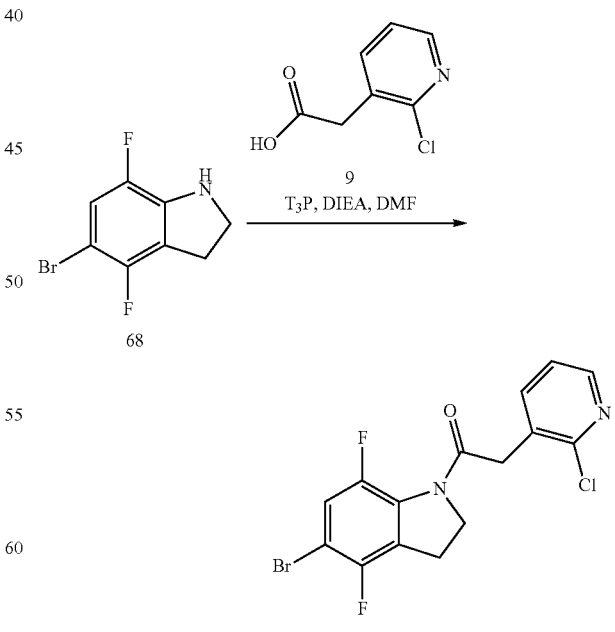

Into a 100 mL flask, Compound 68 (0.43 mg, 0.1.85 mol), ethyl acetate (10 mL), Compound 9 (0.35 g, 2.04 mmol), T₃P (50% solution in ethyl acetate, W/W, 2.83 g, 3.71 mmol), diisopropylethylamine (0.48 g, 3.71 mmol) were sequentially added at room temperature. The reaction was stirred at room temperature for 3 h. After the reaction was completed, the reaction was slowly added with saturated aqueous sodium bicarbonate solution to adjust the pH to 6-7, and was extracted with ethyl acetate (10 mL×4). The combined organic phase was concentrated under reduced pressure. The resulting residue was purified by silica gel column chromatography with eluent system (ethyl acetate petroleum ether=1:3) to give 1-(5-bromo-4,7-difluoro-indolin-1-yl)-2-(2-chloropyridin-3-yl)ethan-1-one 69 (0.56 g, light yellow oil). Yield: 78.2%. LCMS: m/z 386.9/388.9 (M+H).

Step 4. Synthesis of 2-(2-chloropyridin-3-yl)-1-(4,7-difluoro-5-(4,4,5,5-tetramethyl-1,3,2-dioxaborolan-2-yl)indolin-1-yl)ethan-1-one (70)

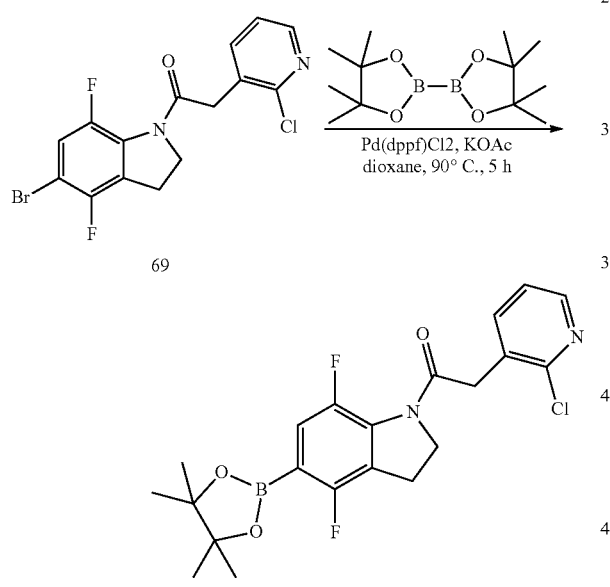

Compound 69 (0.27 g, 0.69 mmol), bis(pinacolato)diboron (0.23 g, 0.89 mol), potassium acetate (0.10 g, 1.02 mmol), (1,1'-bis(diphenyl phosphino)ferrocene)palladium (II) dichloride (0.028 g, 0.89 mmol) were sequentially added into 1,4-dioxane (10 mL) in a dry 100 mL round bottom flask. The reaction was purged with nitrogen gas three times, warmed to 90° C., and stirred for 16 h. After the reaction was completed, the reaction was concentrated under reduced pressure. The resulting residue was purified by silica gel column chromatography with eluent system (ethyl acetate: petroleum ether=1:3) to give the crude product 2-(2-chloropyridin-3-yl)-1-(4,7-difluoro-5-(4,4,5,5-tetramethyl-1,3,2-dioxaborolan-2-yl)indolin-1-yl)ethan-1-one 70 (0.18 g, light yellow solid). LCMS: m/z 434.7/436.8 (M+H).

Intermediate 77: Synthesis of 2-(2-chloropyridin-3-yl)-1-(6,7-difluoro-5-(4,4,5,5-tetramethyl-1,3,2-dioxaborolan-2-yl)indolin-1-yl)ethan-1-one (77)

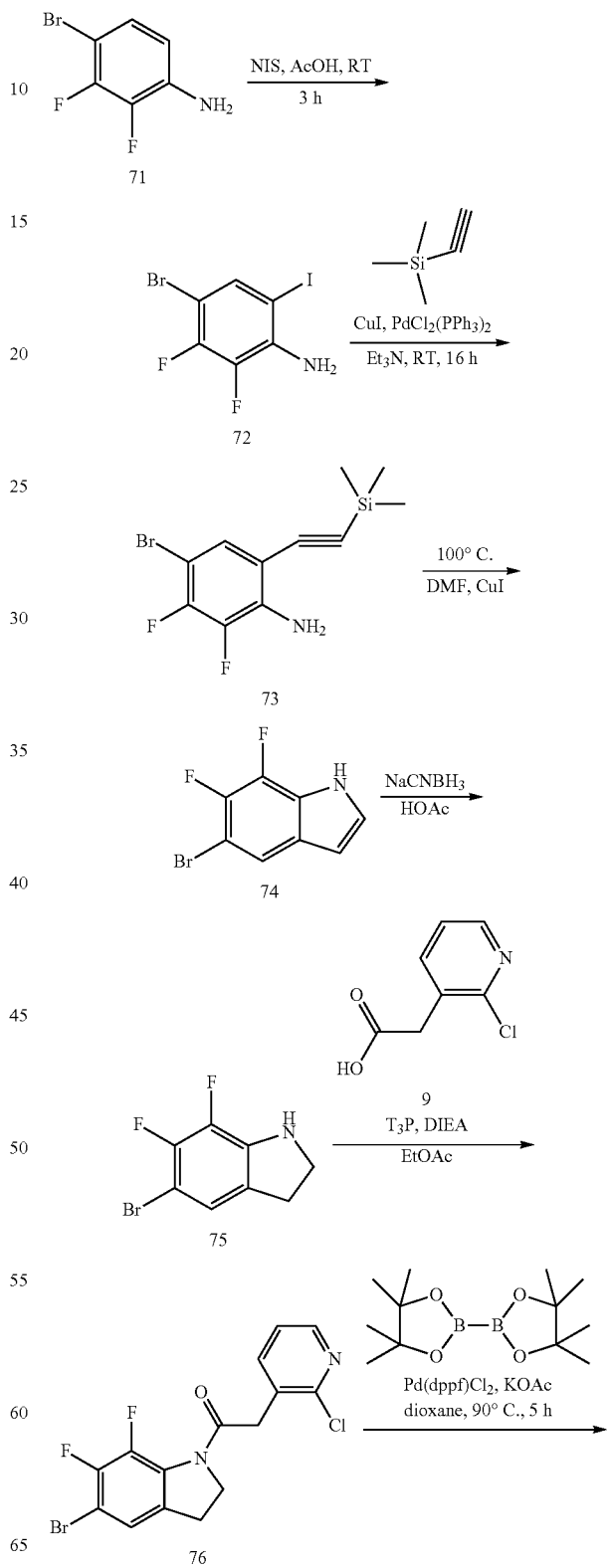

-continued

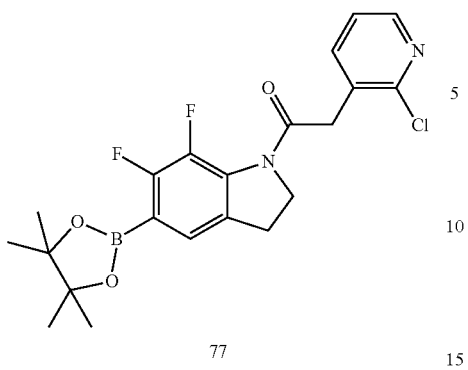

77

Step 1. Synthesis of
4-bromo-2,3-difluoro-6-iodophenylamine (72)

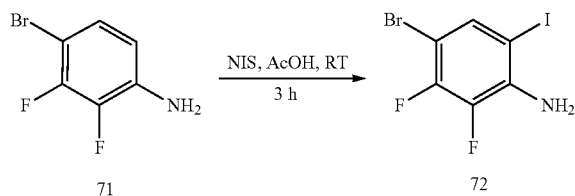 [SMILES: Nc1ccc(Br)c(F)c1F ; Nc1c(I)cc(Br)c(F)c1F]

Into a 100 mL round bottom flask, Compound 71 (0.85 g, 4.1 mmol), glacial acetic acid (15 mL), N-iodosuccinimide (0.97 g, 4.31 mmol) were sequentially added. After completion of the addition, the reaction was stirred at room temperature for 3 h. After the reaction was completed, the reaction was concentrated under reduced pressure. The resulting residue was added with saturated aqueous sodium bicarbonate solution to adjust the pH to 6-7, and extracted with ethyl acetate (20 mL×3). The combined organic phase was concentrated under reduced pressure. The resulting residue was purified by silica gel column chromatography with eluent system (ethyl acetate:petroleum ether=1:10) to give 4-bromo-2,3-difluoro-6-iodophenylamine 72 (1.30 g, light yellow solid). Yield: 95%. LCMS: m/z 333.9/335.8 (M+H).

Step 2. Synthesis of 4-bromo-2,3-difluoro-6-((trimethylsilyl)ethynyl)phenylamine (73)

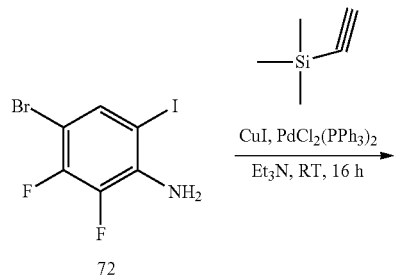

-continued

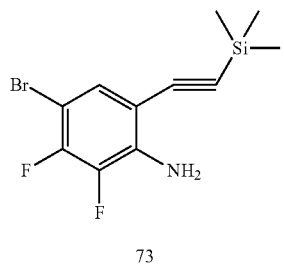

73

Into a 100 mL round bottom flask, Compound 72 (1.30 g, 3.91 mmol), triethylamine (20 mL), cuprous iodide (37.2 mg, 0.20 mol), ethynyltrimethylsilane (460 mg, 4.69 mmol), bis(triphenylphosphine)palladium(II) dichloride (137 mg, 0.20 mmol) were sequentially added. The reaction was stirred at room temperature for 16 h. After the reaction was completed, the reaction was concentrated under reduced pressure. The resulting residue was purified by silica gel column chromatography with eluent system (ethyl acetate:petroleum ether=1:10) to give 4-bromo-2,3-difluoro-6-((trimethylsilyl)ethynyl)phenylamine 73 (1.02 g, pale yellow oil). Yield: 86.2%. $^1$H NMR (DMSO-$d_6$, 400 MHz): δ 7.32 (d, J=7.2, 1H), 5.86 (s, 2H), 0.25 (s, 9H).

Step 3. Synthesis of
5-bromo-6,7-difluoro-1H-indole (74)

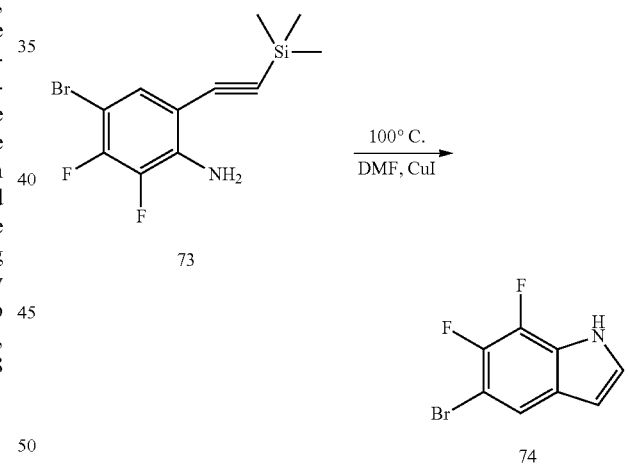

Into a 50 mL eggplant shape flask, Compound 73 (0.85 g, 2.80 mmol), N,N-dimethylformamide (2 mL), cuprous iodide (1.07 g, 5.61 mmol) were added. The reaction was heated to 100° C. under nitrogen gas, and stirred for 4 h. After the reaction was completed, the reaction was cooled to room temperature, added with water (20 mL), and extracted with ethyl acetate (20 mL×3). The combined organic phase was concentrated under reduced pressure. The resulting residue was purified by silica gel column chromatography with eluent system (ethyl acetate:petroleum ether=1:6) to give 5-bromo-6,7-difluoro-1H-indole 74 (560 mg, light yellow oil). Yield: 86%. $^1$H NMR (DMSO-$d_6$, 400 MHz): δ 12.46 (s, 1H), 7.74-7.70 (m, 1H), 7.51 (s, 1H), 3.36 (d, J=5.6 Hz, 1H).

Step 4. Synthesis of 5-bromo-6,7-difluoro-indoline (75)

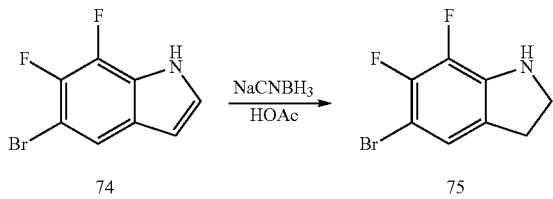

Into a 50 mL round bottom flask in ice-water bath, Compound 74 (0.56 g, 2.42 mmol) and glacial acetic acid (10 mL) were sequentially added, and sodium cyanoborohydride (0.35 g, 4.85 mmol) was added in portions over about 30 min. The reaction was stirred at room temperature for 16 h. After the reaction was completed, the reaction was placed in ice-water bath, slowly added with saturated sodium bicarbonate solution to adjust the pH to 6-7, and then extracted with ethyl acetate (10 mL×3). The combined organic phase was dried over anhydrous sodium sulfate, and filtered. The filtrate was concentrated. The resulting residue was purified by silica gel column chromatography with eluent system (ethyl acetate:petroleum ether=1:6) to give the crude product 5-bromo-6,7-difluoro-indoline 75 (0.23 g) as light yellow oil. LCMS: m/z 233.9/235.9 (M+H); RT=1.470 min (2.5 min).

Step 5. Synthesis of 1-(5-bromo-6,7-difluoro-indolin-1-yl)-2-(2-chloropyridin-3-yl)ethan-1-one (76)

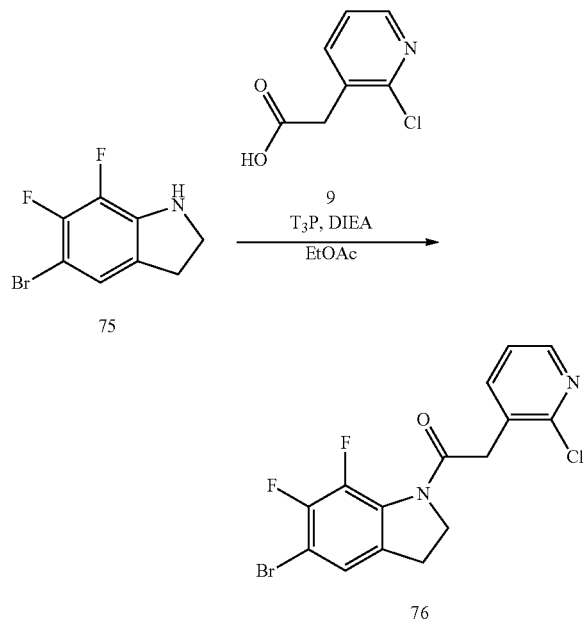

Into a 100 mL flask, Compound 75 (0.23 mg, 0.99 mmol), ethyl acetate (10 mL), Compound 9 (0.20 g, 1.18 mmol), T₃P (50% solution in ethyl acetate, W/W, 1.26 g, 1.98 mmol), diisopropylethylamine (0.38 g, 2.96 mmol) were sequentially added at room temperature. The reaction was stirred at room temperature for 3 h. After the reaction was completed, the reaction was slowly added with saturated aqueous sodium bicarbonate solution to adjust the pH to 6-7, and extracted with ethyl acetate (10 mL×4). The combined organic phase was concentrated under reduced pressure. The resulting residue was purified by silica gel column chromatography with eluent system (ethyl acetate petroleum ether=1:3) to give 1-(5-bromo-6,7-difluoro-indolin-1-yl)-2-(2-chloropyridin-3-yl)ethan-1-one 76 (0.10 g, light yellow oil). Yield: 26.2%. LCMS: m/z 386.9/388.9 (M+H); RT=1.427 min (2.5 min).

Step 6. Synthesis of 2-(2-chloropyridin-3-yl)-1-(6,7-difluoro-5-(4,4,5,5-tetramethyl-1,3,2-dioxaborolan-2-yl)indolin-1-yl)ethan-1-one (77)

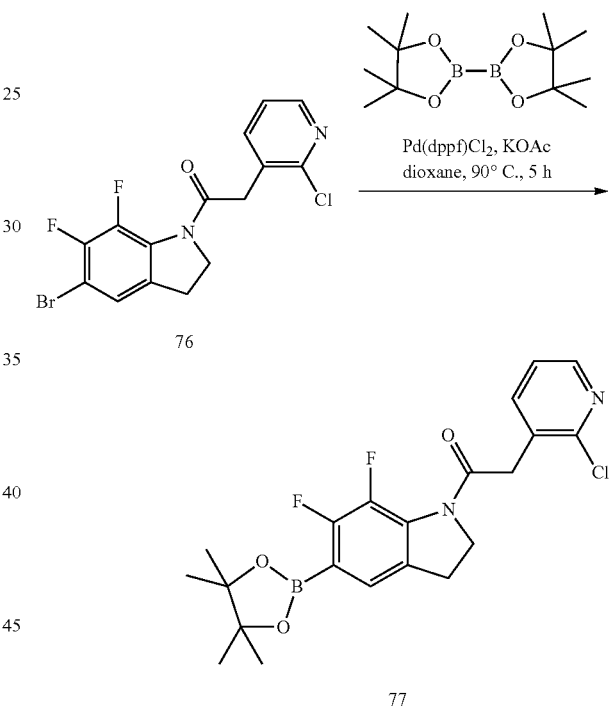

Compound 76 (0.10 g, 0.26 mmol), bis(pinacolato)diboron (0.079 g, 0.31 mmol), potassium acetate (0.038 g, 0.39 mmol), (1,1-bis(diphenylphosphino)ferrocene)palladium (II) dichloride (0.011 g, 0.013 mmol) were sequentially added into 1,4-dioxane (10 ml) in a dry 50 mL round bottom flask. The reaction was purged with nitrogen gas three times, warmed to 90° C., and stirred for 5 h. After the reaction was completed, the reaction was concentrated under reduced pressure. The resulting residue was purified by silica gel column chromatography with eluent system (ethyl acetate: petroleum ether=1:3) to give the crude product 2-(2-chloropyridin-3-yl)-1-(6,7-difluoro-5-(4,4,5,5-tetramethyl-1,3,2-dioxaborolan-2-yl)indolin-1-yl)ethan-1-one 77 (0.065 g, light yellow solid). LCMS: m/z 435.1/437.1 (M+H).

Intermediate 89: Synthesis of 2-(2-chloropyridin-3-yl)-1-(7-fluoro-3-methyl-5-(4,4,5,5-tetramethyl-1,3,2-dioxaborolan-2-yl)indolin-1-yl)ethan-1-one (89)

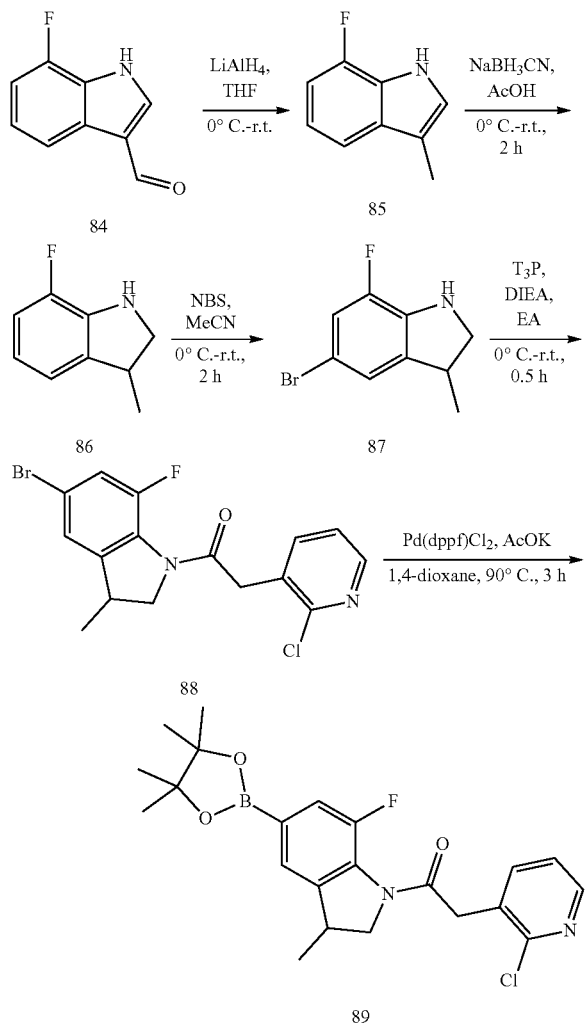

Step 1. Synthesis of 7-fluoro-3-methyl-1H-indole (85)

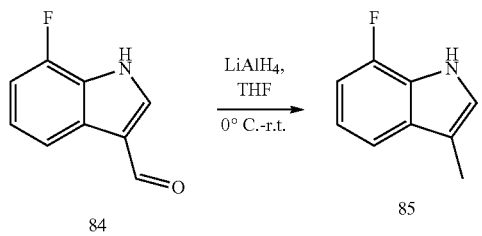

Compound 84 (200.0 mg, 1.23 mmol) was added into tetrahydrofuran (15 mL). The mixture was purged with nitrogen gas three times, cooled to 0° C., and added with lithium aluminum hydride (140.0 mg, 3.69 mmol). After completion of the addition, the reaction was naturally warmed to room temperature, and stirred for 2 h. After the reaction was completed, the reaction was dropwise added with water (20 mL), and extracted with ethyl acetate (20 mL×3). The combined organic phase was concentrated under reduced pressure. The resulting residue was purified by silica gel column chromatography with eluent system (ethyl acetate:petroleum ether=1:8) to give 7-fluoro-3-methyl-1H-indole 85 (130.0 mg, light yellow oil). Yield: 71.0%.

$^1$H NMR (DMSO-$d_6$, 400 MHz): δ11.21 (s, 1H), 7.29 (d, J=7.6 Hz, 1H), 7.17 (s, 1H), 6.97-6.87 (m, 2H).

Step 2. Synthesis of 7-fluoro-3-methyl-indoline (86)

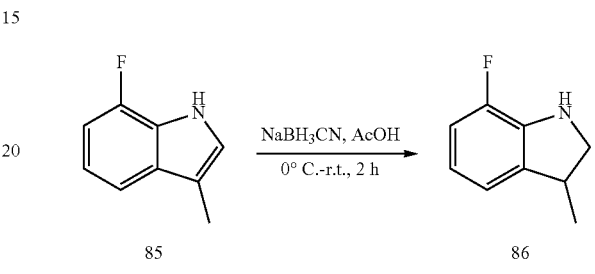

Into a 50 mL round bottom flask in ice-water bath, Compound 85 (819.0 mg, 5.49 mmol) and glacial acetic acid (20 mL) were sequentially added, and added in portions with sodium cyanoborohydride (691.0 mg, 10.99 mol) over about 30 min. The reaction was warmed to room temperature, and stirred for 16 h. After the reaction was completed, the reaction was cooled in ice-water bath, slowly added with saturated sodium bicarbonate solution to adjust the pH to 6-7, and extracted with ethyl acetate (10 mL×3). The combined organic phase was dried over anhydrous sodium sulfate, and filtered. The filtrate was concentrated. The resulting residue was purified by silica gel column chromatography with eluent system (ethyl acetate:petroleum ether=1:6) to give 7-fluoro-3-methyl-indoline 86 (49.0 mg, light yellow oil). LCMS: m/z 152.0 (M+H).

Step 3. Synthesis of 5-bromo-7-fluoro-3-methyl-indoline (87)

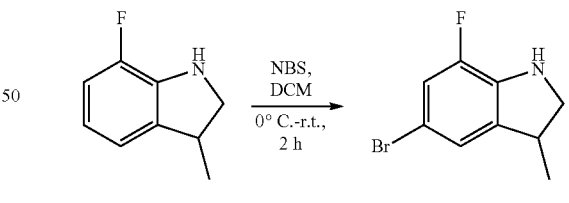

Into a 50 mL flask in ice-water bath, Compound 86 (49.0 mg, 0.324 mmol) and dichloromethane (5 mL) were added, and N-bromosuccinimide (63 mg, 0.356 mmol) was added in portions. The reaction was stirred at room temperature for 4 h. After the reaction was completed, the reaction was concentrated at room temperature under reduced pressure, slowly added with saturated aqueous sodium bicarbonate solution to adjust the pH to 6-7, and extracted with ethyl acetate (10 mL×4). The combined organic phase was concentrated under reduced pressure. The resulting residue was purified by silica gel column chromatography with eluent system (ethyl acetate:petroleum ether=1:5) to give 5-bromo-7-fluoro-3-methyl-indoline 87 (61.0 mg, light yellow solid). Yield: 82.0%. LCMS: m/z 229.8/231.8 (M+H).

Step 4. Synthesis of 1-(5-bromo-7-fluoro-3-methyl-indolin-1-yl)-2-(2-chloropyridin-3-yl)ethan-1-one (88)

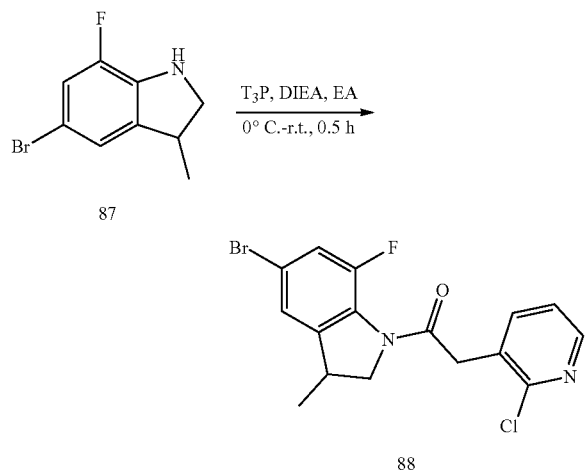

Into a 50 mL flask, Compound 87 (61.0 mg, 0.266 mol), ethyl acetate (5 mL), T₃P (50% solution in ethyl acetate, WAY, 406.0 mg, 0.53 mmol), diisopropylethylamine (103.0 mg, 0.80 mmol) were sequentially added at room temperature. The reaction was stirred for 3 h. After the reaction was completed, the reaction was slowly added with saturated aqueous sodium bicarbonate solution to adjust the pH to 6-7, and was extracted with ethyl acetate (10 mL×4). The solvents were removed from the combined organic phase under reduced pressure. The resulting residue was purified by silica gel column chromatography with eluent system (ethyl acetate:petroleum ether=1:3) to give 1-(5-bromo-7-fluoro-3-methyl-indolin-1-yl)-2-(2-chloropyridin-3-yl)ethan-1-one 88 (79.0 mg, light yellow oil). Yield: 78.0%. LCMS: m/z 382.5/384.6 (M+H).

Step 5. Synthesis of 2-(2-chloropyridin-3-yl)-1-(7-fluoro-3-methyl-5-(4,4,5,5-tetramethyl-1,3,2-dioxaborolan-2-yl)indolin-1-yl)ethan-1-one (89)

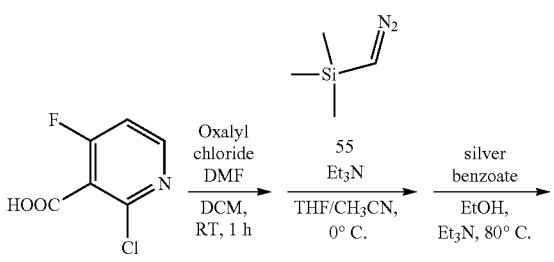

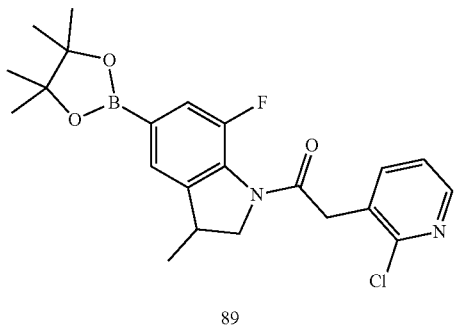

Compound 88 (45.0 mg, 0.12 mmol), bis(pinacolato)diboron (36.0 mg, 0.14 mmol), potassium acetate (17.3 mg, 0.18 mmol), (1,1-bis(diphenylphosphine)ferrocene)palladium (II) dichloride (4.8 mg, 0.0058 mmol) were sequentially added into 1,4-dioxane (10 ml) in a dry 50 mL round bottom flask. The reaction was purged with nitrogen gas three times, warmed to 90° C., and stirred for 3 h. After the reaction was completed, the reaction was concentrated under reduced pressure. The resulting residue was purified by silica gel column chromatography with eluent system (ethyl acetate petroleum ether=1:3) to give 2-(2-chloropyridin-3-yl)-1-(7-fluoro-3-methyl-5-(4,4,5,5-tetramethyl-1,3,2-dioxaborolan-2-yl)indolin-1-yl)ethan-1-one 89 (36.0 mg, pale brown solid). Yield: 76.0%. LCMS: m/z 430.8/432.8 (M+H).

Intermediate 57: Synthesis of 2-(2-chloro-4-fluoropyridin-3-yl)acetic acid (57)

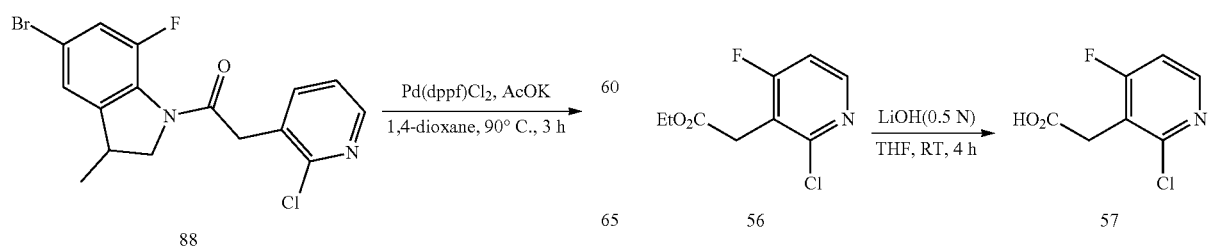

Step 1. Synthesis of ethyl 2-(2-chloro-4-fluoropyridin-3-yl)acetate (56)

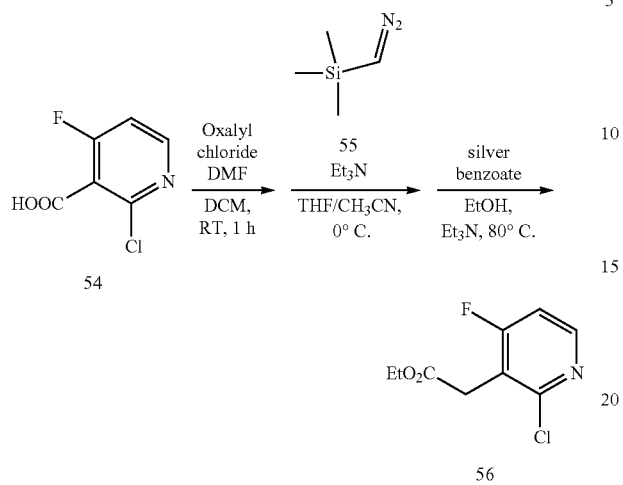

Into a 50 mL round bottom flask, Compound 54 (1.0 g, 5.71 mmol), dichloromethane (25 mL), N,N-dimethylformamide (1 mL) were sequentially added at room temperature, and then the solution of oxalyl chloride (0.90 g, 7.14 mmol) in dichloromethane (10 mL) was added dropwise. After completion of the addition, the reaction was stirred at room temperature for 1 h, and was concentrated under reduced pressure. 15 mL anhydrous tetrahydrofuran was added into the residue. The mixture was added dropwise into the solution of Compound 55 (2M solution in n-hexane, 5.2 mL, 10.3 mmol) and triethylamine (1.04 g, 10.3 mmol) in acetonitrile and tetrahydrofuran (20 mL:20 mL) in ice-water bath. Next, the reaction was stirred at 0° C. for 1 h, then placed into freezing compartment of refrigerator for 16 h, diluted by addition of ethyl acetate (100 mL), and washed with water. The organic phase was adjusted with 0.5 mmol/L hydrochloric acid to pH 4-5, stirred at room temperature for 5 min, then adjusted with 1 mol/L aqueous sodium hydroxide solution to pH 8-9, washed with saturated brine, dried over anhydrous sodium sulfate, and filtered. The filtrate was concentrated under reduced pressure. The resulting residue was dissolved in 20 mL ethanol, added with triethylamine (692 mg, 6.85 mmol), added in portions with silver benzoate (197 mg, 0.86 mmol) at room temperature, stirred for 10 min, heated to 80° C., stirred for 10 min, and cooled to room temperature. After suction filtration, the filtrate was concentrated. The resulting residue was purified by column chromatography with eluent system (ethyl acetate:petroleum ether=1:7) to give ethyl 2-(2-chloro-4-fluoropyridin-3-yl)acetate 56 (250 mg, colorless oil). Yield: 20.0%. LCMS: m/z 217.8/219.8 (M+H).

Step 2. Synthesis of 2-(2-chloro-4-fluoro-pyridin-3-yl)acetic acid (57)

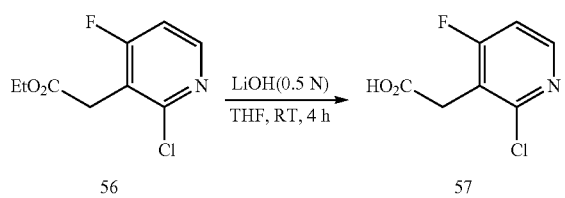 [SMILES: CCOC(=O)Cc1c(F)ccnc1Cl ; O=C(O)Cc1c(F)ccnc1Cl]

At room temperature, Compound 56 (250 mg, 1.15 mmol) was dissolved in tetrahydrofuran (10 mL), and added with aqueous lithium hydroxide solution (10 mL, 0.5 mol/L). The reaction was stirred at room temperature for 1 h. After the reaction was completed as detected by LCMS, ethyl acetate (10 mL) was added. The aqueous phase was adjusted with 0.5 mol/L diluted hydrochloric acid to pH 3-4. After suction filtration, the filter cake washed with water, and dried to give 2-(2-chloro-4-fluoro-pyridin-3-yl)acetic acid 57 (220 mg, crude, light yellow oil). LCMS: m/z 189.9/191.9 (M+H).

Intermediates 65 and 83 were obtained analogously to the preparation of Intermediate 57 from the corresponding starting materials listed in the table below:

| Intermediate No. | Starting material | Structure of the Intermediate | Analytical data |
|---|---|---|---|
| 65 | ![](hooc-2-methylpyridine-3-carboxylic acid) | acetic acid) | LCMS: m/z 152.1 (M + H) |
| 83 | ![](4-chloropyridine-3-carboxylic acid) | acetic acid) | LCMS: m/z 171.9 (M + H) |

Intermediate 82: Synthesis of 3-(2-chloropyridin-3-yl)propionic acid (82)

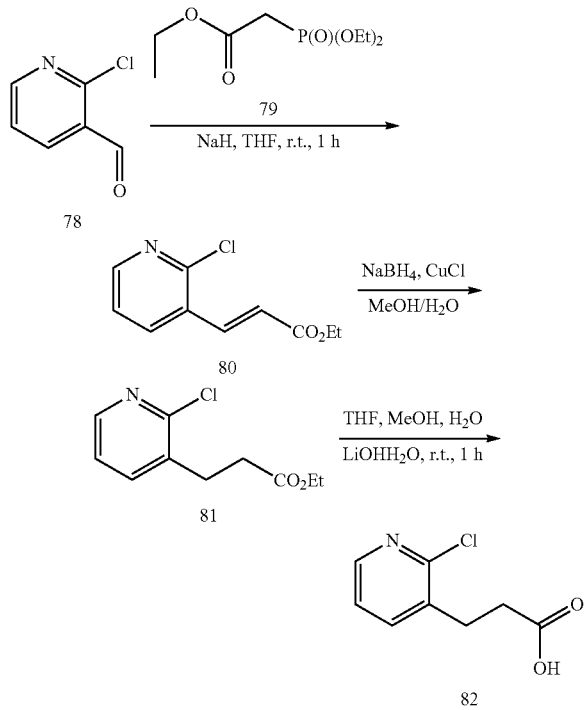

Step 1. Synthesis of ethyl (E)-3-(2-chloropyridin-3-yl)acrylate (80)

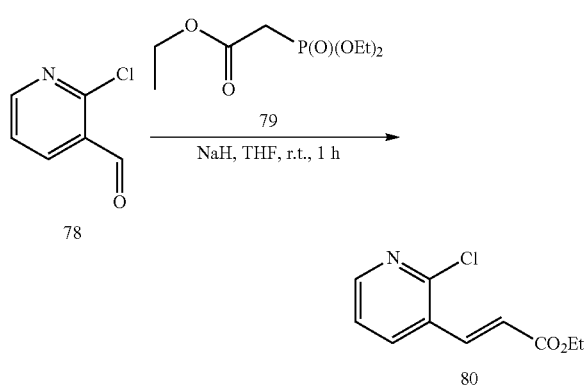

Into a dry 100 mL round bottom flask in ice bath, Compound 79 (634 mg, 4.46 mmol), tetrahydrofuran (50 mL), sodium hydride (357 mg, 8.93 mmol) were added. The reaction was stirred in ice bath for 0.5 h, added with Compound 78 (1000 mg, 4.46 mmol), gradually warmed to room temperature, and stirred for 1 h. The reaction was carried out under monitoring by LCMS, quenched with saturated aqueous ammonium chloride solution, and extracted with ethyl acetate (50 mL×3). The organic phase was dried and concentrated. The resulting readiue was purified by silica gel column chromatography (petroleum ether:ethyl acetate=5:1) to give ethyl (E)-3-(2-chloropyridin-3-yl)acrylate 80 (300 mg, white solid). Yield: 20%. LCMS: m/z 212.0(M+H).

Step 2. Synthesis of ethyl 3-(2-chloropyridin-3-yl)propionate (81)

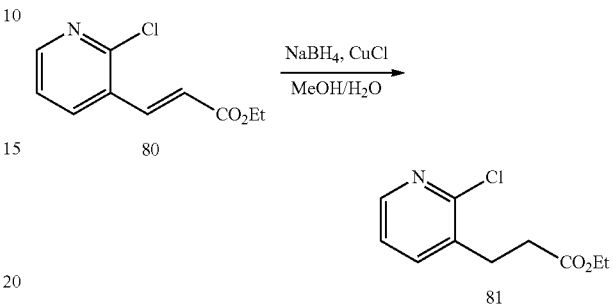

Into a dry 100 mL round bottom flask, Compound 80 (300 mg, 1.4 mmol), methanol (12 mL), water (3 mL), cuprous chloride (140 mg, 1.4 mmol), sodium borohydride (54 mg, 1.4 mmol) were added at room temperature. After the reaction was stirred at 0° C. for 1 h, additional sodium borohydride (54 mg, 1.4 mmol) was added. The reaction was gradually warmed to room temperature and stirred for 1 h, The reaction was completed as monitored by LCMS. The reaction was quenched with ice-water, and extracted with ethyl acetate (50 mL×3). The organic phase was dried and concentrated. The resulting residue was purified by silica gel column chromatography (petroleum ether:ethyl acetate=5:1) to give ethyl 3-(2-chloropyridin-3-yl)propionate 81 (260 mg, white solid). Yield: 86%. LCMS: m/z 214.0(M+H).

Step 3. Synthesis of 3-(2-chloropyridin-3-yl)propionic Acid (82)

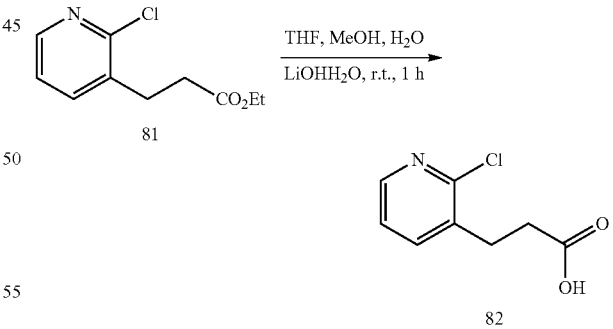

Into a dry 100 mL round bottom flask, Compound 81 (260 mg, 1.21 mmol), lithium hydroxide monohydrate (153 mg, 3.64 mmol), tetrahydrofuran (20 mL), methanol (4 mL), water (4 mL) were added at room temperature. The reaction was stirred for 2 h. After the reaction was completed as monitored by TLC, the reaction was concentrated and lyophilized to give 3-(2-chloropyridin-3-yl)propionic acid 82 (300 mg, white solid), which was used directly in the next step without purification. LCMS: m/z 185.9(M+H).

EXAMPLE

Example P1

Synthesis of Compound 2-(2-chloropyridin-3-yl)-1-(7-fluoro-5-(2-((1-hydroxylprop-2-yl)amino)pyrimidin-4-yl)indolin-1-yl)ethan-1-one (P1)

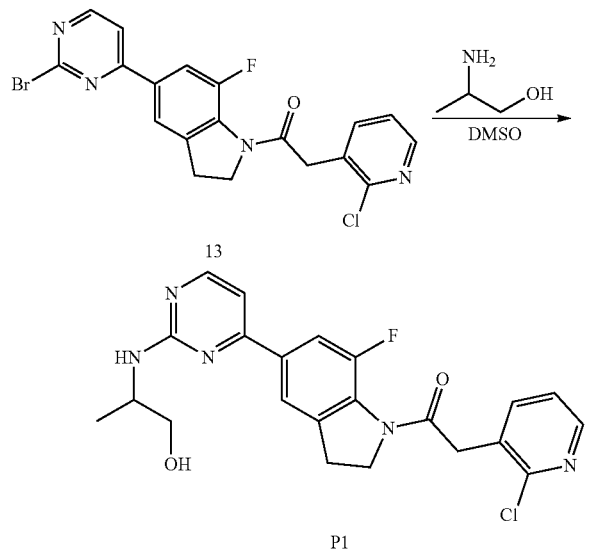

Into a dry 100 mL round bottom flask, Intermediate 13 (100 mg, 0.22 mmol), DL-aminopropanol (84 mg, 1.10 mmol) and DMSO (0.5 mL) were added at room temperature. The reaction was warmed to 90° C. and stirred for 1 h. After the reaction was completed, the reaction was concentrated under reduced pressure, added with 100 mL water, and extracted with ethyl acetate (150 mL×3). The combined organic phase was dried over anhydrous sodium sulfate, and filtered. The filtrate was concentrated under reduced pressure. The resulting residue was purified by silica gel column chromatography with eluent system (ethyl acetate) to give the product P1 (10 mg, white solid). Yield: 10.0%. LCMS: m/z 441.9 (M+H). $^1$H-NMR (DMSO-d6, 400 MHz): δ 8.334 (s, 1H), 8.333 (d, J=10.4 Hz, 1H), 7.91 (s, 1H), 7.76 (m, 3H), 7.84 (m, 1H), 7.83 (d, J=10.4 Hz, 1H), 7.43 (dd, J=7.6 Hz, 5.2 Hz, 1H), 7.14 (d, J=5.2 Hz, 1H), 6.85 (d, J=8.0 Hz, 1H), 4.71 (t, J=5.6 Hz, 1H), 4.29 (t, J=8.0 Hz, 2H), 4.08 (s, 2H), 3.50 (m, 1H), 3.31 (m, 2H), 3.23 (t, J=8.4 Hz, 2H), 1.16 (d, J=6.4 Hz, 2H).

Examples P2-P7 were obtained analogously to the preparation of Example P1 in accordance with the general scheme A as shown in FIG. 1 from Intermediate 13 and the corresponding amines

| Ex. | Structure | Name | Analytical data |
|---|---|---|---|
| P2 | 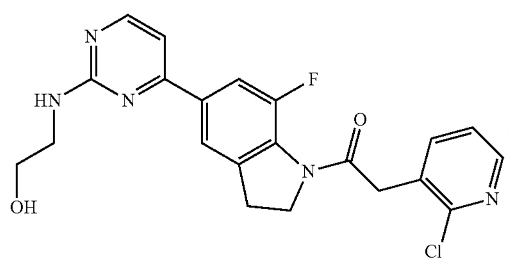 [SMILES: O=C(Cc1cccnc1Cl)N1CCc2cc(-c3ccnc(NCCO)n3)cc(F)c21] | 2-(2-chloropyridin-3-yl)-1-(7-fluoro-5-(2-((2-hydroxylethyl)amino)pyrimidin-4-yl)indolin-1-yl)ethan-1-one | $^1$H-NMR (DMSO-d6, 400 MHz): δ 8.34 (d, J = 2.8 Hz, 2H), 7.98-7.75 (m, 3H), 7.43 (dd, J = 7.4, 4.8 Hz, 1H), 7.16 (d, J = 5.2 Hz, 1H), 7.07 (t, J = 5.6 Hz, 1H), 4.70 (s, 0H), 4.29 (t, J = 7.9 Hz, 2H), 4.08 (s, 2H), 3.55 (s, 2H), 3.42 (s, 1H), 3.23 (t, J = 7.9 Hz, 2H). LCMS: m/z 427.9 (M + H). |
| P3 | 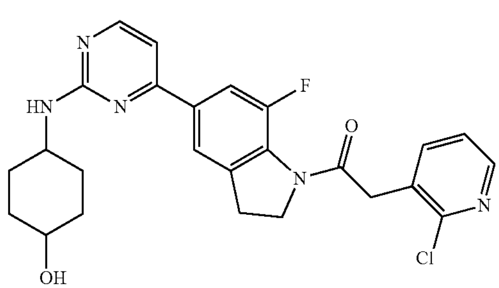 [SMILES: O=C(Cc1cccnc1Cl)N1CCc2cc(-c3ccnc(NC4CCC(O)CC4)n3)cc(F)c21] | 2-(2-chloropyridin-3-yl)-1-(7-fluoro-5-(2-((4-hydroxylcyclohexyl)amino)pyrimidin-4-yl)indolin-1-yl)ethan-1-one | $^1$H-NMR (DMSO-d6, 400 MHz): δ 8.36-8.31 (m, 2H), 7.92-7.87 (m, 2H), 7.81 (d, J = 12.3 Hz, 1H), 7.43 (dd, J = 7.5, 4.8 Hz, 1H), 7.12 (d, J = 5.2 Hz, 1H), 7.05 (d, J = 8.0 Hz, 1H), 4.56 (s, 1H), 4.29 (t, J = 7.9 Hz, 2H), 4.08 (s, 2H), 3.73 (s, 1H), 3.41 (s, 1H), 3.23 (t, J = 7.9 Hz, 2H), 1.95-1.81 (m, 4H), 1.35-1.20 (m, 4H). LCMS: m/z 481.6. |

-continued

| Ex. | Structure | Name | Analytical data |
|---|---|---|---|
| P4 | 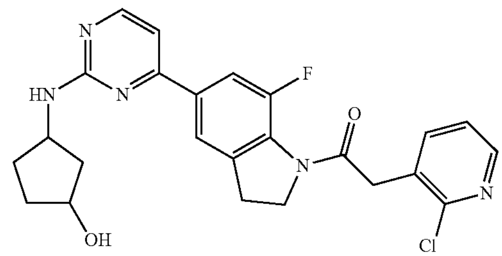 [SMILES: O=C(Cc1cccnc1Cl)N1CCc2cc(-c3ccnc(NC4CCC(O)C4)n3)cc(F)c21] | 2-(2-chloropyridin-3-yl)-1-(7-fluoro-5-(2-((3-hydroxylcyclopentyl)amino)pyrimidin-4-yl)indolin-1-yl)ethan-1-one | $^1$H-NMR (DMSO-$d_6$, 400 MHz): δ 8.34 (d, J = 4.7 Hz, 2H), 7.93-7.79 (m, 3H), 7.43 (dd, J = 7.4, 4.7 Hz, 1H), 7.14 (t, J = 5.3 Hz, 3H), 4.44 (s, 1H), 4.28 (t, J = 7.8 Hz, 2H), 4.22 (s, 1H), 4.13 (s, 1H), 4.07 (s, 2H), 3.58 (s, 0H), 3.25-3.20 (m, 1H), 1.91 (s, 2H), 1.68 (s, 4H), 1.48 (d, J = 6.0 Hz, 2H). LCMS: m/z 467.9 (M + H). |
| P5 | 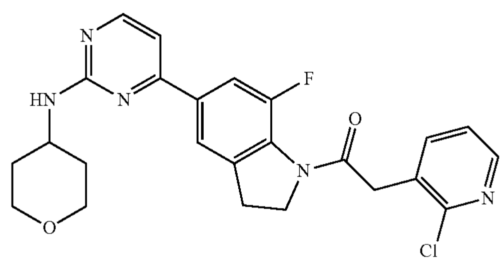 [SMILES: O=C(Cc1cccnc1Cl)N1CCc2cc(-c3ccnc(NC4CCOCC4)n3)cc(F)c21] | 2-(2-chloropyridin-3-yl)-1-(7-fluoro-5-(2-((tetrahydro-2H-pyran-4-yl)amino)pyrimidin-4-yl)indolin-1-yl)ethan-1-one | $^1$H-NMR (CDCl$_3$, 400 MHz): δ 8.33 (br, 2H), 7.77-7.68 (m, 3H), 7.24 (s, 1H), 6.94 (d, J = 4.76 Hz, 1H), 4.33 (t, J = 7.8 Hz, 2H), 4.15 (br, 1H), 4.07-3.95 (m, 4H), 3.61 (t, J = 11.0 Hz, 2H), 3.20 (t, J = 7.8 Hz, 2H), 2.13-2.04 (m, 2H), 1.67-1.57 (m, 2H). LCMS: m/z 454.0 (M + H). |
| P6 | 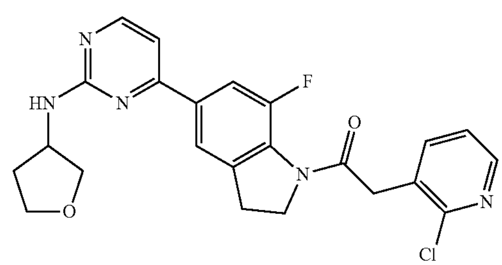 [SMILES: O=C(Cc1cccnc1Cl)N1CCc2cc(-c3ccnc(NC4CCOC4)n3)cc(F)c21] | 2-(2-chloropyridin-3-yl)-1-(7-fluoro-5-(2-((tetrahydrofuran-3-yl)amino)pyrimidin-4-yl)indolin-1-yl)ethan-1-one | $^1$H-NMR (CDCl$_3$, 400 MHz): δ 8.33 (br, 2H), 7.79-7.68 (m, 3H), 7.24 (s, 1H), 6.97 (d, J = 4.68 Hz, 1H), 4.69 (br, 1H), 4.34 (t, J = 7.72 Hz, 2H), 4.08-4.02 (m, 2H), 3.99 (s, 2H), 3.94-3.86 (m, 1H), 3.79 (dd, J = 3.0 Hz, 9.1 Hz, 1H), 3.20 (t, J = 7.70 Hz, 2H), 2.43-2.32 (m, 1H), 2.00-1.91 (m, 1H). LCMS: m/z 454.0 (M + H). |
| P7 | 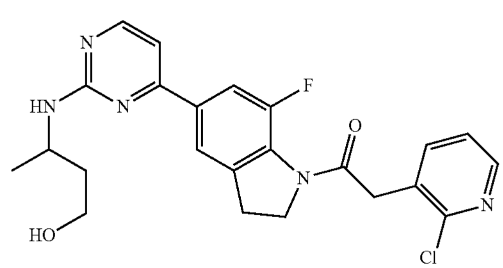 [SMILES: CC(CCO)Nc1nccc(-c2cc(F)c3c(c2)CCN3C(=O)Cc2cccnc2Cl)n1] | 2-(2-chloropyridin-3-yl)-1-(7-fluoro-5-(2-((4-hydroxylbutan-2-yl)amino)pyrimidin-4-yl)indolin-1-yl)ethan-1-one | $^1$H-NMR (DMSO-$d_6$, 400 MHz): δ 8.36-8.30 (m, 2H), 7.93-7.86 (m, 2H), 7.84 (d, J = 12.7 Hz, 1H), 7.45 (dd, J = 7.5, 4.8 Hz, 1H), 7.12 (d, J = 5.1 Hz, 1H), 7.02 (d, J = 8.1 Hz, 1H), 4.42 (br, 1H), 4.30 (t, J = 7.92 Hz, 2H), 4.16 (br, 1H), 4.07 (s, 2H), 3.53-3.49 (m, 2H), 3.24 (t, J = 7.84 Hz, 2H), 1.79-1.68 (m, 1H), 1.68-1.57 (m, 1H), 1.17 (d, J = 6.3 Hz, 3H). LCMS: m/z 456.0 (M + H). |

Example P8

Synthesis of 2-(2-chloropyridin-3-yl)-1-(7-fluoro-5-(2-((1-hydroxylprop-2-yl)amino)pyridin-4-yl)indolin-1-yl)ethan-1-one (P8)

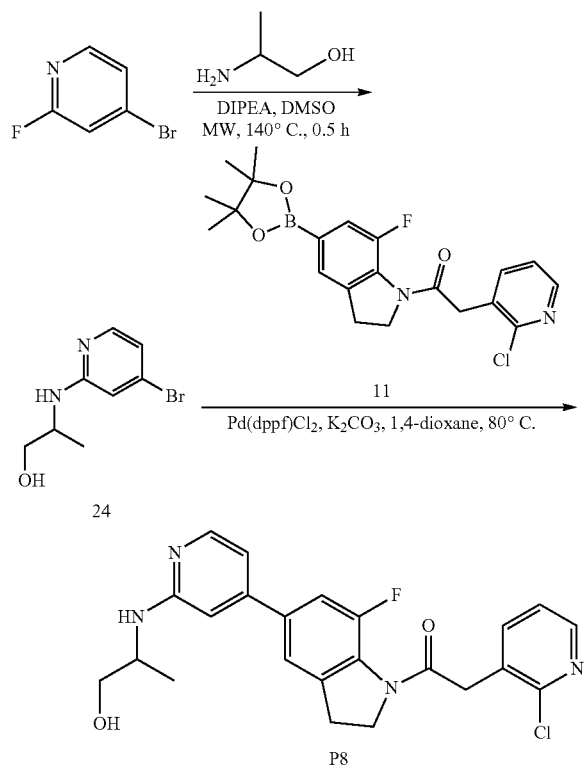

Step 1. Synthesis of 2-((4-bromopyridin-2-yl)amino)propan-1-ol (24)

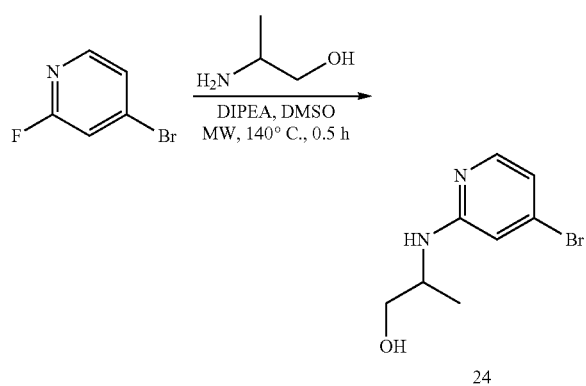

Into a dry 20 mL microwave vial, dimethyl sulfoxide (8 mL), Compound 4-bromo-2-fluoropyridine (1 g, 0.0057 mol), Compound 2-aminopropanol (0.65 g, 0.0085 mol) and N,N-diisopropylethylamine (1.1 g, 0.0085 mol) were added. The reaction was warmed to 140° C., and stirred for 0.5 h. After the reaction was completed as monited by LCMS, the reaction was poured into water (10 mL), and extracted with ethyl acetate (10 mL×3). The combined organic phase washed with saturated brine (10 mL×3), dried over anhydrous sodium sulfate, and filtered. The filtrate was concentrated under reduced pressure. The residue was purified by flash chromatography with eluent system (ethyl acetate: petroleum ether=1:1) to give Compound 24 2-((4-bromopyridin-2-yl)amino)propan-1-ol (0.8 g, yellow solid). Yield: 61%. LCMS: 230.8/232.8 (M+H).

Step 2. Synthesis of 2-(2-chloropyridin-3-yl)-1-(7-fluoro-5-(2-((1-hydroxylprop-2-yl)amino)pyridin-4-yl)indolin-1-yl)ethan-1-one (P8)

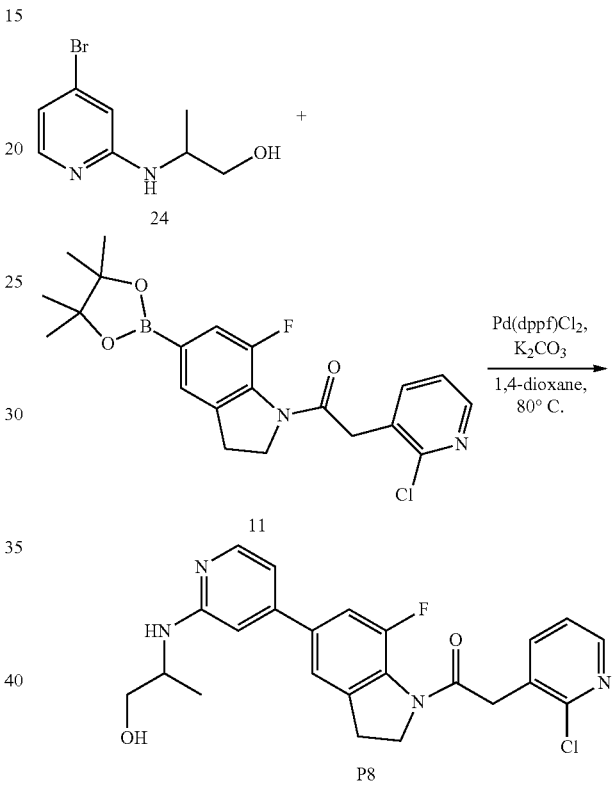

Into a dry 100 mL round bottom flask, Intermediate 24 (0.05 g, 0.00021 mol), K$_2$CO$_3$ (0.058 g, 0.00042 mol), Intermediate 11 (0.108 g, 0.00026 mol), Pd(dppf)Cl$_2$ (15 mg, 0.000021 mol), 1,4-dioxane (20 mL) and distilled water (2 mL) were added at room temperature. The mixture was purged with nitrogen gas three times, warmed to 80° C. and stirred for 5 h under nitrogen gas. After the reaction was completed, the reaction was concentrated under reduced pressure. The crude product was purified by thin-layer chromatography (ethyl acetate) to give Compound P8 (0.04 g, white solid). Yield: 43%. LCMS: m/z 440.7 (M+H).

$^1$H-NMR (DMSO-d$_6$, 400 MHz): δ 8.34 (d, J=3.6 Hz, 1H), 7.98 (d, J=5.8 Hz, 1H), 7.89 (d, J=6.8 Hz, 1H), 7.51 (s, 1H), 7.45-7.40 (m, 2H), 6.96 (br s, 1H), 6.88 (br s, 1H), 4.91 (br s, 1H), 4.28 (t, J=7.8 Hz, 2H), 4.08 (s, 2H), 4.05-3.96 (m, 1H), 3.52-3.44 (m, 1H), 3.37 (s, 1H), 3.22 (t, J=7.8 Hz, 2H), 1.15 (d, J=6.5 Hz, 3H).

Figure 2:
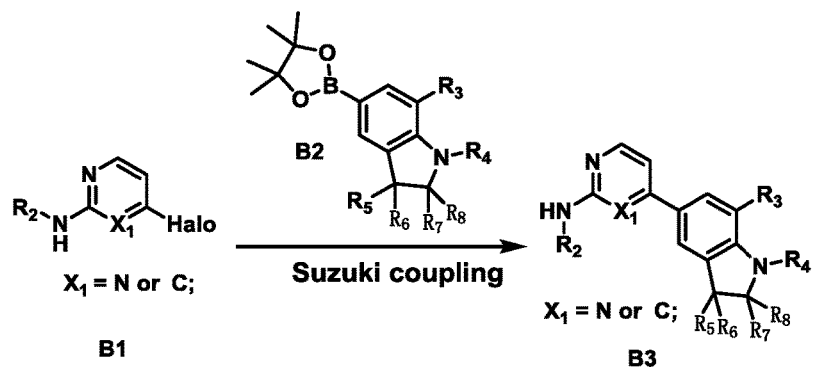
FIG. 2 shows the general synthetic scheme B for the synthesis of the compounds of the invention, wherein individual variables are as defined herein.

Examples P10-P16, P32, P34, P36, P44, P47-51, P53 and P58-59 were obtained analogously to the preparation of Example P8 in accordance with the general scheme B as shown in FIG. 2 from Intermediate 11, 53 or a borate intermediate analogous to Intermediate 11.

| Ex. | Structure | Name | Analytical data |
|---|---|---|---|
| P10 | 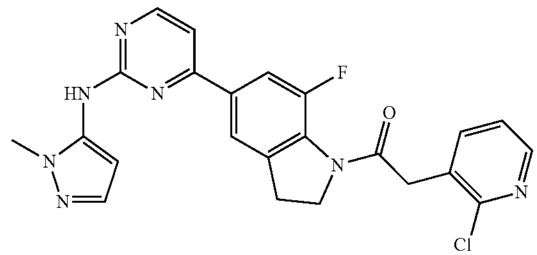 | 2-(2-chloropyridin-3-yl)-1-(7-fluoro-5-(2-((1-methyl-1H-pyrazol-5-yl)amino)pyrimidin-4-yl)indolin-1-yl)ethan-1-one | ¹H-NMR (400 MHz, DMSO-d6) δ 9.43 (s, 1H), 8.47 (d, J = 5.2 Hz, 1H), 8.31 (dd, J = 4.8, 1.8 Hz, 1H), 7.89 (s, 1H), 7.87-7.71 (m, 2H), 7.46-7.36 (m, 2H), 7.34 (d, J = 1.8 Hz, 1H), 6.24 (d, J = 1.7 Hz, 1H), 4.26 (t, J = 7.9 Hz, 2H), 4.04 (s, 2H), 3.66 (s, 3H), 3.20 (t, J = 7.8 Hz, 2H). LCMS: m/z 464.1 (M + H). |
| P11 | 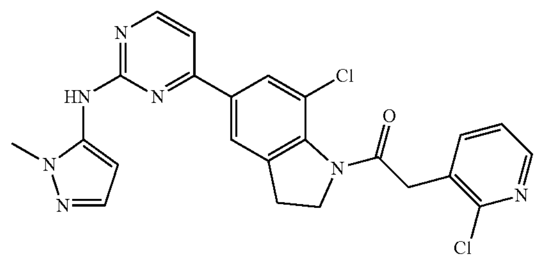 | 1-(7-chloro-5-(2-((1-methyl-1H-pyrazol-5-yl)amino)pyrimidin-4-yl)indolin-1-yl)-2-(2-chloropyridin-3-yl)ethan-1-one | ¹H-NMR (400 MHz, DMSO-d₆) δ 9.44 (s, 1H), 8.47 (d, J = 5.2 Hz, 1H), 8.31 (dd, J = 4.6, 1.5 Hz, 1H), 8.00 (d, J = 2.3 Hz, 2H), 7.88-7.80 (m, 1H), 7.50-7.37 (m, 2H), 7.33 (d, J = 1.5 Hz, 1H), 6.23 (d, J = 1.3 Hz, 1H), 4.26 (t, J = 7.6 Hz, 2H), 4.07 (s, 2H), 3.66 (s, 3H), 3.17 (t, J = 7.5 Hz, 2H). LCMS: m/z 482.0 (M + H). |
| P12 | 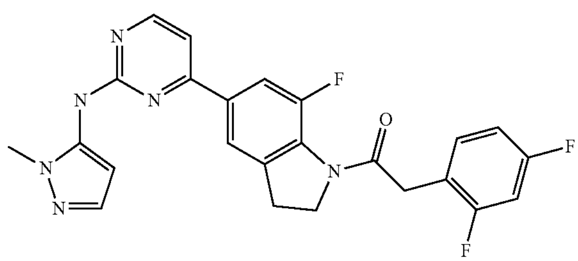 [SMILES: Cn1nccc1Nc1nccc(-c2cc(F)c3c(c2)CCN3C(=O)Cc2ccc(F)cc2F)n1] | 2-(2,4-difluorophenyl)-1-(7-fluoro-5-(2-((1-methyl-1H-pyrazol-5-yl)amino)pyrimidin-4-yl)indolin-1-yl)ethan-1-one | ¹H-NMR (400 MHz, DMSO-d₆) δ 9.44 (s, 1H), 8.47 (d, J = 5.2 Hz, 1H), 8.31 (dd, J = 4.6, 1.5 Hz, 1H), 8.00 (d, J = 2.3 Hz, 2H), 7.88-7.80 (m, 1H), 7.50-7.37 (m, 2H), 7.33 (d, J = 1.5 Hz, 1H), 6.23 (d, J = 1.3 Hz, 1H), 4.26 (t, J = 7.6 Hz, 2H), 4.07 (s, 2H), 3.66 (s, 3H), 3.17 (t, J = 7.5 Hz, 2H). LCMS: m/z 482.0 (M + H). |
| P13 | 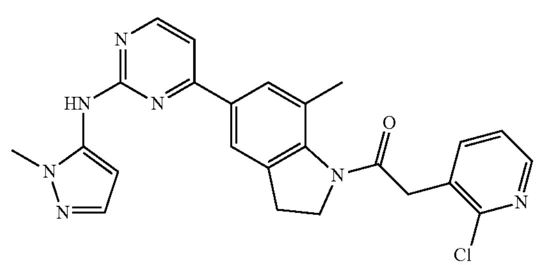 [SMILES: Cc1cc(-c2ccnc(Nc3ccnn3C)n2)cc2c1N(C(=O)Cc1cccnc1Cl)CC2] | 2-(2-chloropyridin-3-yl)-1-(7-methyl-5-(2-((1-methyl-1H-pyrazol-5-yl)amino)pyrimidin-4-yl)indolin-1-yl)ethan-1-one | ¹H NMR (DMSO-d₆, 400 MHz): δ 9.41 (s, 1H), 8.46 (d, J = 5.2 Hz, 1H), 8.35 (d, J = 4.5 Hz, 1H), 7.94-7.75 (m, 3H), 7.51-7.32 (m, 3H), 6.28 (s, 1H), 4.25 (t, J = 7.7 Hz, 2H), 4.11 (s, 3H), 3.70 (s, 3H), 3.15 (s, 2H), 2.20 (s, 3H). LCMS: m/z 460.2 (M + H). |
| P14 | 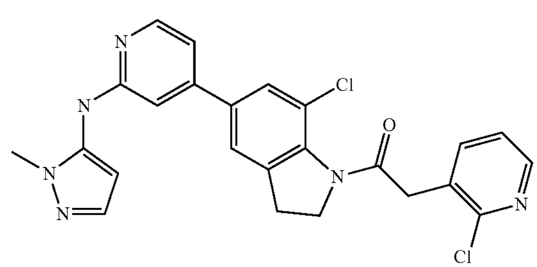 [SMILES: Cn1nccc1Nc1cc(-c2cc(Cl)c3c(c2)CCN3C(=O)Cc2cccnc2Cl)ccn1] | 1-(7-chloro-5-(2-((1-methyl-1H-pyrazol-5-yl)amino)pyridin-4-yl)indolin-1-yl)-2-(2-chloropyridin-3-yl)ethan-1-one | ¹H NMR (600 MHz, DMSO-d₆) δ 8.83 (s, 1H), 8.35 (d, J = 4.5 Hz, 1H), 8.16 (d, J = 5.1 Hz, 1H), 7.88 (d, J = 7.4 Hz, 1H), 7.62 (s, 1H), 7.55 (s, 1H), 7.48-7.41 (m, 1H), 7.34 (s, 1H), 7.09 (d, J = 5.2 Hz, 1H), 7.02 (s, 1H), 6.28 (s, 1H), 4.28 (t, J = 7.3 Hz, 2H), 4.11 (s, 2H), 3.68 (s, 3H), 3.20 (t, J = 7.3 Hz, 2H). LCMS: m/z 479.1 (M + H). |

| Ex. | Structure | Name | Analytical data |
|---|---|---|---|
| P15 | 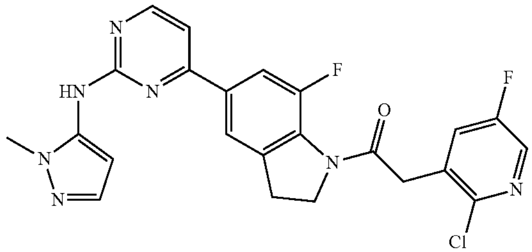 [SMILES: Cn1nccc1Nc1nccc(-c2cc(F)c3c(c2)CCN3C(=O)Cc2cc(F)cnc2Cl)n1] | 2-(2-chloro-5-fluoropyridin-3-yl)-1-(7-fluoro-5-(2-((1-methyl-1H-pyrazol-5-yl)amino)pyrimidin-4-yl)indolin-1-yl)ethan-1-one | $^1$H-NMR (CD$_3$OD, 400 MHz) δ 8.47 (d, J = 5.2, 1H), 8.28 (d, J = 2.8 Hz, 1H), 7.93 (s, 1H), 7.86 (d, J = 12.8 Hz, 1H), 7.77 (dd, J = 8.4 Hz, 2.8 Hz, 1H), 7.49 (s, 1H), 7.39 (d, J = 5.2 Hz, 1H), 6.36 (s, 1H), 4.37 (t, J = 8.0 Hz, 2H), 4.15 (s, 2H), 3.78 (s, 3H), 3.28 (t, J = 7.6 Hz, 2H). LCMS: m/z 481.9/483.9 (M + H). |
| P16 (racemate) | | 2-(2-chloropyridin-3-yl)-1-(7-fluoro-2-methyl-5-(2-((1-methyl-1H-pyrazol-5-yl)amino)pyridin-4-yl)indolin-1-yl)ethan-1-one | $^1$H-NMR (DMSO-d$_6$, 400 MHz) δ 8.85 (s, 1H), 8.35 (d, J = 4.0 Hz, 1H), 8.17 (d, J = 5.2 Hz, 1H), 7.90 (d, J = 7.2 Hz, 1H), 7.53 (s, 1H), 7.48-7.41 (m, 2H), 7.36 (s, 1H), 7.10 (d, J = 5.2 Hz, 1H), 7.02 (s, 1H), 6.28 (s, 1H), 4.97-4.89 (m, 1H), 4.19 (d, J = 16.8 Hz, 1H), 3.98 (d, J = 17.2 Hz, 1H), 3.69 (s, 3H), 3.55 (dd, J = 9.2 Hz, 16.8 Hz, 1H), 2.73 (d, J = 16.4 Hz, 1H), 1.28 (d, J = 6.0 Hz, 3H). LCMS: m/z 476.9 (M + H). |
| P32 | 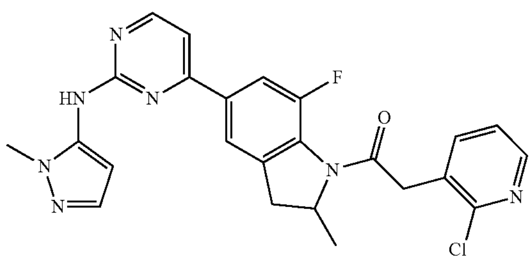 [SMILES: CC1Cc2cc(-c3ccnc(Nc4ccnn4C)c3)cc(F)c2N1C(=O)Cc1cccnc1Cl] | 2-(2-chloropyridin-3-yl)-1-(7-fluoro-2-methyl-5-(2-((1-methyl-1H-pyrazol-5-yl)amino)pyrimidin-4-yl)indolin-1-yl)ethan-1-one | $^1$H-NMR (DMSO, 400 MHz): 9.46 (s, 1H), 8.53 (d, J = 5.2 Hz, 1H), 8.35 (d, J = 4.4 Hz, 1H), 7.96 (s, 1H), 7.93-7.83 (m, 2H), 7.49-7.35 (m, 3H), 6.28 (s, 1H), 4.99-4.90 (m, 1H), 4.20 (d, J = 16.4 Hz, 1H), 3.98 (d, J = 16.8 Hz, 1H), 3.70 (s, 3H), 3.57 (dd, J = 8.8 Hz, 16.8 Hz, 1H), 2.74 (d, J = 16.4 Hz, 1H), 1.29 (d, J = 6.4 Hz, 3H). LCMS: m/z 478.0 (M + H). |
| P34 | 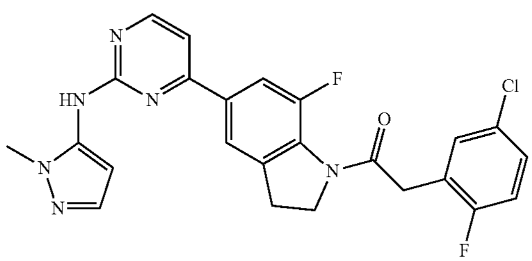 [SMILES: Cn1nccc1Nc1nccc(-c2cc(F)c3c(c2)CCN3C(=O)Cc2cc(Cl)ccc2F)n1] | 2-(5-chloro-2-fluorophenyl)-1-(7-fluoro-5-(2-((1-methyl-1H-pyrazol-5-yl)amino)pyrimidin-4-yl)indolin-1-yl)ethan-1-one | $^1$H-NMR (CD3OD, 400 MHz): 8.46 (d, J = 5.2 Hz, 1H), 7.90 (s, 1H), 7.84 (d, J = 13.2 Hz, 1H), 7.48 (d, J = 2.4 Hz, 1H), 7.39 (dd, J = 10.4 Hz, 6.4 Hz, 1H), 7.38 (d, J = 5.6 Hz, 1H), 7.33 (m, 1H), 6.36 (d, J = 2.0 Hz, 1H), 4.33 (t, J = 8.0 Hz, 2H), 4.02 (s, 2H), 3.78 (s, 3H), 3.27 (t, J = 8.0 Hz, 2H). LCMS: m/z 480.5/482.6 (M + H). |
| P36 | 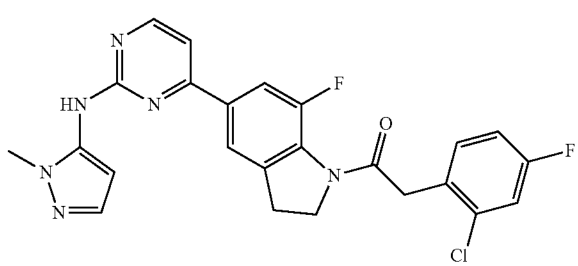 [SMILES: Cn1nccc1Nc1nccc(-c2cc(F)c3c(c2)CCN3C(=O)Cc2ccc(F)cc2Cl)n1] | 2-(2-chloro-4-fluorophenyl)-1-(7-fluoro-5-(2-((1-methyl-1H-pyrazol-5-yl)amino)pyrimidin-4-yl)indolin-1-yl)ethan-1-one | $^1$H NMR (CD3OD, 400 MHz): 8.47 (d, J = 5.2 Hz, 1H), 7.91 (s, 1H), 7.86 (d, J = 12.4 Hz, 1H), 7.48 (s, 1H), 7.44 (t, J = 8.4 Hz, 1H), 7.39 (d, J = 5.6 Hz, 1H), 7.27 (dd, J = 11.2 Hz, 2.8 Hz, 1H), 7.10 (t, J = 5.6 Hz, 1H), 6.35 (s, 1H), 4.34 (t, J = 8 Hz, 2H), 4.08 (s, 2H), 3.78 (s, 3H), 3.26 (t, J = 8 Hz, 2H). LCMS: m/z 480.8/482.8 (M + H). |

-continued

| Ex. | Structure | Name | Analytical data |
|---|---|---|---|
| P53 | (racemate) | 2-(2-chloropyridin-3-yl)-1-(7-fluoro-5-(2-((3-hydroxylcyclobutyl)amino)pyridin-4-yl)indolin-1-yl)ethan-1-one | $^1$H NMR (CD$_3$OD, 400 MHz): 8.34 (d, J = 4.4 Hz, 1H), 7.97 (d, J = 6 Hz, 1H), 7.90 (d, J = 7.6 Hz, 1H), 7.52 (s, 1H), 7.44-7.39 (m, 2H), 6.96-6.93 (m, 1H), 6.82 (s, 1H), 4.50-4.49 (m, 0.5 H), 4.37 (t, J = 8 Hz, 2H), 4.33-4.27 (m, 0.5 H), 4.14 (s, 2H), 4.09-4.05 (m, 1H), 3.84-3.79 (m, 1H), 3.29 (t, J = 8 Hz, 2H), 2.88-2.87 (m, 2H), 2.42-2.34 (m, 2H), 1.89-1.87 (m, 2H). LCMS: m/z 452.8/454.9 (M + H). |
| P44 | 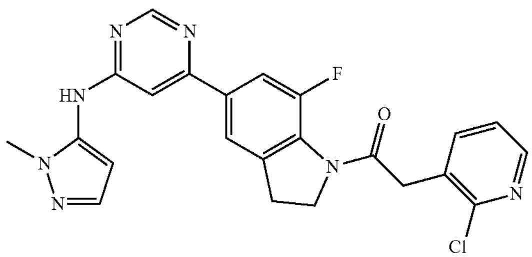 [SMILES: Cn1nccc1Nc1cc(-c2cc(F)c3c(c2)CCN3C(=O)Cc2cccnc2Cl)ncn1] | 2-(2-chloropyridin-3-yl)-1-(7-fluoro-5-(6-((1-methyl-1H-pyrazol-5-yl)amino)pyrimidin-4-yl)indolin-1-yl)ethan-1-one | $^1$H NMR (DMSO_d$_6$, 300 MHz): 9.51 (s, 1H), 8.65 (s, 1H), 8.34 (s, 1H), 7.87 (d, J = 6.6 Hz, 1H), 7.80 (s, 1H), 7.73 (d, J = 12.3 Hz, 1H), 7.41 (s, 2H), 7.14 (s, 1H), 6.33 (s, 1H), 4.28 (t, J = 7.2 Hz, 2H), 4.07 (s, 2H), 3.68 (s, 3H), 3.23 (t, J = 7.2 Hz, 2H) LCMS: m/z 463.8/465.9 (M + H). |
| P47 | 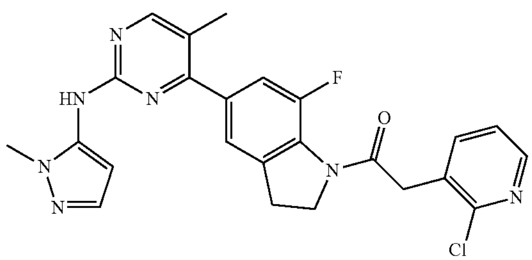 [SMILES: Cc1cnc(Nc2ccnn2C)nc1-c1cc(F)c2c(c1)CCN2C(=O)Cc1cccnc1Cl] | 2-(2-chloropyridin-3-yl)-1-(7-fluoro-5-(5-methyl-2-((1-methyl-1H-pyrazol-5-yl)amino)pyrimidin-4-yl)indolin-1-yl)ethan-1-one | $^1$H NMR (DMSO-d$_6$, 400 MHz): 9.36 (s, 1H), 8.39 (s, 1H), 8.35 (d, J = 4.4 Hz, 1H), 7.89 (d, J = 7.6 Hz, 1H), 7.46-7.37 (m, 3H), 7.32 (s, 1H), 6.24 (s, 1H), 4.29 (t, J = 7.6 Hz, 2H), 4.09 (s, 2H), 3.68 (s, 3H), 3.22 (t, J = 8.4 Hz, 2H), 2.25 (s, 3H). LCMS: m/z 478.0/480.0 (M + H) |
| P48 | 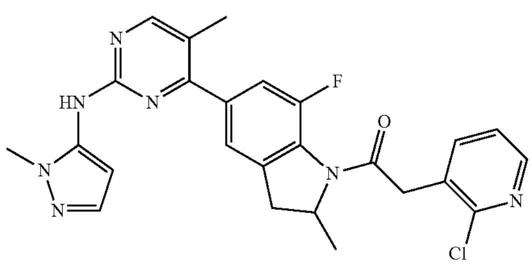 [SMILES: Cc1cnc(Nc2ccnn2C)nc1-c1cc(F)c2c(c1)CC(C)N2C(=O)Cc1cccnc1Cl] | 2-(2-chloropyridin-3-yl)-1-(7-fluoro-2-methyl-5-(5-methyl-2-((1-methyl-1H-pyrazol-5-yl)amino)pyrimidin-4-yl)indolin-1-yl)ethan-1-one | $^1$H NMR (DMSO-d$_6$, 400 MHz): 9.34 (s, 1H), 8.39 (s, 1H), 8.35 (d, J = 4.8 Hz, 1H), 7.90 (d, J = 7.2 Hz, 1H), 7.49 (s, 1H), 7.44-7.39 (m, 2H), 7.33 (s, 1H), 6.25 (s, 1H), 4.94 (t, J = 7.2 Hz, 1H), 4.20 (d, J = 16.8 Hz, 1H), 3.98 (d, J = 16.8 Hz, 1H), 3.69 (s, 3H), 3.59-3.53 (m, 1H), 2.71 (d, J = 16.4 Hz, 1H), 2.26 (s, 3H), 1.29 (d, J = 6.0 Hz, 3H). LCMS: m/z 492.1/494.1 (M + H). |
| P49 | 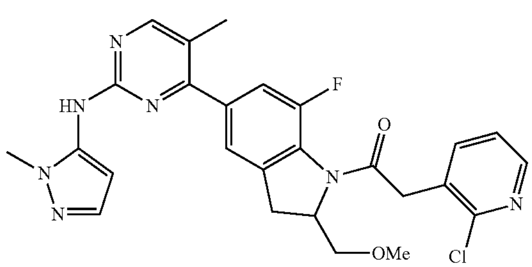 [SMILES: COCC1Cc2cc(-c3nc(Nc4ccnn4C)ncc3C)cc(F)c2N1C(=O)Cc1cccnc1Cl] | 2-(2-chloropyridin-3-yl)-1-(7-fluoro-2-(methoxymethyl)-5-(5-methyl-2-((1-methyl-1H-pyrazol-5-yl)amino)pyrimidin-4-yl)indolin-1-yl)ethan-1-one | $^1$H NMR (DMSO-d$_6$, 400 MHz): 9.34 (s, 1H), 8.39 (s, 1H), 8.35 (d, J = 4.4 Hz, 1H), 7.87 (d, J = 7.2 Hz, 1H), 7.46-7.40 (m, 3H), 7.33 (s, 1H), 6.24 (s, 1H), 5.01 (m, 1H), 4.20 (t, J = 16.8 Hz, 2H), 3.69 (s, 3H), 3.54-3.48 (m, 1H), 3.35 (d, J = 6.0 Hz, 2H), 3.31 (s, 3H), 2.86 (d, J = 16.0 Hz, 1H), 2.25 (s, 3H). LCMS: m/z 522.1/524.1 (M + H). |
| P50 | 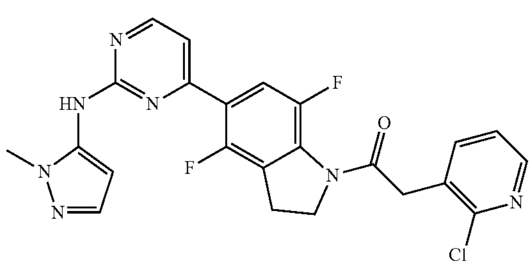 [SMILES: Cn1nccc1Nc1nccc(-c2cc(F)c3c(c2F)CCN3C(=O)Cc2cccnc2Cl)n1] | 2-(2-chloropyridin-3-yl)-1-(4,7-difluoro-5-(2-((1-methyl-1H-pyrazol-5-yl)amino)pyrimidin-4-yl)indolin-1-yl)ethan-1-one | $^1$H-NMR (CD$_3$OD, 400 MHz): δ 8.49 (d, J =5.6 Hz, 1H), 8.33 (d, J = 4.8 Hz, 1H), 7.89-7.83 (m, 2H), 7.46-7.38 (m, 3H), 7.35 (s, 1H), 4.43 (t, J = 8.0 Hz, 2H), 4.14 (s, 2H), 3.78 (s, 3H), 3.29 (t, J = 8.0, 2H). LCMS: m/z 482.0/484.0 (M + H). |

| Ex. | Structure | Name | Analytical data |
|---|---|---|---|
| P51 | 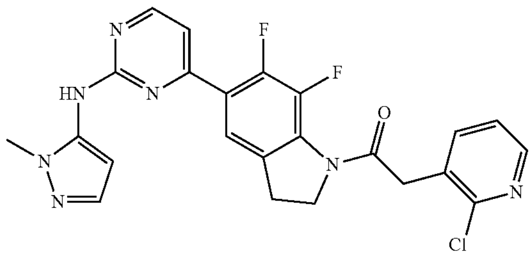 [SMILES: Cn1nccc1Nc1nccc(-c2cc3c(c(F)c2F)N(C(=O)Cc2cccnc2Cl)CC3)n1] | 2-(2-chloropyridin-3-yl)-1-(6,7-difluoro-5-(2-((1-methyl-1H-pyrazol-5-yl)amino)pyrimidin-4-yl)indolin-1-yl)ethan-1-one | $^1$H NMR (CD$_3$OD, 400 MHz): δ 8.52 (s, 1H), 8.35 (s, 1H), 7.90 (d, J = 8.0 Hz, 1H), 7.81 (s, 1H), 7.54 (s, 1H), 7.45 (s, 1H), 7.35 (s, 1H), 6.44 (s, 1H), 4.40 (t, J = 8.0 Hz, 2H), 4.17 (s, 2H), 3.81 (s, 3H), 3.26 (t, J = 8.0 Hz, 2H). LCMS: m/z 481.6/483.6 (M + H). |
| P58 | 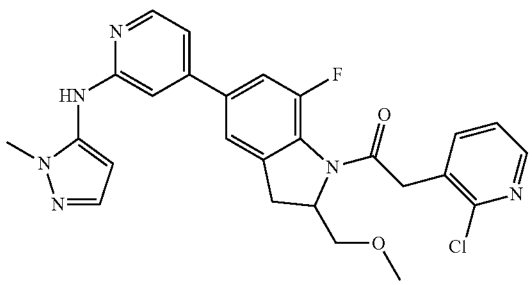 [SMILES: COCC1Cc2cc(-c3ccnc(Nc4ccnn4C)c3)cc(F)c2N1C(=O)Cc1cccnc1Cl] | 2-(2-chloropyridin-3-yl)-1-(7-fluoro-2-(methoxymethyl)-5-(2-((1-methyl-1H-pyrazol-5-yl)amino)pyridin-4-yl)indolin-1-yl)ethan-1-one | $^1$H NMR (400 MHz, CDCl$_3$) δ 8.35 (d, J = 4.0 Hz, 1H), 8.20 (s, 1H), 7.75 (d, J = 7.4 Hz, 1H), 7.56 (s, 1H), 7.27-7.20 (m, 4H), 7.03 (d, J = 5.3 Hz, 1H), 6.72 (s, 1H), 6.24 (s, 1H), 5.05 (d, J = 7.6 Hz, 1H), 4.05 (s, 2H), 3.84 (s, 3H), 3.58-3.51 (m, 1H), 3.47-3.41 (m, 2H), 3.37 (s, 3H), 2.93 (d, J = 16.3 Hz, 1H). LCMS: m/z 507.1/509.1 (M + H). |
| P59 | 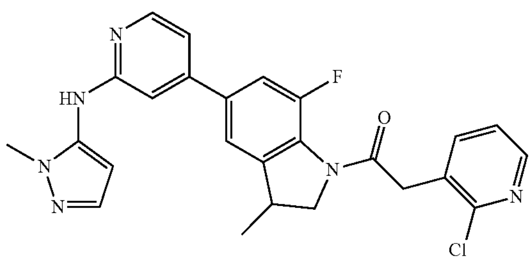 [SMILES: CC1CN(C(=O)Cc2cccnc2Cl)c2c(F)cc(-c3ccnc(Nc4ccnn4C)c3)cc21] | 2-(2-chloropyridin-3-yl)-1-(7-fluoro-3-methyl-5-(2-((1-methyl-1H-pyrazol-5-yl)amino)pyridin-4-yl)indolin-1-yl)ethan-1-one | $^1$H NMR (CD$_3$OD, 400 MHz): δ 8.33 (d, J = 3.6 Hz, 1H), 8.14 (d, J = 5.6 Hz, 1H), 7.88 (d, J = 6.4 Hz, 1H), 7.48 (s, 2H), 7.44-7.39 (m, 2H), 7.11 (d, J = 5.6 Hz, 1H), 6.99 (s, 1H), 6.28 (s, 1H), 4.53 (t, J = 8.4 Hz, 2H), 4.14 (s, 2H), 3.91-3.87 (m, 1H), 3.76 (s, 3H), 3.61-3.59 (m, 1H), 1.42 (d, J = 6.8 Hz, 3H). LCMS: m/z 477.0/479.0 (M + H). |

Example P9

Synthesis of 2-(2-chloropyridin-3-yl)-1-(7-fluoro-5-(2-((1-methyl-1H-pyrazol-5-yl)amino)pyridin-4-yl)indolin-1-yl)ethan-1-one (P9)

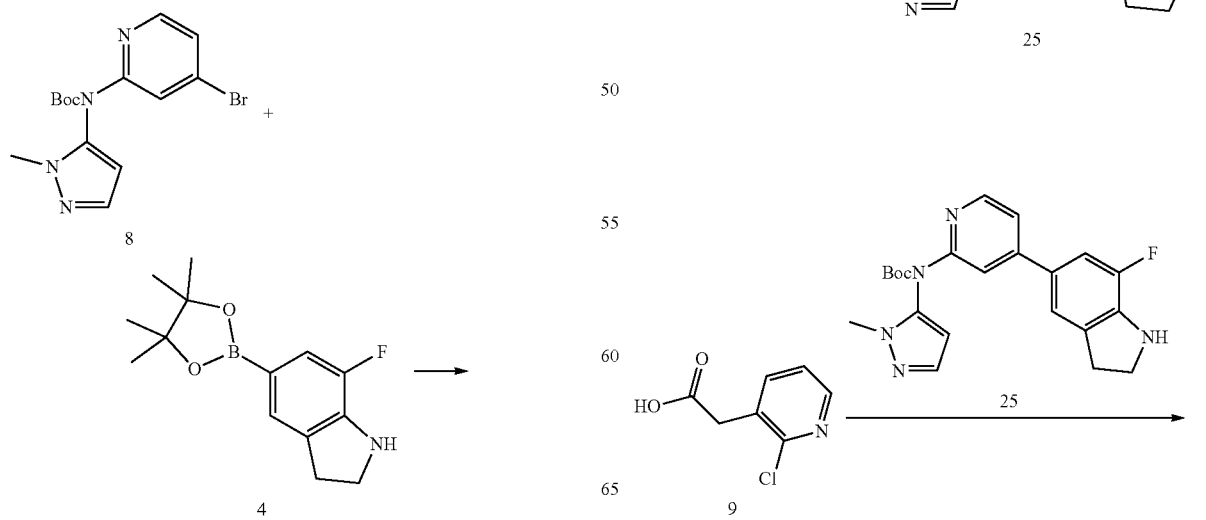

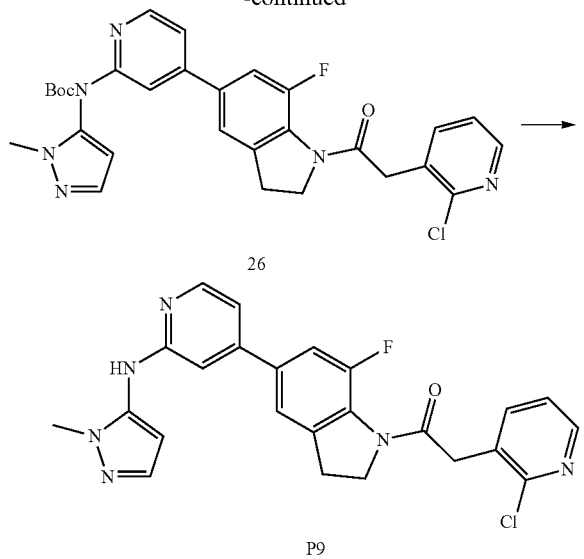

Step 1. Synthesis of t-butyl (4-(7-fluoroindolin-5-yl)pyridin-2-yl)(1-methyl-1H-pyrazol-5-yl)carbamate (25)

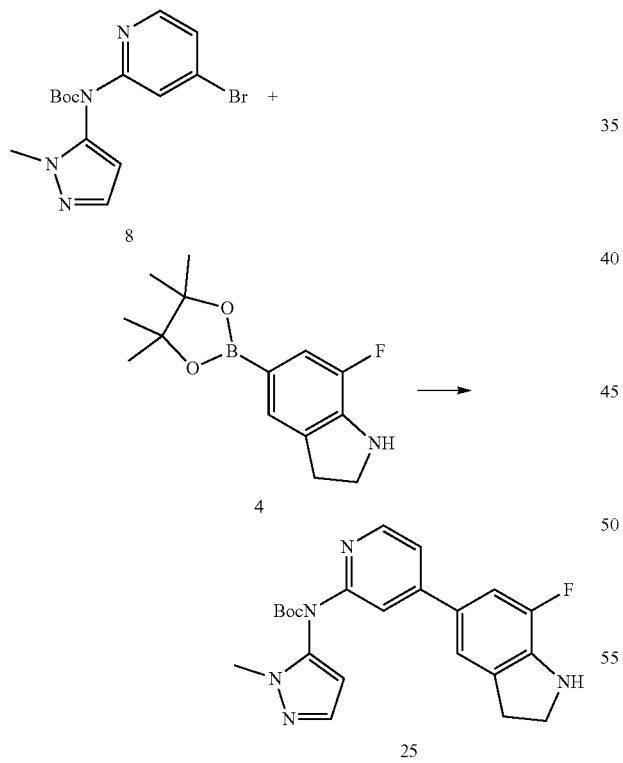

Method I: Into a dry 50 mL round bottom flask, Intermediate 4 (600 mg, 2.279 mmol), 1,4-dioxane (4 mL) and water (0.8 mL), Intermediate 8 (563 mg, 1.595 mmol), Pd(dppf)Cl$_2$ (167 mg, 0.2279 mmol) and sodium bicarbonate (383 mg, 4.56 mmol) were added at room temperature. The mixture was purged with nitrogen gas three times, warmed to 75° C., and stirred for 2 h. After the reaction was completed, the reaction was filtered hot. The filtrated was evaporated under reduced pressure to give the crude product, which was purified by silica gel column chromatography with eluent system (ethyl acetate/petroleum ether=1/5 to 3/1) to give Intermediate 25 t-butyl (4-(7-fluoroindolin-5-yl)pyridin-2-yl)(1-methyl-1H-pyrazol-5-yl)carbamate (620 mg, solid). Yield: 60.45%. $^1$H NMR (400 MHz, DMSO) δ 8.27 (d, J=5.2 Hz, 1H), 7.85 (d, J=1.2 Hz, 1H), 7.49 (dd, J=5.2, 1.6 Hz, 1H), 7.43 (s, 1H), 7.41-7.36 (m, 2H), 6.18 (d, J=2.0 Hz, 1H), 6.14 (s, 1H), 3.70 (s, 3H), 3.57 (t, J=8.8 Hz, 2H), 3.08 (t, J=8.8 Hz, 2H), 1.41 (s, 9H). LCMS: 410.2(M+H).

Method II: At room temperature, into a dry 250 mL round bottom flask, Intermediate 8 (0.984 g, 2.80 mmol), Intermediate 4 (0.88 g, 2.90 mol), triethylamine (1.19 g, 12 mmol), 1,4-dioxane (15 mL), distilled water (3 mL) were sequentially added, and then Pd(dppf)Cl$_2$ (240 mg, 0.3 mol) was added. The reaction was purged with nitrogen gas three times, warmed to 70° C., and stirred for 16 h. After the reaction was completed as monitored by LCMS, the reaction was concentrated under reduced pressure. The resulting residue was purified by silica gel column chromatography with eluent system (ethyl acetate:petroleum ether=1:3-1:5) to give Intermediate 25 t-butyl (4-(7-fluoroindolin-5-yl)pyridin-2-yl)(1-methyl-1H-pyrazol-5-yl)carbamate (1.0 g, solid). Yield 88%. LCMS: m/z 410.1 (M+H).

Method III: In to a round bottom flask (50 mL), Intermediate 8 (1.80 g), Intermediate 4 (2.15 g), methyltetrahydrofuran (15 mL), triethylamine (2.06 g), pure water (3.6 g) and Pd(ddpf)Cl$_2$ (1.25 g) were sequentially added. The mixture was purged with nitrogen gas three times, and reacted for about 15 h, maintaining the temperature at 65-75° C. After the reaction was completed as detected by HPLC, the reaction was concentrated under reduced pressure. The residue was added with MTBE and tap water to dissolve with stirring. The solution was filtered with suction on diatomite. The filter cake washed. The combined filtrate stratified. The organic layer was washed with tap water twice. The combined organic layer was concentrated under reduced pressure. The residue was added dropwise with n-heptane, and stirred at reduced temperature. After suction filtration under reduced pressure, the filter cake was washed with methyl t-butyl ester, and oven-dried under reduced pressure to give Intermediate 25 t-butyl (4-(7-fluoroindolin-5-yl)pyridin-2-yl)(1-methyl-1H-pyrazol-5-yl)carbamate 1.72 g. LCMS: 410.1 (M+H).

Step 2: Synthesis of t-butyl (4-(1-(2-(2-chloropyridin-3-yl)acetyl)-7-fluoroindolin-5-yl)pyridin-2-yl)(1-methyl-1H-pyrazol-5-yl)carbamate (26)

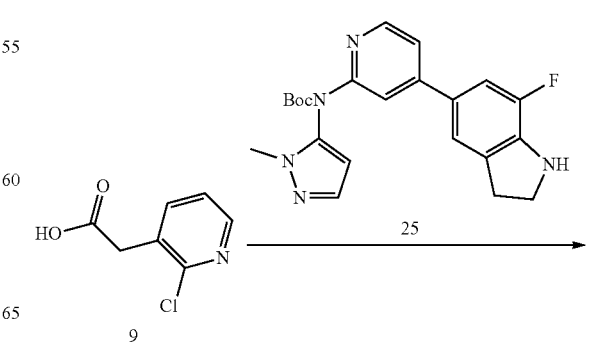

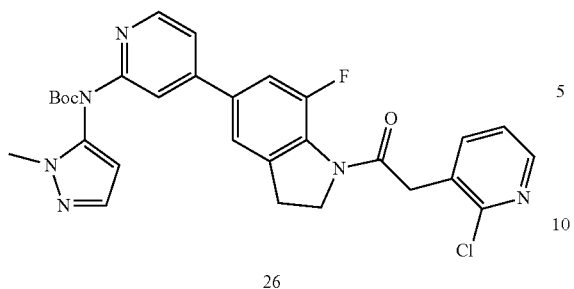

26

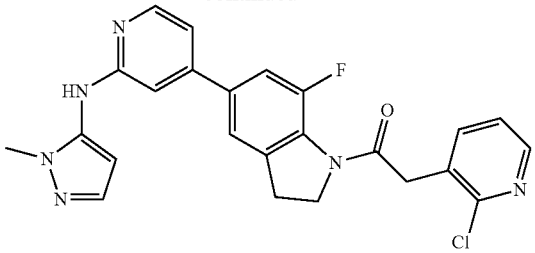

P9

Method I: Into a dry 25 mL round bottom flask, Compound 9 2-chloropyridin-3-acetic acid (493 mg, 2.876 mmol), Ac₂O (285 mg, 2.80 mmol) and THF (3 mL) were added at room temperature. The reaction was carried out at 75° C. for 1 h, and added with additional Intermediate 25 (620 mg, 1.514 mmol), THF (2 mL), DMF (1 mL) and pyridine (240 mg, 3.028 mmol). The reaction was purged with nitrogen gas three times, warmed to 70° C., and stirred for 3 h. After the reaction was completed, the reaction was added with methanol (2 mL), and concentrated under reduced pressure. The resulting residue was purified by silica gel column chromatography with eluent system (ethyl acetate/petroleum ether=1/4 to DCM:MeOH=30/1) to give Intermediate 26 (400 mg, light yellow solid). Yield: 46.9%. LCMS: m/z 564.2(M+H).

Method II: Into a 1000 mL round bottom flask, Compound 25 (1.682 g, 4.1 mmol), diisopropylethylamine (2.121 g, 16.4 mmol), Compound 9 (0.843 g, 4.9 mol), ethyl acetate (20 mL), 1-propylphosphonic anhydride (50% solution in ethyl acetate, 6.54 g, 10 mmol) were sequentially added at room temperature. After completion of the addition, the reaction was stirred at room temperature for 5 h. After the reaction was completed as monitored by LCMS, the reaction was neutralized to pH 7-8 by addition of saturated aqueous sodium bicarbonate solution, and extracted with ethyl acetate (50 mL×3). The combined organic phase was dried over anhydrous sodium sulfate, and filtered with suction. The filtrate was concentrated under reduced pressure to give t-butyl (4-(1-(2-(2-chloropyridin-3-yl) acetyl)-7-fluoroindolin-5-yl)pyridin-2-yl) (1-methyl-1H-pyrazol-5-yl)carbamate (26) (2.033 g, pale yellow oil, crude product). LCMS: m/z 562.5/564.5(M+H).

Step 3. Synthesis of 2-(2-chloropyridin-3-yl)-1-(7-fluoro-5-(2-((1-methyl-1H-pyrazol-5-yl)amino)pyridin-4-yl)indolin-1-yl)ethan-1-one (P9)

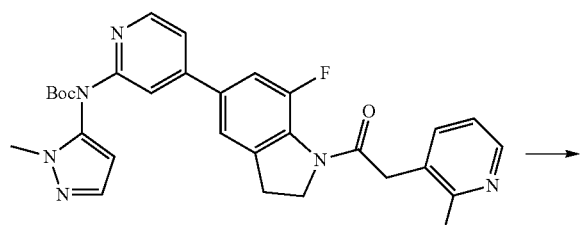

26

Method I: Into a dry 25 mL single-necked flask, Intermediate 26 (350 mg, 0.622 mmol), TFA (709 mg, 6.22 mmol), acetonitrile (5 mL) and H₂O (0.5 mL) were added at room temperature. The reaction was stirred at 40° C. under nitrogen gas for 8 h. After the reaction was completed as detected by LCMS, the crude product was purified by preparative liquid chromatography to give the product P9 2-(2-chloropyridin-3-yl)-1-(7-fluoro-5-(2-((1-methyl-1H-pyrazol-5-yl)amino)pyridin-4-yl)indolin-1-yl)ethan-1-one (135 mg, yellow solid). Yield: 46.9%. LCMS: m/z 463.1(M+H).

¹H-NMR (400 MHz, DMSO-d₆) δ 8.82 (s, 1H), 8.35 (dd, J=4.8, 1.6 Hz, 1H), 8.17 (d, J=5.6 Hz, 1H), 7.88 (dd, J=7.2, 1.2 Hz, 1H), 7.50 (s, 1H), 7.45-7.41 (m, 2H), 7.34 (d, J=1.2 Hz, 1H), 7.10 (d, J=5.2 Hz, 1H), 7.02 (s, 1H), 6.28 (d, J=1.2 Hz, 1H), 4.28 (t, J=8.0 Hz, 2H), 4.08 (s, 2H), 3.69 (s, 3H), 3.21 (t, J=8.0 Hz, 2H).

Method II: Into a dry 50 mL round bottom flask, dichloromethane (15 mL) and Intermediate 26 (2.033 g, 3.6 mmol) were sequentially added, and then trifluoroacetic acid (4 ml) was slowly added. The reaction was stirred at room temperature overnight. After the reaction was completed as monitored by LCMS, saturated aqueous sodium carbonate solution was added dropwise to adjust the pH to 7-8. The reaction stratified, and was extracted with dichloromethane (50 mL×3). The combined organic phase was concentrated under reduced pressure. The resulting suspension was added with water (20 mL) under stirring, and stirred in ice bath for 1-2 h. After suction filtration, the filter cake washed with water (10 mL) once, and oven-dried under reduced pressure to give P9 (2-(2-chloropyridin-3-yl)-1-(7-fluoro-5-(2-((1-methyl-1H-pyrazol-5-yl) amino)pyridin-4-yl)indolin-1-yl) ethan-1-one) 1.63 g. LCMS: m/z 463.1 (M+H).

Figure 3:
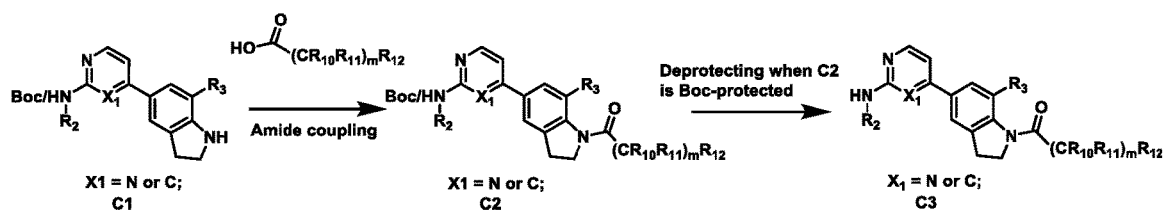
FIG. 3 shows the general synthetic scheme C for the synthesis of the compounds of the invention, wherein individual variables are as defined herein.
Figure 4:
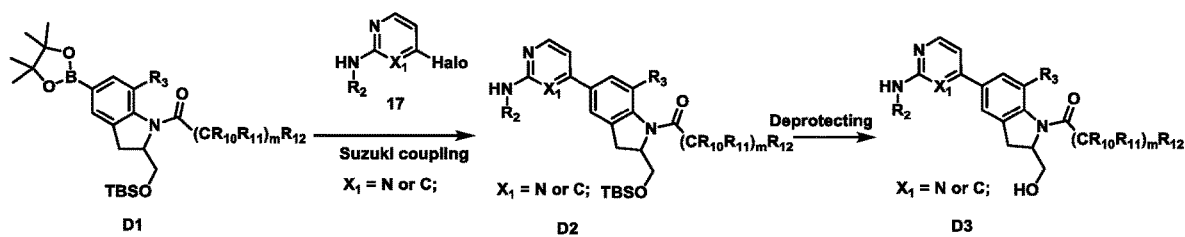
FIG. 4 shows the general synthetic scheme D for the synthesis of the compounds of the invention, wherein individual variables are as defined herein.

Examples P45-46 and P61 were obtained analogously to the preparation of Example P9 in accordance with the general scheme C as shown in FIG. 3 using Intermediate 25 or similar intermediates.

| Ex. | Structure | Name | Analytical data |
|---|---|---|---|
| P45 | 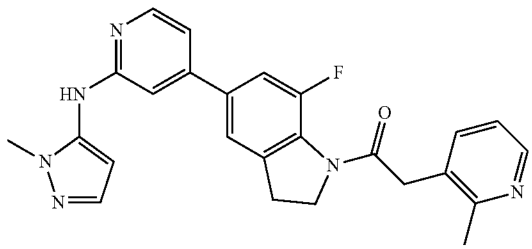 [SMILES: Cc1ncccc1CC(=O)N1CCc2cc(-c3ccnc(Nc4ccnn4C)c3)cc(F)c21] | 1-(7-fluoro-5-(2-((1-methyl-1H-pyrazol-5-yl)amino)pyridin-4-yl)indolin-1-yl)-2-(2-methylpyridin-3-yl)ethan-1-one | $^1$H NMR (DMSO-$d_6$, 400 MHz): δ 8.81 (s, 1H), 8.38 (d, J = 4.8 Hz, 1H), 8.17-8.12 (m, 2H), 7.67 (s, 1H), 7.48 (s, 1H), 7.41 (d, J = 12.2 Hz, 1H), 7.34 (d, J = 2.0 Hz, 1H), 7.26 (s, 1H), 7.09 (dd, J = 5.4, 1.5 Hz, 1H), 7.01 (s, 1H), 6.27 (d, J = 1.8 Hz, 1H), 4.26 (t, J = 8.0 Hz, 2H), 4.01 (s, 2H), 3.68 (s, 3H), 3.22 (t, J = 7.8 Hz, 2H), 2.44 (s, 3H). LCMS: m/z 443.0 (M + H). |
| P46 | 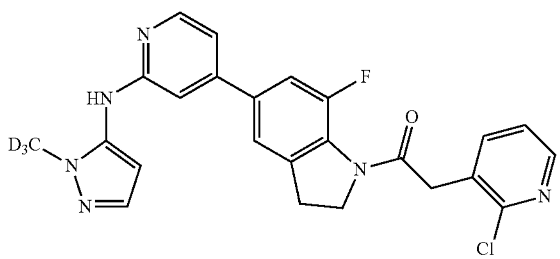 [SMILES: [2H]C([2H])([2H])n1nccc1Nc1cc(-c2cc(F)c3c(c2)CCN3C(=O)Cc2cccnc2Cl)ccn1] | 2-(2-chloropyridin-3-yl)-1-(7-fluoro-5-(2-((1-(deuteriomethyl)-1H-pyrazol-5-yl)amino)pyridin-4-yl)indolin-1-yl)ethan-1-one | $^1$H-NMR (DMSO-$d_6$, 400 MHz): δ 8.83 (s, 1H), 8.35 (d, J = 4.8 Hz, 1H), 8.17 (d, J = 5.2 Hz, 1H), 7.88 (d, J = 7.2 Hz, 1H), 7.51 (s, 1H), 7.46-7.43 (m, 2H), 7.35 (s, 1H), 7.10 (d, J = 5.6 Hz, 1H), 7.02 (s, 1H), 6.28 (s, 1H), 4.29 (t, J = 8.0 Hz, 2H), 4.08 (s, 2H), 3.23 (t, J = 7.6 Hz, 2H). LCMS: m/z 466.0/468.0 (M + H). |
| P61 | 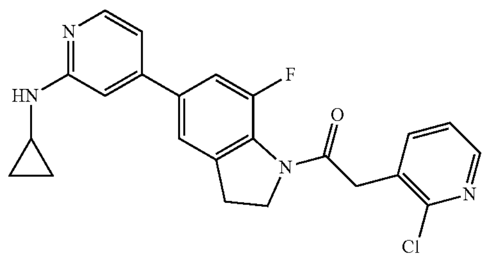 [SMILES: O=C(Cc1cccnc1Cl)N1CCc2cc(-c3ccnc(NC4CC4)c3)cc(F)c21] | 2-(2-chloropyridin-3-yl)-1-(5-(2-(cyclopropylamino)pyridin-4-yl)-7-fluoroindolin-1-yl)ethan-1-one | $^1$H NMR (400 MHz, DMSO-$d_6$) δ 8.34 (d, J = 4.6 Hz, 1H), 8.04 (d, J = 5.2 Hz, 1H), 7.88 (d, J = 7.4 Hz, 1H), 7.51 (s, 1H), 7.45-7.40 (m, 2H), 6.93-6.78 (m, 3H), 4.27 (t, J = 7.6 Hz, 2H), 4.07 (s, 2H), 3.22 (t, J = 7.6 Hz, 2H), 2.59-2.55 (m, 1H), 0.73-0.71 (m, 2H), 0.47-0.42 (m, 2H). LCMS: m/z 422.9 (M + H). |

Example P17

Synthesis of 1-(7-fluoro-5-(2-((1-methyl-1H-pyrazol-5-yl)amino)pyrimidin-4-yl)indolin-1-yl)-2-(2-fluorophenyl)ethan-1-one (P17)

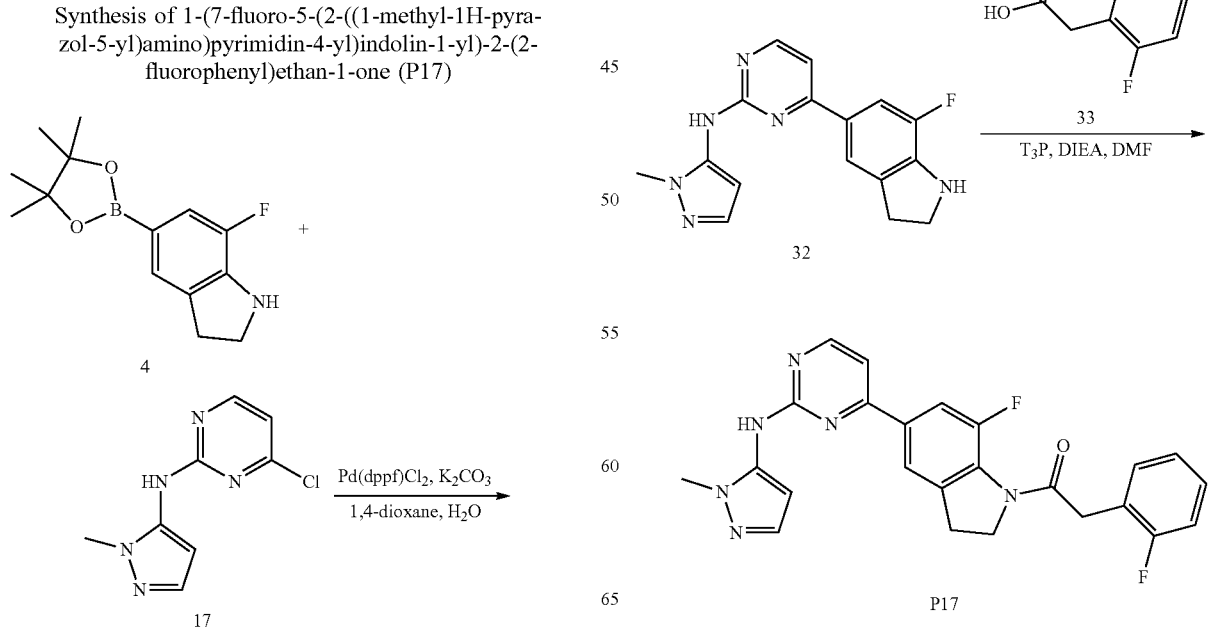

Step 1. Synthesis of N-4-(7-fluoroindolin-5-yl)-N-(1-methyl-1H-pyrazol-5-yl)pyrimidin-2-ylamine (32)

Step 2. Synthesis of 1-(7-fluoro-5-(2-((1-methyl-1H-pyrazol-5-yl)amino)pyrimidin-4-yl)indolin-1-yl)-2-(2-fluorophenyl)ethan-1-one (P17)

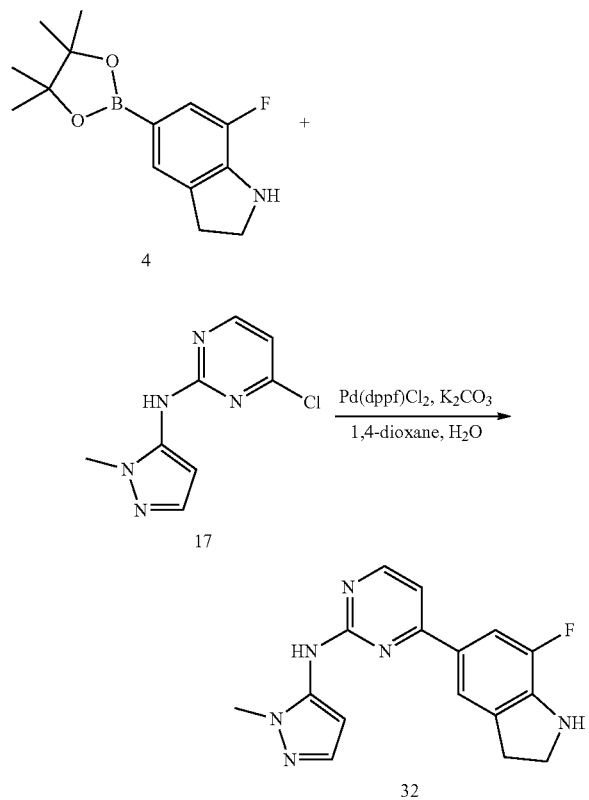

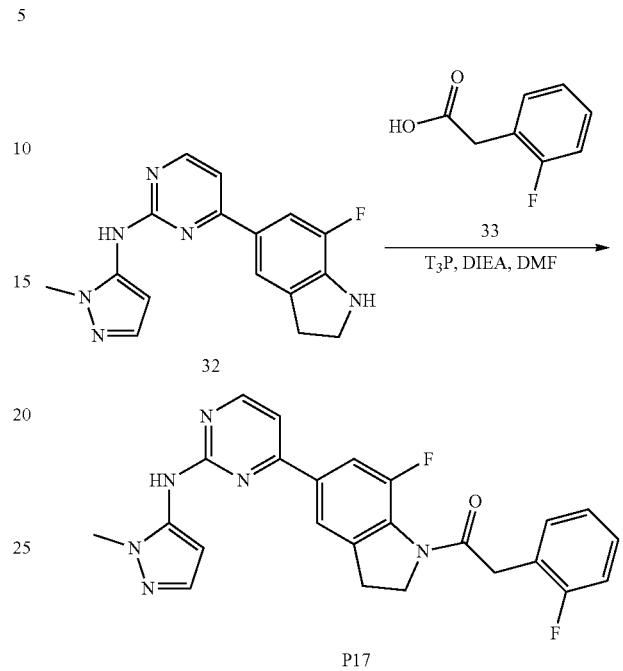

Into a dry 100 mL round bottom flask, Compound 4 7-fluoro-5-(4,4,5,5-tetramethyl-1,3,2-dioxaborolan-2-yl)indoline (900 mg, 3.80 mmol), Compound 17 4-chloro-N-(1-methyl-1H-pyrazol-5-yl)pyrimidin-2-amine (800 mg, 3.80 mmol), potassium carbonate (1.1 g, 7.60 mmol), (1,1-bis (diphenylphosphino)ferrocene)palladium (II) dichloride (278 mg, 0.38 mmol) and 1,4-dioxane (20.0 mL) were added at room temperature, The reaction was purged with nitrogen gas five times, warmed to 80° C., and stirred overnight. After the reaction was completed, the reaction was concentrated under reduced pressure, added with 100 mL water, and extracted with ethyl acetate (150 mL×3). The combined organic phase was dried over anhydrous sodium sulfate, and filtered. The filtrate was concentrated under reduced pressure. The resulting residue was purified by silica gel column chromatography with eluent system (ethyl acetate:petroleum ether=1:10) to give Intermediate 32 N-4-(7-fluoroindolin-5-yl)-N-(1-methyl-1H-pyrazol-5-yl)pyrimidin-2-ylamine (150 mg, white solid). Yield: 12.0%.

LCMS: m/z 311.0 (M+H).

Into a dry 100 mL round bottom flask, Compound 32 N-4-(7-fluoroindolin-5-yl)-N-(1-methyl-1H-pyrazol-5-yl) pyrimidin-2-ylamine (50 mg, 0.16 mmol), Compound 33 2-(2-fluorophenyl)acetic acid (25 mg, 0.16 mmol), N,N-diisopropylethylamine (0.1 mL, 0.64 mmol), 1-propylphosphonic anhydride (407 mg, 50% (wt %) solution in ethyl acetate (0.64 mmol) and N,N-dimethylformamide (1.0 mL) were added at room temperature. The reaction was stirred for 30 min After the reaction was completed, the reaction was concentrated under reduced pressure, added with 100 mL water, and extracted with ethyl acetate (150 mL×3). The combined organic phase washed with saturated brine (50 mL×5), dried over anhydrous sodium sulfate, and filtered. The filtrate was concentrated under reduced pressure. The resulting residue was purified by silica gel column chromatography with eluent system (ethyl acetate:petroleum ether=1:1) to give the product P17 1-(7-fluoro-5-(2-((1-methyl-1H-pyrazol-5-yl) amino)pyrimidin-4-yl)indolin-1-yl)-2-(2-fluorophenyl) ethan-1-one (16.7 mg, light yellow solid). Yield: 20.0%. LCMS: m/z 447.0 (M+H).

$^1$H NMR (DMSO-d6, 400 MHz): δ 9.48 (s, 1H), 8.51 (d, J=5.2 Hz, 1H), 7.91 (s, 1H), 7.83 (d, J=12.4 Hz, 1H), 7.46 (d, J=5.2 Hz, 1H), 7.41-7.31 (m, 3H), 7.19 (q, J=7.6 Hz, 2H), 6.29 (s, 1H), 4.26 (t, J=8.0 Hz, 2H), 3.98 (s, 2H), 3.70 (s, 3H), 3.23 (t, J=8.0 Hz, 2H).

Examples P18-P20, P23-P25, P28-31, P33, P37-39 and P54-57 were obtained in accordance with the general scheme C as shown in FIG. 3 using Intermediate 32 or similar intermediates.

| Ex. | Structure | Name | Analytical data |
|---|---|---|---|
| P18 | 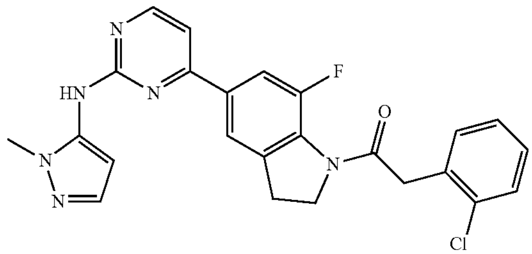 | 2-(2-chlorophenyl)-1-(7-fluoro-5-(2-((1-methyl-1H-pyrazol-5-yl)amino)pyrimidin-4-yl)indolin-1-yl)ethan-1-one | ¹H NMR (DMSO-d6, 400 MHz): δ 9.46 (s, 1H), 8.51 (d, J = 5.2 Hz, 1H), 7.92 (s, 1H), 7.83 (d, J = 12 Hz, 1H), 7.46-7.41 (m, 3H), 7.37 (s, 1H), 7.33-7.30 (m, 2H), 6.28 (s, 1H), 4.27 (t, J =8.0 Hz, 2H), 4.04 (s, 2H), 3.70 (s, 4H), 3.21 (d, J = 7.6 Hz, 3H). LCMS: m/z 462.9 (M + H). |
| P19 | 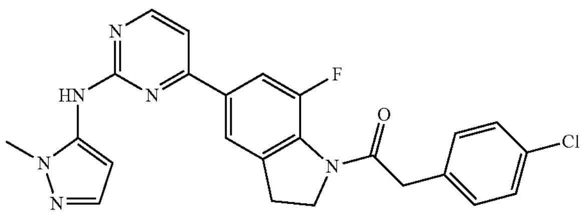 [SMILES: Cn1nccc1Nc1nccc(-c2cc(F)c3c(c2)CCN3C(=O)Cc2ccc(Cl)cc2)n1] | 2-(4-chlorophenyl)-1-(7-fluoro-5-(2-((1-methyl-1H-pyrazol-5-yl)amino)pyrimidin-4-yl)indolin-1-yl)ethan-1-one | ¹H-NMR (DMSO-d6, 400 MHz): δ 9.46 (s, 1H), 8.50 (d, J = 5.6 Hz, 1H), 7.90 (s, 1H), 7.82 (d, J = 12.8 Hz, 1H), 7.47 (d, J = 5.2 Hz, 1H), 7.40 (d, J = 8.4 Hz, 2H), 7.39 (s, 1H), 7.33 (d, J = 8.4 Hz, 2H), 6.28 (s, 1H), 4.23 (t, J = 8.0 Hz, 2H), 3.95 (s, 2H), 3.70 (s, 3H), 3.20 (t, J = 8.0 Hz, 3H). LCMS: m/z 462.9 (M + H). |
| P20 | 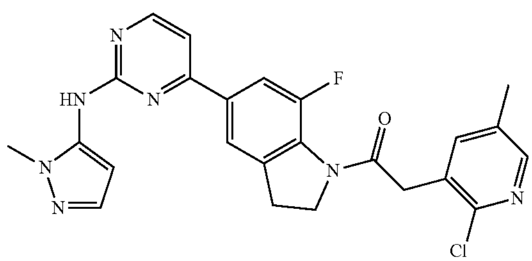 | 2-(2-chloro-5-methylpyridin-3-yl)-1-(7-fluoro-5-(2-((1-methyl-1H-pyrazol-5-yl)amino)pyrimidin-4-yl)indolin-1-yl)ethan-1-one | ¹H-NMR (DMSO-d₆, 400 MHz) δ 9.48 (s, 1H), 8.52 (d, J = 5.2 Hz, 1H), 8.18 (s, 1H), 7.94 (s, 1H), 7.85 (d, J = 12.8 Hz, 1H), 7.71 (s, 1H), 7.47 (d, J = 5.2 Hz, 1H), 7.38 (d, J = 2.0 Hz, 1H), 6.29 (s, 1H), 4.30 (t, J = 7.6 Hz, 2H), 4.03 (s,2H), 3.71 (s, 3H), 3.24 (t, J = 7.6 Hz, 2H), 2.31 (s, 3H). LCMS: m/z 477.9/479.9 (M + H). |
| P23 | 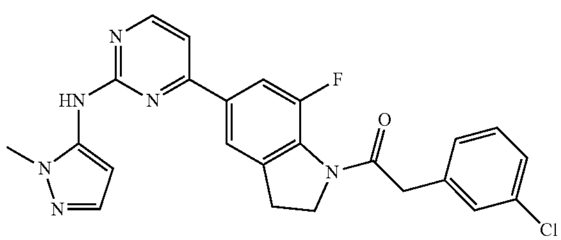 [SMILES: Cn1nccc1Nc1nccc(-c2cc(F)c3c(c2)CCN3C(=O)Cc2cccc(Cl)c2)n1] | 2-(3-chlorophenyl)-1-(7-fluoro-5-(2-((1-methyl-1H-pyrazol-5-yl)amino)pyrimidin-4-yl)indolin-1-yl)ethan-1-one | ¹H-NMR (DMSO-d6, 400 MHz) δ 9.49 (s, 1H), 8.52 (d, J = 5.2 Hz, 1H), 7.91 (s, 1H), 7.83 (d, J = 12.4 Hz, 1H), 7.47 (d, J = 5.2 Hz, 1H), 7.41-7.32 (m, 4H), 7.27 (d, J = 6.8 Hz, 1H), 6.30 (s, 1H), 4.24 (t, J = 8.0 Hz, 2H), 3.97 (s, 2H), 3.71 (s, 3H), 3.21 (t, J = 8.0 Hz, 2H). LCMS: m/z 462.9 (M + H). |
| P24 | 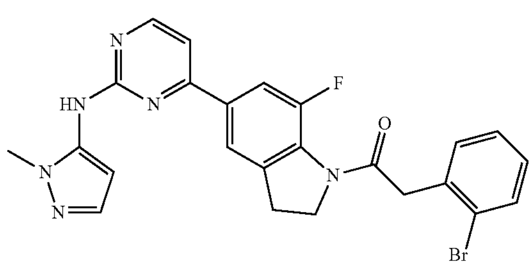 | 2-(2-bromophenyl)-1-(7-fluoro-5-(2-((1-methyl-1H-pyrazol-5-yl)amino)pyrimidin-4-yl)indolin-1-yl)ethan-1-one | ¹HNMR (400 MHz, DMSO-d6) δ 9.46 (s, 1H), 8.51 (d, J = 5.2 Hz, 1H), 7.92 (s, 1H), 7.84 (d, J = 12.6 Hz, 1H), 7.65-7.60 (m, 1H), 7.46 (d, J = 5.3 Hz, 1H), 7.44-7.34 (m, 2H), 7.23 (td, J = 7.7, 1.8 Hz, 1H), 6.27 (d, J = 1.8 Hz, 1H), 4.28 (t, J = 7.9 Hz, 2H), 4.03 (s, 2H), 3.70 (s, 3H), 3.23 (t, J = 7.9 Hz, 2H). LCMS: m/z 507.0/509.0 (M + H). |
| P25 | 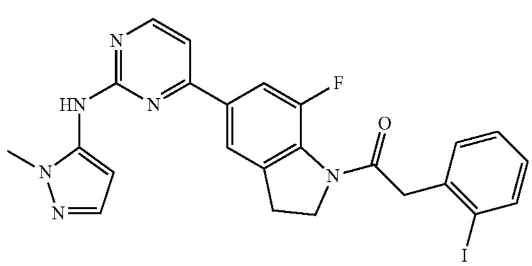 [SMILES: Cn1nccc1Nc1nccc(-c2cc(F)c3c(c2)CCN3C(=O)Cc2ccccc2I)n1] | 1-(7-fluoro-5-(2-((1-methyl-1H-pyrazol-5-yl)amino)pyrimidin-4-yl)indolin-1-yl)-2-(2-iodophenyl)ethan-1-one | ¹H-NMR (400 MHz, DMSO-d6) δ 9.46 (s, 1H), 8.51 (d, J = 5.2 Hz, 1H), 7.93 (s, 1H), 7.85 (d, J = 8.2 Hz, 1H), 7.47 (d, J = 5.3 Hz, 1H), 7.42-7.32 (m, 3H), 7.17-6.92 (m, 1H), 6.28 (d, J = 1.8 Hz, 1H), 4.28 (t, J = 8.0 Hz, 2H), 4.01 (s, 2H), 3.70 (s, 3H), 3.23 (t, J = 8.0 Hz, 2H). LCMS: m/z 555.0 (M + H). |

| Ex. | Structure | Name | Analytical data |
|---|---|---|---|
| P28 | 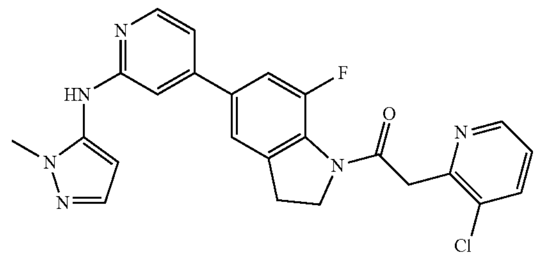 [SMILES: Cn1nccc1Nc1cc(-c2cc(F)c3c(c2)CCN3C(=O)Cc2ncccc2Cl)ccn1] | 2-(3-chloropyridin-2-yl)-1-(7-fluoro-5-(2-((1-methyl-1H-pyrazol-5-yl)amino)pyridin-4-yl)indolin-1-yl)ethan-1-one | $^1$H-NMR (400 MHz, DMSO-d6) δ 8.81 (s, 1H), 8.48 (dd, J = 4.8, 1.4 Hz, 1H), 8.16 (d, J = 5.2 Hz, 1H), 7.94 (dd, J = 8.2, 1.4 Hz, 1H), 7.48 (s, 1H), 7.45-7.36 (m, 2H), 7.34 (d, J = 2.0 Hz, 1H), 7.09 (dd, J = 5.4, 1.6 Hz, 1H), 7.01 (s, 1H), 6.27 (d, J = 2.0 Hz, 1H), 4.25 (t, J = 8.0 Hz, 2H), 4.22 (s, 2H), 3.68 (s, 3H), 3.20 (t, J = 8.0 Hz, 2H). LCMS: m/z 463.0 (M + H). |
| P29 | 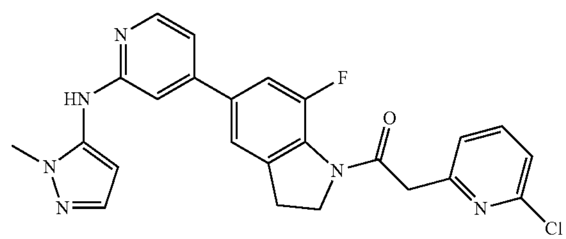 [SMILES: Cn1nccc1Nc1cc(-c2cc(F)c3c(c2)CCN3C(=O)Cc2cccc(Cl)n2)ccn1] | 2-(6-chloropyridin-2-yl)-1-(7-fluoro-5-(2-((1-methyl-1H-pyrazol-5-yl)amino)pyridin-4-yl)indolin-1-yl)ethan-1-one | $^1$H-NMR (400 MHz, DMSO-d6) δ 8.83 (s, 1H), 8.16 (d, J = 5.2 Hz, 1H), 7.85 (t, J = 8.0 Hz, 1H), 7.48 (s, 1H), 7.41 (dd, J = 7.6, 5.2 Hz, 1H), (m, 2H), 7.34 (d, J = 2.0 Hz, 1H), 7.09 (dd, J = 5.4, 1.6 Hz, 1H), 7.01 (s, 1H), 6.27 (d, J = 2.0 Hz, 1H), 4.25 (t, J = 8.0 Hz, 2H), 4.11 (s, 2H), 3.69 (s, 3H), 3.20 (t, J = 8.0 Hz, 2H). LCMS: m/z 463.0 (M + H). |
| P30 | 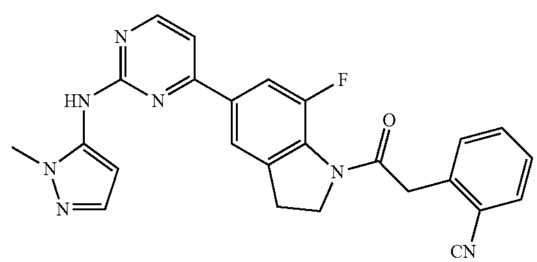 | 2-(2-(7-fluoro-5-(2-((1-methyl-1H-pyrazol-5-yl)amino)pyrimidin-4-yl)indolin-1-yl)-2-oxoethyl)benzonitrile | $^1$H NMR (DMSO-d6, 400 MHz): δ 9.46 (s, 1H), 8.51 (d, J = 5.2 Hz, 1H), 7.93 (s, 1H), 7.84 (d, J = 12 Hz, 1H), 7.69 (td, J = 7.6, 1.6 Hz, 1H), 7.54 (d, J = 7.2 Hz, 1H), 7.51-7.44 (m, 2H), 7.37 (d, J = 2.0 Hz, 1H), 6.28 (d, J = 2.0 Hz, 1H), 4.31 (t, J = 8.0 Hz, 2H), 4.18 (s, 2H), 3.70 (s, 4H), 3.24 (t, J = 8.0 Hz, 2H). LCMS: m/z 454 (M + H). |
| P31 | 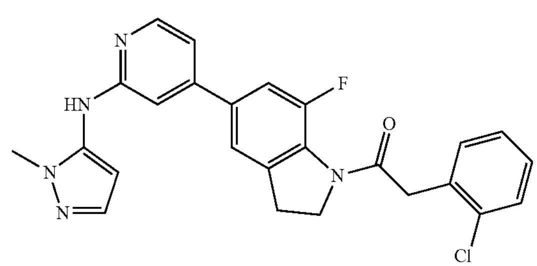 | 2-(2-chlorophenyl)-1-(7-fluoro-5-(2-((1-methyl-1H-pyrazol-5-yl)amino)pyridin-4-yl)indolin-1-yl)ethan-1-one | $^1$H NMR (DMSO-d6, 400 MHz): δ 8.81 (s, 1H), 8.16 (d, J = 5.6 Hz, 1H), 7.49 (s, 1H), 7.47-7.39 (m, 3H), 7.35-7.27 (m, 3H), 7.09 (d, J = 5.2 Hz, 1H), 7.01 (s, 1H), 6.27 (s, 1H), 4.25 (t, J = 8.0 Hz, 2H), 4.03 (s, 2H), 3.68 (s, 3H), 3.21 (t, J = 7.8 Hz, 2H). LCMS: m/z 462.0 (M + H) |
| P33 | 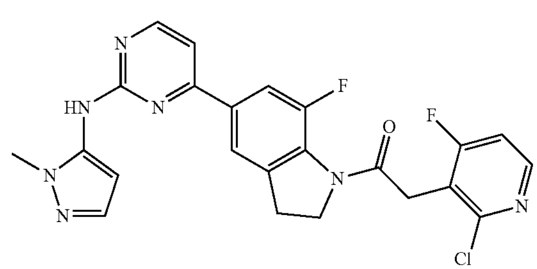 [SMILES: Cn1nccc1Nc1nccc(-c2cc(F)c3c(c2)CCN3C(=O)Cc2c(F)ccnc2Cl)n1] | 2-(2-chloro-4-fluoropyridin-3-yl)-1-(7-fluoro-5-(2-((1-methyl-1H-pyrazol-5-yl)amino)pyrimidin-4-yl)indolin-1-yl)ethan-1-one | $^1$H NMR (CD3OD, 400 MHz): 8.47 (d, J = 5.2 Hz, 1H), 8.37 (t, J = 5.6 Hz, 1H), 7.93 (s, 1H), 7.86 (d, J = 12.8 Hz, 1H), 7.51 (s, 1H), 7.40 (d, J = 5.2 Hz, 1H), 7.31 (t, J = 5.6 Hz, 1H), 6.39 (s, 1H), 4.40 (t, J = 7.6 Hz, 2H), 4.19 (s, 2H), 3.79 (s, 3H), 3.30 (t, J = 7.6 Hz, 2H). LCMS: m/z 481.9/483.9 (M + H). |
| P37 | 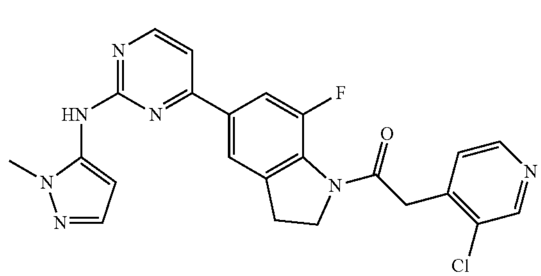 [SMILES: Cn1nccc1Nc1nccc(-c2cc(F)c3c(c2)CCN3C(=O)Cc2ccncc2Cl)n1] | 2-(3-chloropyridin-4-yl)-1-(7-fluoro-5-(2-((1-methyl-1H-pyrazol-5-yl)amino)pyrimidin-4-yl)indolin-1-yl)ethan-1-one | $^1$H NMR (CD3OD, 400 MHz): 8.58 (s, 1H), 8.47 (d, J = 4.8 Hz, 2H), 7.92 (s, 1H), 7.87 (d, J = 13.2 Hz, 1H), 7.51-7.48 (m, 2H), 7.39 (d, J = 5.2 Hz, 1H), 6.39 (d, J = 2.0 Hz, 1H), 4.36 (t, J = 8 Hz, 2H), 4.19 (s, 2H), 3.78 (s, 3H), 3.28 (t, J = 8 Hz, 2H). LCMS: m/z 463.9/466.0 (M + H). |

-continued

| Ex. | Structure | Name | Analytical data |
|---|---|---|---|
| P38 | 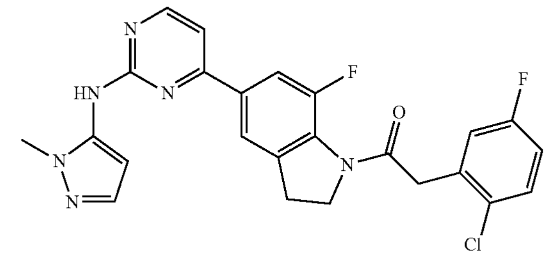 [SMILES: Cn1nccc1Nc1nccc(-c2cc(F)c3c(c2)CCN3C(=O)Cc2cc(F)ccc2Cl)n1] | 2-(2-chloro-5-fluorophenyl)-1-(7-fluoro-5-(2-((1-methyl-1H-pyrazol-5-yl)amino)pyrimidin-4-yl)indolin-1-yl)ethan-1-one | $^1$H NMR (CD$_3$OD, 400 MHz): 8.47 (d, J = 5.6 Hz, 1H), 7.92 (s, 1H), 7.87 (d, J = 12.4 Hz, 1H), 7.49 (d, J = 2.0 Hz, 1H), 7.44 (dd, J = 8.8 Hz, 3.6 Hz, 1H), 7.39 (d, J = 5.2 Hz, 1H), 7.24 (dd, J = 8.8 Hz, 2.8 Hz, 1H), 7.08 (t, J = 8 Hz, 1H), 6.35 (d, J = 2 Hz, 2H), 4.35 (t, J = 8 Hz, 2H), 4.10 (s, 2H), 3.78 (s, 3H), 3.26 (t, J = 7.2 Hz, 2H). LCMS: m/z 481.0/482.9 (M + H) |
| P39 | 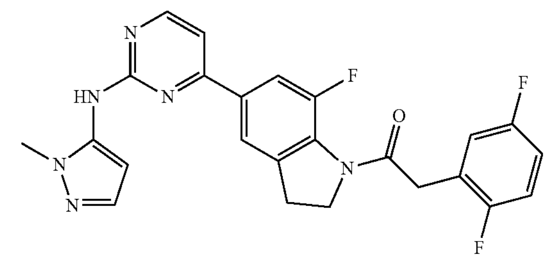 [SMILES: Cn1nccc1Nc1nccc(-c2cc(F)c3c(c2)CCN3C(=O)Cc2cc(F)ccc2F)n1] | 2-(2,5-difluorophenyl)-1-(7-fluoro-5-(2-((1-methyl-1H-pyrazol-5-yl)amino)pyrimidin-4-yl)indolin-1-yl)ethan-1-one | $^1$H NMR (CD$_3$OD, 400 MHz): 8.46 (d, J = 4.0 Hz, 1H), 7.90 (s, 1H), 7.87 (d, J = 12.4 Hz, 1H), 7.48 (d, J = 2.0 Hz, 1H), 7.39 (d, J = 5.6 Hz, 1H), 7.16-7.10 (m, 1H), 7.08-7.04 (m, 1H), 6.35 (d, J = 2.0 Hz, 1H), 4.33 (t, J = 8.0 Hz, 2H), 4.02 (s, 2H), 3.78 (s, 3H), 3.26 (t, J = 8.0 Hz, 2H) LCMS: m/z 465.0 (M + H) |
| P54 | 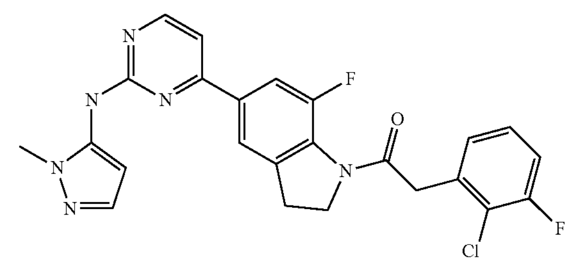 [SMILES: Cn1nccc1Nc1nccc(-c2cc(F)c3c(c2)CCN3C(=O)Cc2cccc(F)c2Cl)n1] | 2-(2-chloro-3-fluorophenyl)-1-(7-fluoro-5-(2-((1-methyl-1H-pyrazol-5-yl)amino)pyrimidin-4-yl)indolin-1-yl)ethan-1-one | $^1$H NMR (400 MHz, DMSO) δ 9.47 (s, 1H),), 8.51 (d, J = 5.2 Hz, 1H), 7.92 (s, 1H), 7.84 (d, J = 12.6 Hz, 1H), 7.46 (d, J = 5.2 Hz, 1H), 7.40-7.33 (m, 3H), 7.31-7.26 (m, 1H), 6.28 (d, J = 1.5 Hz, 1H), 4.28 (t, J = 7.8 Hz, 2H), 4.11 (s, 2H), 3.70 (s, 3H), 3.23 (t, J = 7.8 Hz, 2H). LCMS: m/z 480.9 (M + H). |
| P55 | 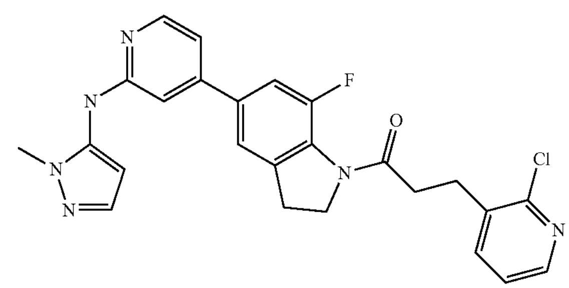 [SMILES: Cn1nccc1Nc1cc(-c2cc(F)c3c(c2)CCN3C(=O)CCc2cccnc2Cl)ccn1] | 3-(2-chloropyridin-3-yl)-1-(7-fluoro-5-(2-((1-methyl-1H-pyrazol-5-yl)amino)pyridin-4-yl)indolin-1-yl)propan-1-one | $^1$H NMR (400 MHz, DMSO) δ 8.82 (s, 1H), 8.28 (d, J = 3.2 Hz, 1H), 8.16 (d, J = 5.6 Hz, 1H), 7.87 (d, J = 7.0 Hz, 1H), 7.46 (s, 1H), 7.44-7.37 (m, 2H), 7.34 (s, 1H), 7.08 (d, J = 5.6 Hz, 1H), 7.00 (s, 1H), 6.27 (s, 1H), 4.16 (t, J = 7.8 Hz, 2H), 3.68 (s, 3H), 3.14 (t, J = 7.8 Hz, 2H), 3.06-2.98 (m, 2H), 2.92-2.85 (m, 2H), LCMS: m/z 476.9 (M + H) |
| P56 | 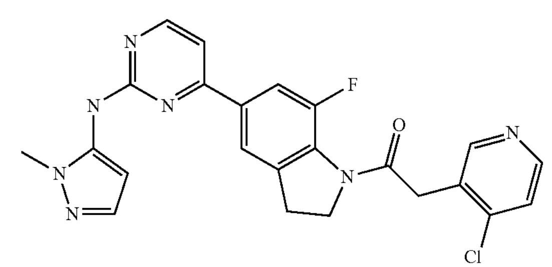 [SMILES: Cn1nccc1Nc1nccc(-c2cc(F)c3c(c2)CCN3C(=O)Cc2cnccc2Cl)n1] | 2-(4-chloropyridin-3-yl)-1-(7-fluoro-5-(2-((1-methyl-1H-pyrazol-5-yl)amino)pyrimidin-4-yl)indolin-1-yl)ethan-1-one | 1H NMR (400 MHz, DMSO) δ 9.47 (s, 1H), 8.57 (s, 1H), 8.51 (d, J = 5.2 Hz, 1H), 8.47 (d, J = 4.8 Hz, 1H), 7.93 (s, 1H), 7.84 (d, J = 12.4 Hz, 1H), 7.57 (d, J = 5.2 Hz, 1H), 7.47 (d, J =5.2 Hz, 1H), 7.37 (d, J = 1.6 Hz, 1H), 6.27 (d, J = 1.2 Hz, 1H), 4.31 (t, J = 8.0 Hz, 2H), 4.11 (s, 2H), 3.70 (s, 3H), 3.25 (t, J = 7.6 Hz, 2H). LCMS: m/z 463.9 (M + H). |

-continued
| Ex. | Structure | Name | Analytical data |
|---|---|---|---|
| P57 | 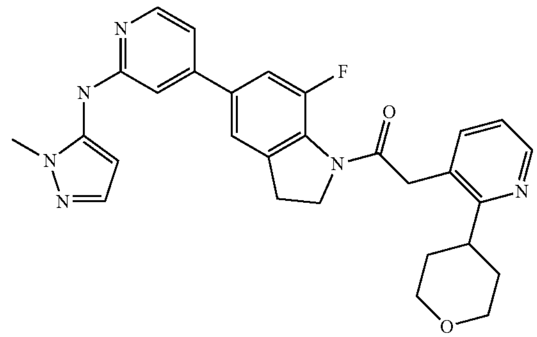 [SMILES: Cn1nccc1Nc1cc(-c2cc(F)c3c(c2)CCN3C(=O)Cc2cccnc2C2CCOCC2)ccn1] | 1-(7-fluoro-5-(2-((1-methyl-1H-pyrazol-5-yl)amino)pyridin-4-yl)indolin-1-yl)-2-(2-(tetrahydro-2H-pyran-4-yl)pyridin-3-yl)ethan-1-one | ¹H NMR (400 MHz, DMSO) δ 8.83 (s, 1H), 8.46 (d, J = 4.4 Hz, 1H), 8.17 (d, J = 7.2 Hz, 1H), 7.61 (d, J = 7.4 Hz, 1H), 7.50 (s, 1H), 7.42 (d, J = 12.01 Hz, 1H), 7.35 (s, 1H), 7.20-7.17 (m, 1H), 7.09 (d, J = 5.2 Hz, 1H), 7.01 (s, 1H), 6.27 (s, 1H), 4.27 (t, J = 7.8 Hz, 2H), 4.05 (s, 2H), 3.93-3.89 (m, 2H), 3.69 (s, 3H), 3.23 (t, J = 7.6 Hz, 2H), 3.04-2.98 (m, 1H), 1.94-1.84 (m, 2H), 1.58-1.55 (m, 2H). LCMS: m/z 513.0 (M + H). |
Example P35
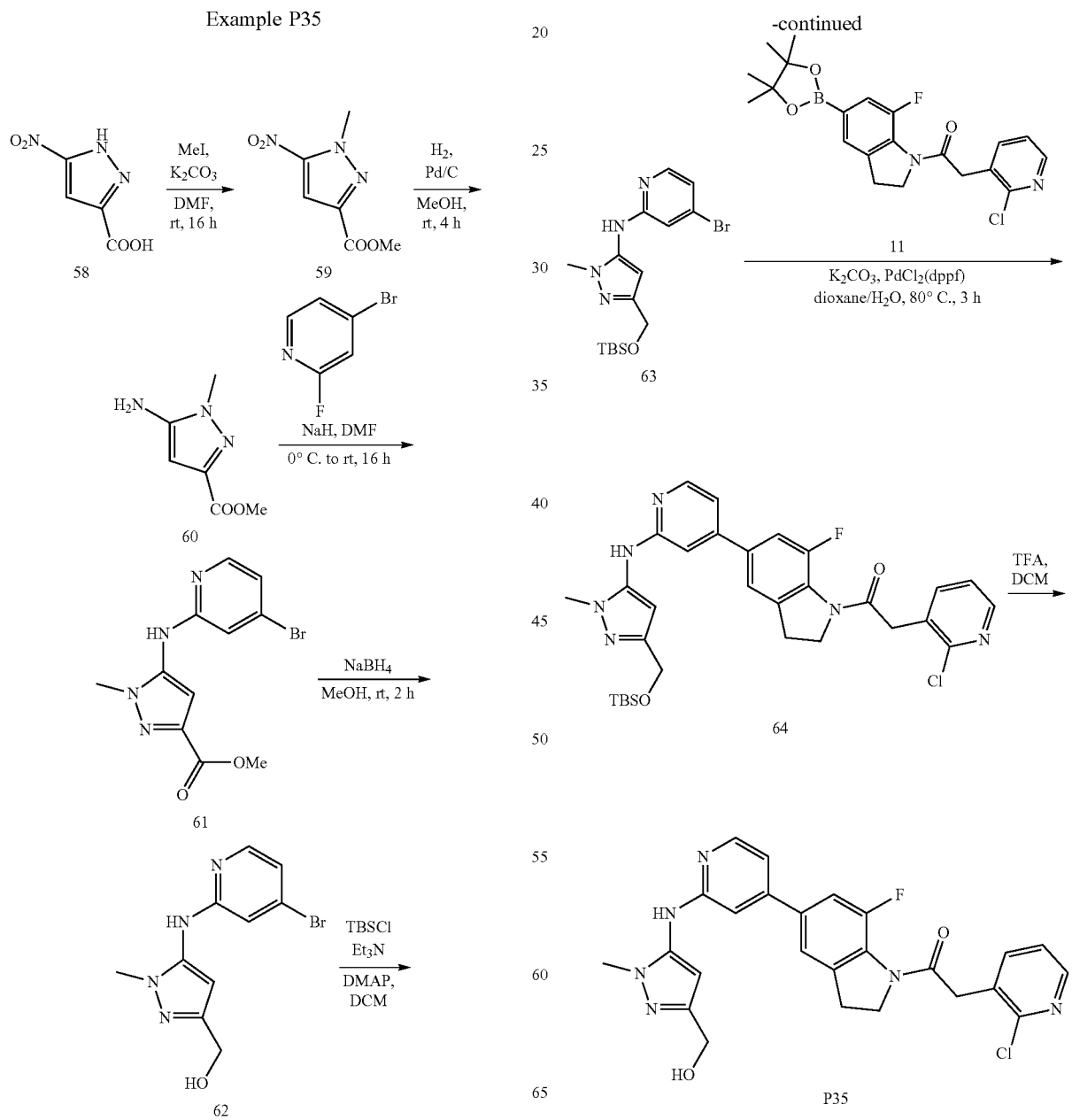

Step 1. Synthesis of methyl 1-methyl-5-nitro-1H-pyrazol-3-carboxylate (59)

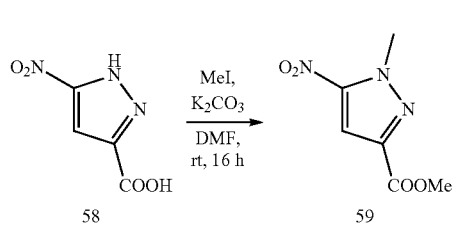

Into a 100 mL round bottom flask in ice-water bath, Compound 58 (5.0 g, 12.74 mmol), potassium carbonate (1.94 g, 14.0 mmol), N,N-dimethylformamide (50 mL) were sequentially added, and solution of iodomethane (3.80 g, 26.75 mmol) in N,N-dimethylformamide (10 mL) was added dropwise. After completion of the dropwise addition, the reaction was stirred for 16 h. After the reaction was completed, the reaction was added with water (150 mL), and extracted with ethyl acetate (50 mL×3). The combined organic phase washed with saturated brine (30 mL×3), dried over anhydrous sodium sulfate, and filtered. The filtrate was concentrated under reduced pressure. The resulting residue was purified by column chromatography with eluent system (ethyl acetate:petroleum ether=1:20) to give methyl 1-methyl-5-nitro-1H-pyrazol-3-carboxylate 59 (1.0 g, white solid). Yield: 17.0%. LCMS: m/z 185.9 (M+H)

Step 2. Synthesis of methyl 5-amino-1-methyl-1H-pyrazol-3-carboxylate (60)

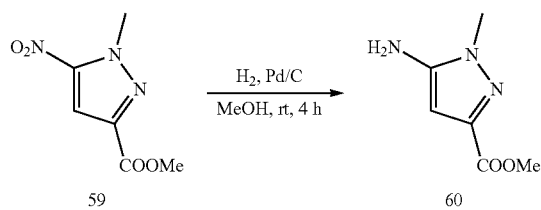

At room temperature, Compound 59 (200 mg, 1.081 mmol) was dissolved in methanol (10 mL) and added with Pd/C (10%, 90 mg). The reaction was stirred for 4 h under 1 atm of hydrogen gas. After the reaction was completed as monitored by LCMS, the reaction was filtered with suction. The filtrate was concentrated under reduced pressure to give methyl 5-amino-1-methyl-1H-pyrazol-3-carboxylate 60 (145 mg, light yellow oil). Yield: 87.0%. LCMS: m/z 156 (M+H).

Step 3. Synthesis of methyl 5-((4-bromopyridin-2-yl)amino)-1-methyl-1H-pyrazol-3-carboxylate (61)

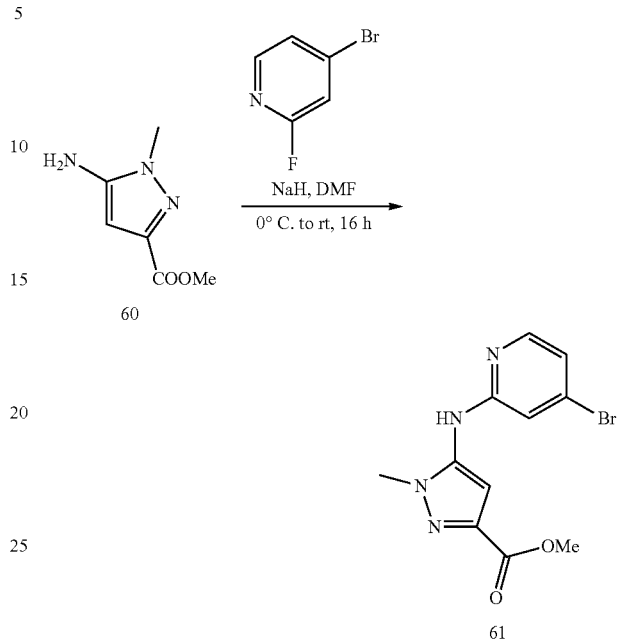

At room temperature, into a 50 mL round bottom flask, Compound 60 (650 mg, 4.19 mmol) and N,N-dimethylformamide (10 mL) were sequentially added, and sodium hydride (335 mg, 8.38 mmol) was added in portions. The reaction was stirred for 0.5 h, added with 2-bromo-4-fluoropyridine (1.47 g, 8.387 mmol), and stirred for 16 h. After the reaction was completed as monitored by LCMS, the reaction was added with water (30 mL), and extracted with ethyl acetate (10 mL×5). The combined organic phase washed with saturated brine (20 mL×3), dried over anhydrous sodium sulfate, and filtered. The filtrate was concentrated under reduced pressure. The resulting residue was purified by column chromatography with eluent system (ethyl acetate petroleum ether=1:4) to give methyl 5-((4-bromopyridin-2-yl)amino)-1-methyl-1H-pyrazol-3-carboxylate 61 (130 mg, pale yellow solid). Yield: 10%. LCMS: m/z 310.9/312.9 (M+H).

Step 4. Synthesis of (5-((4-bromopyridin-2-yl)amino)-1-methyl-1H-pyrazol-3-yl)methanol (62)

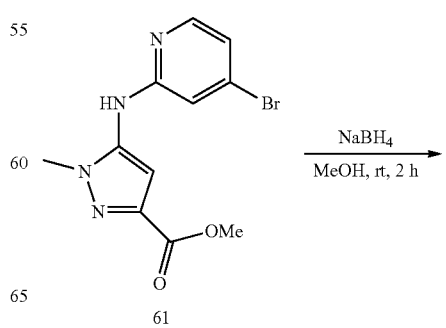

-continued

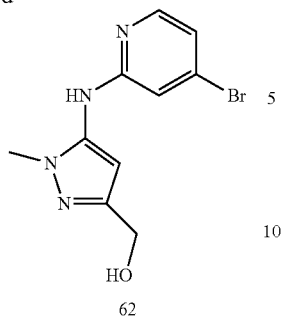

62

At room temperature, Compound 61 (130 mg, 0.418 mmol) was dissolved in anhydrous methanol (25 mL), and added in portions with sodium borohydride (156 mg, 4.18 mmol). After completion of the addition, the reaction was stirred at room temperature for 2 h, and was concentrated under reduced pressure. The resulting residue was purified by column chromatography with eluent system (ethyl acetate:petroleum ether=4:1) to give (5-((4-bromopyridin-2-yl)amino)-1-methyl-1H-pyrazol-3-yl)methanol 62 (100 mg, white gum). Yield: 85%. LCMS: m/z 282.9/284.9 (M+H).

Step 5. Synthesis of N-(3-(((t-butyldimethylsilyl)oxy)methyl)-1-methyl-1H-pyrazol-5-yl)-N-(4-bromopyridin-2-yl)-amine (63)

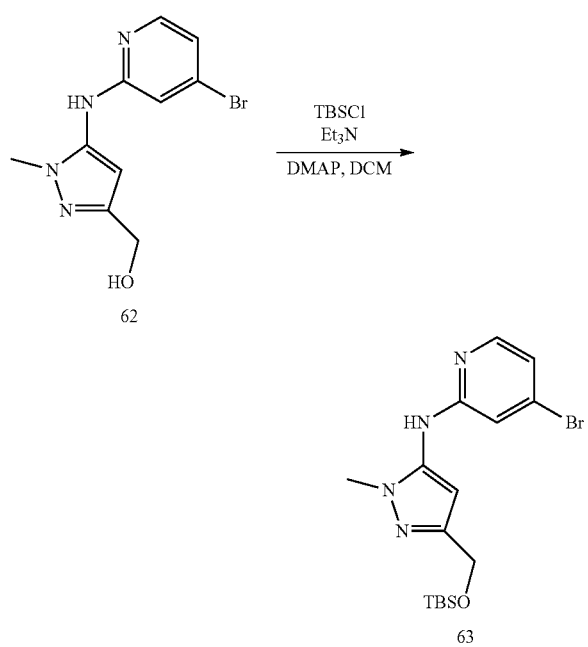

Into a 50 mL round bottom flask, Compound 62 (100 mg, 0.355 mmol), t-butyldimethylsilyl chloride (532 mg, 3.55 mmol), triethylamine (358 mg, 3.55 mmol), 4-dimethylaminopryidine (4.33 mg, 0.036 mmol), dichloromethane (10 mL) were sequentially added at room temperature. The reaction was purged with nitrogen gas three times, and stirred at room temperature for 16 h. After the reaction was completed, the reaction was added with water (30 mL), and extracted with ethyl acetate (10 mL×3). The combined organic phase was dried over anhydrous sodium sulfate, and filtered. The filtrate was concentrated under reduced pressure. The resulting residue was purified by silica gel column chromatography with eluent system (ethyl acetate:petroleum ether=1:5) to give N-(3-(((t-butyldimethylsilyl)oxy)methyl)-1-methyl-1H-pyrazol-5-yl)-N-(4-bromopyridin-2-yl)-amine 63 (50 mg, light yellow oil). Yield: 33.0%. LCMS: m/z 396.9/398.9 (M+H).

Step 6. Synthesis of 1-(5-(24(3-(((t-butyldimethylsilyl)oxy)methyl)-1-methyl-1H-pyrazol-5-yl)amino)pyridin-4-yl)-7-fluoroindolin-1-yl)-2-(2-chloropyridin-3-yl)ethan-1-one (64)

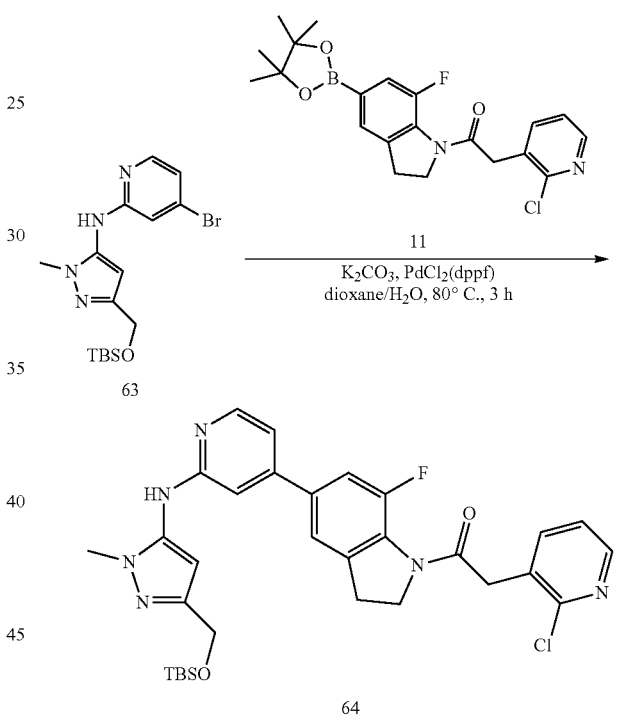

Into a 50 mL round bottom flask, Compound 63 (50 mg, 0.126 mmol), 1,4-dioxane (10 mL), PdCl₂(dppf) (9.2 mg, 0.0126 mmol), potassium carbonate (26.1 mg, 0.189 mmol), Compound 11 (52.5 mg, 0.126 mmol) were sequentially added at room temperature. The reaction was purged with nitrogen gas three times, warmed to 80° C., and stirred for 3 h. After the reaction was completed, the reaction was concentrated under reduced pressure. The resulting residue was purified by silica gel column chromatography with eluent system (ethyl acetate:petroleum ether=5:1) to give 1-(5-(2-((3-(((t-butyldimethylsilyl)oxy)methyl)-1-methyl-1H-pyrazol-5-yl) amino)pyridin-4-yl)-7-fluoroindolin-1-yl)-2-(2-chloropyridin-3-yl)ethan-1-one 64 (60 mg, pale yellow oil). Yield: 78.5%. LCMS: m/z 606.5/608.5, (M+H)

Step 7. Synthesis of 2-(2-chloropyridin-3-yl)-1-(7-fluoro-5-(2-((3-(hydroxylmethyl)-1-methyl-1H-pyrazol-5-yl)amino)pyridin-4-yl)indolin-1-yl)ethan-1-one (P35)

Example P60: Synthesis of 2-(2-chloropyridin-3-yl)-1-(7-fluoro-5-(2-((1-methyl-1H-pyrazol-5-yl)amino)pyridin-4-yl)indolin-1-yl)-2-hydroxylethan-1-one (P60)

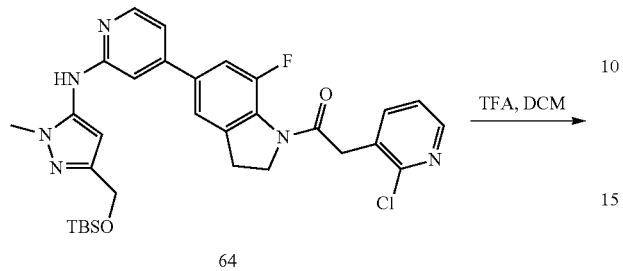

64

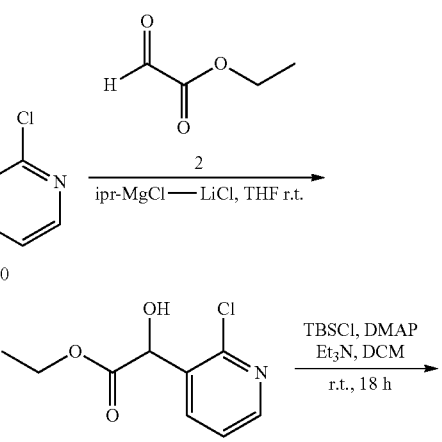

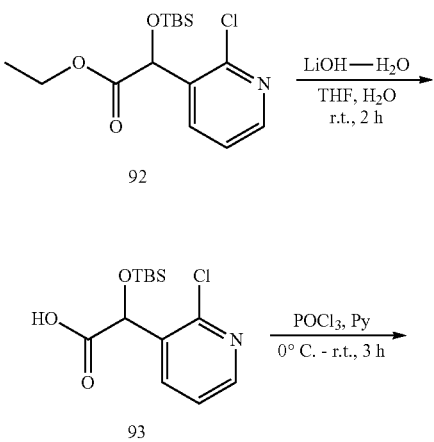

P35

Into a 50 mL flask, Compound 64 (60 mg, 0.099 mmol), trifluoroacetic acid (2 mL), dichloromethane (10 mL) were sequentially added at room temperature. The reaction was stirred at room temperature for 1 h. After the reaction was completed, the reaction was concentrated under reduced pressure, slowly added with saturated aqueous sodium bicarbonate solution (15 mL), and extracted with ethyl acetate (10 mL×5). The combined organic phase was concentrated under reduced pressure. The resulting residue was purified by preparative liquid chromatography (column: -Gemini-C18 150×21.2 mm, Sum; mobile phase: ACN —H$_2$O (0.1% FA), gradient:10-60) to give 2-(2-chloropyridin-3-yl)-1-(7-fluoro-5-(2-((3-(hydroxylmethyl)-1-methyl-1H-pyrazol-5-yl)amino)pyridin-4-yl)indolin-1-yl)ethan-1-one P35 (12 mg, pale yellow solid). Yield: 25%.

$^1$H-NMR (CD$_3$OD, 400 MHz): 8.33 (d, J=3.2 Hz, 1H), 8.15 (d, J=5.6 Hz, 1H), 7.90 (d, J=7.6 Hz, 1H), 7.51 (s, 1H), 7.44-7.38 (m, 2H), 7.12 (d, J=5.6 Hz, 1H), 6.99 (s, 1H), 6.31 (s, 1H), 4.56 (s, 2H), 4.37 (t, J=7.6 Hz, 2H), 4.14 (s, 2H), 3.73 (s, 3H), 3.28 (t, J=7.2 Hz, 2H). LCMS: m/z 492.9/494.9 (M+H)

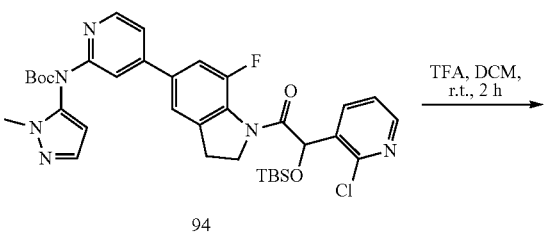

94

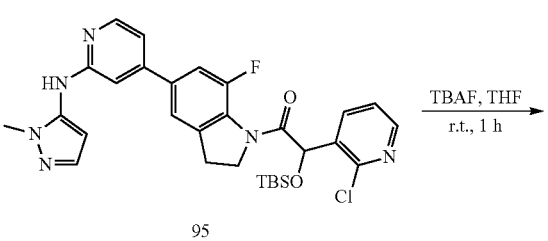

95

-continued

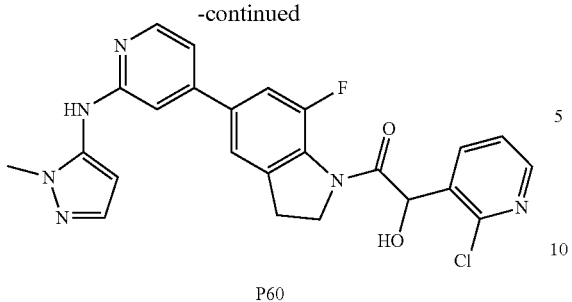

P60

Step 1. Synthesis of ethyl 2-(2-chloropyridin-3-yl)-2-hydroxylacetate (91)

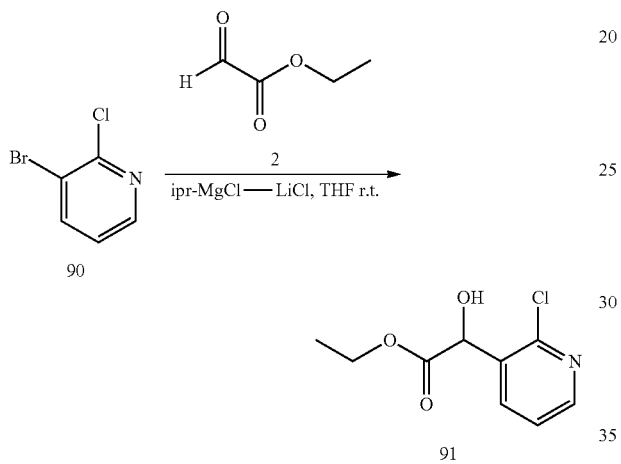

Into a dry 250 mL round bottom flask in ice bath, Compound 90 (6.0 g, 0.031 mol), tetrahydrofuran (100 mL), isopropylmagnesium chloride-lithium chloride complex (31 mL, 40.3 mol) were added. The reaction was purged with nitrogen gas three times, naturally warmed to room temperature, and stirred for 3 h. The reaction was cooled in ice-water bath, added with Compound 2 (3.2 g, 0.031 mol), gradually warmed to room temperature, stirred for 2 h, quenched with saturated ammonium chloride (100 mL), and extracted with ethyl acetate (80 mL×3). The combined organic phase was dried over anhydrous sodium sulfate, and filtered. The filtrate was concentrated under reduced pressure. The resulting residue was purified by silica gel column chromatography (ethyl acetate:petroleum ether=1:10) to give ethyl 2-(2-chloropyridin-3-yl)-2-hydroxylacetate 91 (1.4 g, pale yellow oil). Yield: 21%. LCMS: m/z 216.0 (M+H).

Step 2. Synthesis of ethyl 2-((t-butyldimethylsilyl)oxy)-2-(2-chloropyridin-3-yl)acetate (92)

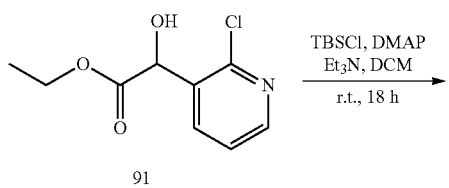

-continued

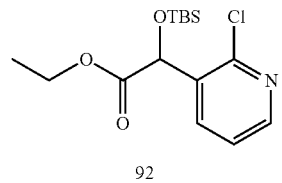

92

Into a dry 100 mL round bottom flask, Compound 91 (800 mg, 3.7 mmol), dichloromethane (50 mL), t-butyldimethylsilyl chloride (2796 mg, 18.5 mmol), 4-dimethylamiopryidine (452 mg, 3.7 mmol), triethylamine (3740 mg, 37.0 mmol) were added at room temperature. The reaction was purged with nitrogen gas three times, and stirred at room temperature for 18 h. After the reaction was completed, the reaction was quenched by addition of ice-water (100 mL), and extracted with dichloromethane (60 mL×3). The combined organic phase was dried over anhydrous sodium sulfate, and filtered. The filtrate was concentrated under reduced pressure. The resulting residue was purified by silica gel column chromatography (ethyl acetate:petroleum ether=1:20) to give ethyl 2-((t-butyldimethylsilyl)oxy)-2-(2-chloropyridin-3-yl)acetate 92 (640 mg, colorless oil). Yield: 52%. LCMS: m/z 330.0 (M+H).

Step 3. Synthesis of 2-((t-butyldimethylsilyl)oxy)-2-(2-chloropyridin-3-yl)acetic acid (93)

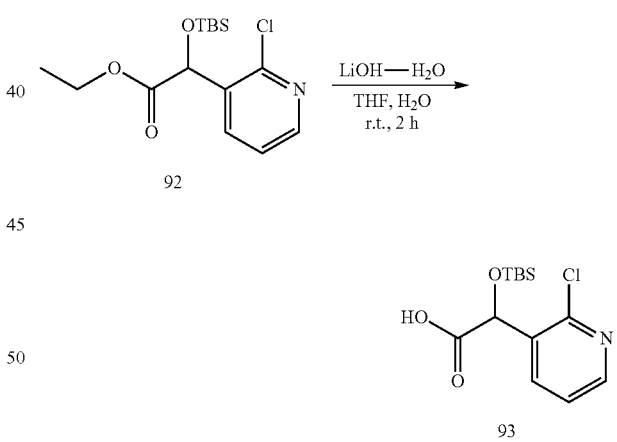

Into a dry 100 mL round bottom flask, Compound 92 (640 mg, 1.94 mmol), lithium hydroxide monohydrate (244 mg, 5.81 mmol), tetrahydrofuran (20 mL), water (4 mL) were added at room temperature. The reaction was stirred for 2 h and filtered. The filtrate was concentrated under reduced pressure, and adjusted with 1 N aqueous hydrochloric acid solution to pH 7. The solid precipitated, was filtered, and dried to give 2-((t-butyldimethylsilyl)oxy)-2-(2-chloropyridin-3-yl)acetic acid 93 (180 mg, white solid). Yield: 31%. LCMS: m/z 302.0 (M+H).

Step 4. Synthesis of t-butyl N-(4-(1-(2-((t-butyldimethylsilyl)oxy)-2-(2-chloropyridin-3-yl)acetyl)-7-fluoroindol-5-yl)pyridin-2-yl)-N-(1-methyl-1H-pyrazol-5-yl)carbamate (94)

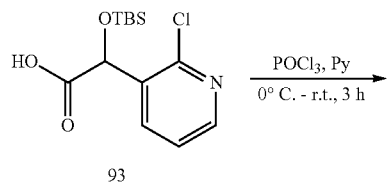

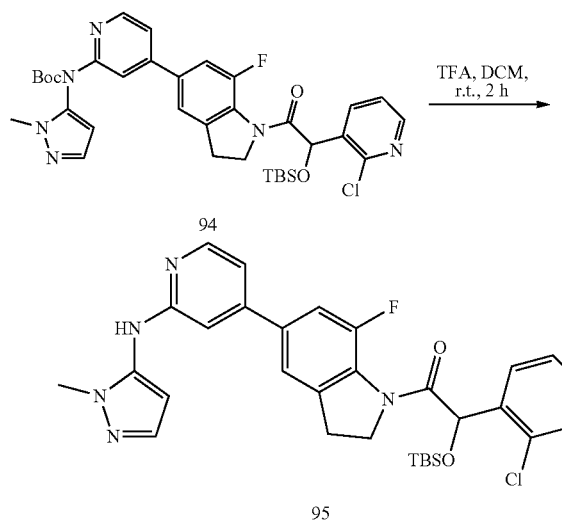

In a dry 100 mL round bottom flask in ice bath, Compound 93 (243 mg, 0.6 mmol), Compound 25 (180 mg, 0.6 mmol), phosphorus oxychloride (273 mg, 1.8 mmol) and pyridine (20 mL) were added. The reason was gradually warmed to room temperature, stirred for 3 h, diluted by addition of ice-water (50 mL), and extracted with ethyl acetate (50 mL×3). The combined organic phase was concentrated under reduced pressure, The resulting residue was purified with preparative TLC (ethyl acetate:petroleum ether=1:3) to give t-butyl N-(4-(1-(2-((t-butyldimethylsilyl)oxy)-2-(2-chloropyridin-3-yl) acetyl)-7-fluoroindol-5-yl) pyridin-2-yl)-N-(1-methyl-1H-pyrazol-5-yl)carbamate 94 (250 mg). Yield: 61%. LCMS: m/z 692.5 (M+H).

Step 5. Synthesis of 2-((t-butyldimethylsilyl)oxy)-2-(2-chloropyridin-3-yl)-1-(7-fluoro-5-(2-01-methyl-1H-pyrazol-5-yl)amino)pyridin-4-yl)indolin-1-yl) ethan-1-one (95)

Into a dry 100 mL round bottom flask, Compound 94 (250 mg, 0.36 mmol), dichloromethane (20 mL) and trifluoroacetic acid (5 mL) were added at room temperature. The reaction was stirred at room temperature for 2 h, cooled in ice bath, neutralized with saturated aqueous sodium bicarbonate solution (50 mL), and extracted with dichloromethane (30 mL×3). The combined organic phase was dried over anhydrous sodium sulfate, and filtered. The filtrate was concentrated under reduced pressure to give ((t-butyldimethylsilyl)oxy)-2-(2-chloropyridin-3-yl)-1-(7-fluoro-5-(2-((1-methyl-1H-pyrazol-5-yl) amino)pyridin-4-yl)indolin-1-yl)ethan-1-one 95 (200 mg, colorless oil). Yield: 93%. LCMS: m/z 593.1 (M+H)

Step 6. Synthesis of 2-(2-chloropyridin-3-yl)-1-(7-fluoro-5-(2-((1-methyl-1H-pyrazol-5-yl)amino)pyridin-4-yl)indolin-1-yl)-2-hydroxyethan-1-one (P60)

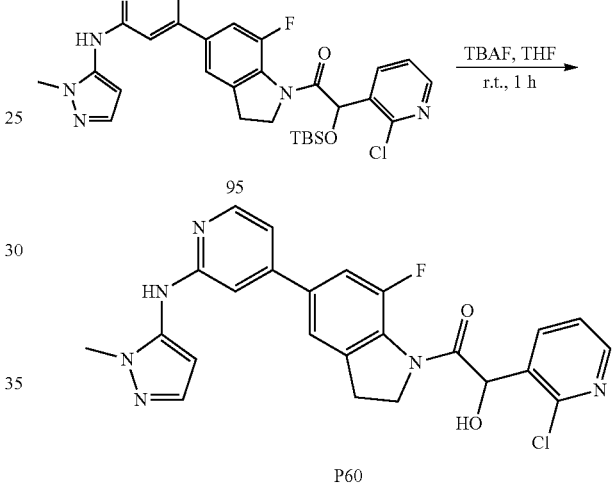

Into a dry 100 mL round bottom flask, Compound 95 (200 mg, 0.34 mmol), tetrahydrofuran (4 mL), tetrabutylammonium fluoride (1N solution in THF, 4 mL) were added at room temperature. The reaction was stirred at room temperature for 1 h, diluted with water (50 mL), and extracted with ethyl acetate (30 mL×3). The combined organic phase was dried over anhydrous sodium sulfate, and filtered. The filtrate was concentrated under reduced pressure. The resulting residue was purified by silica gel column chromatography (ethyl acetate:petroleum ether=1:20) to give 2-(2-chloropyridin-3-yl)-1-(7-fluoro-5-(2-((1-methyl-1H-pyrazol-5-yl) amino)pyridin-4-1-yl)-2-hydroxylethan-1-one P60 (120 mg, white solid), which was recrystallized from ethyl acetate n-hexane=1:2 to give 2-(2-chloropyridin-3-yl)-1-(7-fluoro-5-(2-((1-methyl-1H-pyrazol-5-yl) amino)pyridin-4-1-yl)-2-hydroxylethan-1-one P60 (55 mg, white solid). Yield: 34%.

$^1$H NMR (400 MHz, DMSO-d$_6$) δ 8.82 (s, 1H), 8.38 (dd, J=2.0, 4.8 Hz, 1H), 8.16 (d, J=5.6 Hz, 1H), 8.02 (dd, J=2.0, 7.6 Hz, 1H), 7.55-7.47 (m, 2H), 7.41 (d, J=12 Hz, 1H), 7.34 (d, J=1.6 Hz, 1H), 7.09 (dd, J=1.2, 5.2 Hz, 1H), 7.01 (s, 1H), 6.63 (d, J=6.8 Hz, 1H), 6.27 (d, J=2.0 Hz, 1H), 5.77 (d, J=6.4 Hz, 1H), 4.42-4.33 (m, 1H), 4.24-4.14 (m, 1H), 3.68 (s, 3H), 3.27-3.20 (m, 1H).

LCMS: m/z 479.0 (M+H).

Example P64 was obtained analogously to the preparation of Example 60 using intermediates similar to Intermediate 25.

| Ex. | Structure | Name | Analytical data |
|---|---|---|---|
| P64 | 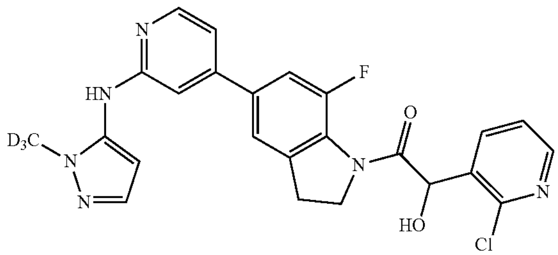 [SMILES: [2H]C([2H])([2H])n1nccc1Nc1cc(-c2cc(F)c3c(c2)CCN3C(=O)C(O)c2cccnc2Cl)ccn1] | 2-(2-chloropyridin-3-yl)-1-(7-fluoro-5-(2-((1-deuteriomethyl-1H-pyrazol-5-yl)amino)pyridin-4-yl)indolin-1-yl)-2-hydroxyethan-1-one | $^1$H NMR (400 MHz, DMSO-d$_6$) δ 8.82 (s, 1H), 8.38 (dd, J = 1.6, 4.8 Hz, 1H), 8.16 (d, J = 5.2 Hz, 1H), 8.02 (dd, J = 1.6, 7.6 Hz, 1H), 7.53 (dd, J = 4.8, 7.6 Hz, 1H), 7.49 (s, 1H), 7.41 (d, J = 12 Hz, 1H), 7.34 (d, J = 1.2 Hz, 1H), 7.09 (dd, J = 1.2, 5.2 Hz, 1H), 7.01 (s, 1H), 6.63 (d, J = 6.4 Hz, 1H), 6.27 (d, J = 1.2 Hz, 1H), 5.77 (d, J = 6.4 Hz, 1H), 4.39-4.35 (m, 1H), 4.24-4.17 (m, 1H), 3.27-3.20 (m, 1H). LCMS: m/z 482.0 (M + H). |

Step 7: Preparation of Compounds P62 and P63 by Resolution of Compound P60

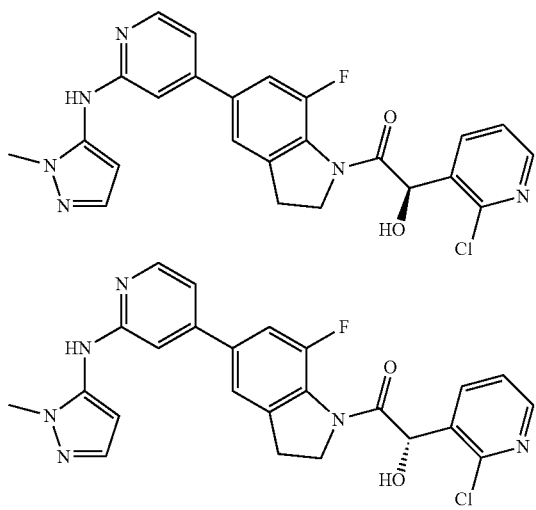

Resolution Conditions:
Chiral column: AD-H, 0.46 cm I.D.X15 cm L
Mobile phase: HEP:IPA (0.1% DEA)=60:40
Flow rate: 0.5 mL
Detection wavelength: UV 254 nm
Column temperature: 25° C.

The compound that was eluted first (Peak 1) was numbered P62

$^1$H NMR (400 MHz, DMSO) δ 8.81 (s, 1H), 8.38 (dd, J=4.8, 1.8 Hz, 1H), 8.16 (d, J=5.4 Hz, 1H), 8.02 (dd, J=7.6, 1.6 Hz, 1H), 7.52 (dd, J=7.6, 4.8 Hz, 1H), 7.48 (s, 1H), 7.40 (d, J=12.0 Hz, 1H), 7.34 (d, J=1.8 Hz, 1H), 7.09 (d, J=4.2 Hz, 1H), 7.00 (s, 1H), 6.61 (s, 1H), 6.27 (d, J=1.6 Hz, 1H), 5.77 (d, J=6.6 Hz, 1H), 4.37-4.41 (m, 1H), 4.26-4.14 (m, 1H), 3.68 (s, 3H), 3.22 (dd, J=13.4, 7.2 Hz, 2H).

LCMS: m/z 479.0 (M+H).

The compound that was eluted second (Peak 2) was numbered P63

$^1$H NMR (400 MHz, DMSO) δ 8.81 (s, 1H), 8.38 (dd, J=4.8, 1.8 Hz, 1H), 8.16 (d, J=5.4 Hz, 1H), 8.02 (dd, J=7.6, 1.8 Hz, 1H), 7.52 (dd, J=7.6, 4.8 Hz, 1H), 7.48 (s, 1H), 7.40 (d, J=12.0 Hz, 1H), 7.34 (d, J=1.8 Hz, 1H), 7.09 (dd, J=5.4, 1.6 Hz, 1H), 7.00 (s, 1H), 6.61 (d, J=6.8 Hz, 1H), 6.27 (d, J=1.8 Hz, 1H), 5.77 (d, J=6.8 Hz, 1H), 4.43-4.35 (m, 1H), 4.25-4.15 (m, 1H), 3.68 (s, 3H), 3.22 (dd, J=13.4, 7.2 Hz, 2H).

LCMS: m/z 479.0 (M+H).

Examples P40 and P41. Preparation of Compounds P40 and P41 by Resolution of Compound P53

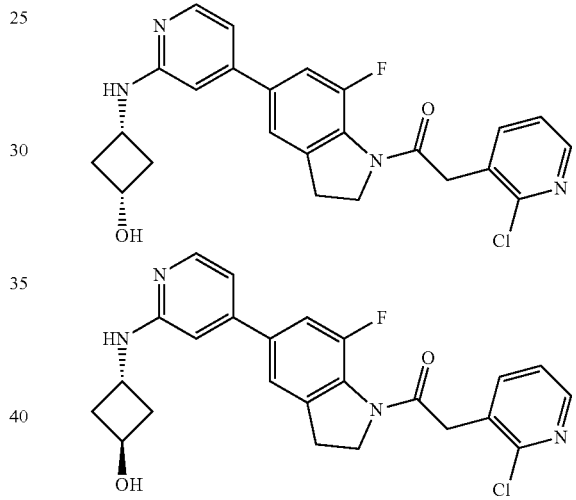

Resolution Conditions:
Chiral column: chiralpak-OJ, 0.46 cm I.D.×25 cm L
Mobile phase: HEX-EtOH (0.2% DEA)=50:50
Flow rate: 0.8 mL
Detection wavelength: UV 214/254 nm
Column temperature: 40° C.

The compound that was eluted first (Peak 1) was numbered P40

$^1$H NMR (CD$_3$OD, 400 MHz): 8.34 (d, J=4.8 Hz, 1H), 7.98 (d, J=5.6 Hz, 1H), 7.90 (d, J=7.6 Hz, 1H), 7.51 (s, 1H), 7.44-7.38 (m, 2H), 6.94-6.92 (m, 1H), 6.79 (s, 1H), 4.51-4.48 (m, 1H), 4.37 (t, J=8 Hz, 2H), 4.30-4.27 (m, 1H), 4.14 (s, 2H), 3.28 (t, J=7.6 Hz, 2H), 2.41-2.38 (m, 2H), 2.35-2.31 (m, 2H).

LCMS: m/z 452.8/454.9 (M+H)

The compound that was eluted second (Peak 2) was numbered P41

$^1$H NMR (CD$_3$OD, 400 MHz): 8.33 (d, J=4.8 Hz, 1H), 7.97 (d, J=6 Hz, 1H), 7.90 (d, J=7.6 Hz, 1H), 7.53 (s, 1H), 7.43-7.40 (m, 2H), 6.96 (d, J=5.6 Hz, 1H), 6.84 (s, 1H), 4.37 (t, J=7.6 Hz, 2H), 4.14 (s, 2H), 4.10-4.03 (m, 1H), 3.85-3.77 (m, 1H), 3.29 (t, J=8 Hz, 2H), 2.91-2.85 (m, 2H), 1.92-1.85 (m, 2H).

LCMS: m/z 452.8/454.9 (M+H)

Examples P42 and P43. Preparation of Compounds P42 and P43 by Resolution of Compound P16

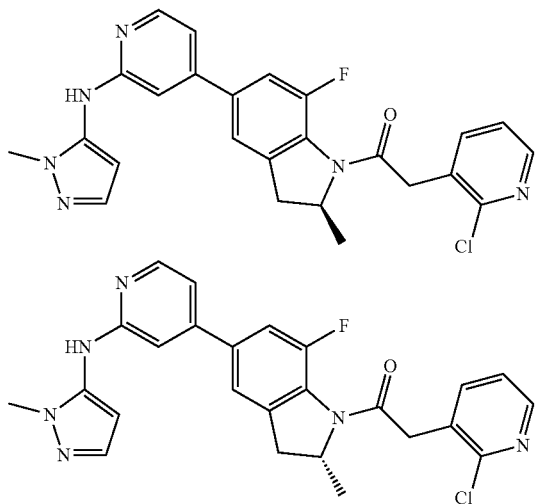

Resolution Conditions:
Chiral column: OJ, 0.46 cm I.D.*25 cm L
Mobile phase: n-hexane:ethanol(0.2% diethylamine)=50:50
Flow rate: 0.8 mL
Detection wavelength: UV 214/254 nm
Column temperature: 40° C.

The compound that was eluted first (Peak 1) was numbered P42

$^1$H NMR (400 MHz, DMSO-d$_6$) δ 8.82 (s, 1H), 8.34 (d, J=3.2 Hz, 1H), 8.16 (d, J=5.2 Hz, 1H), 7.89 (d, J=7.6 Hz, 1H), 7.52 (s, 1H), 7.49-7.41 (m, 2H), 7.34 (d, J=1.4 Hz, 1H), 7.10 (d, J=5.4 Hz, 1H), 7.01 (s, 1H), 6.28 (s, 1H), 4.97-4.89 (m, 1H), 4.18 (d, J=16.8 Hz, 1H), 3.96 (d, J=16.8 Hz, 1H), 3.68 (s, 3H), 3.57-3.51 (m, 1H), 2.72 (d, J=16.0 Hz, 1H), 1.27 (d, J=6.4 Hz, 3H).

LCMS: m/z 476.9 (M+H).

The compound that was eluted second (Peak 2) was numbered P43

$^1$H NMR (400 MHz, DMSO-d6) δ 8.82 (s, 1H), 8.34 (d, J=3.6 Hz, 1H), 8.16 (d, J=5.4 Hz, 1H), 7.89 (d, J=6.8 Hz, 1H), 7.52 (s, 1H), 7.48-7.41 (m, 2H), 7.34 (s, 1H), 7.10 (d, J=5.4 Hz, 1H), 7.01 (s, 1H), 6.27 (s, 1H), 4.98-4.89 (m, 1H), 4.18 (d, J=16.8 Hz, 1H), 3.96 (d, J=16.8 Hz, 1H), 3.68 (s, 3H), 3.57-3.51 (m, 1H), 2.72 (d, J=16.0 Hz, 1H), 1.27 (d, J=6.4 Hz, 3H).

LCMS: m/z 476.9 (M+H).

Effect Example I: Chemical Stability Assay

1. Detection Means and Conditions Used in the Chemical Stability Assay
Detection method: Ultra-high performance liquid chromatography (UPLC)

Chromatographic Conditions:
System: Ultra-high performance liquid chromatography system including pump, automatic sample injector, detector, and column oven
Column Waters Acquity UPLC BEH C18 (2.1*50 mm, 1.7 μm)
Detector: PDA detector
Detection wavelength: 225 nm
Mobile phase: A: 0.05% trifluoroacetic acid in water
B: acetonitrile
Gradient:

| Time (min) | A % | B % |
|---|---|---|
| 0 | 95 | 5 |
| 15 | 50 | 50 |
| 16 | 20 | 80 |
| 19 | 20 | 80 |
| 20 | 95 | 5 |
| 24 | 95 | 5 |

Flow rate: 0.4 ml/min
Column temperature: 40° C.
Injecion volume: 2 μl

2. Study on the Chemical Stability of the Compounds of the Invention (1). Formulation of Solutions of Test Compound P9

Compound P9 was formulated as solutions in different buffer systems at a concentration of 0.2 mg/ml using PEG400 as cosolvent. These solutions were used for chemical stability study. The solutions with various pH values were formulated as follows:

| Type of solutions | Solvent system | Found pH |
|---|---|---|
| Solution, pH 7.4 | 10% PEG400 + 90% phosphate buffer pH 7.4, adjusted with diluted phosphoric acid to pH 7.4 | 7.43 |
| Solution, pH 6.8 | 10% PEG400 + 90% phosphate buffer pH 6.8, adjusted with diluted phosphoric acid to pH 6.8 | 6.81 |
| Solution, pH 2.0 | 10% PEG400 + 90% HCl solution pH 2.0 | 1.99 |

Conditions for the chemical stability assay: the solutions of Compound P9 with various pH values were stored at 37° C. for 24 h. The content of Compound P9 was determined by HPLC at 0, 4, 8, 12, 14 and 24 h.

(2). Results Obtained from the Chemical Stability Assay of Test Compound P9 in Solutions with Various pH Values

| | Time | | | | | |
|---|---|---|---|---|---|---|
| | 0 h | 4 h | 8 h | 12 h | 14 h | 24 h |
| Solution of Compound P9, pH 7.4 | | | | | | |
| Percentage (%) relative to the peak area of the compound at the original point | 100.0 | 100.3 | 101.4 | 100.9 | 101.3 | 101.1 |

-continued

|  | Time | | | | | |
|---|---|---|---|---|---|---|
|  | 0 h | 4 h | 8 h | 12 h | 14 h | 24 h |
| Percentage (%) of the peak area of the total impurity | 0.72 | 0.67 | 0.65 | 0.67 | 0.71 | 0.74 |
| Solution of Compound P9, pH 6.8 | | | | | | |
| Percentage (%) relative to the peak area of the compound at the original point | 100.0 | 101.0 | 101.4 | 101.6 | 100.8 | 101.7 |
| Percentage (%) of the peak area of the total impurity | 0.75 | 0.69 | 0.71 | 0.71 | 0.68 | 0.68 |
| Solution of Compound P9, pH 2.0 | | | | | | |
| Percentage (%) relative to the peak area of the compound at the original point | 100.0 | 100.1 | 101.0 | 100.6 | 100.6 | 101.0 |
| Percentage (%) of the peak area of the total impurity | 0.84 | 0.85 | 0.85 | 0.85 | 0.84 | 0.85 |

(3). Conclusion

The results of this study showed that impurities were not significantly increased after storage of Compound P9 in the solutions with pH 2.0, pH 6.8, and pH 7.4 at 37° C. for 24 h, and Compound P9 had a good chemical stability.

3. Study on the Chemical Stability of the Reference Compound

Similarly, the chemical stability of Compound A107 of WO2017/114510A1 in solutions with pH 1.2, pH 6.8, pH 7.4 was studied using the method above.

(1). Formulation of Solutions of Compound A107

(1.1). Formulation of Compound A107 Solution (pH 1.2):

Solution composition: 10% PEG400+5% Solutol HS-15+ 85% pH 1.2 diluted hydrochloric acid Concentration: 0.2 mg/ml Formulation method: Compound A107 was weighed, added with PEG400 and Solutol HS-15 in the specified amount above, and vortexed to afford a clear solution. Said solution was added with the diluted hydrochloric acid pH 1.2 in the specified amount above and mixed uniformly.

(1.2). Formulation of Compound A107 solution (pH6.8):

Solution composition: 10% PEG400+5% Solutol HS-15+ 85% pH6.8 phosphate buffer

Concentration: 0.2 mg/ml

Formulation method: Compound A107 was weighed, added with PEG400 and Solutol HS-15 in the specified amount above, and vortexed to afford a clear solution. Said solution was added with phosphate buffer pH 6.8 in the specified amount above and mixed uniformly.

(1.3). Formulation of Compound A107 solution (pH7.4):

Solution composition: 10% PEG400+5% Solutol HS-15+ 85% pH 7.4 phosphate buffer

Concentration: 0.2 mg/ml

Formulation method: Compound A107 was weighed, added with PEG400 and Solutol HS-15 in the specified amount above, and vortexed to afford a clear solution. Said solution was added with phosphate buffer pH 7.4 in the specified amount above and mixed uniformly.

(2) Results Obtained from the Chemical Stability Assay of Compound A107 at Various pH Values:

|  | Time | | | | | |
|---|---|---|---|---|---|---|
|  | 0 h | 4 h | 8 h | 12 h | 14 h | 24 h |
| Solution of Compound A107, pH 7.4 | | | | | | |
| Percentage (%) relative to the peak area of the compound at the original point | 100.00 | 98.32 | 97.42 | 95.86 | 94.98 | 84.39 |
| Percentage (%) of the peak area of the total impurity | 0.48 | 2.15 | 3.05 | 4.6 | 5.48 | 16.02 |
| Solution of Compound A107, pH 6.8 | | | | | | |
| Percentage (%) relative to the peak area of the compound at the original point | 100.00 | 99.52 | 99.23 | 98.74 | 98.47 | 95.24 |
| Percentage (%) of the peak area of the total impurity | 0.39 | 0.87 | 1.16 | 1.65 | 1.91 | 5.13 |
| Solution of Compound A107, pH 2.0 | | | | | | |
| Percentage (%) relative to the peak area of the compound at the original point | 100.00 | 99.94 | 99.90 | 99.83 | 99.79 | 99.27 |
| Percentage (%) of the peak area of the total impurity | 0.35 | 0.41 | 0.45 | 0.52 | 0.56 | 1.08 |

The results in the table above showed that impurities were significantly increased after storage of Compound A107 of WO2017/114510A1 in solutions with pH 1.2, pH 6.8 and pH 7.4 at 37° C. for 24 h, and Compound A107 had a poor chemical stability under acidic, neutral, and slightly alkaline conditions.

Effect Example II: In Vitro Enzyme Activity Assay

Half inhibitory activity of the compounds of the invention against ERK2 kinase ($IC_{50}$ value) was determined in this Example.

(1). Materials and Instruments:

Enzyme: extracellular signal-regulated kinase ERK2 kinase (PV3595, Invitrogen)

Kit: Z'-LYTE® Protein Kinase Assay Kit-Ser/Thr 3 Peptide (PV3176, Invitrogen)

Kit components: The substrate Z'-LYTE™ Ser/Thr 3 Peptide (PV3200)

The phosphorylation substrate Z'-LYTE™ Ser/Thr 3 Phospho-peptide (PV3215)

5× kinase buffer: 250 mM HEPES (pH 7.5), 50 mM $MgCl_2$, 5 mM EGTA, 0.05% BRIJ-35 (PV3189, Invitrogen)

ATP (PV3227, Invitrogen)

Development Reagent A (PV3295, Invitrogen)

Development Buffer (P3127, Invitrogen)

Stop Reagent (P3094, Invitrogen)

Microplate reader: The multil-mode microplate reader PerkinElmer EnVision®

Microplate: black shallow 384-well microplate (6008269, PerkinElmer)

(2). Assay Protocol:

The substrate Z'-LYTE™ Ser/Thr 3 Peptide, the phosphorylation substrate Z'-LYTE™ Ser/Thr 3 Phospho-peptide, 1× kinase buffer (5× kinase buffer was diluted with ultra pure water by five times), ATP, Development Reagent A, Development Buffer, Stop Reagent were balanced to room temperature for use. The screening concentrations for detecting the effect of the compounds of the invention on the ERK kinase activity were seven 3-fold serial dilutions starting from 1 μM (from 0.2 μM for the positive drug control) using 4% DMSO as co-solvent. 5 μL enzyme system (50 mM HEPES pH 7.5, 1 mM EGTA, 10 mM $MgCl_2$, 0.01% Brij-35, 4 uM substrate, 0.8 ng/μL enzyme), 2.5 μL Compound, 2.5 μL 400 μM ATP were added into 384 well microplate, followed by incubation at room temperature for 60 min in the dark. After the reaction was completed, 5 μl the developing agent (Development Reagent A) diluted with the developing buffer (Development Buffer) was added to all reaction wells, followed by incubation at the room temperature for 60 min in the dark. 5 μL the terminating agent was added to each well to terminate the reaction. The fluorescence was determined using the multil-mode microplate reader PerkinElmer EnVision® (excitation wavelength 400 nm, emission wavelength 460 nm and 528 nm).

The inhibition rate of each well was calculated from 100% phosphorylation substrate well and 0% phosphorylation substrate well using the data analysis method below:

phosphorylation %=1−{(emission rate×$F_{100\%}$−$C_{100\%}$)/[$C_{0\%}$−$C_{100\%}$+emission rate×($F_{100\%}$−$F_{0\%}$)]}×100 inhibition %=100×(1−phosphorylation % of the test compound well/phosphorylation % of the 0% inhibition control)

wherein:

emission rate=fluorescence emission of the sample at 445 nm/fluorescence emission of the sample at 520 nm $F_{100\%}$=the average fluorescence emission of the control well of 100% phosphorylation substrate at 520 nm $F_{0\%}$=the average fluorescence emission of the control well of 0% phosphorylation substrate at 520 nm $C_{100\%}$=the average fluorescence emission of the control well of 100% phosphorylation substrate at 445 nm $C_{0\%}$=the average fluorescence emission of the control well of 0% phosphorylation substrate at 445 nm Tests were carried out in duplicate. $IC_{50}$ values were calculated from the inhibition of the kinase by the test compounds at a range of different concentrations.

(3). Results

The inhibiton activity data of the compounds of the invention on the ERK2 kinase activity ($IC_{50}$) were listed in the table below, wherein:

A: represented that the $IC_{50}$ of the compound was less than or equal to 10 nM;

B: represented that the $IC_{50}$ of the compound was more than 10 nM and less than 100 nM;

C: represented that the $IC_{50}$ of the compound was more than or equal to 100 nM and less than 1 μM.

The Inhibiton Activity Data of the Compounds of the Invention on the ERK2 Kinase Activity

| Compound No. | ERK2 $IC_{50}$ |
| --- | --- |
| P1 | C |
| P2 | B |
| P3 | B |
| P4 | B |
| P5 | A |
| P6 | B |
| P7 | B |
| P8 | C |
| P9 | A |
| P10 | A |
| P11 | B |
| P12 | B |
| P13 | C |
| P14 | B |
| P17 | B |
| P18 | A |
| P19 | C |
| P28 | B |
| P29 | B |
| P30 | B |
| P31 | A |
| P32 | A |
| P33 | B |
| P34 | B |
| P35 | B |
| P36 | B |
| P37 | B |
| P38 | B |
| P39 | C |
| P40 | B |
| P41 | B |
| P43 | B |
| P44 | B |
| P45 | A |
| P46 | A |
| P47 | A |
| P48 | A |
| P49 | A |
| P50 | C |
| P53 | C |
| P54 | B |
| P55 | B |
| P56 | B |

-continued

| Compound No. | ERK2 IC$_{50}$ |
|---|---|
| P57 | C |
| P58 | A |
| P61 | B |

More specifically, the IC$_{50}$ values of Compounds P5, P9, P10, P18, P42, P59 and P60 in this Example were 8.2 nM, 3.3 nM, 6.1 nM, 3.0 nM, 2.7 nM, 4.8 nM and 10 nM, respectively.

Effect Example III: In Vitro Cell Study

The inhibitory activity of Compound P9 of the invention and the representative compounds of WO2017/114510A1 on the proliferation of human melanoma cell line A375 (IC$_{50}$ value) was determined in this Example.

(1). Materials and Instruments:
 Cell: human melanoma cell line A375 (CRL-1619™, ATCC)
 Detection reagent: sulforhodamine B SRB (S9012, Sigma)
 Microplate: 96 well microplate (3599, Corning)
 Microplate reader: full-wavelength microplate reader (SpectraMax 190, Molecular Devices)

(2). Assay Protocol:

Cells in logarithmic growth phase were seeded at appropriate density (3500/well) into 96-well microplates in the volume of 90 μL per well. After incubation in a CO$_2$ incubator at 37° C. overnight, 10 μL of the compound at various concentrations or saline for medium control was added in triplicate and incubated for 72 h, and a blank well was set. After the end of the action, the culture liquid was removed from the cells, and 10% (w/v) trichloroacetic acid (100 μL/well) was added for fixation at 4° C. for 1 h, followed by five washes with distilled water. After drying in an oven, 100 μL of SRB solution (4 mg/mL, dissolved in 1% glacial acid) was added into each well. After incubation for staining at room temperature for 15 min, the unbound SRB was removed by five washes with 1% glacial acid. The microplates were dried in an oven, and 150 μL of 10 mM Tris solution was added to each well. The optical density (OD value) at the wavelength of 560 nm was measured using a full-wavelength microplate reader SpectraMax 190. The inhibition rate of the drug on the growth of the tumor cells was calculated according to the following formula:

$$\text{Inhibition rate (\%)} = \left(1 - \frac{OD \text{ value of the compound well}}{OD \text{ value of the negative control}}\right) \times 100\%$$

The IC$_{50}$ values were obtained by regression with four-parameter method using the software attached to the microplate reader. The assay was repeated twice.

The assay results were listed in the table below.

Comparison of the Cell-Based Activity Data Between the Representative Compounds of WO2017/114510A1 and Compound P9 of the Invention

| Compound | IC$_{50}$ against A375 cell (μM) |
|---|---|
| Compound A1 of WO2017/114510A1 | 6.10 |
| Compound A179 of WO2017/114510A1 | 0.957 |
| Compound A205 of WO2017/114510A1 | 2.70 |
| Compound A200 of WO2017/114510A1 | 7.80 |
| Compound A180 of WO2017/114510A1 | >10.0 |
| Compound P9 of the invention | 0.363 |

The assay results showed that Compound P9 of the invention had a significantly higher activity than the representative compounds of WO2017/114510A1.

Effect Example IV: Permeability Study

The permeability of Compound P9 of the invention and Compound A107 of WO2017/114510A1 was determined using Caco-2 cell in vitro drug absorption model in this Example (1). Materials and Instruments:
 Cell: human intestinal cancer Caco2 (HTB-37, ATCC)
 Petri dish: 10 cm petri dish (430167, Corning)
  Millicell-24 microplage (PSHT010R$_5$, Millipore)
 Buffer: PBS (14190, Invitrogen)
  HEPES (H0887, Sigma)
  HBSS (H8264, Sigma)
 Substances related to cell culture:
  high glucose DMEM medium (L0103-500, Biowest)
  fetal bovine serum (S1810-500, Biowest)
  trypsin (255200-056, Invitrogen)
  nonessential amino acid (M7145, Sigma)
  penicillin and streptomycin (B-13234, GIBCO)
  sodium pyruvate (11360-070, Invitrogen)
  L-glutamine (25030-081, Invitrogen)
 Relevant reagents: fluorescein (L0144, Sigma)
  propranolol (P831800, Sigma)
  colchicine (C9754, Sigma)
  atenolol (A7655, Sigma)
 Instruments: liquid chromatography (Waters Acquity UPLC I-class, Waters)
  mass spectrometry (Waters xevo TQ-S MS/MS, Waters)
  ohmmeter (Millicell-ERS, Thermo)
  microplate reader (Infinite Pro, Tecan)

(2). Assay Protocol:

Establishment of Caco-2 Cell Monolayer Model

1) The Caco-2 cells were revived, and incubated in a 10 cm petri dish in a 5-6% CO$_2$ and 95% RH incubator at 37° C. The medium was high glucose DMEM medium supplemented with 10% fetal bovine serum, 1% glutamine, 1% non-essential amino acid, 100 U/mL penicillin, and 100 μg/mL streptomycin.
2) When the cell grew to 80-90% confluency, the cells were digested with trypsin, and centrifuged. The supernatant was discarded. The cells were re-suspended in 6 ml complete medium, and counted three times.
3) The cells were harvested by centrifugation at 1000 rpm for 5 min, and diluted in suspension. The cells were seeded in Millicell-24 well microplate at the concentration of $2\times10^5$/mL in the volume of 400 μL per well. 800 μL of the culture liquid was added to the substrate side for incubation in a 5% $CO_2$ incubator at 37° C.

4) The medium was replaced 72 h after the seeding of the cells, and then every other day. The cells were incubated for 21 days.

Evaluation of Caco-2 Monolayer Cells

1) After 21 days of incubation, the integrity of the Caco-2 monolayer cells in each well was assessed by measuring the electric resistance across the membrane during the cell growth.
2) Marker leakage inspection The integrity of the Caco-2 cell monolayer was verified by fluorescent marker Lucifer Yellow. On day 21 of the growth of the cell monolayer, 200 μL of Lucifer Yellow (100 μg/ml) was added to the top side (apical side, AP side) of the cell layer, and 800 μL of HBSS liquid was added to the basal side (basolateral side, BL side). After incubation in 5% $CO_2$ incubator at 37° C. for 1.5 h, sample was collected, and the absorbance was measured at wavelength 485-535 nm. The leakage amount was calculated and generally not more than 0.4%. The blank HBSS solution was used as blank control.

Bilateral Transport Experiment

Under the same conditions, drug transport from the top side (apical side, AP side)→the basal side (basolateral side, BL side) and from BL side→AP side of the Caco-2 cell layer was simultaneously determined.
1) The mother liquids of the compounds were prepared in DMSO at a concentration of 10 mM.
2) The mother liquor was diluted with HBSS solution to 20 μm working concentration.
3) The cells were washed three times with HBSS, and the TEER value was measured with a cell potentiometer.
4) Reference compound or test compound and HBSS were added to both sides of the cells at 400 μL/well on the AP side and 800 μL/well on the BL side, respectively.
5) Samples were respectively collected from the AP side and the BL side after incubation in 5% $CO_2$ incubator at 37° C. for 1.5 h.

(3). Data Analysis:

The apparent permeability coefficients $P_{app}$ of the drugs across the Caco-2 cell model were calculated according to the following formula (1):

$$\text{Papp}=(V_A/(\text{Area}\times\text{Time}))\times([\text{drug}]_{acceptor}/[\text{drug}]_{initial\ donor}) \quad (1)$$

wherein $V_A$ is the volumn at the acceptor side, Area is the film area ($cm^2$), Time is the reaction time, $[\text{drug}]_{acceptor}$ is the drug concentration at the acceptor side, and $[\text{drug}]_{initial\ donor}$ is the drug concentration at the donor side.

The assay results were listed in the table below.

| | Compound A107 of WO2017/114510A1 | Compound P9 of the invention |
|---|---|---|
| apparent permeability coefficient (Caco-2) | From A to B = $1.54 \times 10^{-6}$ cm/s | From A to B = $23.69 \times 10^{-6}$ cm/s |
| Efflux Ratio | 26.2 | 1.3 |

From the assay results of the permeability parameters, it was seen that Compound P9 of the invention had a significantly higher apparent permeability coefficient (Papp, Apical to Basal) than Compound A107 of WO2017/114510A1 in the Caco-2 permeability assay. It is known that a drug is believed to have good permeability if it has Papp$>2\times10^{-6}$ (see, for example, Journal of Pharmacological and Toxicological Methods 44 (2000) 235-249). The apparent permeability coefficient of Compound P9 was significantly higher than this index, but that of Compound A107 was lower than this index. Moreover, Compound A107 had a higher Efflux Ratio, while the Efflux Ratio of Compound P9 was lower. Thus, Compound P9 has a better permeability and is expected to have a better intestinal absorption property and a better oral absorption degree in vivo.

Effect Example V: Solubility Assay

The thermodynamic solubility of the compounds of the invention was determined in this Example
(1). Reagents and Materials:

| Name | Supplier | Catalog No./Batch No. |
|---|---|---|
| DPBS | Corning | R21-031-CV |
| HBSS | Sigma | RNBC5907 |
| ACN | Merck | JA054630 |
| NaOH | SinoPharm Group | 20120515 |
| HCl | SinoPharm Group | 20160503 |
| 384 well microplate | Greiner | B16093FV |
| DMSO | Merck | K42958652 225 |

(2) Instruments and Equipments:

| Name | Source |
|---|---|
| ThermoMixer | Eppendorf |
| Centrifuge | Eppendorf 5424R centrifuge, Eppendorf |
| Centrifuge | Eppendorf 581 OR centrifuge, Eppendorf |
| Plate sealer | Plate Loc sealer, Agilent |
| Oscillator | IKA MS3 digital oscillator, IKA |
| Liquid chromatograph | Waters ACQUITY I-Class System, Waters |
| pH meter | Sartorius PB-10, Sartorius |
| Vortex generator | MS3 digital vortex generator, IKA |
| Analytical balance | Sartorius MSE125P-100-DA analytical balance |
| MS/MS system | Waters ACQUITY XEVO TQ-S (ESI source), Waters |

(3) Assay Protocol:
Blank Vehicle with Different pH Values:
　　PH7.4: DPBS
　　PH6.8: 9900 μL HBSS+100 μL HEPS+5 μL 2N NaOH
　　PH7.4: DPBS adjusted with 2N HCl to pH 2.0
Incubation:
　　About 3 mg of the compound was weighed, added with 500 μL of blank vehicle, and shaked at 37° C. for 24 h.
Sample Treatment:
　　After incubation, the samples were centrifuged for 30 min, and the supernatant was transferred to a new EP tube and further centrifuged for 30 min
　　After centrifugation, the samples were diluted by 100 times with $ACN/H_2O$ (V/V, 1:1).
　　Linear concentration range from 12.5 nM to 1 mM was configured with $ACN/H_2O$ (V/V, 1:1).
Biological Analysis:
　　All samples were mixed with water at the 1:1 ratio by volume, centrifuged at 4000 rpm for 5 min, and analyzed by LC-MS/MS.

Analysis Methods:
Chromatography Conditions:
Analysis column: Acquity BEH C18 (1.7 μm; 2.1×50 mm, Waters)
Mobile phase A: 0.1% FA in $H_2O$
Mobile phase B: 0.1% FA in CAN/MEOH (9:1, V/V)
Gradient: as shown in the table below.

| Time (h) | Flow rate (mL/min) | A % | B % | Curve (h) |
|---|---|---|---|---|
| original | 0.5 | 80 | 20 | original |
| 1.2 | 0.5 | 40 | 60 | 6 |
| 1.5 | 0.5 | 10 | 90 | 6 |
| 2.0 | 0.5 | 80 | 20 | 1 |

MS/MS System
Multiple Reaction Monitoring (MRM) mode was used:

| Compound | Ionization mode | MRM |
|---|---|---|
| Compound P9 of the invention | ESI, positive | 463.047 > 307.588 |

(4) Results:

| Compound No. | Maximum solubility in pH 2.0 PBS (uM) | Maximum solubility in pH 6.8 HBSS/ HEPES 10 mM/ BSA 0.1% (uM) | Maximum solubility in pH 7.4 PBS (uM) |
|---|---|---|---|
| Compound A65 of WO2017/114510A1 | 43.0 ± 2.33 | 31.7 ± 0.229 | 11.9 ± 1.36 |
| Compound A107 of WO2017/114510A1 | 1011 ± 11.2 | 4.53 ± 1.13 | 2.53 ± 0.175 |
| Compound P9 of the invention | 2847 ± 62 | 267 ± 3 | 544 ± 5.3 |

The results above showed that at the three pH values examined, Compound P9 of the invention had much higher solubility than the compounds of WO2017/114510A1, and was advantageous for formulation into a medicament.

Effect Example VI: Pharmacokinetic Study in Animal Model

The pharmacokinetic parameters of Compound P9 of the invention and the representative compounds of WO2017/114510A1 in mice were determined in this Example.
(1) In Vivo Pharmacokinetics Protocol for Single Intravenous (IV) and Oral (PO) Administration to ICR Mice (1.1) Formulation of Test Substances The concentration during formulation of test substances was calculated on the basis of pure free base.
Intravenous Injection (IV)
The test substance was accurately weighed, and added with the excipients (5% DMSO+5% Solutol+90% saline) in the specified amounts. After complete dissolution, the dosing solution for intravenous injection was obtained at the concentration of 0.2 mg/mL.
Oral Administration by Gavage (PO)
The test compound was accurately weighed, and added with the excipients (0.4% methylcellulose (viscosity: 400 cps)) in the specified amount. After sufficiently mixing, the dosing solution for oral administration was obtained at the concentration of 1 mg/mL.

(1.2) Animal Reception and Adaptation

Forty male SPF grade ICR mice were purchased from Shanghai Xipuer-Bikai Laboratory Animal Co., Ltd., and 30 normal healthy ICR mice of them passed the physical examination and were used in this study. Animal weight: 20.12-25.56 g.

(1.3) Administration to Animals

The experiments were conducted in the 30 male ICR mice as shown in the table below.

| Group | Number of animals M | Administration dosage mg/kg | Administration concentration mg/mL | Administration volumn mL/kg | Adiministration mode |
|---|---|---|---|---|---|
| 1 | 15 | 1 | 0.2 | 5 | Intravenous injection |
| 2 | 15 | 10 | 1 | 10 | Oral administration by gavage* |

*All animals were fasted for 10-14 h prior to the administration, and fed 2 h after the administration.

(1.4) Collection and Treatment of Samples

Blood was collected through the orbit or through cardiac puncture after carbon dioxide ($CO_2$) euthanasia. About 0.20 milliliter (mL) of blood was collected for each sample with heparin sodium as anticoagulant agent. The samples were placed on ice after collection.
Blood collecting time points in the intravenous and oral administration groups: before administration as well as 5 min, 15 min, 30 min, 1 h, 2 h, 4 h, 6 h, 8 h and 24 h after administration, as shown in the table below.

| IV & PO | before adminis- tration | 5 min | 15 min | 30 min | 1 h | 2 h | 4 h | 6 h | 8 h | 24 h |
|---|---|---|---|---|---|---|---|---|---|---|
| 3 mice | X | | | | | X | | | | |
| 3 mice | | X | | | | | X | | | |
| 3 mice | | | X | | | | | X | | |
| 3 mice | | | | X | | | | | X | |
| 3 mice | | | | | X | | | | | X |

Blood samples were placed on ice upon collection. The plasma was separated by centrifugation (centrifugation conditions: 8000 rpm, 6 minutes, 2-8° C.). The collected plasma was stored at −80° C. for analysis.
The biological samples of the test substances were analyzed by LC-MS/MS. The analysis method used was described under (1.7). The LLOQ for the detection of the samples was 1 ng/mL. The sample analysis for standard curve and quality control was also conducted during the detection of test substances.

(1.5) Aminal Disposal

After the end of the experiment, all animals were euthanized according to the institutional SOP.

(1.6) Pharmacokinetic Analysis

The pharmacokinetic parameters were calculated from the blood concentration data of the drug, using WinNonlin 7.0 to provide the parameters such as $AUC_{0-t}$, $AUC_{0-\infty}$, $MRT_{0-\infty}$, $C_{max}$, $T_{max}$, and $T_{1/2}$, and the average and standard deviation thereof.

For those samples with concentrations below the lower limit of quantitation, when calculating the pharmacokinetic parameters, samples collected before $C_{max}$ should be calculated as zero, and samples collected at the points after $C_{max}$ should be calculated as being below the limit of qualitification (BLQ).

(1.7) Analysis Method a. Instruments and Equipments
LC-MS/MS

Ultra high performance liquid chromatography system (Waters, ACQUITY UPLC), including binary solvent manager (ACQUITY UPLC Binary Solvent Manager), sample manager (ACQUITY UPLC Autosampler Mod.), high-throughput sample organizer (ACQUITY UPLC Sample Organizer), high temperature column oven (ACQUITY UPLC Column Heater HT).

Mass spectrometer (API 4000, Applied Biosystems), electrospray ionization source (ESI), tandem quadrupole mass analyzer.

The data processing system was Analyst software (Applied Biosystems, software version no. 1.5.1).

Micro-analytical balance (XP26, METTLER TOLEDO Instruments (Shanghai) Co., Ltd.); vortex oscillator (SI-A256, Scientific Industries, Inc.); small desktop high-speed refrigerated centrifuge (5417R, Eppendorf); ultra-pure water machine (Millipore); pipette (Eppendorf).

Reagents

Methanol (Burdick & Jackson, HPLC), acetonitrile (Burdick & Jackson, HPLC), formic acid (J & K), ultra pure water.

b. LC-MS/MS Conditions

The liquid chromatography conditions are as follows:

| column: ACQUITY UPLC HSS T3 1.8 μm (50 mm × 2.10 mm) mobile phase: | | |
|---|---|---|
| Time (min) | A(%) | B(%) |
| 0.00 | 80 | 20 |
| 0.40 | 10 | 90 |
| 0.80 | 10 | 90 |
| 0.81 | 80 | 20 |
| 1.20 | 80 | 20 |

A: 0.1% aqueous formic acid
B: 0.1% formic acid in methanol
Column temperature: 40° C.
Autosampler temperature: 4° C.
Flow rate: 500 μL/min
Injection volumn: 1 μL The mass spectrometry conditions are as follows:

| Scan mode: positive ion multiple reaction monitoring mode | |
|---|---|
| Ion source: ESI source | Spray mode: electrospray |
| Q1 resolution: Unit | Q3 resolution: Unit |
| Spray gas (Gas 1): 65 psi | Heater gas (Gas2): 65 psi |
| Curtain gas (CUR): 35 psi | Collision gas (CAD): 10 |
| Ion source voltage (IS): 5500 v | Ion source temperature (TEM): 550° C. | c. Formulation of Samples for Standard Curve and Samples for Quality Control

An amount of test substance was weighed, added with methanol to completely dissolve it to prepare a stock solution with a concentration of 569,000 ng/mL. An amount of the stock solution was taken and diluted with methanol to a working solution with a concentration of 200,000 ng/mL. The 200,000 ng/mL standard solution was added to blank plasma at the ratio of 1:39 to prepare the sample for standard curve with a concentration of 5000 ng/mL. The 5000 ng/mL standard curve sample was diluted with blank plasma sequentially to obtain 1000, 500, 100, 50, 10, 5, 1 ng/mL standard curve samples, and 800, 200, 2.5 ng/mL quality control samples. The specific formulation process was shown in Table I.

TABLE I

Formulation of samples for standard curve and QC

| Standard sample | Sample taken | Concentration taken (ng/mL) | Volumn taken (μL) | Volumn of vehicle (μL) | Final volumn (μL) | Final concentration (ng/mL) |
|---|---|---|---|---|---|---|
| STD-PRE | NA | 200,000 | 20 | 780 | 800 | 5000 |
| STD-7 | STD-PRE | 5000 | 100 | 400 | 500 | 1000 |
| STD-6 | STD-7 | 1000 | 200 | 200 | 400 | 500 |
| STD-5 | STD-6 | 500 | 100 | 400 | 500 | 100 |
| STD-4 | STD-5 | 100 | 200 | 200 | 400 | 50 |
| STD-3 | STD-4 | 50 | 100 | 400 | 500 | 10 |
| STD-2 | STD-3 | 10 | 200 | 200 | 400 | 5 |
| STD-1 | STD-2 | 5 | 100 | 400 | 500 | 1 |
| DQC | STD-PRE | 5000 | 5 | 45 | 50 | 500 |
| QCH | STD-PRE | 5000 | 80 | 420 | 500 | 800 |
| QCM | QCH | 800 | 100 | 300 | 400 | 200 |
| QCL | STD-2 | 5 | 100 | 100 | 200 | 2.5 |

Working solution of the internal standard: Pipette an amount of tolbutamide stock solution with a concentration of 767,000 ng/mL into a volumetric flask, make up to volume with methanol, and mix well to obtain the working solution of the internal standard.

d. Treatment of Plasma Sample

50 μL sample (samples for standard curve/samples for quality control/biological samples) was taken into a 1.5 mL centrifuge tube, added with 250 μL internal standard solution (added with the same volume of methanol, instead of the internal standard, for blank control), and mixed well by vortex. The mixture was centrifuged at 14000 rpm for 5 minutes. 200 μL of the supernatant was taken and added into the corresponding 96-well sample plate for LC-MS/MS analysis.

(2) Results

The pharmacokinetic data of the representative compounds of WO2017/114510A1 and Compound P9 of the invention were compared as follows.

| Compound | Pharmacokinetic parameters |
|---|---|
| Compound A1 of WO2017/114510A1 | $nAUC_{0-t}$/(ng · h/ mL, po): 145.0<br>$CL_z$/(L/hr/kg): 4.81<br>F/(%, po): 70.07 |
| Compound A35 of WO2017/114510A1 | $nAUC_{0-t}$/(ng · h/ mL, po): 66.97<br>$CL_z$/(L/hr/kg): 4.69<br>F/(%, po): 32.07 |
| Compound A179 of WO2017/114510A1 | $nAUC_{0-t}$/(ng · h/ mL, po): 0.00<br>$CL_z$/(L/hr/kg): 60.11<br>F/(%, po): 0.00 |

| Compound | Pharmacokinetic parameters |
| --- | --- |
| Compound A114 of WO2017/114510A1 | nAUC$_{0-t}$/(ng · h/ mL, po): 180.44<br>CL$_z$/(L/hr/kg): 2.61<br>F/(%, po): 49.46 |
| Compound P9 of the invention | nAUC$_{0-t}$/(ng · h/ mL, po): 1696.3<br>CL$_z$/(L/hr/kg): 0.36<br>F/(%, po): 60.55 |

From the measured results of in vivo pharmacokinetic parameters in these mice, it was seen that Compound P9 of the invention had a significantly greater area under curve (AUC), lower in vivo clearance (CLz), and better bioavailability in mice, compared with the compounds of WO2017/114510A1. Thus, this compound is expected to have better absorption after oral administration and better drugability.

Formulation Example I

An amount of Compound P9 was accurately weighed, added with 5% DMSO+5% Solutol+90% saline or the like, to completely dissolve it to give the dosing solution with a concentration of 0.2 mg/mL, which was filtered sterile for intravenous injection administration.

Formulation Example II

An amount of Compound P9 was accurately weighed, added with 0.4% methylcellulose (viscosity: 400 cps) to the final volumn. After sufficiently mixing, the dosing solution for oral administration was obtained at the concentration of 1 mg/mL.

All documents mentioned in the present disclosure are incorporated herein by reference in their entirety, as if they are individually listed. It is noted that based on the present disclosure, various changes or modifications to the invention are obvious to those skilled in the art, and these equivalent forms also fall within the scope defined by the claims appended to this application.

The invention claimed is:

1. A compound of Formula (Ie), or a stereoisomer, racemate, geometric isomer, tautomer, hydrate, solvate or pharmaceutically acceptable salt thereof, (Ie)

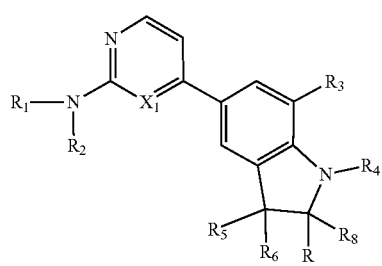

wherein, $X_1$ is selected from the group consisting of CH, CD, and N;

$R_1$ is selected from the group consisting of H and D;

$R_2$ is selected from the group consisting of $C_{1-6}$alkyl optionally substituted with one or more hydroxyl, $C_{3-8}$cycloalkyl optionally substituted with one or more hydroxyl, 3-8 membered heterocyclyl, and 5-7 membered heteroaryl optionally substituted with one or more substituents selected from —CD$_3$, $C_{1-6}$alkyl and hydroxyl$C_{1-6}$alkyl;

$R_3$ is selected from the group consisting of halo and $C_{1-6}$alkyl;

$R_4$ is —CO(CR$_{10}$R$_{11}$)$_m$R$_{12}$; wherein m is 0, 1, 2 or 3, and wherein $R_{10}$ and $R_{11}$ are each independently selected from the group consisting of H, D, and $C_{1-4}$alkyl optionally substituted with hydroxyl; and $R_{12}$ is each independently selected from optionally substituted phenyl and optionally substituted pyridinyl, wherein the optional substituent is one or more substituents independently selected from the group consisting of D, halo, $C_{1-4}$alkyl, cyano, and $C_{3-8}$heterocyclyl-(CH$_2$)$_{0-4}$—; and $R_5$, $R_6$, $R_7$ and $R_8$ are each independently selected from the group consisting of —H, and $C_{1-6}$alkyl optionally substituted with hydroxyl or —O$C_1$-$C_6$alkyl, provided that the compound is not 2-(2-chloropyridin-3-yl)-1-(7-fluoro-2-(hydroxylmethyl)-5-(2-(isopropylamino)pyrimidin-4-yl)indolin-1-yl)ethan-1-one.

2. The compound according to claim 1, wherein $R_2$ is selected from the group consisting of $C_{1-4}$alkyl optionally substituted with one or more hydroxyl;

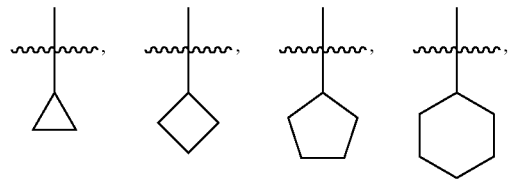

which are optionally substituted with one or more hydroxyl;

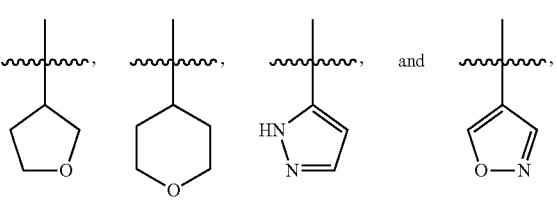

which are optionally substituted with one or more substituents independently selected from the group consisting of $C_{1-4}$alkyl, —CD$_3$ and hydroxyl$C_{1-4}$alkyl.

3. The compound according to claim 1, wherein $R_3$ is selected from the group consisting of fluoro, chloro, bromo, iodo, —CH$_3$, —CH$_2$CH$_3$, —CH(CH$_3$)$_2$, and —CH$_2$CH$_2$CH$_3$.

4. The compound according to claim 1, wherein $R_{12}$ is selected from the group consisting of

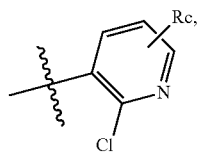

wherein Rc is selected from the group consisting of halo, C$_{1-4}$alkyl,

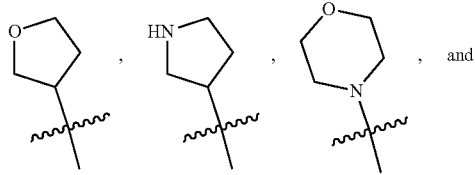, and

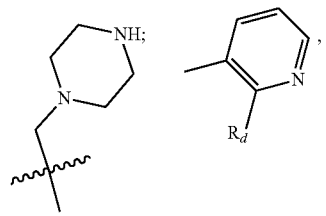

wherein R$_d$ is selected from the group consisting of H, C$_{1-4}$alkyl, and

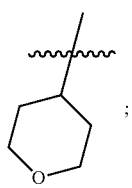;

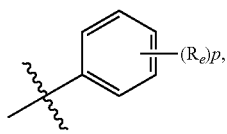

wherein R$_e$ is selected from the group consisting of halo, and p is 1 or 2; and

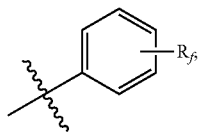

wherein R$^f$ is selected from the group consisting of

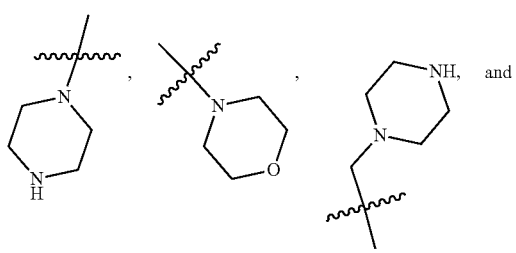

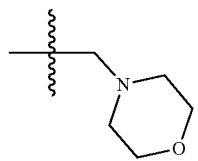

5. The compound according to claim 1, wherein R$_4$ is selected from the group consisting of —CO(CR$_{10}$R$_{11}$)$_m$R$_{12}$, wherein m is 0, 1, 2 or 3, and wherein
R$_{10}$ and R$_{11}$ are each independently H; and
R$_{12}$ is selected from the group consisting of

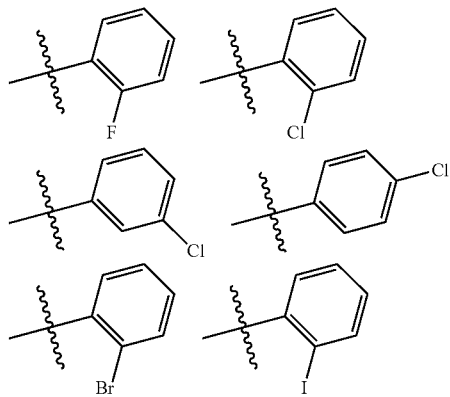

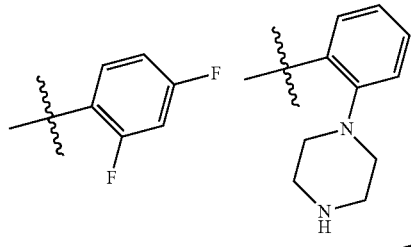

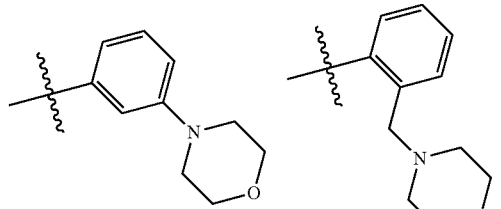

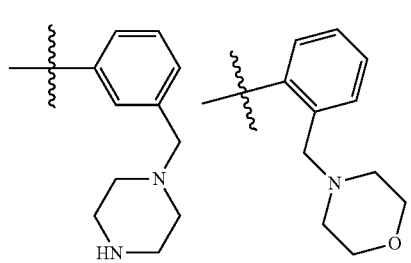

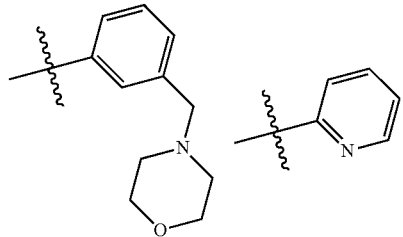

141
-continued

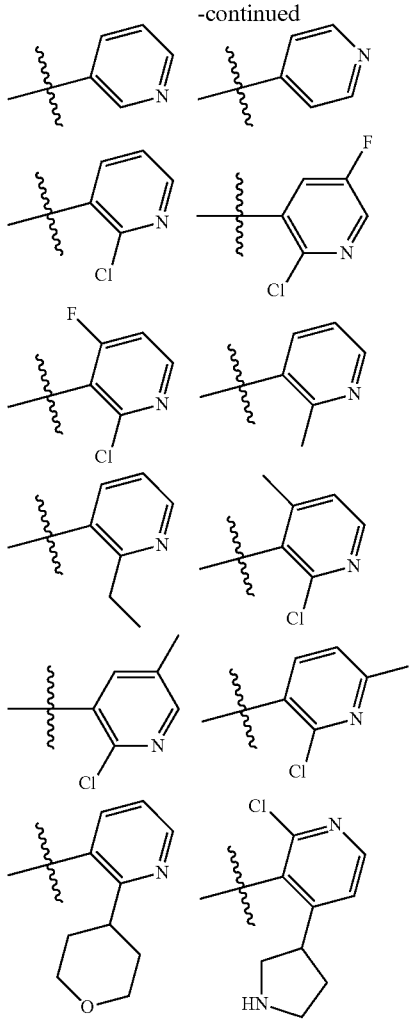

142
-continued

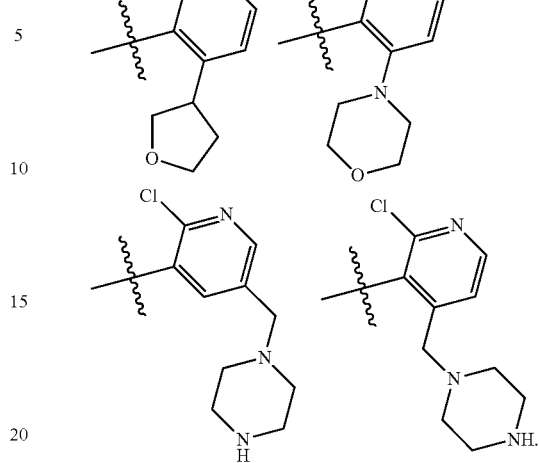

6. The compound according to claim 1, wherein $R_4$ is selected from the group consisting of —CO(CR$_{10}$R$_{11}$)$_m$R$_{12}$, wherein m is 0, 1, 2 or 3, and wherein $R_{10}$ and $R_{11}$ are each independently H; $R_{12}$ is selected from the group consisting of 2-cyanophenyl, 5-chloro-2-fluorophenyl, 2-chloro-3-fluorophenyl, 2-chloro-4-fluorophenyl, 2-chloro-5-fluorophenyl, 2,5-difluorophenyl, 3-chloropyridin-2-yl, 6-chloropyridin-2-yl, 3-chloropyridin-4-yl, or 4-chloropyridin-3-yl.

7. The compound according to claim 1, wherein
$R_5$ and $R_6$ are each independently selected from the group consisting of H and $C_{1-6}$alkyl; and $R_7$ and $R_8$ are each independently selected from the group consisting of H and $C_{1-6}$alkyl optionally substituted with hydroxyl or —OC$_1$-C$_6$alkyl.

8. A compound selected from the group consisting of Examples P1-P20, P23-P25, P28-51, P53-P64, or a pharmaceutically acceptable salt thereof, P1
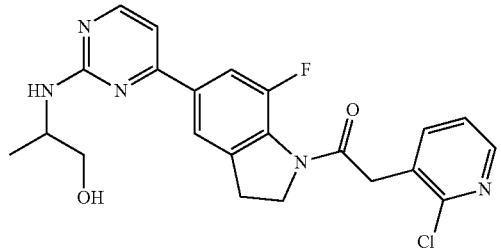
P1

P2
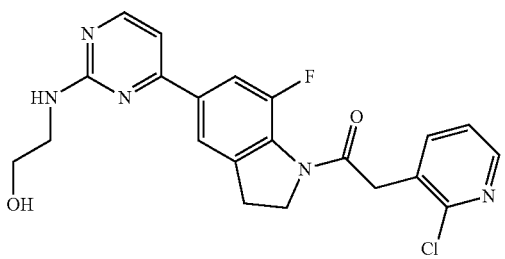
P2

P3
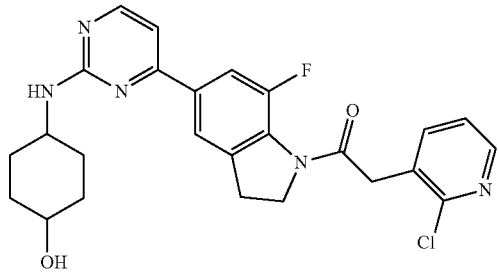
P3
P4
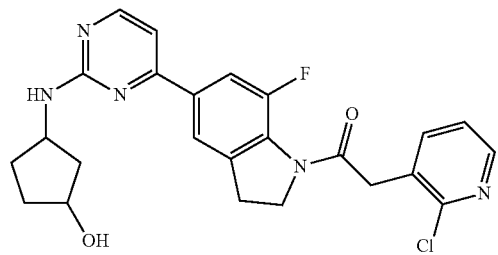
P4
P5
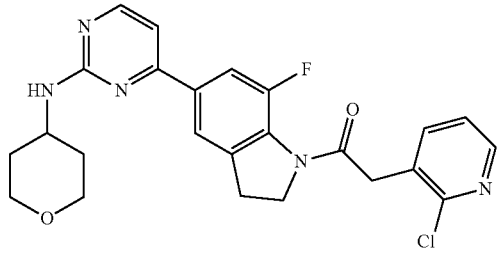
P5
P6
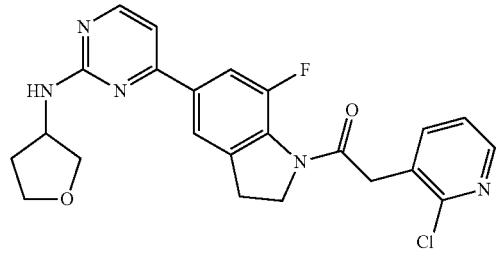
P6
P7
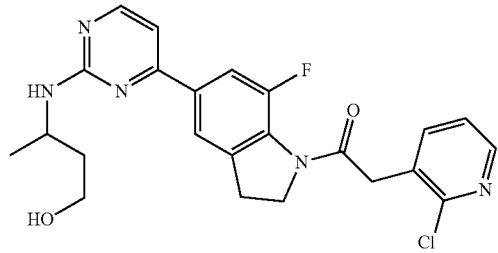
P7

-continued
P8
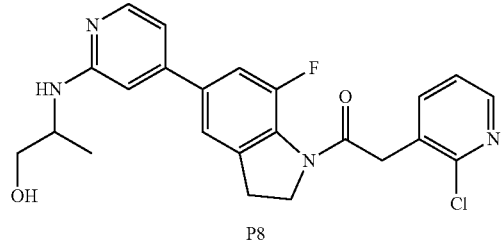
P8
P9
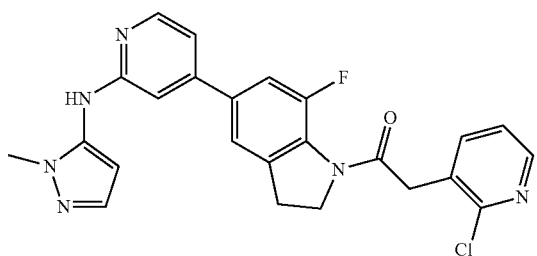
P9
P10
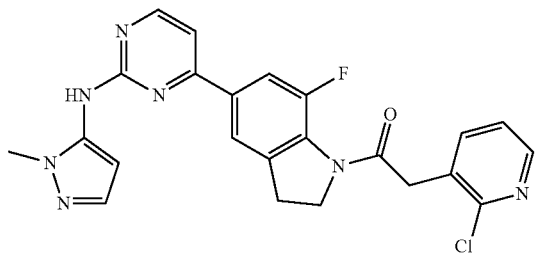
P10
P11
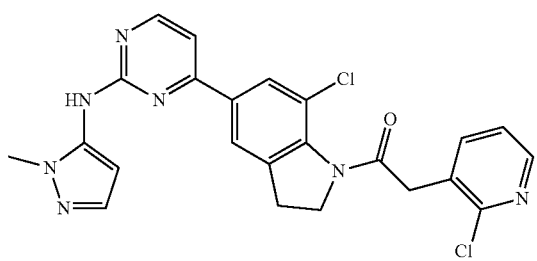
P11
P12
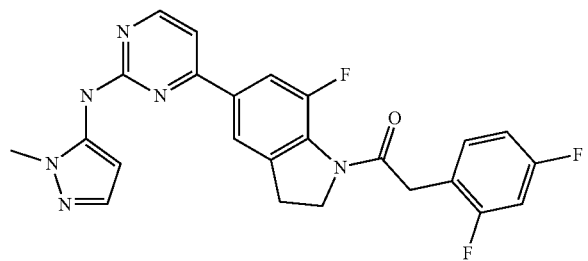 [SMILES: Cn1nccc1Nc1nccc(-c2cc(F)c3c(c2)CCN3C(=O)Cc2ccc(F)cc2F)n1]
P12

P13 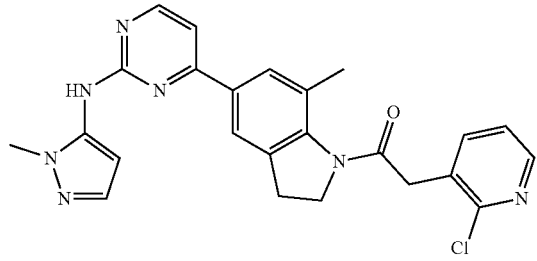 [SMILES: Cc1cc(-c2ccnc(Nc3ccnn3C)n2)cc2c1N(C(=O)Cc1cccnc1Cl)CC2]
P14 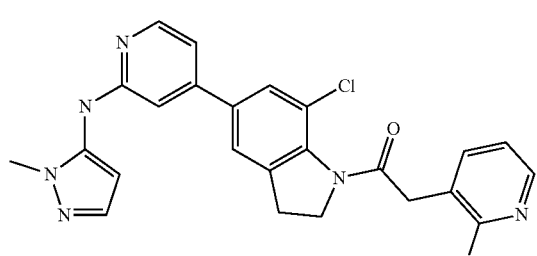
P15 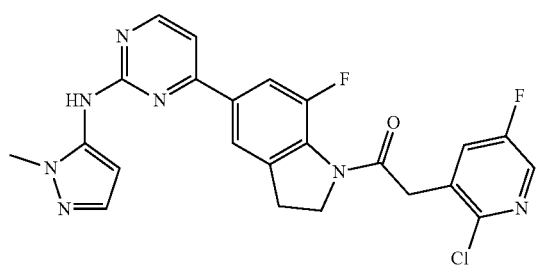 [SMILES: Cn1nccc1Nc1nccc(-c2cc(F)c3c(c2)CCN3C(=O)Cc2cc(F)cnc2Cl)n1]
P16 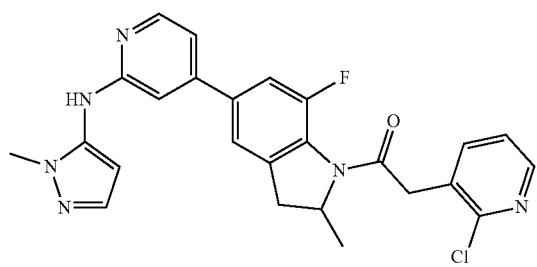 [SMILES: CC1Cc2cc(-c3ccnc(Nc4ccnn4C)c3)cc(F)c2N1C(=O)Cc1cccnc1Cl]
P17 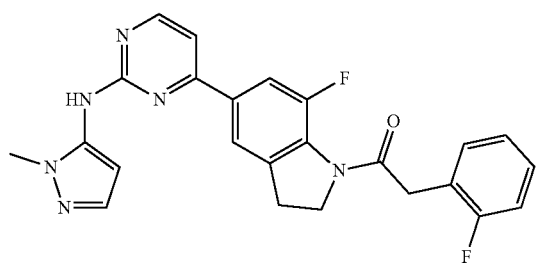

P18
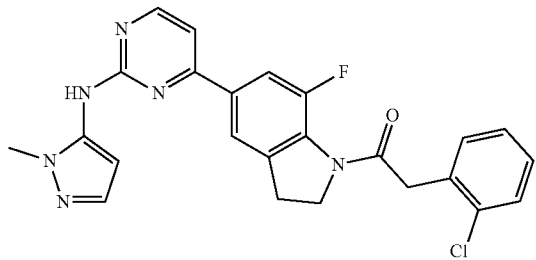 [SMILES: Cn1nccc1Nc1nccc(-c2cc(F)c3c(c2)CCN3C(=O)Cc2ccccc2Cl)n1]
P18
P19
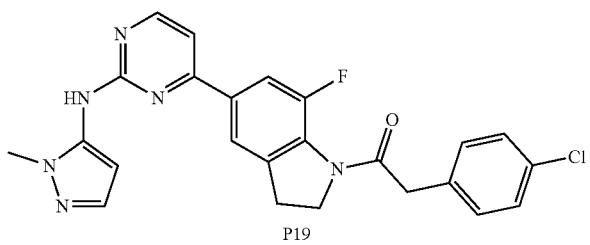
P19
P20
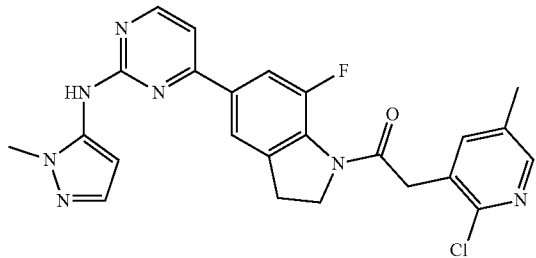 [SMILES: Cc1cnc(Cl)c(CC(=O)N2CCc3cc(-c4ccnc(Nc5ccnn5C)n4)cc(F)c32)c1]
P23
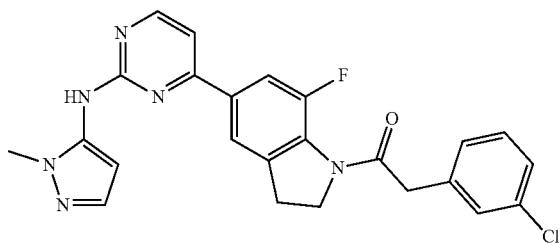 [SMILES: Cn1nccc1Nc1nccc(-c2cc(F)c3c(c2)CCN3C(=O)Cc2cccc(Cl)c2)n1]
P24
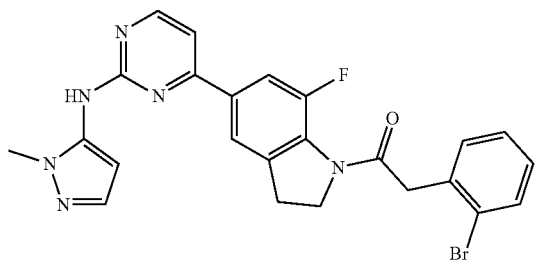
P25
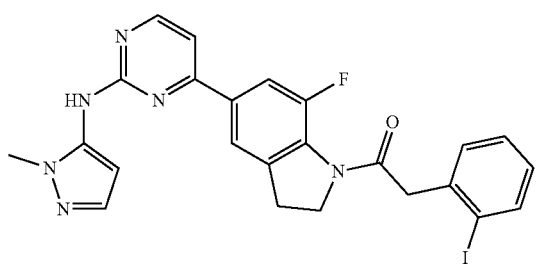 [SMILES: Cn1nccc1Nc1nccc(-c2cc(F)c3c(c2)CCN3C(=O)Cc2ccccc2I)n1]

-continued
P28
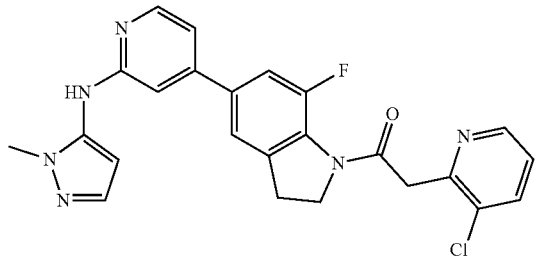 [SMILES: Cn1nccc1Nc1cc(-c2cc(F)c3c(c2)CCN3C(=O)Cc2ncccc2Cl)ccn1]
P29
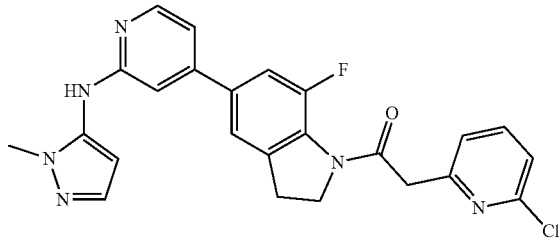 [SMILES: Cn1nccc1Nc1cc(-c2cc(F)c3c(c2)CCN3C(=O)Cc2cccc(Cl)n2)ccn1]
P30
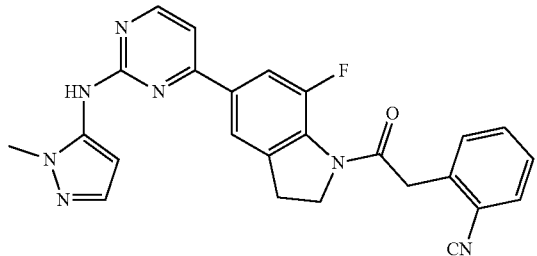
P31
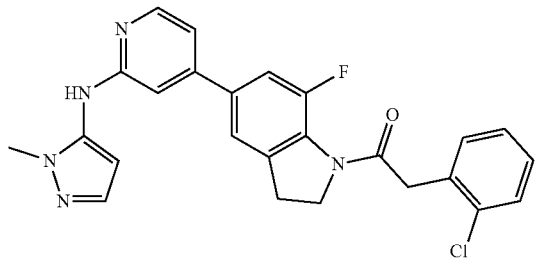
P32
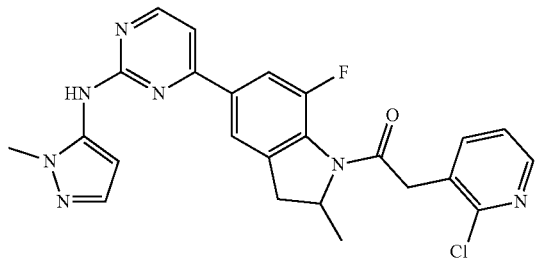 [SMILES: CC1Cc2cc(-c3ccnc(Nc4ccnn4C)n3)cc(F)c2N1C(=O)Cc1cccnc1Cl]
P33
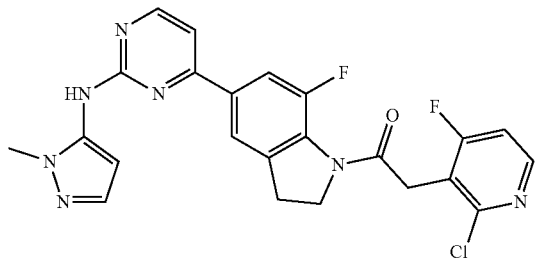 [SMILES: Cn1nccc1Nc1nccc(-c2cc(F)c3c(c2)CCN3C(=O)Cc2c(F)ccnc2Cl)n1]

-continued
P34
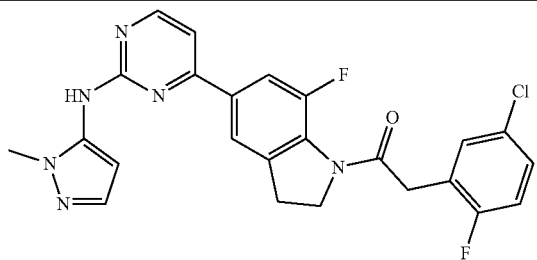
P35
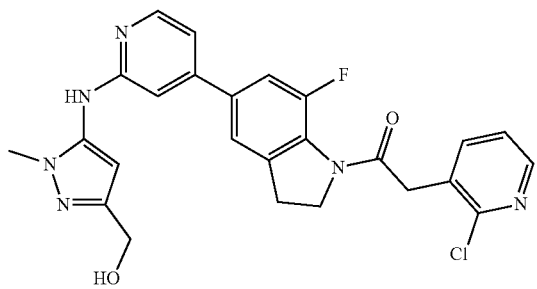 [SMILES: Cn1nc(CO)cc1Nc1cc(-c2cc(F)c3c(c2)CCN3C(=O)Cc2cccnc2Cl)ccn1]
P36
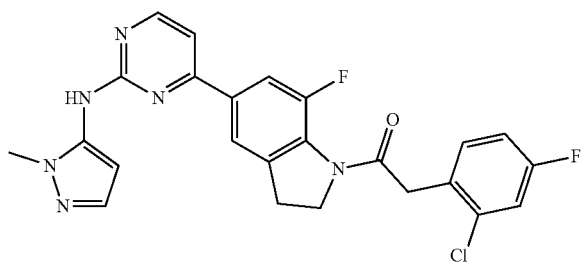 [SMILES: Cn1nccc1Nc1nccc(-c2cc(F)c3c(c2)CCN3C(=O)Cc2ccc(F)cc2Cl)n1]
P37
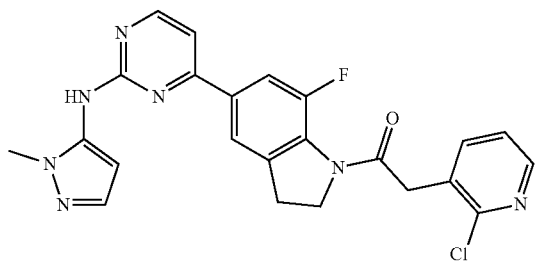
P38
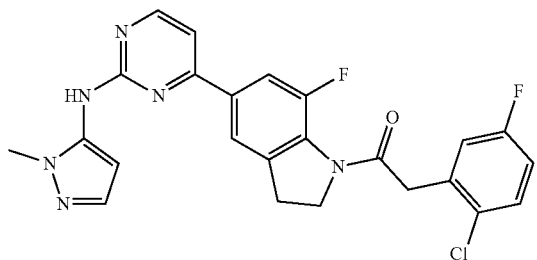
P39
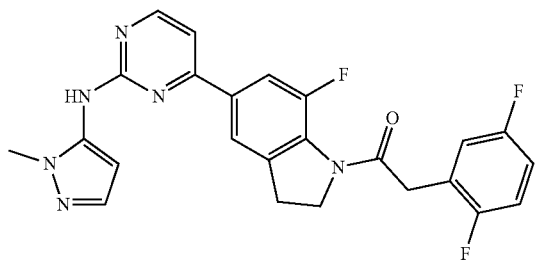 [SMILES: Cn1nccc1Nc1nccc(-c2cc(F)c3c(c2)CCN3C(=O)Cc2cc(F)ccc2F)n1]

P40 and P41
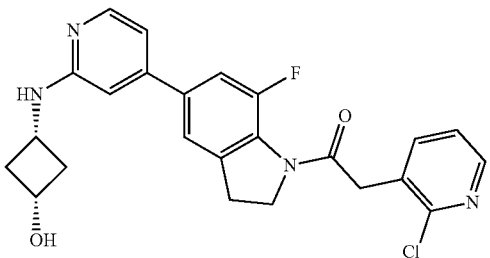
P42 and P43
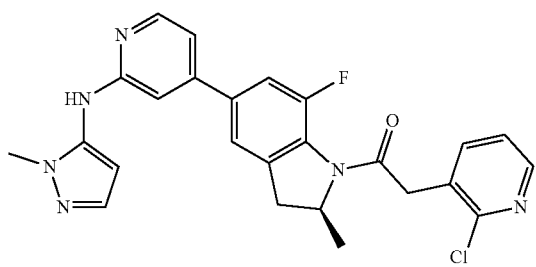
P44
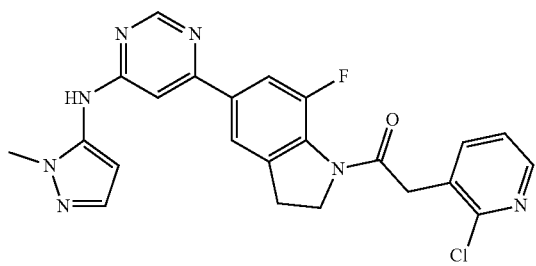 [SMILES: Cn1nccc1Nc1cc(-c2cc(F)c3c(c2)CCN3C(=O)Cc2cccnc2Cl)ncn1]
P45
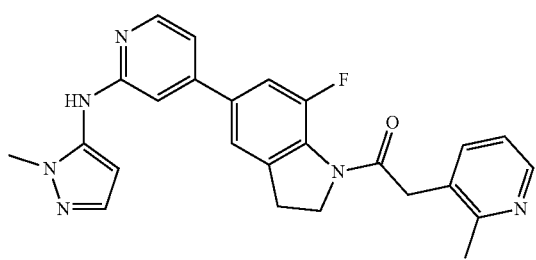 [SMILES: Cc1ncccc1CC(=O)N1CCc2cc(-c3ccnc(Nc4ccnn4C)c3)cc(F)c21]

-continued
P46
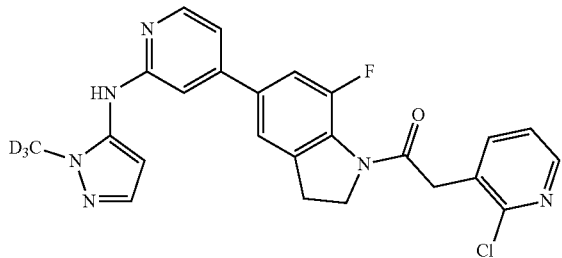 [SMILES: [2H]C([2H])([2H])n1nccc1Nc1cc(-c2cc(F)c3c(c2)CCN3C(=O)Cc2cccnc2Cl)ccn1]
P47
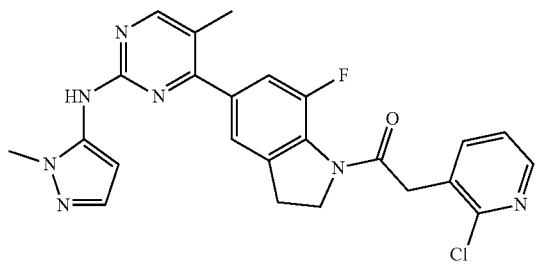 [SMILES: Cc1cnc(Nc2ccnn2C)nc1-c1cc(F)c2c(c1)CCN2C(=O)Cc1cccnc1Cl]
P48
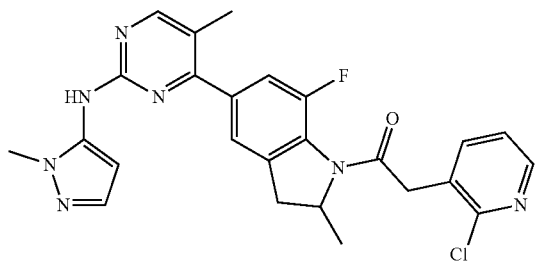 [SMILES: Cc1cnc(Nc2ccnn2C)nc1-c1cc(F)c2c(c1)CC(C)N2C(=O)Cc1cccnc1Cl]
P49
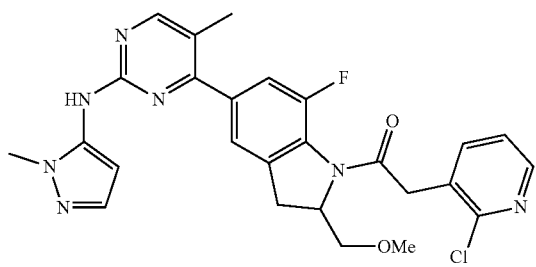 [SMILES: COCC1Cc2cc(-c3nc(Nc4ccnn4C)ncc3C)cc(F)c2N1C(=O)Cc1cccnc1Cl]
P50
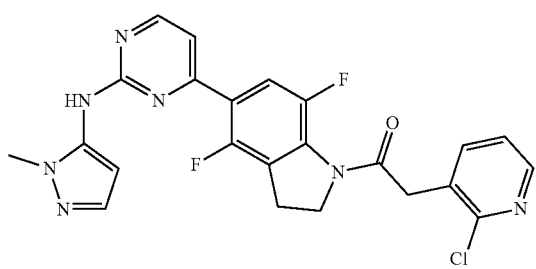 [SMILES: Cn1nccc1Nc1nccc(-c2cc(F)c3c(c2F)CCN3C(=O)Cc2cccnc2Cl)n1]
P51
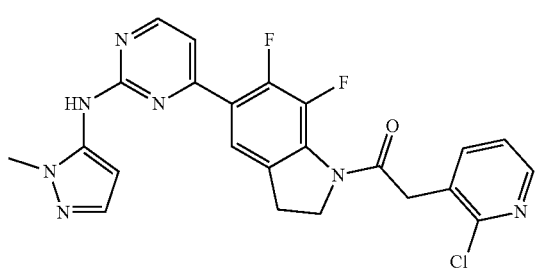 [SMILES: Cn1nccc1Nc1nccc(-c2cc3c(c(F)c2F)N(C(=O)Cc2cccnc2Cl)CC3)n1]

P53
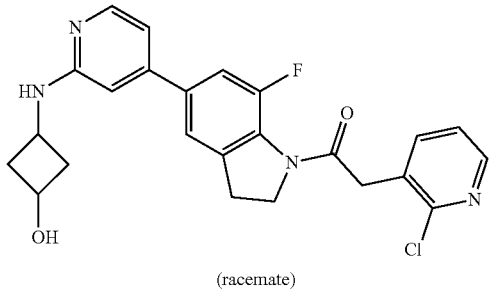 [SMILES: O=C(Cc1cccnc1Cl)N1CCc2cc(-c3ccnc(NC4CC(O)C4)c3)cc(F)c21]
(racemate)
P54
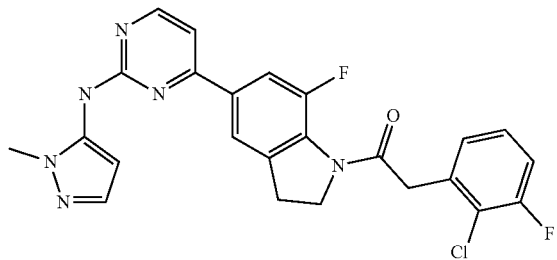 [SMILES: Cn1nccc1Nc1nccc(-c2cc(F)c3c(c2)CCN3C(=O)Cc2cccc(F)c2Cl)n1]
P55
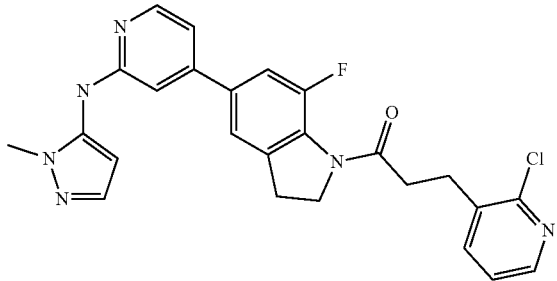 [SMILES: Cn1nccc1Nc1cc(-c2cc(F)c3c(c2)CCN3C(=O)CCc2cccnc2Cl)ccn1]
P56
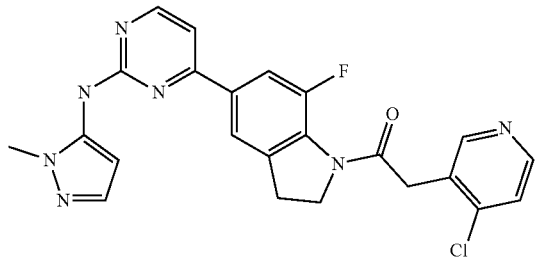 [SMILES: Cn1nccc1Nc1nccc(-c2cc(F)c3c(c2)CCN3C(=O)Cc2cnccc2Cl)n1]
P57
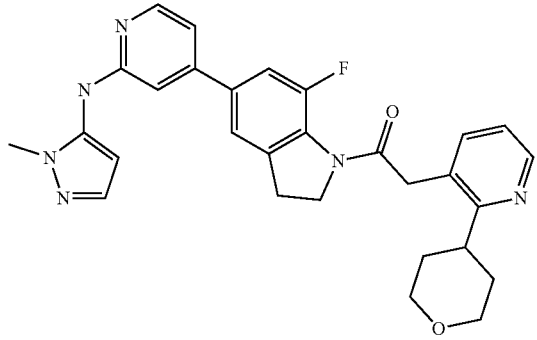 [SMILES: Cn1nccc1Nc1cc(-c2cc(F)c3c(c2)CCN3C(=O)Cc2cccnc2C2CCOCC2)ccn1]

-continued
P58
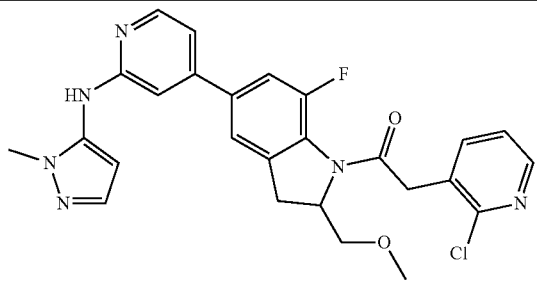
P59
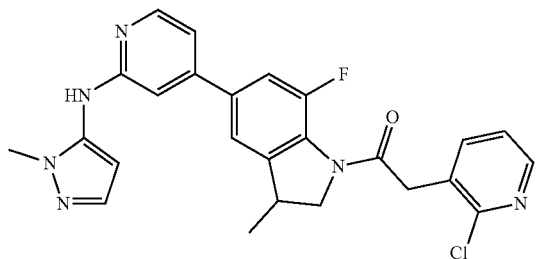 [SMILES: CC1CN(C(=O)Cc2cccnc2Cl)c2c(F)cc(-c3ccnc(Nc4ccnn4C)c3)cc21]
P60
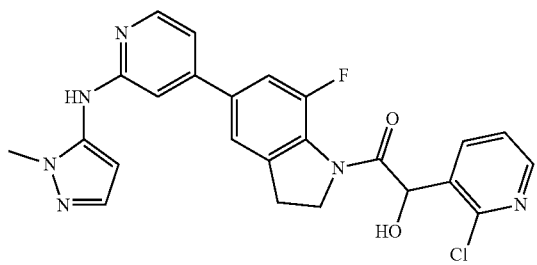 [SMILES: Cn1nccc1Nc1cc(-c2cc(F)c3c(c2)CCN3C(=O)C(O)c2cccnc2Cl)ccn1]
P61
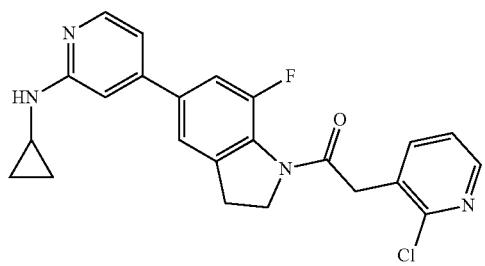 [SMILES: O=C(Cc1cccnc1Cl)N1CCc2cc(-c3ccnc(NC4CC4)c3)cc(F)c21]
P62 and P63
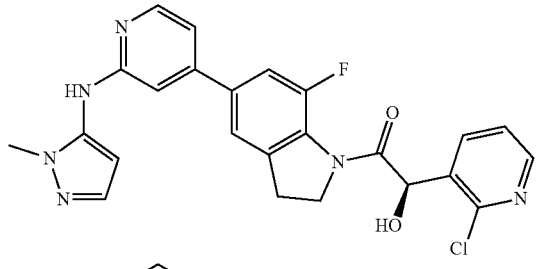
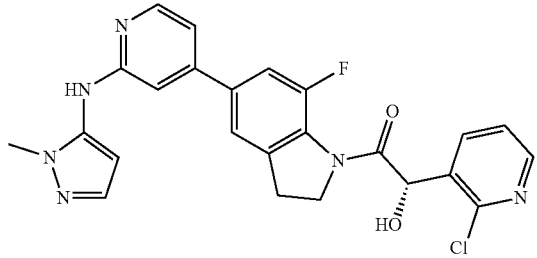

-continued

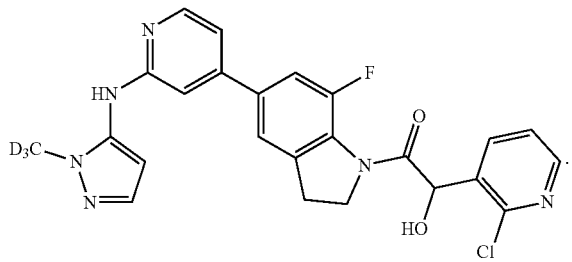 [SMILES: [2H]C([2H])([2H])n1nccc1Nc1cc(-c2cc(F)c3c(c2)CCN3C(=O)C(O)c2cccnc2Cl)ccn1]

P64

9. A compound t-butyl (4-(7-fluoroindolin-5-yl)pyridin-2-yl)(1-methyl-1H-pyrazol-5-yl)carbamate represented by the formula:

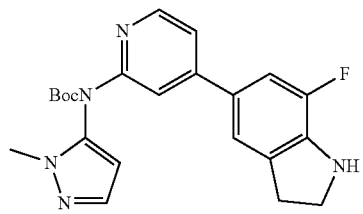 [SMILES: Cn1nccc1N(C(=O)OC(C)(C)C)c1cc(-c2cc(F)c3c(c2)CCN3)ccn1]

or a stereoisomer, racemate, geometric isomer, tautomer, hydrate, solvate, or pharmaceutically acceptable salt thereof.

10. The compound according to claim 1, wherein $R_2$ is selected from the group consisting of isopropyl,

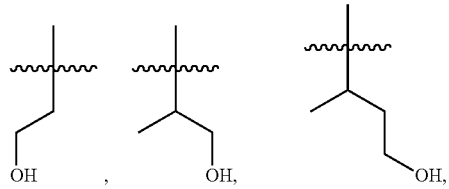

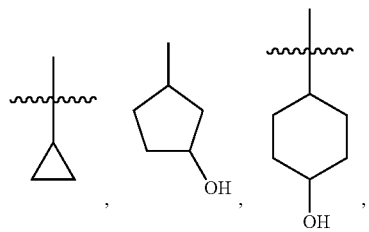

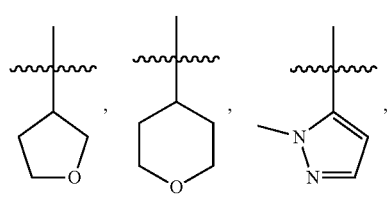

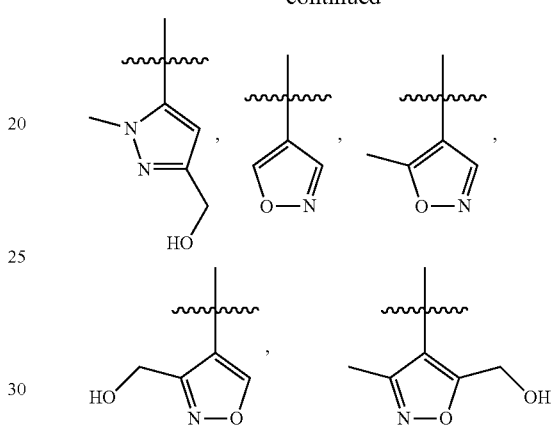

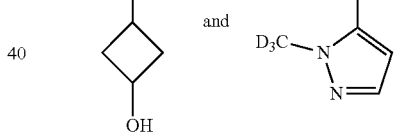

11. The compound according to claim 1, wherein $R_3$ is selected from the group consisting of fluoro, chloro and —$CH_3$.

12. The compound according to claim 1, wherein $R_3$ is selected from the group consisting of fluoro.

13. The compound according to claim 1, wherein $R_5$, $R_6$, $R_7$ and $R_8$ are each independently selected from the group consisting of —H, —$CH_3$, and —$CH_2OH$.

14. A pharmaceutical composition, comprising the compound according to claim 1 or a pharmaceutically acceptable salt thereof, and optionally a pharmaceutically acceptable carrier.

15. A non-therapeutic method of inhibiting ERK kinase activity, comprising contacting an effective amount of the compound according to claim 1 or a pharmaceutically acceptable salt thereof, with an ERK kinase, thereby inhibiting the ERK kinase.

16. A method for preparing the compound of formula (Ie) according to claim 1, wherein said compound of formula (Ie) is the compound of formula C3:

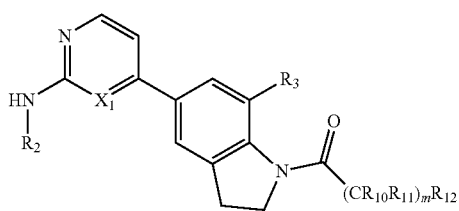

wherein $X_1$, $R_2$, $R_3$, $R_{10}$, $R_{11}$, $R_{12}$ and m are as defined in claim 1, comprising the steps of:

(a) subjecting the compound of formula C1

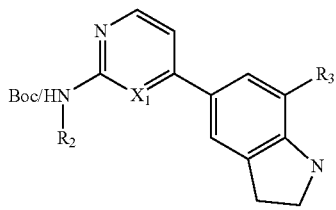

and the compound

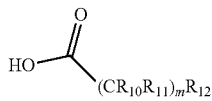

to amide coupling reaction, to give the compound of formula C2,

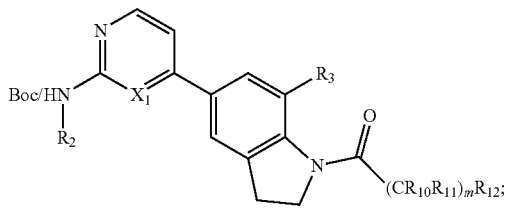

and (b) When the compound of C2 is Boc-protected, deprotecting it, to give the compound of formula C3,

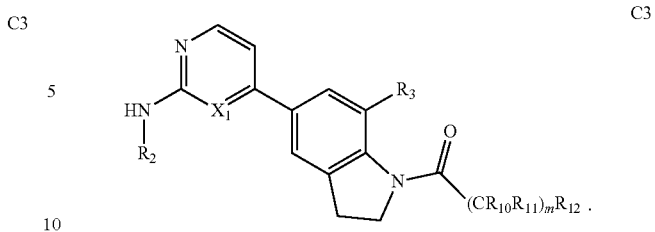

17. The method according to claim 16, wherein the amide coupling reaction is carried out in the presence of a condensing agent and a base in an inert solvent.

18. The method according to claim 16, wherein the deprotection is carried out in the presence of an acid in an inert solvent.

19. The method according to claim 17, wherein the inert solvent is selected from the group consisting of ethyl acetate, tetrahydrofuran, methyltetrahydrofuran, acetonitrile, dimethyl sulfoxide, N,N-dimethylformamide, dichloromethane, 1,2-dichloroethane, N-methyl-2-pyrolidone, or a combination thereof.

20. The method according to claim 17, wherein the condensing agent is one or more selected from the group consisting of 1-hydroxylbenzotriazole (HOBT), 1-hydroxyl-7-azobenzotriazole (HOAT), benzotriazol-1-yl-oxytripyrrolidino-phosphonium hexafluorophosphate (PyBOP), benzotriazol-1-yloxytris(dimethylamino)phosphonium hexafluorophosphate (BOP), 1,1-carbonyldiimidazole (CDI), 1-propylphosphonic anhydride ($T_3P$), 1-ethyl-3-(3-dimethylaminopropyl)carbodiimide hydrochloride (EDC.HCl), N,N-dicyclohexylcarbodiimide (DCC), acetic anhydride, acetyl chloride, oxalyl chloride, O-(7-azabenzotriazol-1-yl)-N,N,N',N'-tetramethyluronium hexafluorophosphate (HATU), and O-(benzotriazol-1-yl)-N,N,N',N'-tetramethyluronium hexafluorophosphate (HBTU).

21. The method according to claim 17, wherein the base is one or more selected from the group consisting of triethylamine, DIPEA, pyridine, 2,4-dimethylpyridine, NaOH, KOH, LiOH, $Na_2CO_3$, $K_2CO_3$, $NaHCO_3$, $Cs_2CO_3$, $Na_3PO_4$, or $K_3PO_4$.

22. The method according to claim 16, wherein the amide coupling reaction is carried out at a temperature from room temperature to reflux for 0.5-24 h.

23. The method according to claim 18, wherein the acid is one or more selected from the group consisting of hydrochloric acid, sulfuric acid, trifluoroacetic acid, acetic acid, formic acid, and phosphoric acid.

24. The method according to claim 16, wherein the deprotection is carried out at a temperature from −10° C. to 80° C. for 0.5-24 h.

25. The method according to claim 18, wherein the inert solvent is selected from the group consisting of ethyl acetate, tetrahydrofuran, methyltetrahydrofuran, acetonitrile, dimethyl sulfoxide, N,N-dimethylformamide, dichloromethane, 1,2-dichloroethane, N-methyl-2-pyrolidone, or a combination thereof.

* * * * *